(12) United States Patent
Odagami et al.

(10) Patent No.: US 10,017,522 B2
(45) Date of Patent: Jul. 10, 2018

(54) ALPHA HELIX MIMETICS AND METHODS RELATING THERETO

(71) Applicant: PRISM BioLab Co., Ltd., Yokohama-shi, Kanagawa (JP)

(72) Inventors: Takenao Odagami, Yokohama (JP); Yuji Kogami, Yokohama (JP); Hiroyuki Kouji, Yokohama (JP)

(73) Assignee: PRISM BioLab Co., Ltd., Yokohama-shi (JP)

( * ) Notice: Subject to any disclaimer, the term of this patent is extended or adjusted under 35 U.S.C. 154(b) by 0 days.

(21) Appl. No.: 14/720,690

(22) Filed: May 22, 2015

(65) Prior Publication Data

US 2015/0368262 A1 Dec. 24, 2015

Related U.S. Application Data

(62) Division of application No. 13/319,071, filed as application No. PCT/JP2010/058141 on May 7, 2010, now Pat. No. 9,040,531.

(60) Provisional application No. 61/176,348, filed on May 7, 2009, provisional application No. 61/176,363, filed on May 7, 2009.

(51) Int. Cl.
| | | |
|---|---|---|
| *C07D 495/14* | (2006.01) | |
| *C07D 401/14* | (2006.01) | |
| *C07D 403/14* | (2006.01) | |
| *C07D 487/04* | (2006.01) | |
| *C07D 498/04* | (2006.01) | |
| *C07D 471/14* | (2006.01) | |
| *C07D 487/14* | (2006.01) | |

(52) U.S. Cl.
CPC ......... *C07D 495/14* (2013.01); *C07D 401/14* (2013.01); *C07D 403/14* (2013.01); *C07D 471/14* (2013.01); *C07D 487/04* (2013.01); *C07D 487/14* (2013.01); *C07D 498/04* (2013.01)

(58) Field of Classification Search
CPC .................................................. C07D 495/14
See application file for complete search history.

(56) References Cited

U.S. PATENT DOCUMENTS

| | | | |
|---|---|---|---|
| 5,440,013 A | 8/1995 | Kahn | |
| 5,929,237 A | 7/1999 | Kahn | |
| 6,013,458 A | 1/2000 | Kahn | |
| 6,762,185 B1 | 7/2004 | Kahn | |
| 7,067,507 B2* | 6/2006 | Pulley | C07D 273/02 514/183 |
| 7,232,822 B2* | 6/2007 | Moon | C07D 487/04 514/243 |

| | | | |
|---|---|---|---|
| 2005/0004131 A1 | 1/2005 | Flohr | |
| 2005/0209256 A1 | 9/2005 | Andres, Jr. | |
| 2005/0222158 A1 | 10/2005 | Andres, Jr. | |

FOREIGN PATENT DOCUMENTS

| | | |
|---|---|---|
| WO | 1994/003494 A1 | 2/1994 |
| WO | 2001/000210 A1 | 1/2001 |
| WO | 2001/016135 A2 | 3/2001 |
| WO | 2003/031448 A1 | 4/2003 |
| WO | 2004/035587 A1 | 4/2004 |
| WO | 2004/072077 A1 | 8/2004 |
| WO | 2004/093828 A2 | 11/2004 |
| WO | 2005/021025 A2 | 3/2005 |
| WO | 2005/116032 A2 | 12/2005 |
| WO | 2006/101858 A1 | 9/2006 |
| WO | 2007/056513 A1 | 5/2007 |
| WO | 2007/056593 A2 | 5/2007 |
| WO | 2009/051397 A1 | 4/2009 |
| WO | 2009/148192 A1 | 12/2009 |
| WO | 2010/044485 A1 | 4/2010 |

OTHER PUBLICATIONS

Drugs.com. "Taxol." © Feb. 12, 2008. Available from: < http://web.archive.org/web/20080212085332/http://www.drugs.com/taxol.html >.*
Mayo Clinic. "Healthy Lifestyle: Adult Health." © 2016, Available from: < http://www.mayoclinic.org/healthy-lifestyle/adult-health/in-depth/cancer-prevention/art-20044816?p=1 >.*
"List of Cancer Chemotherapy Drugs." (2013), Available from: https://www.navigatingcancer.com/library/all/chemotherapy_drugs >.*
Cystic Fibrosis Foundation. "Treatments." © 2014. Available from: < https://www.cff.org/What-is-CF/About-Cystic-Fibrosis/ >.*
Drugs.com "Cystic Fibrosis." (c) 2014. Available from: < https://www.drugs.com/health-guide/cystic-fibrosis.html >.*
Mayo Clinic. "Pulmonary fibrosis." © 2014. Available from: < http://www.mayoclinic.org/diseases-conditions/pulmonary-fibrosis/basics/definition/con-20029091?p=1 >.*
MacDonald, B.T., et al. "Wnt/β-catenin signaling: components, mechanisms, and diseases." Dev. Cell. (Jul. 2009), vol. 17(1): pp. 9-26.*
Mandal, A. "Types of Fibrosis." (c) 2016. Medical News Life Sciences & Medicine. Available from: < http://www.news-medical.net/health/Types-of-Fibrosis.aspx >, pp. 1-3 of 3.*
Monkley, S.J., et al., "Targeted Disruption of the Wnt2 Gene Results in Placentation Defects," Development 122:3343-3353, 1996.
Moon, R.T., et al., WNTs Modulate Cell Fate and Behavior During Vertebrate Development, Trends in Genetics 13(4):157-162, Apr. 1997.
Morin, P.J., et al., "Apoptosis and APC in Colorectal Tumorigenesis," Proceedings of the National Academy of Sciences of USA 93:7950-7954, Jul. 1996.

(Continued)

*Primary Examiner* — Noble E Jarrell
*Assistant Examiner* — John S Kenyon
(74) *Attorney, Agent, or Firm* — Barry L. Davison; Davis Wright Tremaine LLP

(57) ABSTRACT

Alpha-helix mimetic structures and compounds represented by the formula (I) wherein the general formula and the definition of each symbol are as defined in the specification, a chemical library relating thereto, and methods relating thereto, are disclosed. Applications of these compounds in the treatment of medical conditions, e.g., cancer diseases, fibrotic diseases, and pharmaceutical compositions comprising the mimetics are further disclosed.

17 Claims, 8 Drawing Sheets

(56) References Cited

OTHER PUBLICATIONS

Morin, P.J., et al, "Activation of β-Catenin-Tcf Signaling in Colon Cancer by Mutations in β-Catenin or APC," Science 275:1787-1790, Mar. 21, 1997.
Moss, J., et al., "Prevalence and Clinical Characteristics of Lymphangioleiomyomatosis (LAM) in Patients With Tuberous Sclerosis Complex," American Journal of Respiratory and Critical Care Medicine 164:669-671, 2001.
Motoyama, J., et al., "Essential Function of Gli2 and Gli3 in the Formation of Lung, Trachea and Oesophagus," Nature Genetics 20:54-57, Sep. 1998.
Müller-Spahn, F., and D. Hock, "Risk Factors and Differential Diagnosis of Alzheimer's Disease," European Archives of Psychiatry and Clinical Neuroscience 249(Suppl. 3):37-42, 1999.
Muñoz-Elias, G., et al., "Marrow Stromal Cells, Mitosis, and Neuronal Differentiation: Stem Cell and Precursor Functions," Stem Cells 21:437-448, 2003.
Nicolaou, K.C., et al., "Calicheamicin θI1: A Rationally Designed Molecule With Extremely Potent and Selective DNA Cleaving Properties and Apoptosis Inducing Activity," Angewandte Chemie International Edition in English 33(2):183-186, 1994.
Nilsson, E.E., et al., "An in Vivo Mouse Reporter Gene (Human Secreted Alkaline Phosphatase) Model to Monitor Ovarian Tumor Growth and Response to Therapeutics," Cancer Chemotherapy and Pharmacology 49:93-100, 2002.
Nusse, R., and H.E. Varmus, "Wnt Genes," Cell 69:1073-1087, Jun. 26, 1992.
Ogawa, M., et al., "Rice Gibberellin-Insensitive Gene Homolog, OsGAI, Encodes a Nuclear-Localized Protein Capable of Gene Activation at Transcriptional Level," Gene 245:21-29, 2000.
Okanami, M., et al., "HALF-1, a bZIP-Type Protein, Interacting With the Wheat Transcription Factor HBP-1a Contains a Novel Transcriptional Activation Domain," Genes to Cells 1:87-99, 1996.
Orford, K., et al., "Exogenous Expression of β-Catenin Regulates Contact Inhibition, Anchorage-Independent Growth, Aniokis, and Radiation-Induced Cell Cycle Arrest," The Journal of Cell Biology 146(4):855-867, Aug. 23, 1999.
O'Shea, K.S., et al., "Thrombospondin and a 140 kd Fragment Promote Adhesion and Neurite Outgrowth From Embryonic Central and Peripheral Neurons and From PC12 Cells," Neuron 7:231-237, Aug. 1991.
Pacherník, J., et al., "Neural Differentiation of Mouse Embryonic Stem Cells Grown in Monolayer," Reproduction Nutritional Development 42:317-326, 2002.
Parr, B.A., and A.P. McMahon, "Wnt Genes and Vertebrate Development," Current Opinion in Genetics and Development 4:523-528, 1994.
Parr, B.A., et al., "Wnt7b Regulates Placental Development in Mice," Developmental Biology 237:324-332, 2001.
Peifer, M., and P. Polakis, "Wnt Signaling in Oncogenesis and Embryogenesis—A Look Outside the Nucleus," Science 287:1606-1609, Mar. 3, 2000.
Pellitteri, P., et al., "Schwann Cell-Derived Factors Support Serotoninergic Neuron Survival and Promote Neurite Outgrowth," European Journal of Histochemistry 45:367-376, 2001.
Pepicelli, C.V., et al., "Sonic Hedgehog Regulates Branching Morphogenesis in the Mammalian Lung," Current Biology 8(19):1083-1086, Sep. 24, 1998.
Piergentili, A., et al., "Solution-Phase Synthesis of ICG-001, a β-Turn Peptidomimetic Molecule Inhibitor of β-Catenin-Tcf-Mediated Transcription," Tetrahedron 63(52):12912-12916, Oct. 13, 2007.
Polakis, P., "Wnt Signaling and Cancer," Genes & Development, 14:1837-1851, 2000.
Polakis, P. et al., 2000, "Colon Cancer Prevention: Dietary Modulation of Cellular and Molecular Mechanisms," Advances in Experimental Medicine and Biology 470:23-32, 2000.
Randolph, J.T., et al., "Major Simplifications in Oligosaccharide Syntheses Arising From a Solid-Phase Based Method: An Application to the Synthesis of the Lewis b Antigen," Journal of the American Chemical Society 117:5712-5719, 1995.
Robyr, D., et al., "Nuclear Hormone Receptor Coregulators in Action: Diversity for Shared Tasks," Molecular Endocrinology 14(3):329-347, 2000.
Rocchi, A., et al, "Causative and Susceptibility Genes for Alzheimer's Disease: A Review," Brain Research Bulletin 61(1):1-24, Jun. 30, 2003.
Rodova, M., et al., "The Polycystic Kidney Disease-1 Promoter is a Target of the β-Catenin/T-Cell Factor Pathway," The Journal of Biological Chemistry 277(33):29577-29583, Aug. 16, 2002.
Roose, J., et al., "Synergy Between Tumor Suppressor APC and the β-Catenin-Tcf4 Target Tcf1," Science 285(5435):1923-1926, Sep. 17, 1999.
Rowan, M.J., et al., "Synaptic Plasticity in Animal Models of Early Alzheimer's Disease," Philosophical Transactions of the Royal Society B: Biological Sciences 358(1432):821-828, Apr. 2003.
Rubinfeld, B., et al., "Binding of GSK3beta to the APC-Beta-Catenin Complex and Regulation of Complex Assembly," Science 272(5264):1023-1026, May 17, 1996.
Rubinfeld, B., et al, "Stabilization of β-Catenin by Genetic Defects in Melanoma Cell Lines," Science 275(5307):1790-1792, Mar. 21, 1997.
Rydel, R.E., and L.A. Greene, "cAMP Analogs Promote Survival and Neurite Outgrowth in Cultures of Rat Sympathetic and Sensory Neurons Independently of Nerve Growth Factor," Proceedings of the National Academy of Sciences of USA 5(4):1257-1261, Feb. 1988.
Sakanaka, C., and L.T. William, "Functional Domains of Axin," The Journal of Biological Chemistry 274(20):14090-14093, May 14, 1999.
Sakanaka, C., et al., "Bridging of β-Catenin and Glycogen Synthase Kinase-3β Axin and Inhibition of β-Catenin-Mediated Transcription," Proceedings of the National Academy of Sciences of USA 95(6):3020-3023, Mar. 1998.
Sant'Angelo, A., et al., "Usefulness of Behavioral and Electrophysiological Studies in Transgenic Models of Alzheimer's Disease," Neurochemical Research 28(7):1009-1015, Jul. 2003.
Sata, M., "Circulating Vascular Progenitor Cells Contribute to Vascular Repair, Remodeling, and Lesion Formation," Trends in Cardiovascular Medicine 13(6):249-253, Aug. 2003.
Sata, M., et al., "Hematopoietic Stem Cells Differentiate Into Vascular Cells That Participate in the Pathogenesis of Atherosclerosis," Nature Medicine 8(4):403-409, May 2002.
Satoh, T., et al., "Prostaglandin J2 and Its Metabolites Promote Neurite Outgrowth Induced by Nerve Growth Factor in PC12 Cells," Biochemical and Biophysical Research Communications 258(1):50-53, Apr. 29, 1999.
Selman, et al., "TIMP-1, -2, -3, and -4 in Idiopathic Pulmonary Fibrosis. A Prevailing Nondegradative Lung Microenvironment?," American Journal of Physoiology—Lung Cellular and Molecular Physiology 279(3):L562-L574, Sep. 1, 2000.
Shawler, D.L., et al., "Comparison of Gene Therapy With Interleukin-2 Gene Modified Fibroblasts and Tumor Cells in the Murine CT-26 Model of Colorectal Carcinoma," Journal of Immunotherapy with Emphasis on Tumor Immunology 17(4):201-208, May 1995.
Shih, H.-M., et al., "A Positive Genetic Selection for Disrupting Protein-Protein Interactions: Identification of Creb Mutations That Prevent Association With the Coactivator CBP," Proceedings of the National Academy of Sciences of USA 93(24):13896-13901, Nov. 1996.
Shikama, N., "The p300/CBP Family: Integrating Signals With Transcription Factors and Chromatin" Trends in Cell Biology 7(6):230-236, Jun. 1997.
Shtutman, M., et al., "The Cyclin D1 Gene is a Target of the β-Catenin/LEF-1 Pathway," Proceedings of the National Academy of Sciences of USA 96(10):5522-5527, May 1999.
Shu, W., et al., "Wnt7b Regulates Mesenchymal Proliferation and Vascular Development in the Lung," Development 129:4831-4842, 2002.

(56) References Cited

OTHER PUBLICATIONS

Simonet, W.S., et al., "Pulmonary Malformation in Transgenic Mice Expressing Human Keratinocyte Growth Factor in the Lung," Proceedings of the National Academy of Sciences of USA 92(26):12461-12465, Dec. 1995.
Simosa, H.F., et al., "Survivin Expression is Up-Regulated in Vascular Injury and Identifies a Distinct Cellular Phenotype," Journal of Vascular Surgery 41(4):682-690, Apr. 2005.
Skubitz, A.P.N., et al., "Synthetic Peptides From the Carboxy-Terminal Globular Domain of the A Chain of Laminin: Their Ability to Promote Cell Adhesion and Neurite Outgrowth, and Interact With Heparin and the β1 Integrin Subunit," The Journal of Cell Biology 115(4):1137-1148, Nov. 15, 1991.
Smalley, M.J., and T.C. Dale, "Wnt Signalling in Mammalian Development and Cancer," Cancer and Metastasis Reviews 18(2):215-230, May 1999.
Song, D.H., et al., "Endogenous Protein Kinase CK2 Participates in Wnt Signaling in Mammary Epithelial Cells," The Journal of Biological Chemistry 275(31):23790-23797, Aug. 4, 2000.
Guo, Y., et al., "An Antiangiogenic Urokinase-Derived Peptide Combined With Tamoxifen Decreases Tumor Growth and Metastasis in a Syngeneic Model of Breast Cancer," Cancer Research 62:4678-4684, Aug. 15, 2002.
Gurwitz, D., "New Imaging Techniques for Early Diagnosis of Alzheimer's Disease," Trends in Neurosciences 23 (9):386, 2000.
Hanai, J.-I., et al., "Endostatin is a Potential Inhibitor of Wnt Signaling," The Journal of Cell Biology 158(3):529-539, Aug. 5, 2002.
Hayashi, S., et al., "A *Drosophila* Homolog of the Tumor Suppressor Gene Adenomatous Polyposis Coli Down-Regulates β-Catenin but its Zygotic Expression is not Essential for the Regulation of Armadillo," Proceedings of the National Academy of Sciences of USA 94:242-247, Jan. 1997.
He, T.C., et al., "Identificatioin of c-MYC as a Target of the APC Pathway," Science 281:1509-1512, Sep. 4, 1998.
He, T.C., et al., "PPARδ Is an APC-Regulated Target of Nonsteroidal Anti-Inflammatory Drugs," Cell 99:335-345, Oct. 29, 1999.
Hecht, A., et al, "The p300/CBP Acetyltransferases Function as Transcriptional Coactivators of β-Catenin in Vertebrates," The EMBO Journal 19(9):1839-1850, 2000.
Hirata, T., and H. Fujisawa, "Cortex-Specific Distribution of Membrane-Bound Factors That Promote NeuriteOutgrowth of Mitral Cells in Culture," Journal of Neurobiology 32:415-425, 1997.
Hobo, T., et al., "A bZIP Factor, TRAB1, Interacts With BP1 and Mediates Abscisic Acid-Induced Transcription," Proceedings of the National Academy of Sciences of USA 96(26):15348-15353, Dec. 21, 1999.
Hollenberg, S.M., et al., "Identification of a New Family of tissue-Specific Basic Helix-Loop-Helix Proteins With a Two-Hybrid System," Molecular and Cellular Biology 15(7):3813-3822, Jul. 1995.
Hsu, S.-C., et al., "Modulation of Transcriptional Regulation by LEF-1 in Response to Wnt-1 Signaling and Association With β-Catenin," Molecular and Cellular Biology 18(8):4807-4818, Aug. 1998.
Hunter, W.L., "Drug-Eluting Stents: Beyond the Hyperbole," Advanced Drug Delivery Reviews 58:347-349, 2006.
Janknecht, R., and T. Hunter, "A Growing Coactivator Network," Nature 383:22-23, Sep. 5, 1996.
Jue, S.F., et al., "The Mouse Wnt-1 Gene Can Act via a Paracrine Mechanism in Transformation of Mammary Epithelial Cells," Molecular and Cellular Biology 12(1):321-328, Jan. 1992.
Kapanci, Y., et al., "Cytoskeletal Protein Modulation in Pulmonary Alveolar Myofibroblasts During Idiopathic Pulmonary Fibrosis," American Journal of Respiratory and Critical Care Medicine 152:2163-2169, 1994.
Kasper, M., and G. Haroske, "Alterations in the Alveolar Epithelium After Injury Leading to Pulmonary Fibrosis," Histology and Histopatholgy 11:463-483, 1996.
Kato, S., et al., "Effect of Sodium Fluorescein on Neurite Outgrowth From the Retinal Explant Culture: An in Vitro Model for Retinal Toxicity," Developmental Brain Research 11:143-147, 1983.
Kawamorita, M., et al., "In Vitro Differentiation of Mouse Embryonic Stem Cells After Activation by Retinoic Acid," Human Cell 15(3):178-182, 2002.
Kawanami, O., "Structure of Alveolar Epithelial Cells in Patients With Fibrotic Lung Disorders," Laboratory Investigation 46(1):39-53, 1982.
Khalil, N., et al., "Increased Production and Immunohistochemical Localization of Transforming Growth Factor-β in Idiopathic Pulmonary Fibrosis," American Journal of Respiratory Cell and Molecular Biology 5:155-162, 1991.
Kinzler, K.W., and B. Vogelstein, "Lessons From Hereditary Colorectal Cancer," Cell 87:159-170, Oct. 18, 1996.
Kispert, A., et al., "Proteoglycans are Required for Maintenance of Wnt-11 Expression in the Ureter Tips," Development 122:3627-3637, 1996.
Kolligs, R.T., et al., "Neoplastic Transformation of RK3E by Mutant β-Catenin Requires Deregulation of Tcf/Lef Transcription but Not Activation of c-myc Expression," Molecular and Cellular Biology 19(8):5696-5706, Aug. 1999.
Koo, E.H., et al., "Amyloid β-Protein as Substrate Interacts With Extracellular Matrix to Promote Neurite Outgrowth," Proceedings of the National Academy of Sciences of USA 90:4748-4752, May 1993.
Koutsourakis, M., et al., "Branching and Differentiation Defects in Pulmonary Epithelium With Elevated Gata6 Expression," Mechanisms of Development 105:105-114, 2001.
Kril, J.J. and G.M. Halliday, "Alzheimer's Disease: Its Diagnosis and Pathogenesis," International Review of Neurobiology 48:167-217, 2001.
Kudo, C., et al., "Diclofenac Inhibits Proliferation and Differentiation of Neural Stem Cells," Biochemical Pharmacology 66:289-295, 2003.
Kurz, A., et al., "The Role of Biological Markers in the Early and Differential Diagnosis of Alzheimer's Disease," Journal of Neural Transmission (Supplementum) 62:238-133, 2002.
Labonté, P., et al., "Inhibition of Tumor Growth With Doxorubicin in a New Orthotopically Implanted Human Hepatocellular Carcinoma Model," Hepatology Research 18:72-85, 2000.
Lacza, Z., et al., "Neural Stem Cell Transplantation in Cold Lesion: A Novel Approach for the Investigation of Brain Trauma and Repair," Brain Research Protocols 11:145-154, 2003.
Lam, K.S., et al., "A New Type of Synthetic Peptide Library for Identifying Ligand-Binding Activity," Nature 354:82-84, Nov. 7, 1991.
Landesman-Bollag, E., "Protein Kinase CK2 in Mammary Gland Tumorigenesis," Onogene 20:3247-3257, 2001.
Lemere, C.A., et al., "Amyloid-Beta Immunization in Alzheimer's Disease Transgenic Mouse Models and Wildtype Mice," Neurochemical Research 28(7):1017-1027, Jul. 2003.
Lemon, B.D., and L.P. Freedman, "Nuclear Receptor Cofactors as Chromatin Remodelers," Current Opinion in Genetics & Development 9:499-504, 1999.
Leo, C., and J.D. Chen, "The SRC Family of Nuclear Receptor Coactivators," Gene 245:1-11, 2000.
Li, C., et al., "Wnt5a Participates in Distal Lung Morphogenesis," Developmental Biology 248:68-81, 2002.
Lin Y., et al., Induction of Ureter Branching as a Response to Wnt-2b Signaling During Early Kidney Organogenesis, Developmental Dynamics 222:26-39, 2001.
Litingtung, Y., et al., "Sonic Hedgehog is Essential to Foregut Development," Nature Genetics 20:58-61, Sep. 1998.
Lu, Q., et al., "The effect of Combining Aromatase Inhibitors With Antestrogens on Tumor Growth in a Nude Mouse Model for Breast Cancer," Breast Cancer Research and Treatment 57:183-92, 1999.
Mak, B.C., et al., "The Tuberin-Hamartin Complex Negatively Regulates β-Catenin Signaling Activity," The Journal of Biological Chemistry 278(8):5947-5951, Feb. 21, 2003.
Malik, S., and R.G. Roeder, "Transcriptional Regulation Through Mediator-Like Coactivators in Yeast and Metazoan Cells," Trends in Biochemical Sciences, 25:277-283, Jun. 2000.

(56) References Cited

OTHER PUBLICATIONS

Manteuffel-Cymborowska, M., "Nuclear Receptors, Their Coactivators and Modulation of Transcription," Acta Biochimica Polonica 46(1):77-89, 1999.
Marin, D.B., et al., "Alzheimer's Desease: Accurate and Early Diagnosis in the Primary Care Setting," Geriatrics 57(2):36-40, Feb. 2002.
McGregor, J.R., and S.W. Dahill, "Effect of Fibrin Sealant on Perianastomotic Tumor Growth in an Experimental Model of Colorectal Cancer Surgery," Disease of the Colon & Rectum 36(9):834-839, Sep. 1993.
McKenna, N.J., et al., "Nuclear Receptor Coactivators: Multiple Enzymes, Multiple Complexes, Multiple Functions," The Journal of Steroid Biochemistry & Molecular Biology 69:3-12, 1999.
McMurtry, M.S., et al., "Gene Therapy Targeting Survivin Selectively Induces Pulmonary Vascular Apoptosis and Reverses Pulmonary Arterial Hypertension," The Journal of Clinical Investigation 115(6):1479-1491, Jun. 2005.
Miller, J.R., et al., "Mechanism and Function of Signal Transduction by the Wnt/β-Catenin and Wnt/Ca2+ Pathways," Oncogene 18:7860-7872, 1999.
Miloloza, A., et al., "The TSC1 Gene Product, Hamartin, Negatively Regulates Cell Proliferation," Human Molecular Genetics 9(12):1721-1727, 2000.
Min, H., et al., "Fgf-10 is Required for Both Limb and Lung Development and Exhibits Striking Functional Similarity to *Drosophila* Branchless," Genes & Development 12:3156-3161, 1998.
Molenaar, M., et al., "XTcf-3 Transcription Factor Mediates β-Catenin-Induced Axis Formation in Xenopus Embryos," Cell 86:391-399, Aug. 9, 1996.
Adnot, S., "Lessons Learned From Cancer May Help in the Treatment of Pulmonary Hypertension," The Journal of Clinical Investigation 115(6):1461-1463, Jun. 2005.
Albranches, E., et al., "Expansion and Neural Differentiation of Embryonic Stem Cells in Adherent and Suspension Cultures," Biotechnology Letters 25:725-730, 2003.
Bao, R., et al., "Use of a Surrogate Marker (Human Secreted Alkaline Phosphatase) to Monitor in Vivo Tumor Growth and Anticancer Drug Efficacy in Ovarian Cancer Xenografts," Gynecologic Oncology 78(3):373:379, Sep. 2000.
Behrens, J., et al., "Functional Interaction of β-Catenin With the Transcription Factor LEF-1," Nature 382:638-642, Aug. 15, 1996.
Bellusci, S., et al., "Fibroblast Growth Factor 10 (FGF10) and Branching Morphogenesis in the Embryonic Mouse Lung," Development 124:4867-4878, 1997.
Bienz, M., and H. Clevers, "Linking Colorectal Cancer to Wnt Signaling," Cell 103:311-320, Oct. 13, 2000.
Blanc-Brude, O.P., et al., "Inhibitor of Apoptosis Protein Survivin Regulates Vascular Injury," Nature Medicine 8:987-994, 2002.
Borok, Z., et al., "Rat Serum Inhibits Progression of Alveolar Epithelial Cells Toward the Type I Cell Phenotype In Vitro," American Journal of Respiratory Cell and Molecular Biology 12(1):50-55, 1995.
Bouvet, M., et al., "Real-Time Optical Imaging of Primary Tumor Growth and Multiple Metastatic Events in a Pancreatic Cancer Orthotopic Model," Cancer Research 62:1534-1540, Mar. 1, 2000.
Brown, W.A., et al., "5-Aminosalicylic Acid and Olsalazine Inhibit Tumor Growth I a Rodent Model of Colorectal Cancer," Digestive Diseases and Sciences 45(8):1578-1584, Aug. 2000.
Caca, K., et al, "β- and γ-Catenin Mutations, but Not E-Cadherin Inactivation, Underlie T-Cell Factor/Lymphoid Enhancer Factor Transcriptionial Deregulation in Gastric and Pancreatic Cancer," Cell Growth & Differentiation 10:369-376, Jun. 1999.
Cadigan, K.M., and R. Nusse, "Wnt Signaling: A Common Theme in Animal Development," Genes & Development 11:3286-3305, 1997.
Cao, S., et al., "Persistent Induction of Apoptosis and Suppression of Mitosis as the Basis for Curative Therapy With S-1, an Oral 5-Fluorouracil Prodrug in a Colorectal Tumor Model," Clinical Cancer Research 5:267-274, Feb. 1999.
Carri, N.G., et al., "Choroid Coat Extract and Ciliary Neurotrophic Factor Strongly Promote Neurite Outgrowth in the Embryonic Chick Retina," International Journal of Developmental Neuroscience 12(6):567-578, 1994.
Chauvet, N., et al., "Aged Median Eminence Glial Cell Cultures Promote Survival and Neurite Outgrowth of Cocultured Neurons," Glia 18:211-223, 1996.
Chen, S., et al., "Wnt-1 Signaling Inhibits Apoptosis by Activating β-Catenin/T Cell Factor-Mediated Transcription," The Journal of Cell Biology 152(1):87-96, Jan. 8, 2001.
Chilosi, M., et al., "Aberrant Wnt/β-Catenin Pathway Activation in Idiopathic Pulmonary Fibrosis," American Journal of Pathology 162(5):1495-1502, May 2003.
Cho, S., et al., "Analysis of the C-Terminal Region of *Arabidopsis thaliana* APETALA1 as a Transcription Activation Domain," Plant Molecular Biology 40:419-429, 1999.
Chrivia, J.C., et al, "Phosphorylated CREB Binds Specifically to the Nuclear Protein CBP," Nature 365:855-859, Oct. 28, 1993.
Chu, K., et al., "Human Neural Stem Cells Can Migrate, Differentiate, and Integrate After Intravenous Transplantation in Adult Rats With Transient Forebrain Ischemia," Neuroscience Letters 343:129-133, 2003.
Clark, J.C., et al., "FGF-10 Disrupts Lung Morphogenesis and Causes Pulmonary Adenomas in Vivo," American Journal of Lung Cell Molecular Physiology 280:L705-L715, 2001.
Collingwood, T.N., et al., "Nuclear Receptors: Coactivators, Corepressors and Chromatin Remodeling in the Contro of Transcription," Journal of Molecular Endocrinology 23:255-275, 1999.
Crawford, H.C., et al., "The Metalloproteinase Matrilysin is a Target of β-Catenin Transactivation in Intestinal Tumors," Oncogene 18:2883-2891, 1999.
Crispino, J.D., et al., "Use of Altered Specificity Mutants to Probe a Specific Protein-Protein Interaction in Differentiation: The GATA-1:FOG Complex," Molecular Cell 3:219-228, Feb. 1999.
Daniels, D.L., et al., "β-Catenin: Molecular Plasticity and Drug Design," Trends in Biochemical Sciences 28(11):672-678, Nov. 2001.
Danto, S.I., et al., "Reversible Transdifferentiation of Alveolar Epithelial Cells," American Journal of Respiratory Cell and Molecular Biology 12:497-502, 1995.
Dasgupta, R. and E. Fuchs, "Multiple Roles for Activated LEF/TCF Transcription Complexes During Hair Follicle Development and Differentiation," Development 128:4557-4568, 1999.
Davis, P.D., et al., "ZD6126: A Novel Vascular-Targeting Agent That Causes Selective Destruction of Tumor Vasculature," Cancer Research 62:7247-7253, Dec. 15, 2002.
Demidem, A., et al., "Cystemustine Induces Redifferentiation of Primary Tumors and Confers Protection Against Secondary Tumor Growth in a Melanoma Murine Model," Cancer Research 61:2294-2300, Mar. 1, 2001.
Deng, J., et al., "Neural Trans-Differentiation Potential of Hepatic Oval Cells in the Neonatal Mouse Brain," Experimental Neurology 182:373-382, 2003.
Dinsmore, S.T., "Alzheimer's Disease Diagnosis," Journal of the American Osteopathic Association 99(9) (Supplement 15):Abstract, Sep. 1, 1999.
Dinsmore, S.T., "Treatment Options for Alzheimer's Disease," Journal of the American Osteopathic Association 99(9)(Supplement 65):Abstract, Sep. 1, 1999.
Eckner, R., et al., "Molecular Cloning and Functional Analysis of the Adenovirus E1A-Associated 300-kD Protein (p300) Reveals a Protein With Properties of a Transcriptional Adaptor," Genes & Development 8:869-884, 1994.
Eguchi, M., et al., "Design, Synthesis, and Evaluation of Opioid Analogues With Non-Peptidic β-Turn Scaffold: Enkephalin and Endomorphin Mimetics," Journal of Medicinal Chemistry 45(7):1395-1398, Mar. 3, 2002.
Eguchi, M., et al., "Solid-Phase Synthesis and Solution Structure of Bicyclic β-Turn Peptidoimetics: Diversity at the i Position," Tetrahedron Letters 42(7):1237-1239, Feb. 12, 2001.

(56) References Cited

OTHER PUBLICATIONS

Eguchi, M., et al., "Solid-Phase Synthesis and Structural Analysis of Bicyclic β-Turn Mimetics Incorporating Functionality at the i to i + 3 Positions," Journal of the American Chemical Society 121(12):12204-12205, Jan. 1, 1999.
El Bitar, F., et al., "Neuroblastoma B104 Cell Line as a Model for Analysis of Neurite Outgrowth and Neuronal Aggregation Induced by Reissner's Fiber Material," Cell and Tissue Research 298(2):233-242, Nov. 1999.
Fleisher, D., et al., "Improved Oral Drug Delier: Solubility Limitations Overcome by the Use of Prodrugs," Advanced Drug Delivery Reviews 19:115-130, 1996.
Fox, N.C., and M.N. Rossor, "Diagnosis of Early Alzheimer's Disease," Revue Neurologique (Paris) 155:4S33-4S37, 1999.
Fraser, P.E., et al., "Presenilin Function: Connections to Alzheimer's Disease and Signal Transduction," Biochemical Society Symposia 67:89-100, 2001.
Fuchs, E., "Beauty is Skin Deep: The Fascinating Biology of the Epidermis and its Appendages," The Harvey Lectures, Series 94, 2001, pp. 47-78.
Fujimuro, M., et al., "A Novel Viral Mechanism for Dysregulation of β-Catenin in Kaposi's Sarcoma-Associated Herpesvirus Latency," Nature Medicine 9(3):300-306, Mar. 2003.
Fukunaga, A., et al., "Differentiation and Angiogenesis of Central Nervous System Stem Cells Implanted With Mesenchyme Into Ischemic Rat Brain," Cell Transplantation 8:435-441, 1999.
Gallop, M.A., et al., "Applications of Combinatorial Technologies to Drug Discovery. 1. Background and Peptide Combinatorial Libraries," Journal of Medicinal Chemistry 37(9):1233-1251, Apr. 29, 1994.
Gat, U., et al., "De Novo Hair Follicle Morphogenesis and Hair Tumors in Mice Expressing a Truncated β-Catenin in Skin," Cell 95:605-614, Nov. 25, 1998.
Goff, S.A., et al., "Identification of Functional Domains in the Maize Transcriptional Activator C1: Comparison of Wild-Type and Dominant Inhibitor Proteins," Genes & Development 5:298-309, 1991.
Gomez, M.R., "History of the Tuberous Sclerosis Complex," Brain & Development 17(Supplement):55-57, 1995.
Gong, Z.-Z., et al., "A Constitutively Expressed Myc-Like Gene Involved in Anthocyanin Biosynthesis From Perilla Frutescens: Molecular Characterization, Heterologous Expression in Transgenic Plants and Transactivation Yeast Cells," Plant Molecular Biology 41:33-44, 1999.
Graminski, G.F., and M.R. Lerner, "A Rapid Bioassay for Platelet-Derived Growth Factor β-Receptor Tyrosine Kinase Function," Biotechnology 12:1008-1011, Oct. 1994.
Grube, E., and L. Buellesfeld, "Rapamycin Analogs for Stent-Based Local Drug Delivery," Herz 29(2):162-166, 2004.
Sprenger-Haussels, M., and B. Weisshaar, "Transactivation Properties of Parsley Proline-Rich bZIP Transcription Factors," Plant Journal 22(1):1-8, 2000.
Stavridis, M.P., and A.G. Smith, "Neural Differentiation of Mouse Embryonic Stem Cells," Biochemical Society Transactions 31(Part 1):45-49, Feb. 1, 2003.
Stein, R.W., et al., "Analysis of E1A-Mediated Growth Regulation Functions: Binding of the 300-Kilodalton Cellular Product Correlates With E1A Enhancer Repression Function and DNA Synthesis-Inducing Activity," Journal of Virology 64(9):4421-4427, Sep. 1990.
Storey, E., et al., "Patterns of Cognitive Impairment in Alzheimer's Disease: Assessment and Differential Diagnosis," Frontiers in Bioscience 7:e155-e184, May 1, 2002.
Strovel, E.T., and D.J. Sussman, "Transient Overexpression of Murine Dishevelled Genes Results in Apoptotic Cell Death," Experimental Cell Research 253:637-648, 1999.
Su, L.-K., et al., "Association of the APC Tumor Suppressor Protein With Catenins," Science 262:1734-1737, Dec. 10, 1993.
Takahashi, Y., et al., "α-Difluoromethylornithine Induces Apoptosis as well as Anti-Angiogenesis in the Inhibition of Tumor Growth and Metastasis in a Human Gastric Cancer Model," International Journal of Cancer 85(2):243-247, Jan. 15, 2000.
Takemaru, K.-I., and R.T. Moon, "The Transcriptional Coactivator CBP Interacts With β-Catenin to Activate Gene Expression," The Journal of Cell Biology 149(2):249-254, Apr. 17, 2000.
Tapia, J.C., "Casein Kinase 2 (CK2) Increases Survivin Expression via Enhanced β-Catenin-T Cell Factor/Lymphoid Enhancer Binding Factor-Dependent Transcription," Proceeding of the National Academy of Sciences USA 103(41):15079-15084, Oct. 10, 2006.
Tebar, M., "Expression of Tcf/Lef and sFrp and Localization of β-Catenin in the Developing Mouse Lung," Mechanisms of Development 109(2):437-440, Dec. 2001.
Tetsu, O., and F. McCormick, "β-Catenin Regulates Expression of Cyclin D1 in Colon Carcinoma Cells," Nature 398:422-426, Apr. 1, 1999.
Tsukamoto, A.S., "Expression of the int-1 Gene in Transgenic Mice is Associated With Mammary Gland Hyperplasia and Adenocarcinomas in Male and Female Mice," Cell 55(4):619-625, Nov. 18, 1988.
Tsunoda, A., et al., "Effect of Povidone-Iodine on Anastomotic Tumor Growth in an Experimental Model of Colorectal Cancer Surgery," Anticancer Research 19:1149-1152, 1999.
Uhal, B.D., et al., "Fibroblasts Isolated After Fibrotic Lung Injury Induce Apoptosis of Alveolar Epithelial Cells in Vitro," American Journal of Physiology—Lung Cellular and Molecular Physiology 269(6):L819-L828, Dec. 1, 1995.
Uhal, B.D., et al., "Alveolar Epithelial Cell Death Adjacent to Underlying Myofibroblasts in Advanced Fibrotic Human Lung," American Journal of Physiology—Lung Cellular and Molecular Physiology 275(6):L1192-L1199, Dec. 1, 1998.
Ulmasov, T., et al., "Activation and Repression of Transcription by Auxin-Response Factors," Proceedings of the National Academy of Sciences of USA 96:5844-5849, May 1999.
Vanhems, E., et al., "Insulin and Neuroparsin Promote Neurite Outgrowth in Cultured Locust CNS," European Journal of Neuroscience 2(9):776-782 Sep. 1990.
Verstijnen, C.P.H.J., et al., "Culturing and Xenografting of Primary Colorectal Carcinoma Cells: Comparison of in Vitro, and in Vivo Model and Primary Tumor," Anticancer Research 8(6):1193-1200, 1988.
Vetter, M.L., and J.M. Bishop, "β PDGF Receptor Mutants Defective for Mitogenesis Promote Neurite Outgrowth in PC12 Cells," Current Biology 5(2):168-178, Feb. 1995.
Wan, H., et al., "Differentiation of Rat Embryonic Neural Stem Cells Promoted by Co-Cultured Schwann Cells," Chinese Medical Journal 116(3):428-431, 2003.
Wang, G.J., et al., "Regulation of Vein Graft Hyperplasia by Survivin, an Inhibitor of Apoptosis Protein," Arteriosclerosis, Thrombosis, and Vascular Biology 25:2081-2087, Oct. 2005.
Warburton, D., et al., "The Molecular Basis of Lung Morphogenesis," Mechanisms of Development 92(1):55-81, Mar. 15, 2000.
Weaver, M., et al., "Bmp Signaling Regulates Proximal-Distal Differentiation of Endoderm in Mouse Lung Development," Development 128:4005-4015, 1999.
Weeraratna, A.T., et al., "Wnt5a Signaling Directly Affects Cell Motility and Invasion of Metastatic Melanoma," Cancer Cell 1(3):279-288, Apr. 2002.
Weidenfeld, J., et al., "The WNT7b Promoter is Regulated by TTF-1, GATA6, and Foxa2 in Lung Epithelium," The Journal of Biological Chemistry 277(23):21061-21070, Jun. 7, 2002.
Weiner, M.F., "Alzheimer's Disease: Diagnosis and Treatment," Harvard Review of Psychiatry 4(6):306-316, Mar./Apr. 1997.
Willert, K., and R. Nusse, "β-Catenin: A Key Mediator of Wnt Signaling," Current Opinion in Genetics & Development 8(1):95-102, Feb. 1998.
Xia, X., et al., "Loss of Presenilin 1 is Associated With Enhanced β-Catenin Signaling and Skin Tumorigenesis," Proceedings of the National Academy of Sciences USA 98(19):10863-10868, Sep. 11, 2001.
Yamaguchi, T.P., et al., "A Wnt5a Pathway Underlies Outgrowth of Multiple Structures in the Vertebrate Embryo," Development 126:1211-1223, 1999.

(56) References Cited

OTHER PUBLICATIONS

Yost, C., et al., "The Axis-Inducing Activity, Stability, and Subcellular Distribution of β-Catenin is Regulatedin Xenopus Embryos by Glycogen Synthase Kinase 3," Genes & Development 10:1443-1454, 1996.

Zaloom, J., and D.C. Roberts, "Preparation of Azido Derivatives From Amino Acids and Peptides by Diazo Transfer," The Journal of Organic Chemistry 46:5173-5176, 1981.

Zhang, T., et al., "Evidence That APC Regulates Survivin Expression: A Possible Mechanism Contributing to the Stem Cell Origin of Colon Cancer," Cancer Research 61:8664-8667, Dec. 15, 2001.

Zhou, L., et al., Hepatocyte Nuclear Factor-3b Limits Cellular Diversity in the Developing Respiratory Epithelium and Alters Lung Morphogenesis In Vivo, Developmental Dynamics 210(3):305-314, 1997.

Chang-Moore Cancer Virology Laboratory, "Kaposi's Sarcoma-Associated Herpesvirus (KSHV)," <http://www.tumorvirology.pitt.edu/kshvrsch.html>, © 2015.

Chemical Abstract Service (CAS) Registry Database, American Chemical Society (ACS), © 1998.

Cystic Fibrosis Foundation, "Treatments," <http://www.cff.org/treatments/> [retrieved Dec. 20, 2014], © 2014.

Dangas, G., et al., "Restenosis: Repeat Narrowing of a Coronary Artery," Circulation 105:2586-2587, 2002.

drugs.com, "Cystic Fibrosis," <http://www.drugs.com/health-guide/cystic-fibrosis.html?printable=1> [retrieved Dec. 20, 2014], © 2014.

"List of Cancer Chemotherapy Drugs," <https://www.navigatingcancer.com/library/all/chemotherapy_drugs> [retrieved Nov. 26, 2013], 2013.

Mayo Clinic, "Alzheimer's Disease," <http://www.mayoclinic.org/diseases-conditions/alzheimers-disease/care-at-mayo-clinic/why-choose-mayo-clinic/con-20023871?p=1> [retrieved Jan. 2, 2015], © 2015.

Mayo Clinic, "Cystic Fibrosis," <http://www.mayoclinic.org/diseases-conditions/cystic-fibrosis/basics/causes/con-20013731?p=1> [retrieved Jan. 2, 2015], © 2015.

Mayo Clinic, "Hair Loss," <http://www.mayoclinic.org/diseases-conditions/hair-loss/basics/definition/con-20027666?p=1> [retrieved Jan. 2, 2015], © 2015.

Mayo Clinic, "Polycystic Kidney Disease," <http://www.mayoclinic.org/diseases-conditions/polycystic-kidney-disease/basics/definition/con-20028831?p=1> [retrieved Dec. 29, 2014], © 2015.

Mayo Clinic, "Pulmonary Fibrosis," <http://www.mayoclinic.org/diseases-conditions/pulmonary-fibrosis/basics/definition/con-20029091?p=1> [retrieved Dec. 29, 2014], © 2015.

Mayo Clinic, "Tuberous Sclerosis," <http://www.mayoclinic.org/diseases-conditions/tuberous-sclerosis/basics/treatment/con-20032953> [retrieved Jan. 2, 2015], © 2015.

National Cancer Institute, "Cancer Prevention Overview," <http://www.cancer.gov/cancertopics/pdq/prevention/overview/patient/page3/print> [retrieved Dec. 15, 2014], © Apr. 17, 2014.

Pulmonary Fibrosis Foundation, "Treatment Options," <http://www.pulmonaryfibrosis.org/life-with-pf/pulmonary-fibrosis-treatment-options>, © 2015.

Shanafelt, T.D., and N. Kay, "The Clinical and Biologic Importance of Neovascularization and Angiogenic Signaling Pathways in Chronic Lymphocytic Leukemia," Semininars in Oncology 33(2):174-185, Apr. 2006.

International Search Report dated May 8, 2012, in International Application No. PCT/JP2012/055489, filed Feb. 27, 2012, 4 pages.

Kouji, H., et al., "Alpha Helix Mimetics and Methods Relating Thereto," U.S. Appl. No. 61/105,088, filed Oct. 14, 2008.

\* cited by examiner

ALPHA HELIX MIMETICS AND METHODS RELATING THERETO

CROSS-REFERENCE TO RELATED APPLICATIONS

This application is a division of U.S. patent application Ser. No. 13/319,071, filed 28 Dec. 2011, and issuing on 26 May 2015, as U.S. Pat. No. 9,040,531, the disclosure of which is hereby incorporated herein by reference in its entirety.

TECHNICAL FIELD

The present invention relates generally to alpha-helix mimetic structures and to a chemical library relating thereto. The invention also relates to applications in the treatment of medical conditions, e.g., cancer diseases, fibrotic diseases, and pharmaceutical compositions comprising the mimetics.

BACKGROUND ART

Recently, non-peptide compounds have been developed which more closely mimic the secondary structure of reverse-turns found in biologically active proteins or peptides. For example, U.S. Pat. No. 5,440,013 to Kahn and published PCT applications nos. WO94/03494, WO01/00210A1, and WO01/16135A2 to Kahn each disclose conformationally constrained, non-peptidic compounds, which mimic the three-dimensional structure of reverse-turns. In addition, U.S. Pat. No. 5,929,237 and its continuation-in-part U.S. Pat. No. 6,013,458, both to Kahn, disclose conformationally constrained compounds which mimic the secondary structure of reverse-turn regions of biologically active peptides and proteins. In relation to reverse-turn mimetics, Kahn disclosed new conformationally constrained compounds which mimic the secondary structure of alpha-helix regions of biologically active peptide and proteins in WO2007/056513 and WO2007/056593.

While significant advances have been made in the synthesis and identification of conformationally constrained, reverse-turn and alpha-helix mimetics, there remains a need in the art for small molecules which mimic the secondary structure of peptides. There is also a need in the art for libraries containing such members, as well as techniques for synthesizing and screening the library members against targets of interest, particularly biological targets, to identify bioactive library members.

The present invention also fulfills these needs, and provides further related advantages by providing conformationally constrained compounds which mimic the secondary structure of alpha-helix regions of biologically active peptides and proteins.

Wnt signaling pathway regulates a variety of processes including cell growth, oncogenesis, and development (Moon et al., 1997, Trends Genet. 13, 157-162; Miller et al., 1999, Oncogene 18, 7860-7872; Nusse and Varmus, 1992, Cell 69, 1073-1087; Cadigan and Nusse, 1997, Genes Dev. 11, 3286-3305; Peifer and Polakis, 2000 Science 287, 1606-1609; Polakis 2000, Genes Dev. 14, 1837-1851). Wnt signaling pathway has been intensely studied in a variety of organisms. The activation of TCF4/β-catenin mediated transcription by Wnt signal transduction has been found to play a key role in its biological functions (Molenaar et al., 1996, Cell 86:391-399; Gat et al., 1998 Cell 95:605-614; Orford et al., 1999 J. Cell. Biol. 146:855-868; Bienz and Clevers, 2000, Cell 103:311-20).

In the absence of Wnt signals, tumor suppressor gene adenomatous polyposis coli (APC) simultaneously interacts with the serine kinase glycogen synthase kinase (GSK)-3β and β-catenin (Su et al., 1993, Science 262, 1734-1737: Yost et al., 1996 Genes Dev. 10, 1443-1454: Hayashi et al., 1997, Proc. Natl. Acad. Sci. USA, 94, 242-247: Sakanaka et al., 1998, Proc. Natl. Acad. Sci. USA, 95, 3020-3023: Sakanaka and William, 1999, J. Biol. Chem 274, 14090-14093). Phosphorylation of APC by GSK-3β regulates the interaction of APC with β-catenin, which in turn may regulate the signaling function of β-catenin (B. Rubinfeld et al., Science 272, 1023, 1996). Wnt signaling stabilizes β-catenin allowing its translocation to the nucleus where it interacts with members of the lymphoid enhancer factor (LEF1)/T-cell factor (TCF4) family of transcription factors (Behrens et al., 1996 Nature 382, 638-642: Hsu et al., 1998, Mol. Cell. Biol. 18, 4807-4818: Roose et al., 1999 Science 285, 1923-1926).

Recently c-myc, a known oncogene, was shown to be a target gene for β-catenin/TCF4-mediated transcription (He et al., 1998 Science 281 1509-1512: Kolligs et al., 1999 Mol. Cell. Biol. 19, 5696-5706). Many other important genes, including cyclin Dl, and metalloproteinase, which are also involved in oncogenesis, have been identified to be regulated by TCF4/β-catenin transcriptional pathway (Crawford et al., 1999, Oncogene 18, 2883-2891: Shtutman et al., 1999, Proc. Natl. Acad. Sci. USA., 11, 5522-5527: Tetsu and McCormick, 1999 Nature, 398, 422-426). Moreover, overexpression of several downstream mediators of Wnt signaling has been found to regulate apoptosis (Moris et al., 1996, Proc. Natl. Acad. Sci. USA, 93, 7950-7954: He et al., 1999, Cell 99, 335-345: Orford et al., 1999 J. Cell. Biol., 146, 855-868: Strovel and Sussman, 1999, Exp. Cell. Res., 253, 637-648). Overexpression of APC in human colorectal cancer cells induced apoptosis (Moris et al., 1996, Proc. Natl. Acad. Sci. USA., 93, 7950-7954), ectopic expression of β-catenin inhibited apoptosis associated with loss of attachment to extracellular matrix (Orford et al., 1999, J. Cell Biol. 146, 855-868). Inhibition of TCF4/β-catenin transcription by expression of dominant-negative mutant of TCF4 blocked Wnt-1-mediated cell survival and rendered cells sensitive to apoptotic stimuli such as anti-cancer agent (Shaoqiong Chen et al., 2001, J. Cell. Biol., 152, 1, 87-96) and APC mutation inhibits apoptosis by allowing constitutive surviving expression, a well-known anti-apoptotic protein (Tao Zhang et al., 2001, Cancer Research, 62, 8664-8667).

Although mutations in the Wnt gene have not been found in human cancer, a mutation in APC or β-catenin, as is the case in the majority of colorectal tumors, results in inappropriate activation of TCF4, overexpression of c-myc and production of neoplastic growth (Bubinfeld et al., 1997, Science, 275, 1790-1792: Morin et al., 1997, Science, 275, 1787-1790: Casa et al., 1999, Cell. Growth. Differ. 10, 369-376). The tumor suppressor gene (APC) is lost or inactivated in 85% of colorectal cancers and in a variety of other cancers as well (Kinzler and Vogelstein, 1996, Cell 87, 159-170). APCs principal role is that of a negative regulator of the Wnt signal transduction cascade. A center feature of this pathway involves the modulation of the stability and localization of a cytosolic pool of β-catenin by interaction with a large Axin-based complex that includes APC. This interaction results in phosphorylation of β-catenin thereby targeting it for degradation.

CREB binding proteins (CBP)/p300 were identified initially in protein interaction assays, first through its association with the transcription factor CREB (Chrivia et al., 1993, Nature, 365, 855-859) and later through its interaction with the adenoviral-transforming protein E1A (Stein et al., 1990, J. Viol., 64, 4421-4427: Eckner et al., 1994, Genes. Dev., 8, 869-884). CBP had a potential to participate in variety of cellular functions including transcriptional coactivator function (Shikama et al., 1997, Trends. Cell. Biol., 7, 230-236: Janknecht and Hunter, 1996, Nature, 383, 22-23). CBP/p300 potentiates β-catenin-mediated activation of the siamois promoter, a known Wnt target (Hecht et al., 2000, EMBO J. 19, 8, 1839-1850). β-catenin interacts directly with the CREB-binding domain of CBP and β-catenin synergizes with CBP to stimulate the transcriptional activation of TCF4/β-catenin (Ken-Ichi Takemaru and Randall T. Moon, 2000 J. Cell. Biol., 149, 2, 249-254).

SUMMARY OF THE INVENTION

The present invention relates generally to alpha-helix mimetic structures and to a chemical library relating thereto. The invention also relates to applications in the treatment of medical conditions, e.g., cancer diseases, fibrotic diseases, and pharmaceutical compositions comprising the mimetics.

From the above background discussions, it is seen that TCF4/β-catenin and CBP complex of Wnt pathway can be taken as target molecules for the regulation of cell growth, oncogenesis and apoptosis of cells, etc. Accordingly, the present invention also addresses a need for compounds that block TCF4/β-catenin transcriptional pathway by inhibiting CBP, and therefore can be used for treatment of cancer, especially colorectal cancer, and fibrotic diseases. In aspects thereof, the present invention is directed to a new type of conformationally constrained compounds, which mimic the secondary structure of alpha-helix regions of biologically active peptides and proteins. This invention also discloses libraries containing such compounds, as well as the synthesis and screening thereof.

(1) A compound having the following general formula (I):

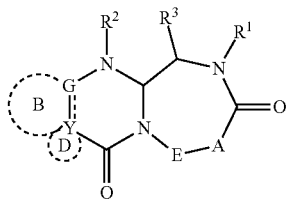

wherein
- - - - is single bond or double bond;
A is —CHR$^7$—,
  wherein
    R$^7$ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl or optionally substituted heterocycloalkylalkyl;
E is bond, —CHR$^5$—, —O— or —NR$^8$—,
  wherein
    R$^5$ is hydrogen, optionally substituted alkyl, optionally substituted alkenyl, optionally substituted alkynyl, optionally substituted arylalkyl or optionally substituted heteroarylalkyl; and
    R$^8$ is hydrogen, optionally substituted alkyl, optionally substituted alkenyl or optionally substituted alkynyl;

B is void or optionally substituted monocyclic ring formed together with G and Y;
D is void or optionally substituted spiro ring formed together with Y;
with the proviso that
B and D are not both present;
when B is present, then G and Y are independently carbon atom or nitrogen atom,
when D is present, then Y is carbon atom and G is —NR$^6$—, —O—, —CHR$^6$— or —C(R$^6$)$_2$—,
when both B and D are void, then G and Y are the same or different and each is —NR$^6$—, —O—, —CHR$^6$— or —C(R$^6$)$_2$—,
  wherein
    each R$^6$ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl, and
when E is bond, then D is void, B is optionally substituted monocyclic ring, and G and Y are independently carbon atom or nitrogen atom;
R$^1$ is optionally substituted alkyl, optionally substituted alkenyl, optionally substituted alkynyl, optionally substituted arylalkyl, optionally substituted heteroarylalkyl, optionally substituted cycloalkylalkyl or optionally substituted heterocycloalkylalkyl;
R$^2$ is —W$^{21}$—W$^{22}$—Rb—R$^{20}$,
  wherein
    W$^{21}$ is —(CO)— or —(SO$_2$)—,
    W$^{22}$ is bond, —O—, —NH— or optionally substituted lower alkylene,
    Rb is bond or optionally substituted alkylene, and
    R$^{20}$ is optionally substituted alkyl, optionally substituted alkenyl, optionally substituted alkynyl, optionally substituted aryl, optionally substituted heteroaryl, optionally substituted cycloalkyl or optionally substituted heterocycloalkyl;
R$^3$ is hydrogen, optionally substituted alkyl, optionally substituted alkenyl or optionally substituted alkynyl;
with the proviso that
when D is void, E is bond, B is benzene, and R$^2$ is —W$^{21}$—W$^{22}$—Rb—R$^{20}$, wherein W$^{21}$ is —(CO)—, W$^{22}$ is —NH—, and Rb is bond, then R$^{20}$ should not be optionally substituted phenyl;
or a pharmaceutically acceptable salt thereof.

(2) The compound according to (1) mentioned above, wherein, in the formula (I),
D is void, and
B is optionally substituted 3-, 4-, 5-, 6- or 7-membered saturated or unsaturated mono cyclic ring formed together with G and Y.

(3) The compound according to (1) mentioned above, wherein, in the formula (I),
D is void, and
B is optionally substituted 4-, 5-, 6- or 7 membered saturated or unsaturated heterocyclic ring formed together with G and Y and the hetero atom is selected from S, N and O and the number of hetero atoms is an integer of 1-3.

(4) The compound according to (1) mentioned above, wherein, in the formula (I),
D is void;
B is optionally substituted 5- or 6-membered saturated or unsaturated heterocyclic ring formed together with G and Y and the hetero atom is selected from S, N and O and the number of hetero atoms is an integer of 1-3.

(5) The compound according to (1) mentioned above, wherein, in the formula (I),
B is void;
D is optionally substituted spiro ring; and
G is —NR$^{6'}$—, —CHR$^6$—, —C(R$^6$)$_2$— or —O—,
   wherein
      each R$^6$ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl, and
      R$^{6'}$ is optionally substituted cyclic or noncyclic lower alkyl, optionally substituted aryl, optionally substituted heteroaryl, optionally substituted arylalkyl or optionally substituted heteroarylalkyl.

(6) The compound according to (1) mentioned above, wherein, in the formula (I),
B is void;
D is optionally substituted C$_{3-8}$ cycloalkane; and
G is —NR$^{6'}$—, —CHR$^6$—, —C(R$^6$)$_2$— or —O—,
   wherein
      each R$^6$ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl, and
      R$^{6'}$ is optionally substituted cyclic or noncyclic lower alkyl, optionally substituted aryl, optionally substituted heteroaryl, optionally substituted arylalkyl or optionally substituted heteroarylalkyl.

(7) The compound according to (1) mentioned above, wherein, in the formula (I),
both B and D are void, and
at least one of G and Y is —NR$^{6'}$—, —CHR$^6$—, —C(R$^6$)$_2$— or —O—,
   wherein
      each R$^6$ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl, and
      R$^{6'}$ is optionally substituted cyclic or noncyclic lower alkyl, optionally substituted aryl, optionally substituted heteroaryl, optionally substituted arylalkyl or optionally substituted heteroarylalkyl.

(8) The compound according to (1) mentioned above, wherein, in the formula (I),
both B and D are void; and
G is —NR$^{6'}$—, —CHR$^{6'}$—, —C(R$^{6'}$)$_2$—, or —O—,
   wherein
      each R$^{6'}$ is independently optionally substituted cyclic or noncyclic lower alkyl, optionally substituted aryl, optionally substituted heteroaryl, optionally substituted arylalkyl or optionally substituted heteroarylalkyl.

(9) The compound according to (1) mentioned above, wherein, in the formula (I),
both B and D are void;
G is —NR$^{6'}$— or —O—,
   wherein
      R$^{6'}$ is optionally substituted lower alkyl, optionally substituted alkenyl or optionally substituted aryl; and
Y is —CHR$^6$— or —C(R$^6$)$_2$—,
   wherein
      each R$^6$ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl.

(10) The compound according to (1) mentioned above, wherein, in the formula (I),
both B and D are void;
is —NR$^{6'}$—, or —O—,
   wherein
      R$^{6'}$ is optionally substituted lower alkyl, or optionally substituted alkenyl; and
Y is —CHR$^6$— or —C(R$^6$)$_2$—,
   wherein
      R$^6$ is hydrogen, optionally substituted alkyl, optionally substituted alkenyl or optionally substituted alkynyl.

(11) The compound according to (1) mentioned above, wherein, in the formula (I),
E is —CHR$^5$—, —O—, or —NR$^8$—,
   wherein
      R$^5$ is hydrogen, optionally substituted lower alkyl, optionally substituted lower alkenyl or optionally substituted lower alkynyl, and
      R$^8$ is hydrogen, lower alkyl, lower alkenyl or lower alkynyl.

(12) The compound according to (1) mentioned above, wherein, in the formula (I),
E is —CHR$^5$—, —O—, or —NR$^8$—,
   wherein
      R$^5$ is hydrogen or optionally substituted lower alkyl, and
      R$^8$ is hydrogen, lower alkyl, lower alkenyl or lower alkynyl.

(13) The compound according to (1) mentioned above, wherein, in the formula (I),
E is —CHR$^5$—, —O—, or —NR$^8$—,
   wherein
      R$^5$ is hydrogen, or lower alkyl, and
      R$^8$ is hydrogen, lower alkyl, lower alkenyl or lower alkynyl.

(14) The compound according to (1) mentioned above, wherein, in the formula (I),
E is —CHR$^5$—, —O—, or —NR$^8$—,
   wherein
      R$^5$ is hydrogen, lower alkyl, lower alkenyl or lower alkynyl, and
      R$^8$ is hydrogen or alkyl.

(15) The compound according to (1) mentioned above, wherein, in the formula (I),
E is —CHR$^5$—, —O—, or —NR$^8$—,
   wherein
      R$^5$ is hydrogen or lower alkyl, and
      R$^8$ is hydrogen or lower alkyl.

(16) The compound according to (1) mentioned above, wherein, in the formula (I),
E is —O—, or —NR$^8$—,
   wherein
      R$^8$ is hydrogen or lower alkyl.

(17) The compound according to (1) mentioned above, wherein, in the formula (I), D is void, B is optionally substituted monocyclic ring and E is bond.

(18) The compound according to (1) mentioned above, wherein, in the formula (I),
$R^3$ is hydrogen or $C_{1-4}$ alkyl group.

(19) The compound according to (1) mentioned above, wherein, in the formula (I),
$R^3$ is hydrogen.

(20) The compound according to (1) mentioned above, wherein, in the formula (I),
D is void; and
B is selected from optionally substituted cyclopropane, optionally substituted cyclobutane, optionally substituted cyclopentane, optionally substituted cyclohexane, optionally substituted cycloheptane, optionally substituted pyrrolidine, optionally substituted pyrazole, optionally substituted cyclopropene, optionally substituted cyclobutene, optionally substituted cyclopentene, optionally substituted cyclohexene, optionally substituted cycloheptene, optionally substituted cyclopentadiene, optionally substituted dihydro-pyrrole, optionally substituted pyrrole, optionally substituted dihydro-pyrazole, optionally substituted imidazole, optionally substituted thiophene, optionally substituted thiazole, optionally substituted isothiazole, optionally substituted thiadiazole, optionally substituted furan, optionally substituted oxazole, optionally substituted isoxazole, optionally substituted oxadiazole, optionally substituted benzene, optionally substituted pyridine, optionally substituted pyridazine, optionally substituted pyrimidine, optionally substituted pyrazine and optionally substituted triazine formed together with G and Y.

(21) The compound according to any one of (1)-(4) and (11)-(20) mentioned above, wherein, in the formula (I),
B is present and is optionally substituted by one or more of the chemical moieties selected from the group consisting of —$R^9$, —$OR^9$, —$COR^9$, —$COOR^9$, —$CONR^9R^4$, —$NR^9R^4$, —$SR^9$, —$SO_2R^9$, —$SO_2NR^9R^4$, —$SO_3R^9$, —$NHC(NHR^9)NR^4$, and halogen,
wherein
$R^9$ and $R^4$ are independently selected from hydrogen atom, optionally substituted, cyclic or noncyclic alkyl, aryl, heteroaryl, arylalkyl and heteroarylalkyl.

(22) The compound according to (1) mentioned above, wherein, in the formula (I),
B is void; and
D is optionally substituted cycloalkane.

(23) The compound according to (22) mentioned above, wherein, in the formula (I),
B is void; and
D is optionally substituted $C_{3-8}$ cycloalkane.

(24) The compound according to (22) mentioned above, wherein, in the formula (I),
B is void;
D is optionally substituted $C_{3-6}$ cycloalkane.

(25) The compound according to (1) mentioned above, wherein, in the formula (I),
$R^1$ is —Ra—$R^{10}$,
wherein
Ra is optionally substituted lower alkylene and
$R^{10}$ is hydrogen, optionally substituted alkyl, optionally substituted cycloalkyl, optionally substituted aryl or optionally substituted heteroaryl.

(26) The compound according to (23) mentioned above, wherein, in the formula (I),
$R^1$ is —Ra—$R^{10}$,
wherein
Ra is optionally substituted lower alkylene and
$R^{10}$ is hydrogen, optionally substituted aryl or optionally substituted heteroaryl.

(27) The compound according to (25) mentioned above, wherein, in the formula (I),
$R^{10}$ is hydrogen, optionally substituted methyl, optionally substituted ethyl, optionally substituted propyl, optionally substituted isopropyl, optionally substituted isobutyl, optionally substituted cyclohexyl, optionally substituted benzhydryl, optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furanyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuranyl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(28) The compound according to (26) mentioned above, wherein, in the formula (I),
$R^{10}$ is hydrogen, optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furanyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuranyl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(29) The compound according to (1) mentioned above, wherein, in the formula (I),
$R^2$ is —$W^{21}$—$W^{22}$—Rb—$R^{20}$;
wherein
$W^{21}$ is —(CO)— or —($SO_2$)—,
$W^{22}$ is bond, —O—, —NH— or optionally substituted lower alkylene,
Rb is bond or optionally substituted lower alkylene, and
$R^{20}$ is optionally substituted alkyl, optionally substituted cycloalkyl, optionally substituted aryl or optionally substituted heteroaryl.

(30) The compound according to (29) mentioned above, wherein, in the formula (I),
$R^2$ is —$W^{21}$—$W^{22}$—Rb—$R^{20}$;
wherein
$W^{21}$ is —(CO)— or —($SO_2$)—,
$W^{22}$ is —O— or —NH—,
Rb is bond or optionally substituted lower alkylene, and
$R^{20}$ is optionally substituted alkyl, optionally substituted cycloalkyl, optionally substituted aryl or optionally substituted heteroaryl.

(31) The compound according to (29) and (30) mentioned above, wherein, in the formula (I),
$R^{20}$ is optionally substituted methyl, optionally substituted ethyl, optionally substituted propyl, optionally substituted butyl, optionally substituted isopropyl, optionally substituted isobutyl, optionally substituted cyclohexyl, optionally substituted benzhydryl, optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furanyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuranyl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl, optionally substituted benzodioxolyl or optionally substituted imidazopyridinyl.

(32) The compound according to (1) mentioned above, wherein, in the formula (I),
$R^7$ of A is —Rc—$R^{70}$,
wherein
Rc is bond or optionally substituted lower alkylene, and
$R^{70}$ is hydrogen, optionally substituted alkyl, optionally substituted aryl or optionally substituted heteroaryl.

(33) The compound according to (32) mentioned above, wherein, in the formula (I),
$R^7$ of A is —Rc—$R^{70}$
wherein
Rc is bond or optionally substituted lower alkylene, and
$R^{70}$ is hydrogen, optionally substituted aryl or optionally substituted heteroaryl.

(34) The compound according to (32) mentioned above, wherein, in the formula (I),
$R^{70}$ is hydrogen, optionally substituted methyl, optionally substituted ethyl, optionally substituted propyl, optionally substituted butyl, optionally substituted isopropyl, optionally substituted isobutyl, optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furanyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuranyl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(35) The compound according to (33) mentioned above, wherein, in the formula (I),
$R^{70}$ is hydrogen, optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furanyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuranyl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(36) The compound according to (1) mentioned above, wherein, in the formula (I),
D is void;
B is optionally substituted 4-, 5-, 6- or 7 membered saturated or unsaturated heterocyclic ring formed together with G and Y and the hetero atom is selected from S, N and O and the number of hetero atoms is an integer of 1-3;
$R^1$ is —Ra—$R^{10}$,
  wherein
  Ra is optionally substituted lower alkylene and
    $R^{10}$ is Hydrogen, optionally substituted alkyl, optionally substituted cycloalkyl, optionally substituted aryl or optionally substituted heteroaryl;
$R^2$ is —$W^{21}$—$W^{22}$—Rb—$R^{20}$,
  wherein
  $W^{21}$ is —(CO)— or —($SO_2$)—,
  $W^{22}$ is bond, —O—, —NH— or optionally substituted lower alkylene,
  Rb is bond or optionally substituted lower alkylene, and
  $R^{20}$ is optionally substituted alkyl, optionally substituted cycloalkyl, optionally substituted aryl or optionally substituted heteroaryl; and
$R^7$ of A is —Rc—$R^{70}$,
  wherein
    Rc is bond or optionally substituted lower alkylene, and
    $R^{70}$ is hydrogen, optionally substituted alkyl, optionally substituted aryl or optionally substituted heteroaryl.

(37) The compound according to (1) mentioned above, wherein, in the formula (I),
B is void;
D is optionally substituted $C_{3-8}$ cycloalkane;
G is —$NR^{6'}$—, —$C(R^{6'})_2$—, or —O—,
  wherein
    each $R^{6'}$ is independently hydrogen, optionally substituted cyclic or noncyclic lower alkyl, optionally substituted aryl, optionally substituted heteroaryl, optionally substituted arylalkyl or optionally substituted heteroarylalkyl;
$R^1$ is —Ra—$R^{10}$,
  wherein
  Ra is optionally substituted lower alkylene and
    $R^{10}$ is Hydrogen, optionally substituted alkyl, optionally substituted cycloalkyl, optionally substituted aryl or optionally substituted heteroaryl;
$R^2$ is —$W^{21}$—$W^{22}$—Rb—$R^{20}$,
  wherein
  $W^{21}$ is —(CO)— or —($SO_2$)—,
  $W^{22}$ is bond, —O—, —NH— or optionally substituted lower alkylene,
Rb is bond or optionally substituted lower alkylene, and
$R^{20}$ is optionally substituted alkyl, optionally substituted cycloalkyl, optionally substituted aryl or optionally substituted heteroaryl; and
$R^7$ of A is —Rc—$R^{70}$,
  wherein
Rc is bond or optionally substituted lower alkylene, and
$R^{70}$ is hydrogen, optionally substituted alkyl, optionally substituted aryl or optionally substituted heteroaryl.

(38) The compound according to (1) mentioned above, wherein, in the formula (I),
both B and D are void;
G is —$NR^{6'}$—, —$CHR^{6'}$—, —$C(R^{6'})_2$—, or —O—,
  wherein
    each $R^{6'}$ is independently hydrogen, optionally substituted cyclic or noncyclic lower alkyl, optionally substituted aryl, optionally substituted heteroaryl, optionally substituted arylalkyl or optionally substituted heteroarylalkyl;
$R^1$ is —Ra—$R^{10}$,
  wherein
  Ra is optionally substituted lower alkylene and
    $R^{10}$ is hydrogen, optionally substituted alkyl, optionally substituted cycloalkyl, optionally substituted aryl or optionally substituted heteroaryl;
$R^2$ is —$W^{21}$—$W^{22}$—Rb—$R^{20}$,
  wherein
  $W^{21}$ is —(CO)— or —($SO_2$)—,
  $W^{22}$ is bond, —O—, —NH— or optionally substituted lower alkylene,
  Rb is bond or optionally substituted lower alkylene, and
  $R^{20}$ is optionally substituted alkyl, optionally substituted cycloalkyl, optionally substituted aryl or optionally substituted heteroaryl; and
$R^7$ of A is —Rc—$R^{70}$,
  wherein
    Rc is bond or optionally substituted lower alkylene, and
    $R^{70}$ is hydrogen, optionally substituted alkyl, optionally substituted aryl or optionally substituted heteroaryl.

(39) The compound according to (1) mentioned above, wherein, in the formula (I),
E is —$CHR^5$—, —O—, or —$NR^8$—,
  wherein
  $R^5$ is hydrogen or optionally substituted lower alkyl, and
  $R^8$ is hydrogen, lower alkyl, lower alkenyl or lower alkynyl;
$R^1$ is —Ra—$R^{10}$,
  wherein
  Ra is optionally substituted lower alkylene and $R^{10}$ is hydrogen, optionally substituted alkyl, optionally substituted cycloalkyl, optionally substituted aryl or optionally substituted heteroaryl;
$R^2$ is $W^{21}$—$W^{22}$—Rb—$R^{20}$,
  wherein
  $W^{21}$ is —(CO)— or —($SO_2$)—,
  $W^{22}$ is bond, —O—, —NH— or optionally substituted lower alkylene,
  Rb is bond or optionally substituted lower alkylene, and
  $R^{20}$ is optionally substituted alkyl, optionally substituted cycloalkyl, optionally substituted aryl or optionally substituted heteroaryl; and
$R^7$ of A is —Rc—$R^{70}$,
  wherein
    Rc is bond or optionally substituted lower alkylene, and
    $R^{70}$ is hydrogen, optionally substituted alkyl, optionally substituted aryl or optionally substituted heteroaryl.

(40) The compound according to (1) mentioned above, wherein, in the formula (I),
D is void and E is bond;
$R^1$ is —Ra—$R^{10}$,
  wherein
  Ra is optionally substituted lower alkylene and
    R" is Hydrogen, optionally substituted alkyl, optionally substituted cycloalkyl, optionally substituted aryl or optionally substituted heteroaryl;
$R^2$ is —$W^{21}$—$W^{22}$—Rb—$R^{20}$,
  wherein
  $W^{21}$ is —(CO)— or —($SO_2$)—,
  $W^{22}$ is bond, —O—, —NH— or optionally substituted lower alkylene,
  Rb is bond or optionally substituted lower alkylene, and R²⁰ is optionally substituted alkyl, optionally substituted cycloalkyl, optionally substituted aryl or optionally substituted heteroaryl; and R⁷ of A is —Rc—R⁷⁰,
wherein
Rc is bond or optionally substituted lower alkylene, and
R⁷⁰ is Hydrogen, optionally substituted alkyl, optionally substituted aryl or optionally substituted heteroaryl.

(41) The compound according to (1) mentioned above, wherein, in the formula (I),
both B and D are void;
G is —NR⁶'—, —CHR⁶'—, —C(R⁶')₂—, or —O—,
wherein
each R⁶' is independently hydrogen, optionally substituted cyclic or noncyclic lower alkyl, optionally substituted aryl, optionally substituted heteroaryl, optionally substituted arylalkyl or optionally substituted heteroarylalkyl; and
E is —CHR⁵—, —O—, or —NR⁸—,
wherein
R⁵ is hydrogen or optionally substituted lower alkyl, and
R⁸ is hydrogen, lower alkyl, lower alkenyl or lower alkynyl.

(42) The compound according to (1) mentioned above, wherein, in the formula (I),
B is void;
D is optionally substituted $C_{3-8}$ cycloalkane;
G is —NR⁶'—, —CHR⁶'—, —C(R⁶')₂—, or —O—,
wherein
each R⁶' is independently hydrogen, optionally substituted cyclic or noncyclic lower alkyl, optionally substituted aryl, optionally substituted heteroaryl, optionally substituted arylalkyl or optionally substituted heteroarylalkyl;
E is —CHR⁵—, —O—, or —NR⁸—
wherein
R⁵ is hydrogen or optionally substituted lower alkyl, and
R⁸ is hydrogen, lower alkyl, lower alkenyl or lower alkynyl;
R¹ is —Ra—R¹⁰,
wherein
Ra is optionally substituted lower alkylene and R¹⁰ is hydrogen, optionally substituted alkyl, optionally substituted cycloalkyl, optionally substituted aryl or optionally substituted heteroaryl;
R² is —W²¹—W²²—Rb—R²⁰;
wherein
W²¹ is —(CO)— or —(SO₂)—,
W²² is bond, —O—, —NH— or optionally substituted lower alkylene,
Rb is bond or optionally substituted lower alkylene, and
R²⁰ is optionally substituted alkyl, optionally substituted cycloalkyl, optionally substituted aryl or optionally substituted heteroaryl; and
R⁷ of A is —Rc—R⁷⁰,
wherein
Rc is bond or optionally substituted lower alkylene, and
R⁷⁰ is Hydrogen, optionally substituted alkyl, optionally substituted aryl or optionally substituted heteroaryl.

(43) The compound according to (1) mentioned above, wherein, in the formula (I),
both B and D are void;
G is —NR⁶'—, —CHR⁶'—, —C(R⁶')₂—, or —O—,
wherein
each R⁶' is independently hydrogen, optionally substituted cyclic or noncyclic lower alkyl, optionally substituted aryl, optionally substituted heteroaryl, optionally substituted arylalkyl or optionally substituted heteroarylalkyl;
E is —CHR⁵—, —O—, or —NR⁸—,
wherein
R⁵ is hydrogen or optionally substituted lower alkyl, and
R⁸ is hydrogen, lower alkyl, lower alkenyl or lower alkynyl;
R¹ is —Ra—R¹⁰,
wherein
Ra is optionally substituted lower alkylene and R¹⁰ is hydrogen, optionally substituted alkyl, optionally substituted cycloalkyl, optionally substituted aryl or optionally substituted heteroaryl.
R² is —W²¹—W²²—Rb—R²⁰,
wherein
W²¹ is —(CO)— or —(SO₂)—,
W²² is bond, —O—, —NH— or optionally substituted lower alkylene,
Rb is bond or optionally substituted lower alkylene, and
R²⁰ is optionally substituted alkyl, optionally substituted cycloalkyl, optionally substituted aryl or optionally substituted heteroaryl.
R⁷ of A is —Rc—R⁷⁰,
wherein
Rc is bond or optionally substituted lower alkylene, and
R⁷⁰ is hydrogen, optionally substituted alkyl, optionally substituted aryl or optionally substituted heteroaryl.

In further embodiment of formula (I), such compounds comprise a formula (Ia)

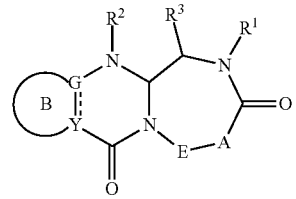

(Ia)

wherein
- - - - is single bond or double bond;
A is —CHR⁷—,
wherein
R⁷ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl or optionally substituted heterocycloalkylalkyl;
E is —CHR⁵—, —O— or —NR⁸—,
wherein
R⁵ is hydrogen, optionally substituted alkyl, optionally substituted alkenyl, optionally substituted alkynyl, optionally substituted arylalkyl or optionally substituted heteroarylalkyl; and
R⁸ is hydrogen, optionally substituted alkyl, optionally substituted alkenyl or optionally substituted alkynyl;
B is optionally substituted monocyclic ring formed together with
G and Y;
G and Y are independently carbon atom or nitrogen atom;

R¹ is optionally substituted alkyl, optionally substituted alkenyl, optionally substituted alkynyl, optionally substituted arylalkyl, optionally substituted heteroarylalkyl, optionally substituted cycloalkylalkyl or optionally substituted heterocycloalkylalkyl;

R² is —W²¹—W²²—Rb—R²⁰,
  wherein
    W²¹ is —(CO)— or —(SO₂)—,
    W²² is bond, —O—, —NH— or optionally substituted lower alkylene,
    Rb is bond or optionally substituted alkylene, and
    R²⁰ is optionally substituted alkyl, optionally substituted alkenyl, optionally substituted alkynyl, optionally substituted aryl, optionally substituted heteroaryl, optionally substituted cycloalkyl or optionally substituted heterocycloalkyl; and R³ is hydrogen, optionally substituted alkyl, optionally substituted alkenyl or optionally substituted alkynyl.

In further another embodiment of formula (I), such compounds comprise a formula (Ib)

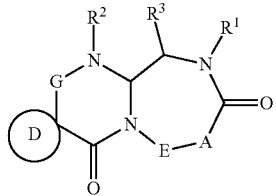

(Ib)

wherein
A is —CHR⁷—,
  wherein
    R⁷ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl or optionally substituted heterocycloalkylalkyl;
E is —CHR⁵—, —O— or —NR⁸—,
  wherein
    R⁵ is hydrogen, optionally substituted alkyl, optionally substituted alkenyl, optionally substituted alkynyl, optionally substituted arylalkyl or optionally substituted heteroarylalkyl; and
  R⁸ is hydrogen, optionally substituted alkyl, optionally substituted alkenyl or optionally substituted alkynyl;
D is optionally substituted spiro ring,
G is —NR⁶—, —O—, —CHR⁶— or —C(R⁶)₂—,
  wherein
    each R⁶ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl;
R¹ is optionally substituted alkyl, optionally substituted alkenyl, optionally substituted alkynyl, optionally substituted arylalkyl, optionally substituted heteroarylalkyl, optionally substituted cycloalkylalkyl or optionally substituted heterocycloalkylalkyl;
R² is —W²¹—W²²—Rb—R²⁰,
  wherein
    W²¹ is —(CO)— or —(SO₂)—,
    W²² is bond, —O—, —NH— or optionally substituted lower alkylene,
    Rb is bond or optionally substituted alkylene, and
    R²⁰ is optionally substituted alkyl, optionally substituted alkenyl, optionally substituted alkynyl, optionally substituted aryl, optionally substituted heteroaryl, optionally substituted cycloalkyl or optionally substituted heterocycloalkyl;
R³ is hydrogen, optionally substituted alkyl, optionally substituted alkenyl or optionally substituted alkynyl.

In further another embodiment of formula (I), such compounds comprise a formula (Ic)

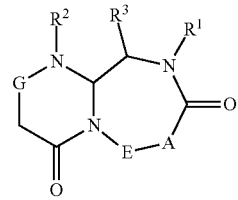

(Ic)

wherein
A is —CHR⁷—,
  wherein
    R⁷ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl or optionally substituted heterocycloalkylalkyl;
E is —CHR⁵—, —O— or —NR⁸—,
  wherein
    R⁵ is hydrogen, optionally substituted alkyl, optionally substituted alkenyl, optionally substituted alkynyl, optionally substituted arylalkyl or optionally substituted heteroarylalkyl, and
  R⁸ is hydrogen, optionally substituted alkyl, optionally substituted alkenyl or optionally substituted alkynyl;
G is —NR⁶—, —O—, —CHR⁶— or —C(R⁶)₂—,
  wherein
    each R⁶ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl;
R¹ is optionally substituted alkyl, optionally substituted alkenyl, optionally substituted alkynyl, optionally substituted arylalkyl, optionally substituted heteroarylalkyl, optionally substituted cycloalkylalkyl or optionally substituted heterocycloalkylalkyl;
R² is —W²¹—W²²—Rb—R²⁰,
  wherein
    W²¹ is —(CO)— or —(SO₂)—,
    W²² is bond, —O—, —NH— or optionally substituted lower alkylene,
    Rb is bond or optionally substituted alkylene,
    R²⁰ is optionally substituted alkyl, optionally substituted alkenyl, optionally substituted alkynyl, optionally substituted aryl, optionally substituted heteroaryl, optionally substituted cycloalkyl or optionally substituted heterocycloalkyl; and $R^3$ is hydrogen or optionally substituted alkyl.

In further another embodiment of formula (I), such compounds comprise a formula (Id)

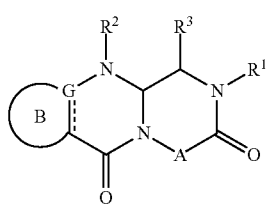

(Id)

wherein
- - - - is single bond or double bond;
A is —CHR$^7$—,
  wherein
    $R^7$ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl or optionally substituted heterocycloalkylalkyl;
B is optionally substituted monocyclic ring;
G is carbon atom or nitrogen atom;
$R^1$ is optionally substituted alkyl, optionally substituted alkenyl, optionally substituted alkynyl, optionally substituted arylalkyl, optionally substituted heteroarylalkyl, optionally substituted cycloalkylalkyl or optionally substituted heterocycloalkylalkyl;
$R^2$ is —W$^{21}$—W$^{22}$—Rb—R$^{20}$,
  wherein
    W$^{21}$ is —(CO)— or —(SO$_2$)—,
    W$^{22}$ is bond, —O—, —NH— or optionally substituted lower alkylene,
    Rb is bond or optionally substituted alkylene, and
    $R^{20}$ is optionally substituted alkyl, optionally substituted alkenyl, optionally substituted alkynyl, optionally substituted aryl, optionally substituted heteroaryl, optionally substituted cycloalkyl or optionally substituted heterocycloalkyl; and
$R^3$ is hydrogen, optionally substituted alkyl, optionally substituted alkenyl or optionally substituted alkynyl;
with the proviso that
when B is benzene, and $R^2$ is —W$^{21}$—W$^{22}$—Rb—R$^{20}$; wherein W$^{21}$ is —(CO)—; W$^{22}$ is —NH—; Rb is bond, then $R^{20}$ should not be optionally substituted phenyl.

In further another embodiment of formula (I), such compounds comprise a formula (II):

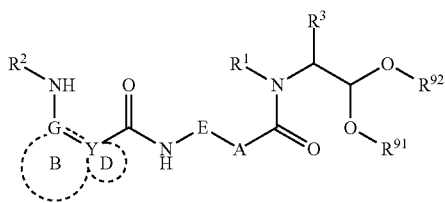

wherein
- - - - is single bond or double bond;
A is —CHR$^7$—,
  wherein
    $R^7$ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl or optionally substituted heterocycloalkylalkyl;
E is bond, —CHR$^5$—, —O— or —NR$^8$—,
  wherein
    $R^5$ is hydrogen, optionally substituted alkyl, optionally substituted alkenyl, optionally substituted alkynyl, optionally substituted arylalkyl or optionally substituted heteroarylalkyl; and
    $R^8$ is hydrogen, optionally substituted alkyl, optionally substituted alkenyl or optionally substituted alkynyl;
B is void or optionally substituted monocyclic ring formed together with G and Y;
D is void or optionally substituted spiro ring formed together with Y;
with the proviso that
B and D are not both present,
when B is present, then G and Y are independently carbon atom or nitrogen atom,
when D is present, then Y is carbon atom and G is —NR$^6$—, —O—, —CHR$^6$— or —C(R$^6$)$_2$—,
when both B and D are void, then G and Y are the same or different and each is —NR$^6$—, —O—, —CHR$^6$— or —C(R$^6$)$_2$—,
  wherein
    each $R^6$ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl, and
when E is bond, then D is void, B is optionally substituted monocyclic ring, and G and Y are independently carbon atom or nitrogen atom;
$R^1$ is optionally substituted alkyl, optionally substituted alkenyl, optionally substituted alkynyl, optionally substituted arylalkyl, optionally substituted heteroarylalkyl, optionally substituted cycloalkylalkyl or optionally substituted heterocycloalkylalkyl;
$R^2$ is —W$^{21}$—W$^{22}$—Rb—R$^{20}$,
  wherein
    W$^{21}$ is —(CO)— or —(SO$_2$)—;
    W$^{22}$ is bond, —O—, —NH— or optionally substituted lower alkylene;
    Rb is bond or optionally substituted alkylene; and
    $R^{20}$ is optionally substituted alkyl, optionally substituted alkenyl, optionally substituted alkynyl, optionally substituted aryl, optionally substituted heteroaryl, optionally substituted cycloalkyl or optionally substituted heterocycloalkyl;
$R^3$ is hydrogen, optionally substituted alkyl, optionally substituted alkenyl or optionally substituted alkynyl;
$R^{91}$ is selected from optionally substituted alkyl, linker and solid support; and
$R^{92}$ is selected from optionally substituted alkyl, linker and solid support;

with the proviso that
when D is void, E is bond, B is benzene, and $R^2$ is —$W^{21}$—$W^{22}$—Rb—$R^{20}$, wherein $W^{21}$ is —(CO)—, $W^{22}$ is —NH—, and Rb is bond, then $R^{20}$ should not be optionally substituted phenyl;

In further another embodiment of formula (I), such compounds comprise a formula (IIa'):

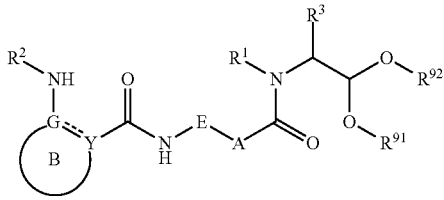

wherein
---- is single bond or double bond;
A is —$CHR^7$—,
wherein
$R^7$ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl or optionally substituted heterocycloalkylalkyl;
E is bond, —$CHR^5$—, —O— or —$NR^8$—,
wherein
$R^5$ is hydrogen, optionally substituted alkyl, optionally substituted alkenyl, optionally substituted alkynyl, optionally substituted arylalkyl or optionally substituted heteroarylalkyl; and
$R^8$ is hydrogen, optionally substituted alkyl, optionally substituted alkenyl or optionally substituted alkynyl;
B is void or optionally substituted monocyclic ring formed together with G and Y;
G and Y are independently carbon atom or nitrogen atom;
with the proviso that
when E is bond, then B is optionally substituted monocyclic ring, and G and Y are independently carbon atom or nitrogen atom;
$R^1$ is optionally substituted alkyl, optionally substituted alkenyl, optionally substituted alkynyl, optionally substituted arylalkyl, optionally substituted heteroarylalkyl, optionally substituted cycloalkylalkyl or optionally substituted heterocycloalkylalkyl;
$R^2$ is —$W^{21}$—$W^{22}$—Rb—$R^{20}$,
wherein
$W^{21}$ is —(CO)— or —($SO_2$)—;
$W^{22}$ is bond, —O—, —NH— or optionally substituted lower alkylene;
Rb is bond or optionally substituted alkylene; and
$R^{20}$ is optionally substituted alkyl, optionally substituted alkenyl, optionally substituted alkynyl, optionally substituted aryl, optionally substituted heteroaryl, optionally substituted cycloalkyl or optionally substituted heterocycloalkyl;
$R^3$ is hydrogen, optionally substituted alkyl, optionally substituted alkenyl or optionally substituted alkynyl;
$R^{91}$ is selected from optionally substituted alkyl, linker and solid support; and
$R^{92}$ is selected from optionally substituted alkyl, linker and solid support;

with the proviso that
when E is bond, B is benzene, and $R^2$ is —$W^{21}$—$W^{22}$—Rb—$R^{20}$, wherein $W^{21}$ is —(CO)—, $W^{22}$ is —NH—, and Rb is bond, then $R^{20}$ should not be optionally substituted phenyl;

In further another embodiment of formula (I), such compounds comprise a formula (IIb'):

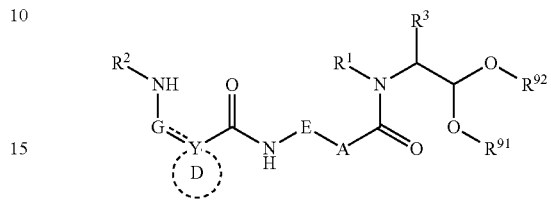

wherein
---- is single bond or double bond;
A is —$CHR^7$—,
wherein
$R^7$ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl or optionally substituted heterocycloalkylalkyl;
E is —$CHR^5$—, —O— or —$NR^8$—,
wherein
$R^5$ is hydrogen, optionally substituted alkyl, optionally substituted alkenyl, optionally substituted alkynyl, optionally substituted arylalkyl or optionally substituted heteroarylalkyl; and
$R^8$ is hydrogen, optionally substituted alkyl, optionally substituted alkenyl or optionally substituted alkynyl;
D is void or optionally substituted spiro ring formed together with Y;
with the proviso that
when D is present, Y is carbon atom and G is —$NR^6$—, —O—, —$CHR^6$— or —$C(R^6)_2$—, and
when D is void, then G and Y are the same or different and each is —$NR^6$—, —O—, —$CHR^6$— or —$C(R^6)_2$—,
wherein
each $R^6$ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl;
$R^1$ is optionally substituted alkyl, optionally substituted alkenyl, optionally substituted alkynyl, optionally substituted arylalkyl, optionally substituted heteroarylalkyl, optionally substituted cycloalkylalkyl or optionally substituted heterocycloalkylalkyl;
$R^2$ is —$W^{21}$—$W^{22}$—Rb—$R^{20}$,
wherein
$W^{21}$ is —(CO)— or —($SO_2$)—;
$W^{22}$ is bond, —O—, —NH— or optionally substituted lower alkylene;
Rb is bond or optionally substituted alkylene; and
$R^{20}$ is optionally substituted alkyl, optionally substituted alkenyl, optionally substituted alkynyl, optionally substituted aryl, optionally substituted heteroaryl, optionally substituted cycloalkyl or optionally substituted heterocycloalkyl;

$R^3$ is hydrogen, optionally substituted alkyl, optionally substituted alkenyl or optionally substituted alkynyl;

$R^{91}$ is selected from optionally substituted alkyl, linker and solid support; and $R^{92}$ is selected from optionally substituted alkyl, linker and solid support;

or a salt thereof.

The present invention is also directed to libraries containing one or more compounds of formula (I) above, as well as methods for synthesizing such libraries and methods for screening the same to identify biologically active compounds.

In another embodiment, a pharmaceutical composition comprises the compound of formula (I) or pharmaceutically acceptable salt thereof, and, if necessary, together with a pharmaceutical acceptable carrier or diluent. Compositions containing a compound of this invention in combination with a pharmaceutically acceptable carrier or diluent are also disclosed.

In another embodiment, there is a method of treating a cancerous condition or fibrosis by administering the compound of formula (I). The present invention also provides methods for preventing or treating disorders associated with Wnt signaling pathway. Disorders that may be treated or prevented using a compound or composition of the present invention include tumor or cancer (e.g., KSHV-associated tumor), fibrotic diseases, restenosis associated with angioplasty, polycystic kidney disease, aberrant angiogenesis disease, tuberous sclerosis complex, hair loss, and Alzheimer's disease. Such methods comprise administering to a subject in need thereof a compound or composition of the present invention in an amount effective to achieve the desired outcome.

These and other aspects of this invention will be apparent upon reference to the attached figure and following detailed description. To this end, various references are set forth herein, which describe in more detail certain procedures, compounds and/or compositions, and are incorporated by reference in their entirety.

DETAILED DESCRIPTION OF THE INVENTION

Figure 1:
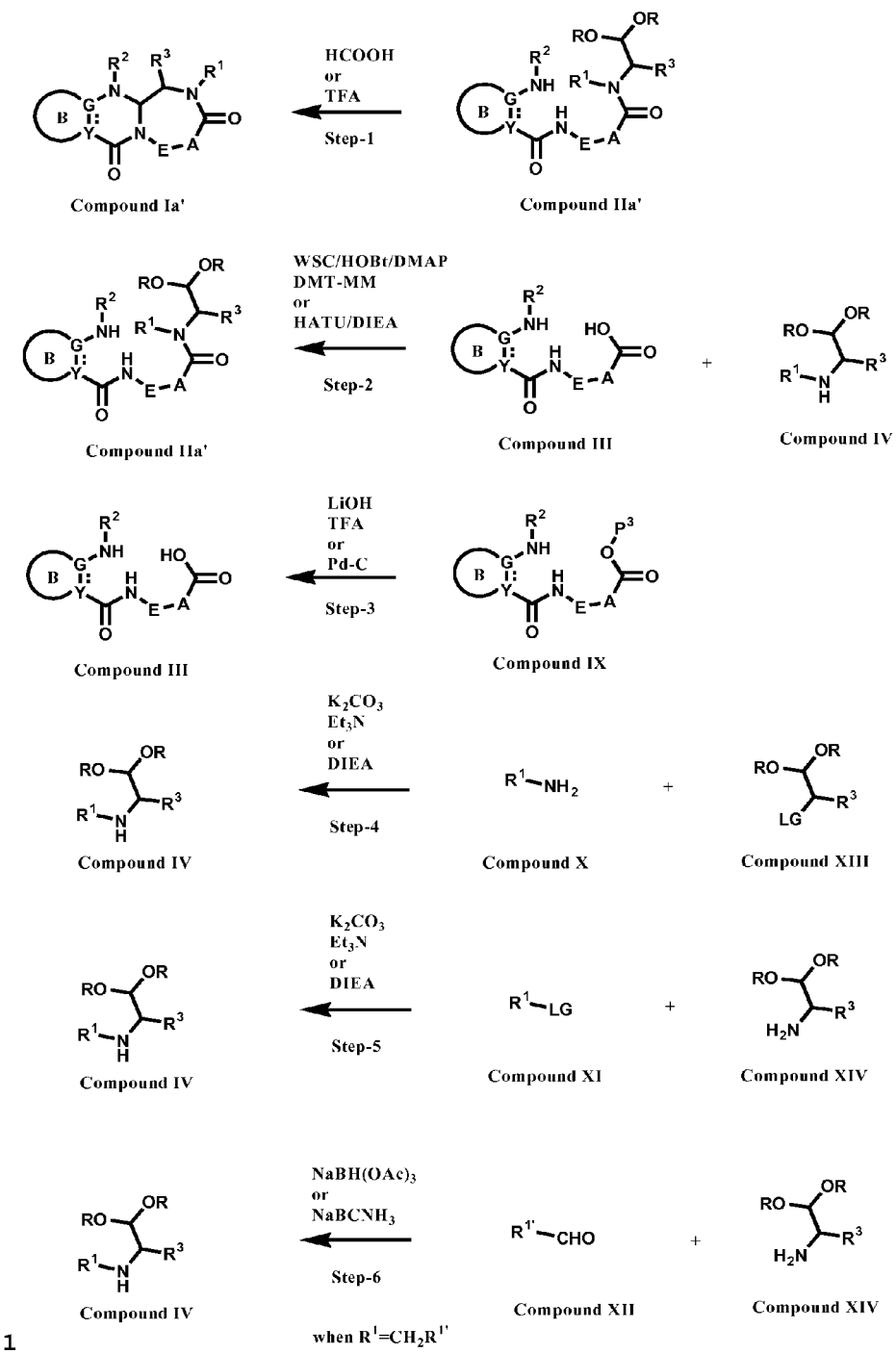
FIG. 1 (including FIGS. 1-1 to 1-6) and
FIG. 2 (including FIGS. 2-1 and 2-2) provide a general synthetic scheme for preparing alpha-helix mimetics of the present invention.

The present invention relates generally to alpha-helix mimetic structures and to a chemical library relating thereto.

The present invention is also directed to conformationally constrained compounds that mimic the secondary structure of alpha-helix regions of biological peptide and proteins (also referred to herein as "alpha-helix mimetics"), and is also directed to chemical libraries relating thereto. The alpha-helix mimetic structures of the present invention are useful as bioactive agents, including (but not limited to) use as diagnostic, prophylactic and/or therapeutic agents. The alpha-helix mimetic structure libraries of this invention are useful in the identification of bioactive agents having such uses. In the practice of the present invention, the libraries may contain from tens to hundreds to thousands (or greater) of individual alpha-helix structures (also referred to herein as "members").

Definitions

Unless otherwise stated, the following terms used in the specification and claims shall have the following meanings for the purposes of this Application.

"Lower", unless indicated otherwise, means that the number of the carbon atoms constituting the given radicals is between one and six.

"Optionally substituted", unless otherwise stated, means that a given radical may consist of only hydrogen substituents through available valencies or may further comprise one or more non-hydrogen substituents through available valencies. In general, a non-hydrogen substituent may be any substituent that may be bound to an atom of the given radical that is specified to be substituted. Examples of substituents include, but are not limited to, —$R^9$, —$OR^9$, —$COR^9$, —$COOR^9$, —$OCOR^9$, —$CONR^9R^4$, —$NR^9R^4$, —$NR^4COR^9$, —$NR^4COOR^9$, —$SR^9$, —$SO_2R^9$, —$SO_2NR^9R^4$, —$SO_3R^9$, —$NHC(NHR^9)NR^4$, —$NHC(NH_2)NH$, —$OPO(OH)_2$, —$OPO(ONa)_2$, —CN, —$NO_2$, halogen and methylenedioxy, wherein $R^9$ and $R^4$ are independently selected from hydrogen, optionally substituted, cyclic or noncyclic, alkyl, aryl, heteroaryl, arylalkyl and heteroarylalkyl.

"Halogen" means fluorine, chlorine, bromine or iodine.

"Halo" means fluoro, chloro, bromo or iodo.

"Alkyl" means a linear or branched, saturated, aliphatic radical having a chain of carbon atoms. $C_{X-Y}$ alkyl is typically used where X and Y indicate the number of carbon atoms in the chain. The number of carbon atoms in the chain is preferably 1 to 10, more preferably 1 to 6, further preferably 1 to 4. Non-exclusive examples of alkyl include methyl, ethyl, propyl, isopropyl, butyl, sec-butyl, isobutyl, tert-butyl, pentyl, isopentyl, neopentyl, tert-pentyl, hexyl, isohexyl, and the like. "Noncyclic alkyl" equals to "alkyl" as used here.

"Alkenyl" means a linear or branched, carbon chain that contains at least one carbon-carbon double bond. $C_{X-Y}$ alkenyl is typically used where X and Y indicate the number of carbon atoms in the chain. The number of carbon atoms in the chain is preferably 2 to 10, more preferably 2 to 6. Non-exclusive examples of alkenyl include ethenyl (vinyl), allyl, isopropenyl, 2-methylallyl, 1-pentenyl, hexenyl, heptenyl, 1-propenyl, 2-butenyl, 2-methyl-2-butenyl, and the like.

"Alkynyl" means a linear or branched, carbon chain that contains at least one carbon-carbon triple bond. $C_{X-Y}$ alkynyl is typically used where X and Y indicate the number of carbon atoms in the chain. The number of carbon atoms in the chain is preferably 2 to 10, more preferably 2 to 6. Non-exclusive examples of alkynyl include ethynyl, propargyl, 3-methyl-1-pentynyl, 2-heptynyl and the like.

"Alkylene", unless indicated otherwise, means a linear or branched, saturated, aliphatic, polyvalent carbon chain. $C_{X-Y}$ alkylene is typically used where X and Y indicate the number of carbon atoms in the chain. The number of carbon atoms in the chain is preferably 1 to 10, more preferably 1 to 6. Non-exclusive examples of alkylene include methylene (—$CH_2$—), ethylene (—$CH_2CH_2$—), methylmethylene (—$CH(CH_3)$—), 1,2-propylene (—$CH_2CH(CH_3)$—), 1,3-propylene (—$CH_2CH_2CH_2$—), 1,2-butylene (—$CH_2CH(CH_2CH_3)$—), 1,3-butylene (—$CH_2CH_2CH(CH_3)$—), 1,4-butylene (—$CH_2CH_2CH_2CH_2$—), 2-methyltetramethylene (—CH$_2$CH(CH$_3$)CH$_2$CH$_2$—) pentamethylene (—CH$_2$CH$_2$CH$_2$CH$_2$CH$_2$—), 1,2,3-propanetriyl, 1,3,3-propanetriyl and the like.

"Oxy" means the radical —O—. It is noted that the oxy radical may be further substituted with a variety of substituents to form different oxy groups including hydroxy, alkoxy, aryloxy, heteroaryloxy and the like.

"Thio" means the radical —S—. It is noted that the thio radical may be further substituted with a variety of substituents to form different thio groups including mercapto, alkylthio, arylthio, heteroarylthio and the like.

"Sulfinyl" means the radical —SO—. It is noted that the sulfinyl radical may be further substituted with a variety of substituents to form different sulfinyl groups including alkylsulfinyl, arylsulfinyl, heteroarylsulfinyl and the like.

"Sulfonyl" means the radical —SO$_2$—. It is noted that the sulfonyl radical may be further substituted with a variety of substituents to form different sulfonyl groups including alkylsulfonyl, arysulfonyl, heteroarylsulfonyl and the like.

"Alkoxy" means an oxygen moiety having a further alkyl substituent. $C_{X-Y}$ alkoxy is typically used where X and Y indicate the number of carbon atoms in the chain. The number of carbon atoms in the chain is preferably 1 to 10, more preferably 1 to 6. Non-exclusive examples of alkoxy include methoxy, ethoxy, propoxy, isopropoxy, butoxy, sec-butoxy, isobutoxy, tert-butoxy, pentoxy, isopentoxy, neopentoxy, tert-pentoxy, hexyloxy, isohexyloxy, and the like.

"Heteroatom" refers to an atom that is not a carbon atom and hydrogen atom. Particular examples of heteroatoms include, but are not limited to nitrogen, oxygen, and sulfur.

"Aryl" means a monocyclic or polycyclic radical wherein each ring is aromatic or when fused with one or more rings forms an aromatic ring. $C_{X-Y}$ aryl is typically used where X and Y indicate the number of carbon atoms in the ring assembly. The number of carbon atoms in the ring is preferably 6 to 14, more preferably 6 to 10. Non-exclusive examples of aryl include phenyl, naphthyl, indenyl, azulenyl, biphenyl, fluorenyl, anthracenyl, phenalenyl and the like. "Aryl" may partially be hydrogenated. Non-exclusive examples of partially hydrogenated aryl include tetrahydronaphthyl, indanyl and the like.

"Heteroaryl" means a monocyclic or polycyclic aromatic radical wherein at least one ring atom is a heteroatom and the remaining ring atoms are carbon. "X-Y membered heteroaryl" is typically used where X and Y indicate the number of carbon atoms and heteroatoms in the ring assembly. The number of carbon atoms and heteroatoms in the ring is preferably 5 to 14, more preferably 5 to 10. Monocyclic heteroaryl groups include, but are not limited to, cyclic aromatic groups having five or six ring atoms, wherein at least one ring atom is a heteroatom and the remaining ring atoms are carbon. The nitrogen atoms can be optionally quaternerized and the sulfur atoms can be optionally oxidized. Non-exclusive examples of monocyclic heteroaryl group of this invention include, but are not limited to, those derived from furan, thiophene, pyrrole, imidazole, isothiazole, isoxazole, oxadiazole, oxazole, 1,2,3-oxadiazole, pyrazine, pyrazole, pyridazine, pyridine, pyrimidine, triazine, pyrroline, thiazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, and another monocyclic heteroaryl or heterocycloalkyl ring. Non-exclusive examples of bicyclic or tricyclic heteroaryl include, but are not limited to, those derived from benzofuran (ex. benzo[b]furan), benzothiophene (ex. benzo[b]thiophene), benzimidazole, benzotriazine (ex. benzo[e][1,2,4]triazine, benzo[d][1,2,3]triazine), pyridopyrimidine (ex. pyrido[4,3-d]pyrimidine, pyrido[3,4-d]pyrimidine, pyrido[3,2-d]pyrimidine, pyrido[2,3-d]pyrimidine), pyridopyrazine (ex. pyrido[3,4-b]pyrazine, pyrido[2,3-b]pyrazine), pyridopyridazine (ex. pyrido[2,3-c]pyridazine, pyrido[3,4-c]pyridazine, pyrido[4,3-c]pyridazine, pyrido[3,2-c]pyridazine), pyridotriazine (ex. pyrido[2,3-d][1,2,3]triazine, pyrido[3,4-d][1,2,3]triazine, pyrido[4,3-d][1,2,3]triazine, pyrido[3,2-d][1,2,3]triazine, pyrido[3,4-e][1,2,4]triazine, pyrido[3,2-e][1,2,4]triazine), benzothiadiazole (ex. benzo[c][1,2,5]thiadiazole), fulopyridine (ex. furo[3,2-b]pyridine, furo[3,2-c]pyridine, furo[2,3-c]pyridine, furo[2,3-b]pyridine), oxazolopyridine (ex. oxazolo[4,5-b]pyridine, oxazolo[4,5-c]pyridine, oxazolo[5,4-c]pyridine, oxazolo[5,4-b]pyridine), thiazolopyridine (ex. thiazolo[4,5-b]pyridine, thiazolo[4,5-c]pyridine, thiazolo[5,4-c]pyridine, thiazolo[5,4-b]pyridine), imidazopyridine (ex. imidazo[1,2-a]pyridine, imidazo[4,5-c]pyridine, imidazo[1,5-a]pyridine), quinazoline, thienopyridine (ex. thieno[2,3-c]pyridine, thieno[3,2-b]pyridine, thieno[2,3-b]pyridine), indolizine, quinoline, isoquinoline, phthalazine, quinoxaline, cinnoline, naphthyridine, quinolizine, indole, isoindole, indazole, indoline, benzoxazole, benzopyrazole, benzothiazole, pyrazolopyridine (ex. pyrazolo[1,5-a]pyridine), imidazopyrimidine (ex. imidazo[1,2-a]pyrimidine, imidazo[1,2-c]pyrimidine, imidazo[1,5-a]pyrimidine, imidazo[1,5-c]pyrimidine), pyrrolopyridine (ex. pyrrolo[2,3-b]pyridine, pyrrolo[2,3-c]pyridine, pyrrolo[3,2-c]pyridine, pyrrolo[3,2-b]pyridine), pyrrolopyrimidine (ex. pyrrolo[2,3-d]pyrimidine, pyrrolo[3,2-d]pyrimidine, pyrrolo[1,2-c]pyrimidine, pyrrolo[1,2-a]pyrimidine), pyrrolopyrazine (ex. pyrrolo[2,3-b]pyrazine, pyrrolo[1,2-a]pyrazine), pyrrolopyridazine (ex. pyrrolo[1,2-b]pyridazine), triazopyridine (ex. triazo[1,5-a]pyridine), pteridine, purine, carbazole, acridine, permidine, 1,10-phenanthroline, phenoxathiin, phenoxazine, phenothiazine, phenazine, benzodioxole, benzodioxolane and the like. The bicyclic or tricyclic heteroaryl rings can be attached to the parent molecule through either the heteroaryl group itself or the aryl, cycloalkyl, or heterocycloalkyl group to which it is fused.

"Cycloalkyl" means a non-aromatic, saturated or partially unsaturated, monocyclic, fused bicyclic or bridged polycyclic ring radical. $C_{X-Y}$ cycloalkyl is typically used where X and Y indicate the number of carbon atoms in the ring assembly. The number of carbon atoms in the ring is preferably 3 to 10, more preferably 3 to 8. Non-exclusive examples of cycloalkyl include cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, bicyclo[2.2.1]hept-1-yl, and the like. "Cyclic alkyl" equals to "cycloalkyl" as used here.

"Heterocycloalkyl" means cycloalkyl, as defined in this Application, provided that one or more of the atoms forming the ring is a heteroatom selected, independently from N, O, and S. $C_{X-Y}$ heterocycloalkyl is typically used where X and Y indicate the number of carbon atoms and heteroatoms in the ring assembly. The number of carbon atoms and heteroatoms in the ring is preferably 3 to 10, more preferably 3 to 8. Non-exclusive examples of heterocycloalkyl include piperidyl, 4-morpholyl, 4-piperazinyl, pyrrolidinyl, perhydropyrrolizinyl, 1,4-diazaperhydroepinyl, 1,3-dioxanyl, 1,4-dioxanyl, tetrazolyl and the like.

Moreover, the above-mentioned definitions can apply to groups wherein the above-mentioned substituents are connected. For example, "arylalkyl" means linear or branched alkyl group which is substituted by one or more aryl groups, such as benzyl, 1-phenylethyl, 2-phenylethyl, 3-phenylpropyl, 1-naphthylmethyl, 2-naphthylmethyl, benzhydryl, 2,2-diphenylethyl, trityl and the like.

"Monocyclic ring" as used herein refers to a monocyclic, saturated or unsaturated carbocyclic ring or a monocyclic, saturated or unsaturated heterocyclic ring. "X- (to, or) Y-membered monocyclic ring" is typically used where X and Y indicate the number of carbon atoms and heteroatoms in the ring assembly. The number of carbon atoms and heteroatoms in the ring is preferably 4 to 7, more preferably 5 or 6. "Monocyclic heterocyclic ring" means a monocyclic, aromatic or nonaromatic ring wherein at least one ring atom is a heteroatom (preferably S, N or O) and the remaining ring atoms are carbon. The nitrogen atoms can be optionally quaternerized and the sulfur atoms can be optionally oxidized.

Non-exclusive examples of monocyclic saturated carbocyclic ring include cyclopropane, cyclobutane, cyclopentane, cyclohexane, cycloheptane and the like.

Non-exclusive examples of monocyclic unsaturated carbocyclic ring include cyclopropene, cyclobutene, cyclopentene, cyclohexene, cycloheptene, cyclopentadiene, benzene, and the like.

Non-exclusive examples of monocyclic saturated heterocyclic ring include pyrrolidine, piperidine, morpholine, piperazine, 1,3-dioxane, 1,4-dioxane and the like.

Non-exclusive examples of monocyclic unsaturated heterocyclic ring include pyrazole, dihydro-pyrrole, pyrrole, dihydro-pyrazole, imidazole, thiophene, thiazole, isothiazole, thiadiazole, furan, oxazole, isoxazole, oxadiazole, pyridine, pyridazine, pyrimidine, pyrazine, triazine and the like.

"Spiro ring" as used herein refers to saturated or unsaturated cycloalkane or saturated or unsaturated heterocycloalkane.

"Cycloalkane" means a non-aromatic, saturated or partially unsaturated, monocyclic, fused bicyclic or bridged polycyclic ring. $C_{X-Y}$ cycloalkane is typically used where X and Y indicate the number of carbon atoms in the ring assembly. The number of carbon atoms in the ring is preferably 3 to 10, more preferably 3 to 8. Non-exclusive examples of cycloalkane include cyclopropane, cyclobutane, cyclopentane, cyclohexane, cycloheptane, cyclooctane and the like.

"Heterocycloalkane" means cycloalkane, as defined in this Application, provided that one or more of the atoms forming the ring is a heteroatom selected, independently from N, O, and S. $C_{X-Y}$ heterocycloalkane is typically used where X and Y indicate the number of carbon atoms and heteroatoms in the ring assembly. The number of carbon atoms and heteroatoms in the ring is preferably 3 to 10, more preferably 3 to 8. Non-exclusive examples of heterocycloalkane include piperidine, morpholine, piperazine, pyrrolidine, perhydropyrrolizine, tetrahydrofuran, tetrahydropyran, 1,3-dioxane, 1,4-dioxane and the like.

"Fused ring" as used herein refers to a ring that is bonded to another ring to form a compound having a bicyclic structure when the ring atoms that are common to both rings are directly bound to each other. Non-exclusive examples of fused rings include decalin, naphthalene, anthracene, phenanthrene, indole, furan, benzofuran, quinoline, and the like. Compounds having fused ring systems may be saturated, partially saturated or aromatic.

"Bridging ring" as used herein refers to a ring that is bonded to another ring to form a compound having a bicyclic structure where two ring atoms that are common to both rings are not directly bound to each other. Non-exclusive examples of common compounds having a bridging ring include adamantine, borneol, norbornane, 7-oxabicyclo[2.2.1]heptane, and the like.

"Protected derivatives" means derivatives of compound in which a reactive site or sites are blocked with protecting groups. A comprehensive list of suitable protecting groups can be found in T. W. Greene, *Protecting Groups in Organic Synthesis*, 3rd edition, John Wiley & Sons, Inc. 1999.

"Isomers" mean any compound having an identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture." A compound that has more than one chiral center has $2^{n1}$ enantiomeric pairs, where n is the number of chiral centers. Compounds with more than one chiral center may exist as either an individual diastereomer or as a mixture of diastereomers, termed a "diastereomeric mixture." When one chiral center is present, a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Animal" includes humans, non-human mammals (e.g., mice, rats, dogs, cats, rabbits, cattle, horses, sheep, goats, swine, deer, and the like) and non-mammals (e.g., birds, and the like).

"Disease" specifically includes any unhealthy condition of an animal or part thereof and includes an unhealthy condition that may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salt" means a salt of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salt also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Amount effective to treat" means that amount which, when administered to an animal for treating a disease, is sufficient to effect such treatment for the disease.

"Amount effective to prevent" means that amount which, when administered to an animal for preventing a disease, is sufficient to effect such prophylaxis for the disease.

"Effective amount" equals to "amount effective to treat" and "amount effective to prevent".

"Treatment" or "treat" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the disease (i.e., arresting further development of the pathology and/or symptomatology), or (3) ameliorating the disease in an animal that is experiencing or displaying the pathology or symptomatology of the disease (i.e., reversing the pathology and/or symptomatology).

It is noted in regard to all of the definitions provided herein that the definitions should be interpreted as being open ended in the sense that further substituents beyond those specified may be included.

Alpha-Helix Mimetic

In one aspect of the present invention, an alpha-helix mimetic structure is disclosed having the following formula (I):

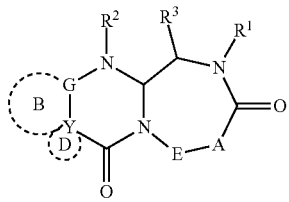

(I)

wherein

- - - - is single bond or double bond;

A is —CHR$^7$—,
  wherein
    R$^7$ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl or optionally substituted heterocycloalkylalkyl;

E is bond, —CHR$^5$—, —O— or —NR$^8$—,
  wherein
    R$^5$ is hydrogen, optionally substituted alkyl, optionally substituted alkenyl, optionally substituted alkynyl, optionally substituted arylalkyl or optionally substituted heteroarylalkyl; and
    R$^8$ is hydrogen, optionally substituted alkyl, optionally substituted alkenyl or optionally substituted alkynyl;

B is void or optionally substituted monocyclic ring formed together with G and Y, D is void or optionally substituted spiro ring formed together with Y, with the proviso that B and D are not both present, when B is present, then G and Y are independently carbon atom or nitrogen atom, when D is present, then Y is carbon atom and G is —NR$^6$—, —O—, —CHR$^6$— or —C(R$^6$)$_2$—, when both B and D are void, then G and Y are the same or different and each is —NR$^6$—, —O—, —CHR$^6$— or —C(R$^6$)$_2$—
  wherein
    each R$^6$ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl; and when E is bond, then D is void, B is optionally substituted monocyclic ring, and G and Y are independently carbon atom or nitrogen atom;

R$^1$ is optionally substituted alkyl, optionally substituted alkenyl, optionally substituted alkynyl, optionally substituted arylalkyl, optionally substituted heteroarylalkyl, optionally substituted cycloalkylalkyl or optionally substituted heterocycloalkylalkyl;

R$^2$ is —W$^{21}$—W$^{22}$—Rb—R$^{20}$,
  wherein
    W$^{21}$ is —(CO)— or —(SO$_2$)—;
    W$^{22}$ is bond, —O—, —NH— or optionally substituted lower alkylene;
    Rb is bond or optionally substituted lower alkylene, and
    R$^{20}$ is optionally substituted alkyl, optionally substituted alkenyl, optionally substituted alkynyl, optionally substituted aryl, optionally substituted heteroaryl, optionally substituted cycloalkyl or optionally substituted heterocycloalkyl; and R$^3$ is hydrogen, optionally substituted alkyl, optionally substituted alkenyl or optionally substituted alkynyl;

with the proviso that when D is void, E is bond, B is benzene, and R$^2$ is —W$^{21}$—W$^{22}$—Rb—R$^{20}$, wherein W$^{21}$ is —(CO)—, W$^{22}$ is —NH—, and Rb is bond, then R$^{20}$ should not be optionally substituted phenyl;

or a pharmaceutically acceptable salt thereof.

In one embodiment of formula (I), A is —CHR$^7$—, wherein R$^7$ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl or optionally substituted heterocycloalkylalkyl.

Examples of optionally substituted alkyl group include methyl, ethyl, propyl, isopropyl, butyl, isobutyl, sec-butyl, tert-butyl, pentyl, isopentyl, neopentyl, tert-pentyl, aminomethyl, aminoethyl, aminopropyl, aminobutyl, carboxymethyl, carboxyethyl, carboxypropyl, carboxybutyl, carbamoylmethyl, carbamoylethyl, carbamoylpropyl, carbamoylbutyl, methoxymethyl, methoxyethyl, methoxypropyl, methoxybutyl, methylthiomethyl, methylthioethyl, methylthiopropyl, methylthiobutyl, hydroxymethyl, hydroxyethyl, hydroxypropyl, hydroxybutyl, ethoxycarbonylmethyl, ethoxycarbonylethyl, benzyloxymethyl, benzyloxyethyl, benzyloxypropyl, benzyloxybutyl and the like.

Examples of alkenyl group include ethenyl, allyl, 1-propenyl, 2-methylallyl and the like.

Examples of alkynyl group include ethynyl, 1-propynyl and the like.

Examples of aryl group and heteroaryl group include biphenyl, phenyl, pyridyl, pyrimidyl, pyridazinyl, pyrazinyl, triazinyl, pyrrolyl, thienyl, furyl, thiazolyl, oxazolyl, imidazolyl, tetrahydronaphthyl, naphthyl, quinolinyl, isoquinolinyl, quinazolinyl, quinoxalinyl, cinnolinyl, naphthyridinyl, benzotriazinyl, indenyl, pyridopyrimidinyl, pyridopyrazinyl, pyridopyridazinyl, pyridotriazinyl, benzofuryl, benzothienyl, indolyl, indazolyl, benzoxazolyl, benzimidazolyl, benzothiazolyl, benzothiadiazolyl, furopyridinyl, thienopyridinyl, pyrropyridinyl, oxazolopyridinyl, thiazolopyridinyl, imidazopyridinyl and the like.

Examples of cycloalkyl and optionally substituted heterocycloalkyl include cyclopropyl, cyclobutyl, cyclopentyl, cyclohexyl, cycloheptyl, adamantyl and the like.

In another embodiment of formula (I), A is —CHR$^7$—, wherein R$^7$ is —Rc—R$^{70}$ wherein Rc is bond or optionally substituted lower alkylene, and R$^{70}$ is hydrogen, optionally substituted alkyl, optionally substituted aryl, optionally substituted heteroaryl, optionally substituted cycloalkyl or optionally substituted heterocycloalkyl.

Examples of lower alkylene group include methylene, ethylene, methylmethylene, 1,2-propylene, 1,3-propylene, 1,2-butylene, 1,3-butylene, 1,4-butylene, 1,2,3-propanetriyl, 1,3,3-propanetriyl and the like.

Examples of optionally substituted alkyl group include methyl, ethyl, propyl, isopropyl, butyl, isobutyl, sec-butyl, tert-butyl, pentyl, isopentyl, neopentyl, tert-pentyl, aminomethyl, aminoethyl, aminopropyl, aminobutyl, carboxymethyl, carboxyethyl, carboxypropyl, carboxybutyl, carbamoylmethyl, carbamoylethyl, carbamoylpropyl, carbamoylbutyl, methoxymethyl, methoxyethyl, methoxypropyl, methoxybutyl, methylthiomethyl, methylthioethyl, methylthiopropyl, methylthiobutyl, hydroxymethyl, hydroxyethyl, hydroxypropyl, hydroxybutyl, ethoxycarbonylmethyl, ethoxycarbonylethyl, benzyloxymethyl, benzyloxyethyl, benzyloxypropyl, benzyloxybutyl and the like.

Examples of aryl group and heteroaryl group include biphenyl, phenyl, pyridyl, pyrimidyl, pyridazinyl, pyrazinyl, triazinyl, pyrrolyl, thienyl, furanyl, thiazolyl, oxazolyl, imidazolyl, tetrahydronaphthyl, naphthyl, quinolinyl, isoquinolinyl, quinazolinyl, quinoxalinyl, cinnolinyl, naphthyridinyl, benzotriazinyl, indenyl, pyridopyrimidinyl, pyridopyrazinyl, pyridopyridazinyl, pyridotriazinyl, benzofuranyl, benzothienyl, indolyl, indazolyl, benzoxazolyl, benzimidazolyl, benzothiazolyl, benzothiadiazolyl, furopyridinyl, thienopyridinyl, pyrropyridinyl, oxazolopyridinyl, thiazolopyridinyl, imidazopyridinyl and the like.

Examples of cycloalkyl group and heterocycloalkyl group include cyclopropyl, cyclobutyl, cyclopentyl, cyclohexyl, cycloheptyl, adamantyl and the like.

In a particular embodiment of formula (I), in the above-mentioned embodiments R$^{70}$ is optionally substituted aryl or optionally substituted heteroaryl.

Examples of aryl group and heteroaryl group include biphenyl, phenyl, pyridyl, pyrimidyl, pyridazinyl, pyrazinyl, triazinyl, pyrrolyl, thienyl, furanyl, thiazolyl, oxazolyl, imidazolyl, tetrahydronaphthyl, naphthyl, quinolinyl, isoquinolinyl, quinazolinyl, quinoxalinyl, cinnolinyl, naphthyridinyl, benzotriazinyl, indenyl, pyridopyrimidinyl, pyridopyrazinyl, pyridopyridazinyl, pyridotriazinyl, benzofuranyl, benzothiopenyl, indolyl, indazolyl, benzoxazolyl, benzimidazolyl, benzothiazolyl, benzothiadiazolyl, furopyridinyl, thienopyridinyl, pyrrolopyridinyl, oxazolopyridinyl, thiazolopyridinyl, imidazopyridinyl and the like.

Preferred examples of aryl group and heteroaryl group include phenyl, pyridyl, pyrimidyl, pyridazinyl, pyrazinyl, triazinyl, pyrrolyl, thienyl, furanyl, thiazolyl, oxazolyl, imidazolyl, naphthyl and the like.

Most preferred example of aryl group include phenyl and the like.

Examples of substituents for R$^7$ include —R$^9$, —OH, —OR$^9$, —OC(O)R$^9$, —OC(O)OR$^9$, —COOH, —COR$^9$, —COOR$^9$, —CONH$_2$, —CONHR$^9$, —CONR$^9$R$^4$, —NH$_2$, —NHR$^9$, —NR$^9$R$^4$, —SH, —SR$^9$, —SO$_2$R$^9$, —SO$_2$NH$_2$, —SO$_2$NHR$^9$, —SO$_2$NR$^9$R$^4$, —SO$_3$H, —SOR$^9$, —NHC(NH$_2$) (=NH), —NHC(NHR$^9$) (=NR$^4$), —OP(=O)(OH)$_2$, —OP(=O) (ONa)$_2$, —OP(=O) (OR$^9$)$_2$, —OP(=O) (OR$^9$)(OH), —OP(=O) (OH)—O—P(=O)(OH)$_2$, —OP(=O)(ONa)—O—OP(=O)(ONa)$_2$, —CN, —NO$_2$ and halogen, wherein R$^9$ and R$^4$ is independently selected from linear or branched chain, cyclic or noncyclic, substituted or unsubstituted, alkyl chain, aryl and arylalkyl moieties.

Preferred examples of the substituents include —OH, —COOH, —OC(O)R$^9$, —OC(O)OR$^9$, —NH$_2$, —SH, —SO$_3$H, —SOR$^9$, —OP(=O)(OH)$_2$, —OP(=O)(OR$^9$)$_2$, —OP(=O)(OR$^9$)(OH), —OP(=O)(ONa)$_2$, —OP(=O)(OH)—O—P(=O)(OH)$_2$, —OP(=O)(ONa)—O—OP(=O)(ONa)$_2$, and halogen.

Most preferred examples of the substituents include —OH, —OR$^9$, —COOH, —OC(O)R$^9$, —COOR$^9$, —NH$_2$, —NHR$^9$, —NR$^9$R$^4$, —CONH$_2$, —CONHR$^9$, —CONR$^9$R$^4$, —OP(=O) (OH)$_2$, —OP(=O) (ONa)$_2$, and halogen.

In a particular embodiment of formula (I), in the above-mentioned embodiments R$^7$ is phenyl, benzyl, phenethyl, 1-naphthyl, 2-naphthyl, 1-naphthylmethyl, 2-naphthylmethyl, 4-hydroxybenzyl, 4-benzyloxybenzyl, imidazolyl-5-methyl, methyl, n-butyl, isopropyl, isobutyl, hydroxymethyl, 4-aminobutyl, carboxymethyl, 2-carboxyethyl, carbamoylmethyl, 2-carbamoylethyl, ethoxycarbonylmethyl, 2-ethoxycarbonylethyl, benzyloxymethyl and the like.

In one embodiment of formula (I), E is bond, —CHR$^5$—, —O— or —NR$^8$—, wherein R$^5$ is hydrogen, optionally substituted alkyl, optionally substituted alkenyl, optionally substituted alkynyl, optionally substituted arylalkyl or optionally substituted heteroarylalkyl; and R$^8$ is hydrogen, optionally substituted alkyl, optionally substituted alkenyl or optionally substituted alkynyl.

In another embodiment of formula (I), in the above-mentioned embodiments R$^5$ is lower alkyl, lower alkenyl, lower alkynyl or lower arylalkyl, and R$^8$ is alkyl, alkynyl or arylalkyl.

Examples of lower alkyl group for R$^5$ include methyl, ethyl, propyl, isopropyl, butyl, isobutyl, sec-butyl, tert-butyl and the like.

Examples of lower alkenyl group for R$^5$ include ethenyl, allyl, 1-propenyl, 2-methylallyl and the like.

Examples of lower alkynyl group for R$^5$ include ethynyl, 1-propynyl and the like.

In another embodiment of formula (I), R$^5$ is arylalkyl or heteroarylalkyl represented by —Rd—R$^{50}$ wherein Rd is optionally substituted lower alkylene, and $R^{50}$ is optionally substituted aryl or optionally substituted heteroaryl.

Examples of lower alkylene group for Rd include methylene, ethylene, methylmethylene, 1,2-propylene, 1,3-propylene, 1,2-butylene, 1,3-butylene, 1,4-butylene, 1,2,3-propanetriyl, 1,3,3-propanetriyl and the like.

Examples of aryl group and heteroaryl group include biphenyl, phenyl, pyridyl, pyrimidyl, pyridazinyl, pyrazinyl, triazinyl, pyrrolyl, thienyl, furanyl, thiazolyl, oxazolyl, imidazolyl, tetrahydronaphthyl, naphthyl, quinolinyl, isoquinolinyl, quinazolinyl, quinoxalinyl, cinnolinyl, naphthyridinyl, benzotriazinyl, indenyl, pyridopyrimidinyl, pyridopyrazinyl, pyridopyridazinyl, pyridotriazinyl, benzofuranyl, benzothienyl, indolyl, indazolyl, benzoxazolyl, benzimidazolyl, benzothiazolyl, benzothiadiazolyl, furopyridinyl, thienopyridinyl, pyrropyridinyl, oxazolopyridinyl, thiazolopyridinyl, imidazopyridinyl and the like.

Examples of alkyl group for $R^8$ include methyl, ethyl, propyl, isopropyl, butyl, isobutyl, sec-butyl, tert-butyl and the like.

Examples of alkenyl group for $R^8$ include ethenyl, allyl, 1-propenyl, 2-methylallyl and the like.

Examples of alkynyl group for $R^8$ include ethynyl, 1-propynyl and the like.

In a particular embodiment of formula (I), in the above-mentioned embodiments E is —CH$_2$—, —O— or —N(CH$_3$)—.

In another embodiment of formula (I), in the above-mentioned embodiments E is bond with the proviso that when E is bond, then D is void, B is optionally substituted monocyclic ring, and G and Y are independently carbon atom or nitrogen atom.

In one embodiment of formula (I), B is void or optionally substituted monocyclic ring formed together with G and Y; when B is present, then D is void, and G and Y are independently carbon atom or nitrogen atom.

B is preferably optionally substituted 3-, 4-, 5-, 6- or 7 membered saturated or unsaturated monocyclic ring and more preferably optionally substituted 5- or 6-membered saturated or unsaturated monocyclic ring formed together with G and Y.

When B is heterocyclic ring formed together with G and Y, the preferable hetero atom is selected from S, N, and O and the number of hetero atoms is preferably an integer of 1-3.

Examples of monocyclic ring group include cyclopropane, cyclobutane, cyclopentane, cyclohexane, cycloheptane, pyrrolidine, pyrazole, cyclopropene, cyclobutene, cyclopentene, cyclohexene, cycloheptene, cyclopentadiene, dihydro-pyrrole, pyrrole, pyrrolidine, dihydro-pyrazole, pyrazole, imidazole, thiophene, thiazole, isothiazole, thiadiazole, furan, oxazole, isooxazole, oxadiazole, benzene, pyridine, pyridazine, pyrimidine, pyrazine, triazine and the like.

In a particular embodiment of formula (I), in the above-mentioned embodiments $Q^1$ designates a structural sector of the compound;

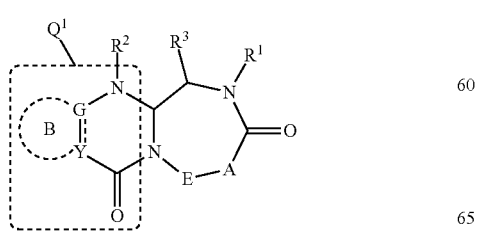

wherein $Q^1$ is selected from one of the following group:

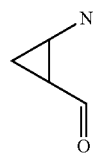

B-1

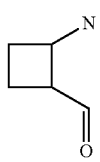

B-2

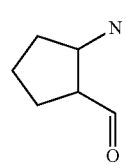

B-3

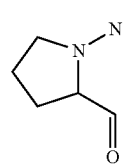

B-4

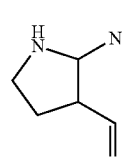

B-5

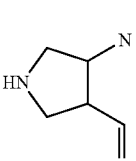

B-6

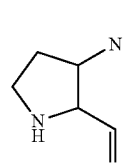

B-7

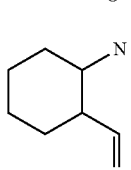

B-8

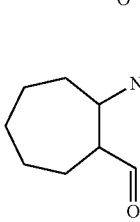

B-9

B-10 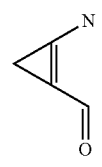
B-11 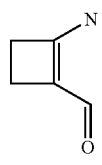
B-12 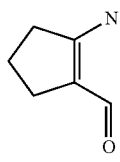
B-13 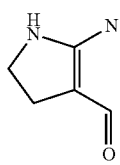
B-14 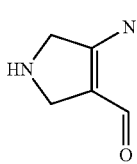
B-15 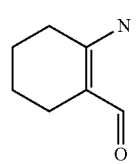
B-16 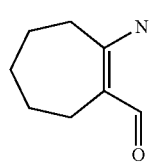
B-17 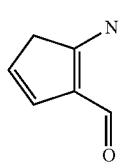
B-18 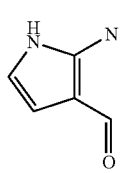
B-19 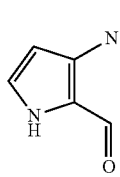
B-20 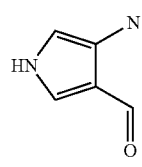
B-21 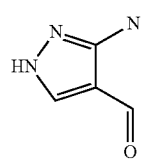
B-22 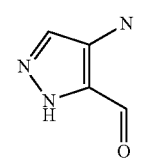
B-23 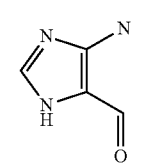
B-24 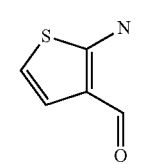
B-25 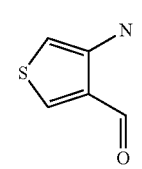
B-26 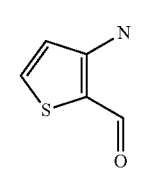
B-27 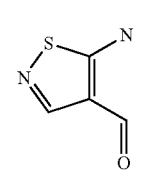
B-28 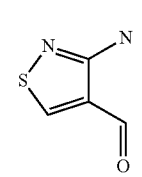
B-29 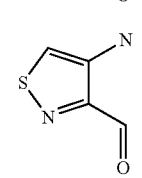

| | |
|---|---|
| B-30 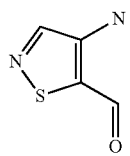 | B-40 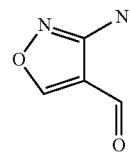 |
| B-31 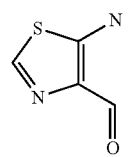 | B-41 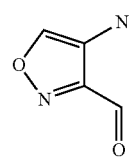 |
| B-32 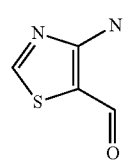 | B-42 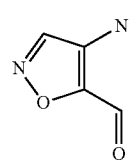 |
| B-33 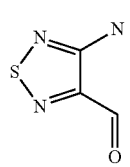 | B-43 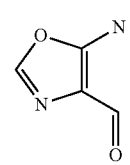 |
| B-34 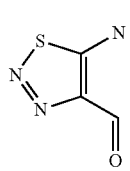 | B-44 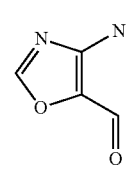 |
| B-35 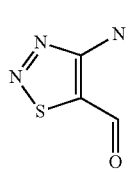 | B-45 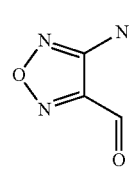 |
| B-36 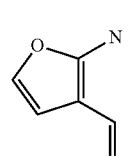 | B-46 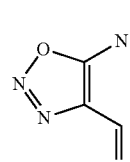 |
| B-37 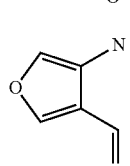 | B-47 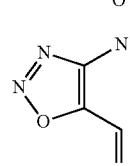 |
| B-38 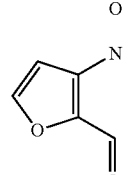 | B-48 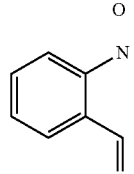 |
| B-39 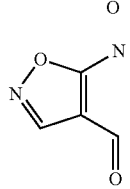 | B-49 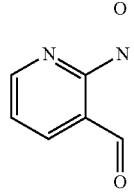 |

B-50 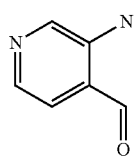
B-51 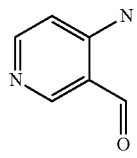
B-52 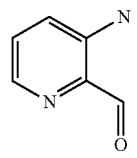
B-53 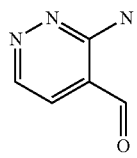
B-54 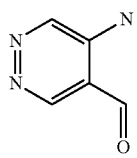
B-55 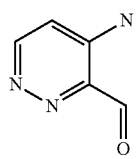
B-56 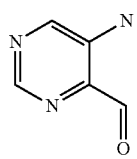
B-57 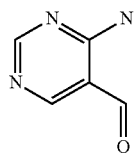
B-58 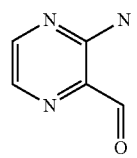
B-59 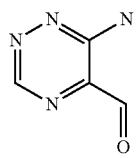

B-60 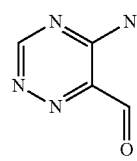
B-61 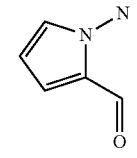
B-62 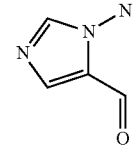
B-63 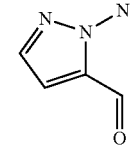

and the like.

In one embodiment of formula (I), D is void or optionally substituted spiro ring formed together with Y; when D is present, then B is void, and Y is carbon atom and G is —$NR^6$—, —O—, —$CHR^6$— or —$C(R^6)_2$—, wherein each $R^6$ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl. Specific embodiments for $R^6$ are explained in detail below.

B and D are not both present.

Examples of spiro ring group include cyclopropane, cyclobutane, cyclopentane, cyclohexane, cycloheptane, pyrrolidine, tetrahydrofuran, tetrahydrothiophene, piperidine, tetrahydropyran, tetrahydro-2H-thiopyran, azepane, cyclopentene and the like.

In another embodiment of formula (I), D is optionally substituted cycloalkane, preferably optionally substituted $C_{3-8}$ cycloalkane.

In a particular embodiment of formula (I), in the above-mentioned embodiments $Q^2$ designates a structural sector of the compound;

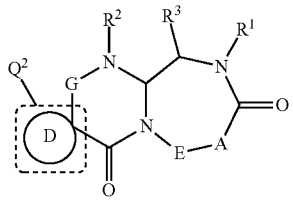

wherein spiro ring of $Q^2$ is selected from one of the following group:

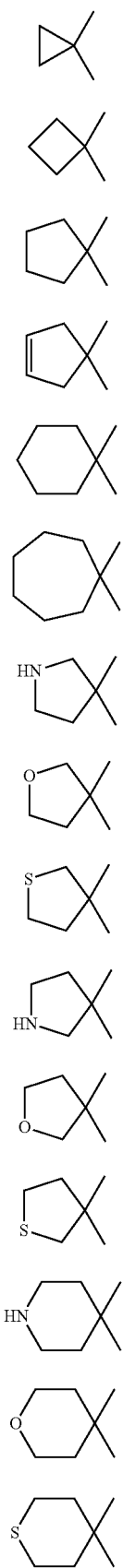

EB-1
EB-2
EB-3
EB-4
EB-5
EB-6
EB-7
EB-8
EB-9
EB-10
EB-11
EB-12
EB-13
EB-14
EB-15

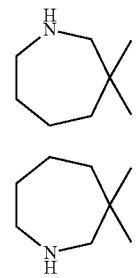

EB-16

EB-17 and the like.

The substituents of B or D are one or more of the chemical moieties selected from the group consisting of —$R^9$, —$OR^9$, —$COR^9$, —$COOR^9$, —$OCOR^9$, —$CONR^9R^4$, —$NR^9R^4$, —$NR^4COR^9$, —$NR^4COOR^9$, —$SR^9$, —$SO_2R^9$, —$SO_2NR^9R^4$, —$SO_3R^9$, —$NHC(NHR^9)NR^4$, halogen and methylenedioxy, wherein $R^9$ and $R^4$ are independently selected from hydrogen atom, optionally substituted, cyclic or noncyclic, alkyl, aryl, heteroaryl, arylalkyl and heteroarylalkyl.

In one embodiment of formula (I), when both B and D are void, G and Y are the same or different and each is —$NR^6$—, —O—, —$CHR^6$— or —$C(R^6)_2$—, wherein each $R^6$ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl.

Examples of alkyl group for $R^6$ include methyl, ethyl, propyl, isopropyl, butyl, isobutyl, sec-butyl, tert-butyl and the like.

Examples of alkenyl group for $R^6$ include ethenyl, allyl, 1-propenyl, 2-methylallyl and the like.

Examples of alkynyl group for $R^6$ include ethynyl, 1-propynyl and the like.

In another embodiment of formula (I), $R^6$ is aryl, heteroaryl, cycloalkyl, heterocycloalkyl, arylalkyl or heteroarylalkyl represented by —Re—$R^{60}$ wherein Re is bond or optionally substituted lower alkylene, and $R^{60}$ is optionally substituted aryl, optionally substituted heteroaryl, optionally substituted cycloalkyl or optionally substituted heterocycloalkyl.

Examples of lower alkylene group for Re include methylene, ethylene, methylmethylene, 1,2-propylene, 1,3-propylene, 1,2-butylene, 1,3-butylene, 1,4-butylene, 1,2,3-propanetriyl, 1,3,3-propanetriyl and the like.

Examples of aryl group and heteroaryl group for $R^{60}$ include biphenyl, phenyl, pyridyl, pyrimidyl, pyridazinyl, pyrazinyl, triazinyl, pyrrolyl, thienyl, furanyl, thiazolyl, oxazolyl, imidazolyl, tetrahydronaphthyl, naphthyl, quinolinyl, isoquinolinyl, quinazolinyl, quinoxalinyl, cinnolinyl, naphthyridinyl, benzotriazinyl, indenyl, pyridopyrimidinyl, pyridopyrazinyl, pyridopyridazinyl, pyridotriazinyl, benzofuranyl, benzothienyl, indolyl, indazolyl, benzoxazolyl, benzimidazolyl, benzothiazolyl, benzothiadiazolyl, furopyridinyl, thienopyridinyl, pyrropyridinyl, oxazolopyridinyl, thiazolopyridinyl, imidazopyridinyl and the like.

Examples of cycloalkyl group and heterocycloalkyl group include cyclopropyl, cyclobutyl, cyclopentyl, cyclohexyl, cycloheptyl, adamantyl and the like.

In another embodiment of formula (I), at least one of G and Y is —$NR^{6'}$—, —$CHR^{6'}$— or —$C(R^{6'})_2$—, wherein each $R^{6'}$ is independently hydrogen, optionally substituted cyclic or noncyclic lower alkyl, optionally substituted aryl, optionally substituted heteroaryl, optionally substituted arylalkyl or optionally substituted heteroarylalkyl.

In a particular embodiment of formula (I), in the above-mentioned embodiments $R^6$ or $R^{6'}$ is hydrogen, lower alkyl (ex. methyl) or lower alkenyl (ex. allyl).

In one embodiment of formula (I), $R^1$ is optionally substituted alkyl, optionally substituted alkenyl, optionally substituted alkynyl, optionally substituted arylalkyl, optionally substituted heteroarylalkyl, optionally substituted cycloalkylalkyl or optionally substituted heterocycloalkylalkyl.

Examples of optionally substituted alkyl group include methyl, ethyl, propyl, isopropyl, butyl, isobutyl, sec-butyl, tert-butyl, pentyl, isopentyl, neopentyl, tert-pentyl, aminomethyl, aminoethyl, aminopropyl, aminobutyl, carboxymethyl, carboxyethyl, carboxypropyl, carboxybutyl, carbamoylmethyl, carbamoylethyl, carbamoylpropyl, carbamoylbutyl, methoxymethyl, methoxyethyl, methoxypropyl, methoxybutyl, methylthiomethyl, methylthioethyl, methylthiopropyl, methylthiobutyl, hydroxymethyl, hydroxyethyl, hydroxypropyl, hydroxybutyl, ethoxycarbonylmethyl, ethoxycarbonylethyl, benzyloxymethyl, benzyloxyethyl, benzyloxypropyl, benzyloxybutyl, 3,3-diphenylpropyl and the like.

Examples of alkenyl group include ethenyl, allyl, 1-propenyl, 2-methylallyl and the like.

Examples of alkynyl group include ethynyl, 1-propynyl and the like.

In another embodiment of formula (I), $R^1$ is —Ra—$R^{10}$, wherein Ra is optionally substituted lower alkylene and $R^{10}$ is hydrogen, optionally substituted alkyl, optionally substituted cycloalkyl, optionally substituted heterocycloalkyl, optionally substituted aryl or optionally substituted heteroaryl.

Examples of optionally substituted alkyl group include methyl, ethyl, propyl, isopropyl, butyl, isobutyl, sec-butyl, tert-butyl, pentyl, isopentyl, neopentyl, tert-pentyl, aminomethyl, aminoethyl, aminopropyl, aminobutyl, carboxymethyl, carboxyethyl, carboxypropyl, carboxybutyl, carbamoylmethyl, carbamoylethyl, carbamoylpropyl, carbamoylbutyl, methoxymethyl, methoxyethyl, methoxypropyl, methoxybutyl, methylthiomethyl, methylthioethyl, methylthiopropyl, methylthiobutyl, hydroxymethyl, hydroxyethyl, hydroxypropyl, hydroxybutyl, ethoxycarbonylmethyl, ethoxycarbonylethyl, benzyloxymethyl, benzyloxyethyl, benzyloxypropyl, benzyloxybutyl, 3,3-diphenylpropyl and the like.

Examples of lower alkylene group include methylene, ethylene, methylmethylene, 1,2-propylene, 1,3-propylene, 1,2-butylene, 1,3-butylene, 1,4-butylene, 1,2,3-propanetriyl, 1,3,3-propanetriyl and the like.

Examples of cycloalkyl group and heterocycloalkyl group include cyclopropyl, cyclobutyl, cyclopentyl, cyclohexyl, cycloheptyl, adamantyl and the like.

Examples of aryl group and heteroaryl group include biphenyl, phenyl, pyridyl, pyrimidyl, pyridazinyl, pyrazinyl, triazinyl, pyrrolyl, thienyl, furanyl, thiazolyl, oxazolyl, imidazolyl, naphthyl, tetrahydronaphthyl, quinolinyl, isoquinolinyl, quinazolinyl, quinoxalinyl, cinnolinyl, naphthyridinyl, benzotriazinyl, pyridopyrimidinyl, pyridopyrazinyl, pyridopyridazinyl, pyridotriazinyl, indenyl, benzofuranyl, benzothienyl, indolyl, indazolyl, benzoxazolyl, benzimidazolyl, benzothiazolyl, benzothiadiazolyl, furopyridinyl, thienopyridinyl, pyrropyridinyl, oxazolopyridinyl, thiazolopyridinyl, imidazopyridinyl and the like.

Preferred examples of lower alkylene group include methylene, ethylene, 1,3-propylene and the like.

Preferred examples of aryl group and heteroaryl group include bicyclic fused aryl group and bicyclic fused heteroaryl group such as naphthyl, quinolinyl, isoquinolinyl, quinazolinyl, quinoxalinyl, cinnolinyl, naphthyridinyl, benzotriazinyl, indenyl, pyridopyrimidinyl, pyridopyrazinyl, pyridopyridazinyl, pyridotriazinyl, benzofuryl, benzothienyl, indolyl, indazolyl, benzoxazolyl, benzimidazolyl, benzothiazolyl, benzothiadiazolyl, furopyridinyl, thienopyridinyl, pyrropyridinyl, oxazolopyridinyl, thiazolopyridinyl, imidazopyridinyl and the like.

Examples of substituents for $R^1$ include —$R^9$, —$OR^9$, —$COR^9$, —$COOR^9$, —$OCOR^9$, —$CONR^9R^4$, —$NR^9R^4$, —$NR^4COR^9$, —$NR^4COOR^9$, —$SR^9$, —$SO_2R^9$, $SO_2NR^9R^4$, —$SO_3R^9$, —$NHC(NHR^9)NR^4$, —$NHC(NH_2)NH$, —$OPO(OH)_2$, —$OPO(ONa)_2$, —$CN$, —$NO_2$, halogen and methylenedioxy, wherein $R^9$ and $R^4$ are independently selected from hydrogen atom, optionally substituted, cyclic or noncyclic, alkyl, aryl, heteroaryl, arylalkyl and heteroaryl.

Preferred examples of the substituents include —$NH_2$, —OH, —$OR^9$, —COOH, —$COOR^9$, —$NR^4COR^9$, —$CONH_2$, —$CONHR^9$, —$CONR^9R^4$, —$NHR^9$, —$NR^9R^4$ and halogen.

More preferred examples of the substituents include —$NH_2$, —OH, —COOH, —$COOR^9$, —$NR^4COR^9$, —$CONH_2$ and halogen.

In a particular embodiment of formula (I), in the above-mentioned embodiments $R^1$ is isopentyl, benzyl, 2,4-difluorobenzyl, 4-hydroxybenzyl, 1-phenylethyl, 2-phenylethyl, 3-phenylpropyl, 3,3-diphenylpropyl, pyridyl-4-methyl, pyridyl-2-methyl, thienyl-2-methyl, thienyl-3-methyl, imidazolyl-5-methyl, 1-naphthylmethyl, 2-naphthylmethyl, 4-quinolinylmethyl, 8-quinolinylmethyl, 1,5-chloroquinolin-8-ylmethyl, 5-isoquinolynylmethyl, 8-isoquinolynylmethyl, 5-chloroisoquinolin-8-ylmethyl, indazolyl-7-ylmethyl, benzothiazol-4-ylmethyl, benzothiazol-7-ylmethyl, 7-fluorobenzothiazol-4-ylmethyl, 4-fluorobenzothiazol-7-ylmethyl, 2-aminobenzothiazol-4-ylmethyl, 2-aminobenzothiazol-7-ylmethyl, 2-amino-7-fluorobenzothiazol-4-ylmethyl, 2-amino-4-fluorobenzothiazol-7-ylmethyl, 2-tert-butoxycarbonylaminobenzothiazol-4-ylmethyl, benzoxazol-4-ylmethyl, benzoxazol-7-ylmethyl, 7-fluorobenzoxazol-4-ylmethyl, 4-fluorobenzoxazol-7-ylmethyl, 2-aminobenzoxazol-4-ylmethyl, 2-aminobenzoxazol-7-ylmethyl, 2-amino-7-fluorobenzoxazol-4-ylmethyl, 2-amino-4-fluorobenzoxazol-7-ylmethyl, benzothiophen-3-ylmethyl, 7-fluorobenzothiophen-3-ylmethyl, benzothiophen-4-ylmethyl, benzothiophen-7-ylmethyl, 7-fluorobenzothiophen-4-ylmethyl, 4-fluorobenzothiophen-7-ylmethyl, benzothiadiazol-4-ylmethyl, benzofuran-3-ylmethyl, 7-fluorobenzofuran-3-ylmethyl, benzofuran-4-ylmethyl, benzofuran-7-ylmethyl, 7-fuorobenzofuran-4-ylmethyl or 4-fluorobenzofuran-7-ylmethyl.

In one embodiment of formula (I), $R^2$ is —$W^{21}$—$W^{22}$—Rb—$R^{20}$, wherein $W^{21}$ is —(CO)— or —($SO_2$)—; $W^{22}$ is bond, —O—, —NH— or optionally substituted lower alkylene; Rb is bond or optionally substituted alkylene; and $R^{20}$ is optionally substituted alkyl, optionally substituted alkenyl, optionally substituted alkynyl, optionally substituted aryl, optionally substituted heteroaryl, optionally substituted cycloalkyl or optionally substituted heterocycloalkyl.

Examples of lower alkylene group for $W^{22}$ include methylene, ethylene, propylene, butylene and the like.

Examples of lower alkylene group for Rb include methylene, ethylene, methylmethylene, 1,2-propylene, 1,3-propylene, 1,2-butylene, 1,3-butylene, 1,4-butylene, 1,2,3-propanetriyl, 1,3,3-propanetriyl and the like.

Examples of optionally substituted alkyl group for $R^{20}$ include methyl, ethyl, propyl, isopropyl, butyl, isobutyl, sec-butyl, tert-butyl, pentyl, isopentyl, neopentyl, tert-pentyl, aminomethyl, aminoethyl, aminopropyl, aminobutyl, carboxymethyl, carboxyethyl, carboxypropyl, carboxybutyl, carbamoylmethyl, carbamoylethyl, carbamoylpropyl, carbamoylbutyl, methoxymethyl, methoxyethyl, methoxypropyl, methoxybutyl, methylthiomethyl, methylthioethyl, methylthiopropyl, methylthiobutyl, hydroxymethyl, hydroxyethyl, hydroxypropyl, hydroxybutyl, ethoxycarbonylmethyl, ethoxycarbonylethyl, benzyloxymethyl, benzyloxyethyl, benzyloxypropyl, benzyloxybutyl, 3,3-diphenylpropyl and the like.

Examples of alkenyl group for $R^{20}$ include ethenyl, allyl, 1-propenyl, 2-methylallyl and the like.

Examples of alkynyl group for $R^{20}$ include ethynyl, 1-propynyl and the like.

Examples of aryl group and heteroaryl group for $R^{20}$ include biphenyl, phenyl, pyridyl, pyrimidyl, pyridazinyl, pyrazinyl, triazinyl, pyrrolyl, thienyl, furanyl, thiazolyl, oxazolyl, imidazolyl, tetrahydronaphthyl, naphthyl, quinolinyl, isoquinolinyl, quinazolinyl, quinoxalinyl, cinnolinyl, naphthyridinyl, benzotriazinyl, indenyl, pyridopyrimidinyl, pyridopyrazinyl, pyridopyridazinyl, pyridotriazinyl, benzofuranyl, benzothienyl, indolyl, indazolyl, benzoxazolyl, benzimidazolyl, benzothiazolyl, benzothiadiazolyl, furopyridinyl, thienopyridinyl, pyrrolopyridinyl, oxazolopyridinyl, thiazolopyridinyl, imidazopyridinyl, benzodioxolyl and the like.

Examples of cycloalkyl group and heterocycloalkyl group include cyclopropyl, cyclobutyl, cyclopentyl, cyclohexyl, cycloheptyl, adamantyl and the like.

In a further embodiment of formula (I), in the above-mentioned embodiments $R^2$ is $—W^{21}—W^{22}—Rb—R^{20}$, wherein $W^{21}$ is —(CO)— or —($SO_2$)—; $W^{22}$ is bond, —O—, —NH—, methylene, ethylene, propylene or butylene; Rb is bond, methylene, ethylene, methylmethylene, 1,2-propylene, 1,3-propylene, 1,2-butylene, 1,3-butylene, 1,4-butylene, 1,2,3-propanetriyl or 1,3,3-propanetriyl; and $R^{20}$ is methyl, ethyl, propyl, isopropyl, butyl, isobutyl, sec-butyl, tert-butyl, pentyl, isopentyl, neopentyl, tert-pentyl, aminomethyl, aminoethyl, aminopropyl, aminobutyl, carboxymethyl, carboxyethyl, carboxypropyl, carboxybutyl, carbamoylmethyl, carbamoylethyl, carbamoylpropyl, carbamoylbutyl, methoxymethyl, methoxyethyl, methoxypropyl, methoxybutyl, methylthiomethyl, methylthioethyl, methylthiopropyl, methylthiobutyl, hydroxymethyl, hydroxyethyl, hydroxypropyl, hydroxybutyl, ethoxycarbonylmethyl, ethoxycarbonylethyl, benzyloxymethyl, benzyloxyethyl, benzyloxypropyl, benzyloxybutyl, 3,3-diphenylpropyl, ethenyl, ethynyl, allyl, 1-propynyl, 2-methylallyl, 1-propynyl, optionally substituted cyclopropyl, optionally substituted cyclobutyl, optionally substituted cyclopentyl, optionally substituted cyclohexyl, optionally substituted cycloheptyl, optionally substituted adamantyl, optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furanyl, optionally substituted thiazolyl, optionally substituted oxazolyl, optionally substituted imidazolyl, optionally substituted naphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted benzofuranyl, optionally substituted benzothiopenyl, optionally substituted indolyl, optionally substituted indenyl, optionally substituted benzooxazolyl, optionally substituted benzimidazolyl, optionally substituted benzothiazolyl, optionally substituted furopyridinyl, optionally substituted thienopyridinyl, optionally substituted pyrropyridinyl, optionally substituted oxazolopyridinyl, optionally substituted thiazolopyridinyl, optionally substituted imidazopyridinyl, optionally substituted benzodioxolyl and the like.

In particular embodiment of formula (I), in the above-mentioned $—W^{21}—W^{22}—Rb—R^{20}$, mentioned embodiments $R^2$ wherein $W^{21}$ is —(CO)—; $W^{22}$ is —NH—; Rb is bond, methylene or ethylene; and $R^{20}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furanyl, optionally substituted thiazolyl, optionally substituted oxazolyl, optionally substituted imidazolyl, optionally substituted naphthyl or optionally substituted benzodioxolyl.

Examples of substituents for $R^{20}$ include, $—R^9$, $—OR^9$, $—COR^9$, $—COOR^9$, $—OCOR^9$, $—CONR^9R^4$, $—NR^9R^4$, $—NR^4COR^9$, $—NR^4COOR^9$, $—SR^9$, $—SO_2R^9$, $SO_2NR^9R^4$, $—SO_3R^9$, $—NHC(NHR^9)NR^4$, $—NHC(NH_2)NH$, $—OPO(OH)_2$, $—OPO(ONa)_2$, $—CN$, $—NO_2$, halogen and methylenedioxy, wherein $R^9$ and $R^4$ are independently selected from hydrogen atom, optionally substituted, cyclic or noncyclic, alkyl, aryl, heteroaryl, arylalkyl and heteroaryl.

Preferred examples of the substituents include $—R^9$, $—NH_2$, $—OH$, $—OR^9$, $—COOH$, $—COOR^9$, $—CONH_2$, $—CONHR^9$, $—CONR^9R^4$, $—NHR^9$, $—NR^9R^4$, halogen and methylenedioxy.

More preferred examples of the substituents include $—R^9$, $—NH_2$, $—OH$, $—COOH$, $—COOR^9$, $—CONH_2$, halogen and methylenedioxy.

In one embodiment of formula (I), $R^3$ is hydrogen, optionally substituted alkyl, optionally substituted alkenyl or, optionally substituted alkynyl.

Preferable examples of alkyl group include $C_{1-4}$ alkyl group such as methyl, ethyl, propyl, isopropyl, butyl, isobutyl, sec-butyl, tert-butyl and the like.

Examples of alkenyl group include ethenyl, allyl, 2-methylallyl and the like.

Examples of alkynyl group include 1-propynyl, ethynyl and the like.

$R^3$ is preferably hydrogen or $C_{1-4}$ alkyl such as methyl, ethyl, propyl, isopropyl, butyl, isobutyl, sec-butyl or tert-butyl, more preferably methyl or ethyl.

In particular embodiment of formula (I), in the above-mentioned embodiments $R^3$ is hydrogen or methyl.

In a further embodiment of formula (I), in the above-mentioned embodiments $R^7$ is 4-hydroxy-benzyl; and $R^2$ represents $—W^{21}—W^{22}—Rb—R^{20}$, wherein $W^{21}$ is —(CO)— or —($SO_2$)—; $W^{22}$ is bond, —O—, —NH— or optionally substituted lower alkylene; Rb is bond or optionally substituted alkylene; and $R^{20}$ is optionally substituted alkyl, optionally substituted alkenyl, optionally substituted alkynyl, optionally substituted aryl, optionally substituted heteroaryl, optionally substituted cycloalkyl or optionally substituted heterocycloalkyl.

In order to avoid an accidental anticipation, the following proviso is added to the formula (I);
when D is void, E is bond, B is benzene, $R^2$ is $-W^{21}-W^{22}-Rb-R^{20}$, wherein $W^{21}$ is $-(CO)-$, and Rb is bond, then $R^{20}$ should is $W^{22}$ is $-NH-$, not be optionally substituted phenyl.

Figures 1, 2:
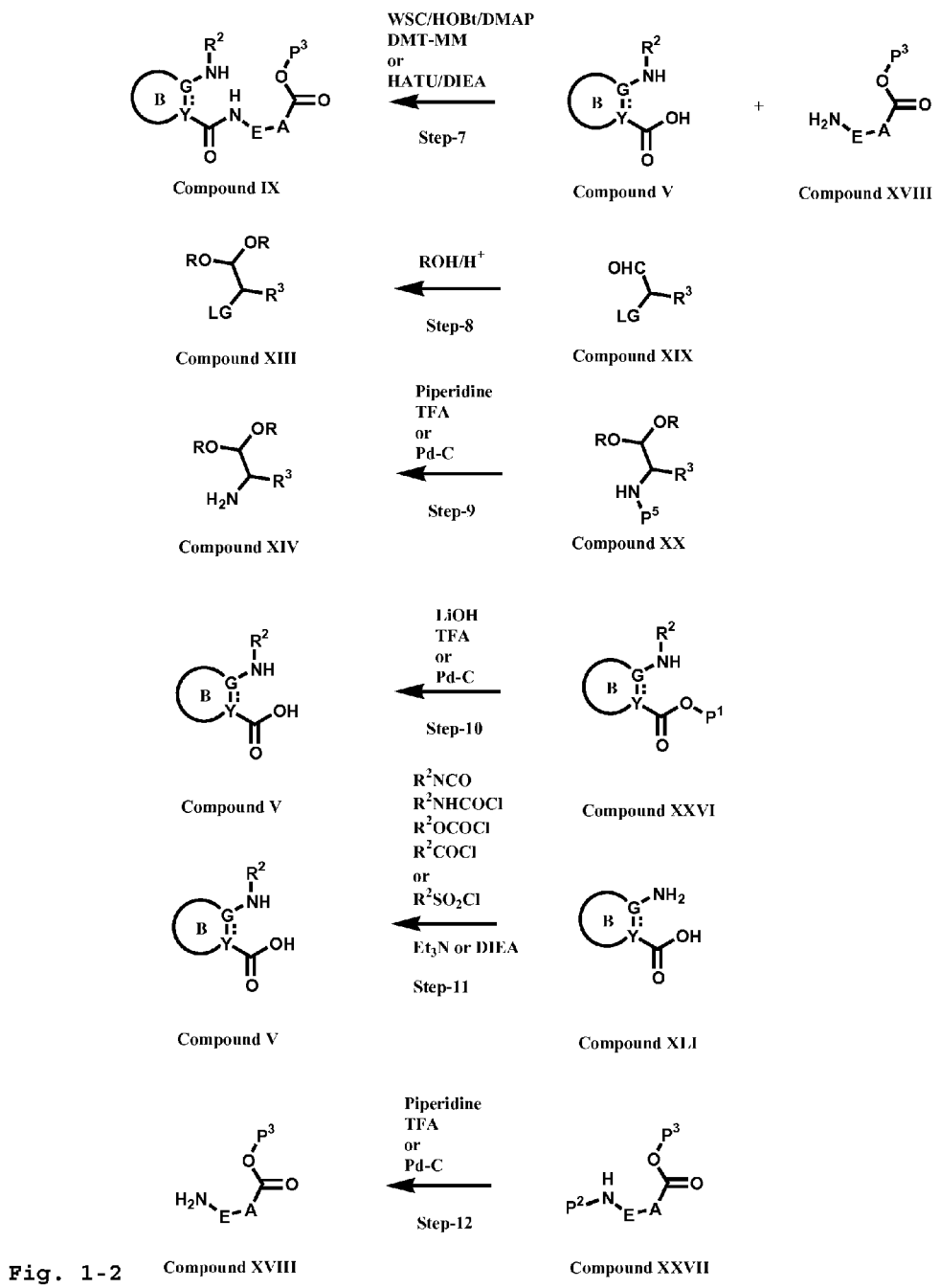
Figures 1, 2, 3:
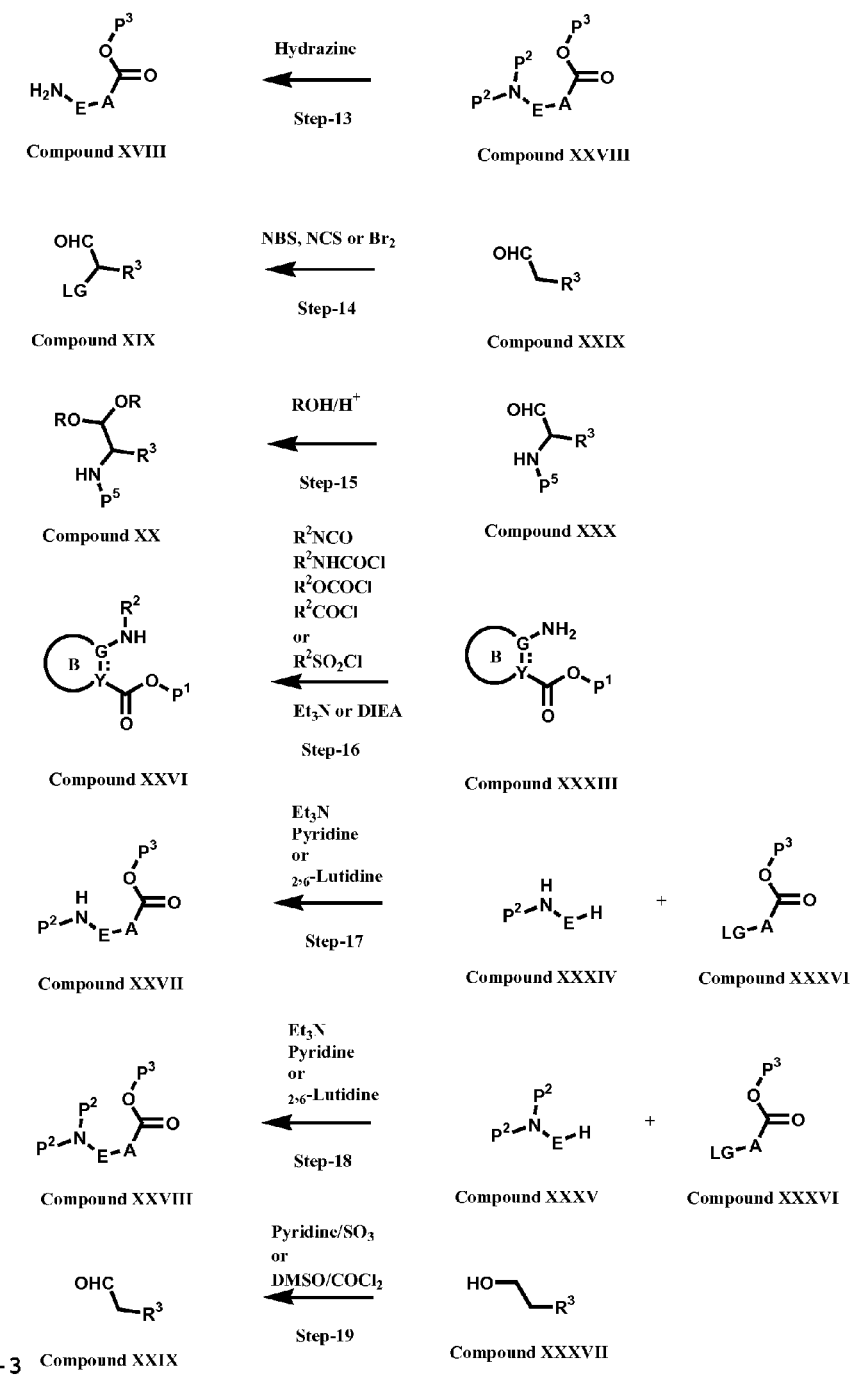
Figures 1, 2, 3, 4:
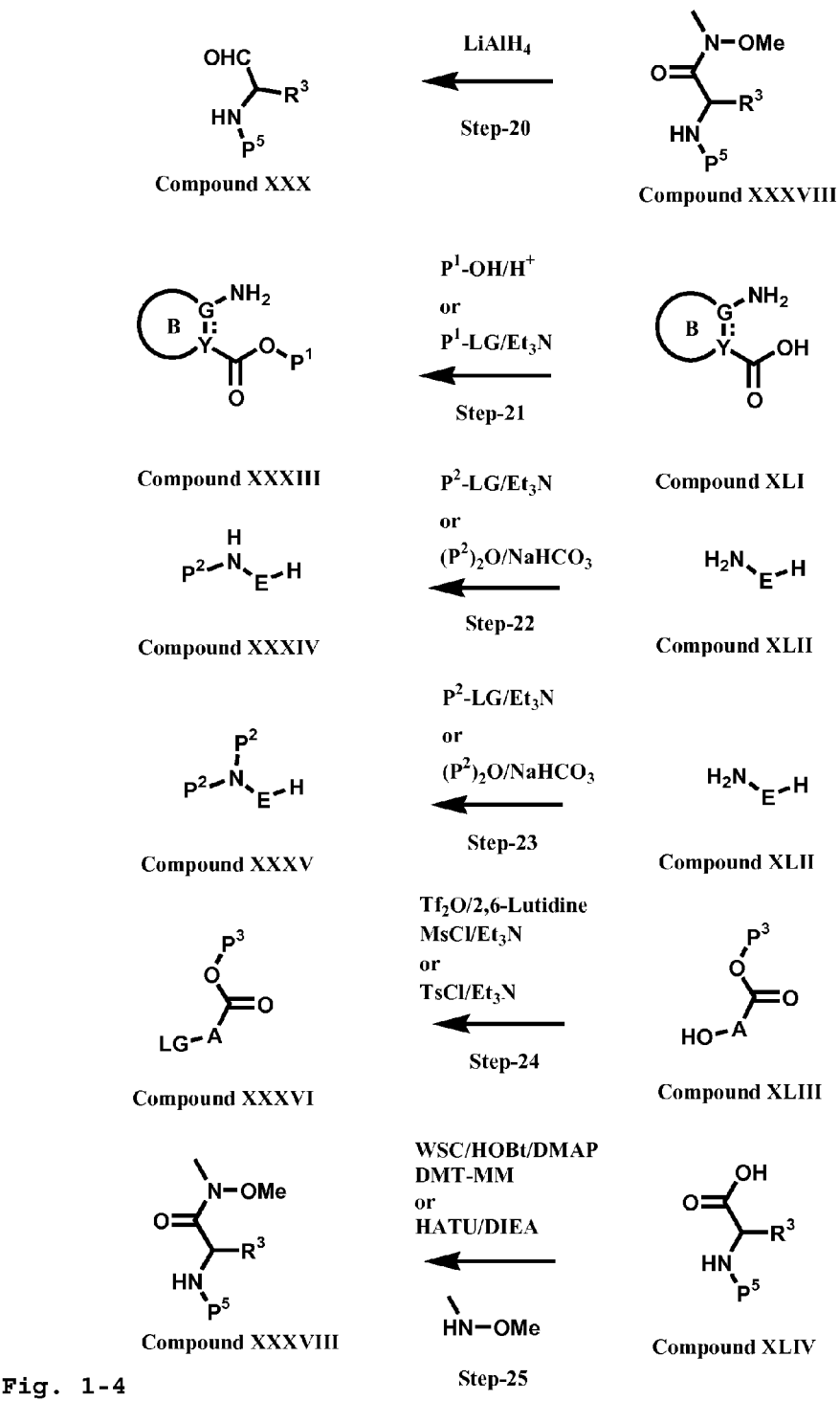
Figures 1, 2, 3, 4, 5:
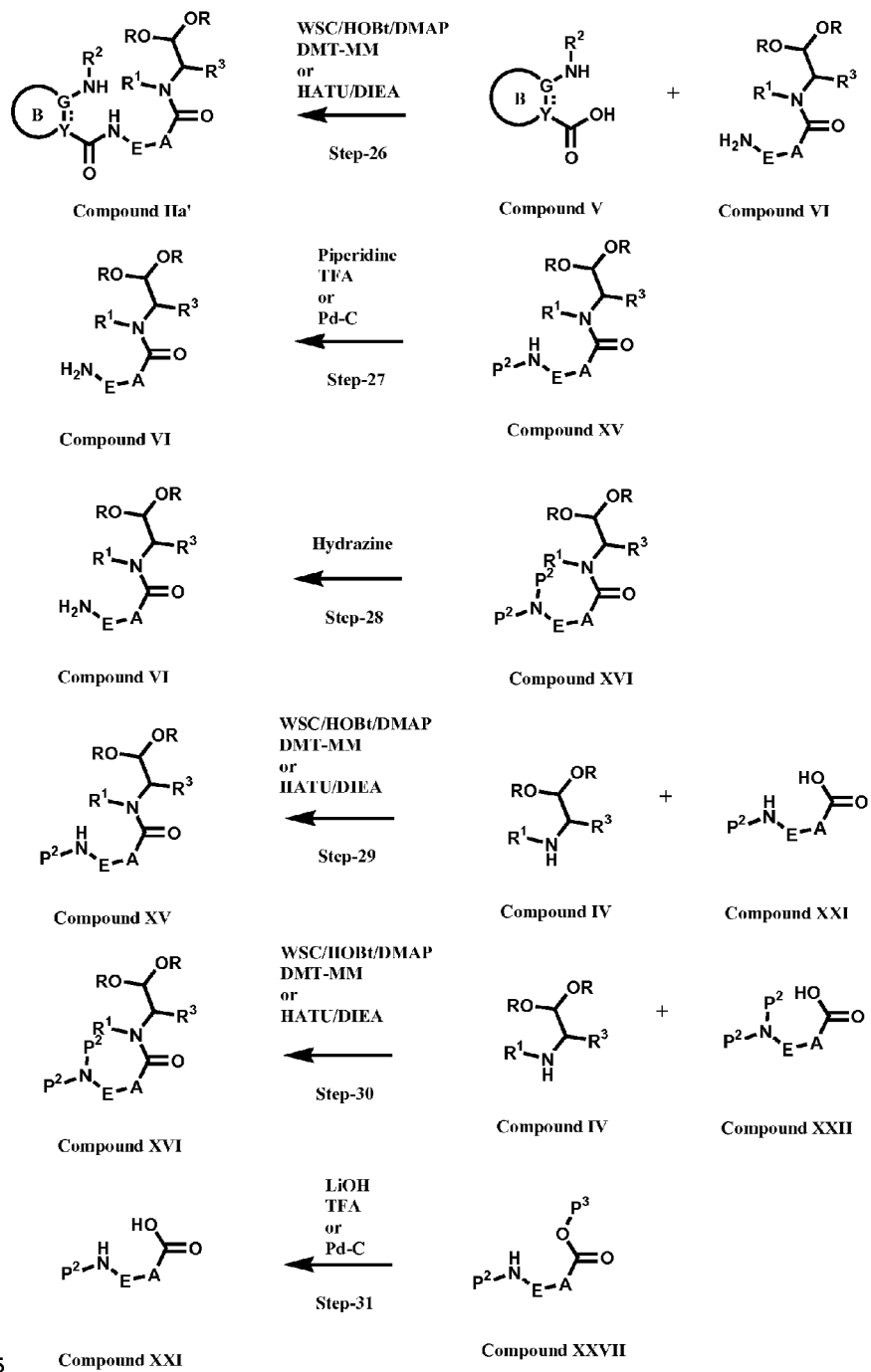
Figures 1, 2, 3, 4, 5, 6:
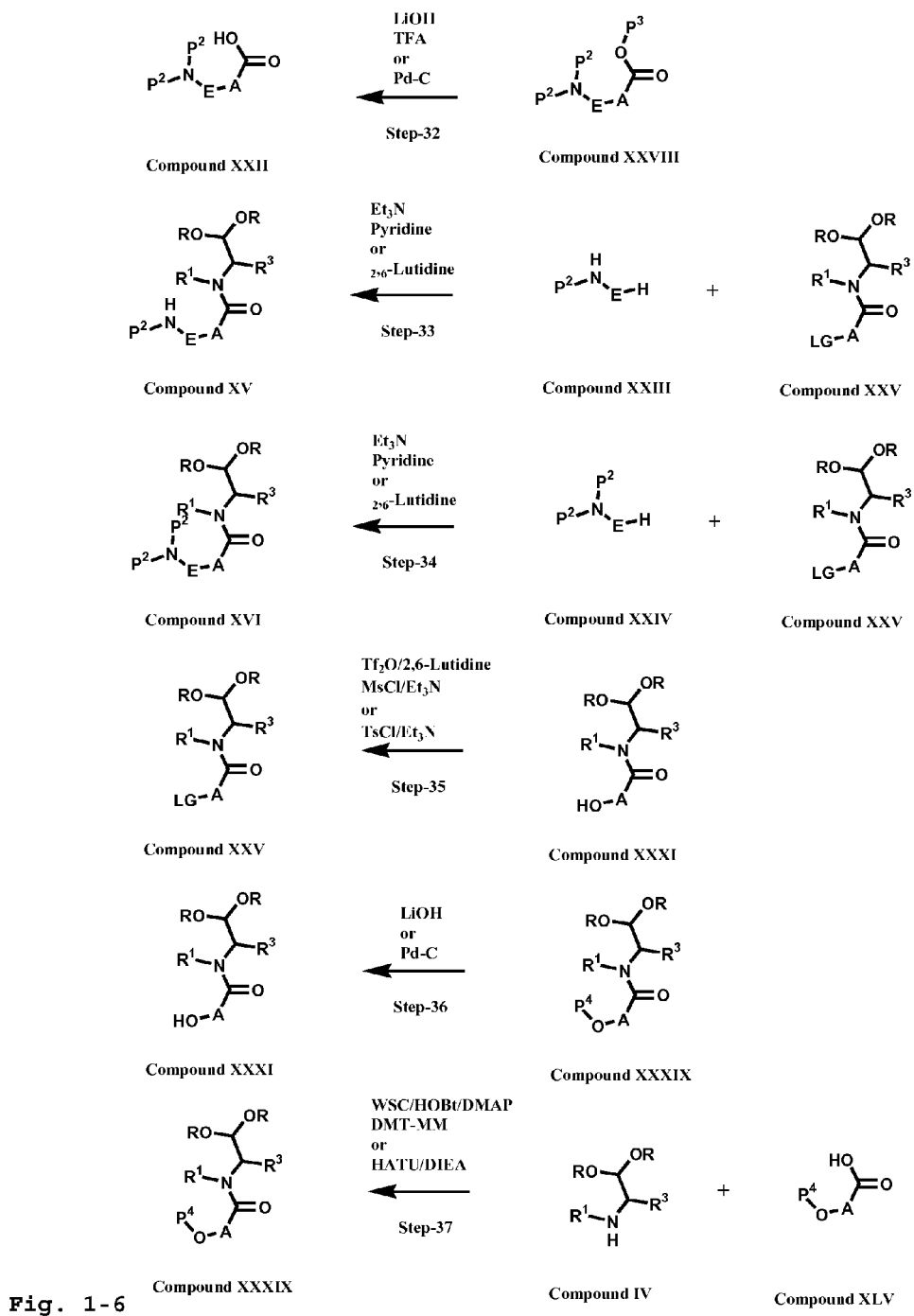
Figures 1, 2:
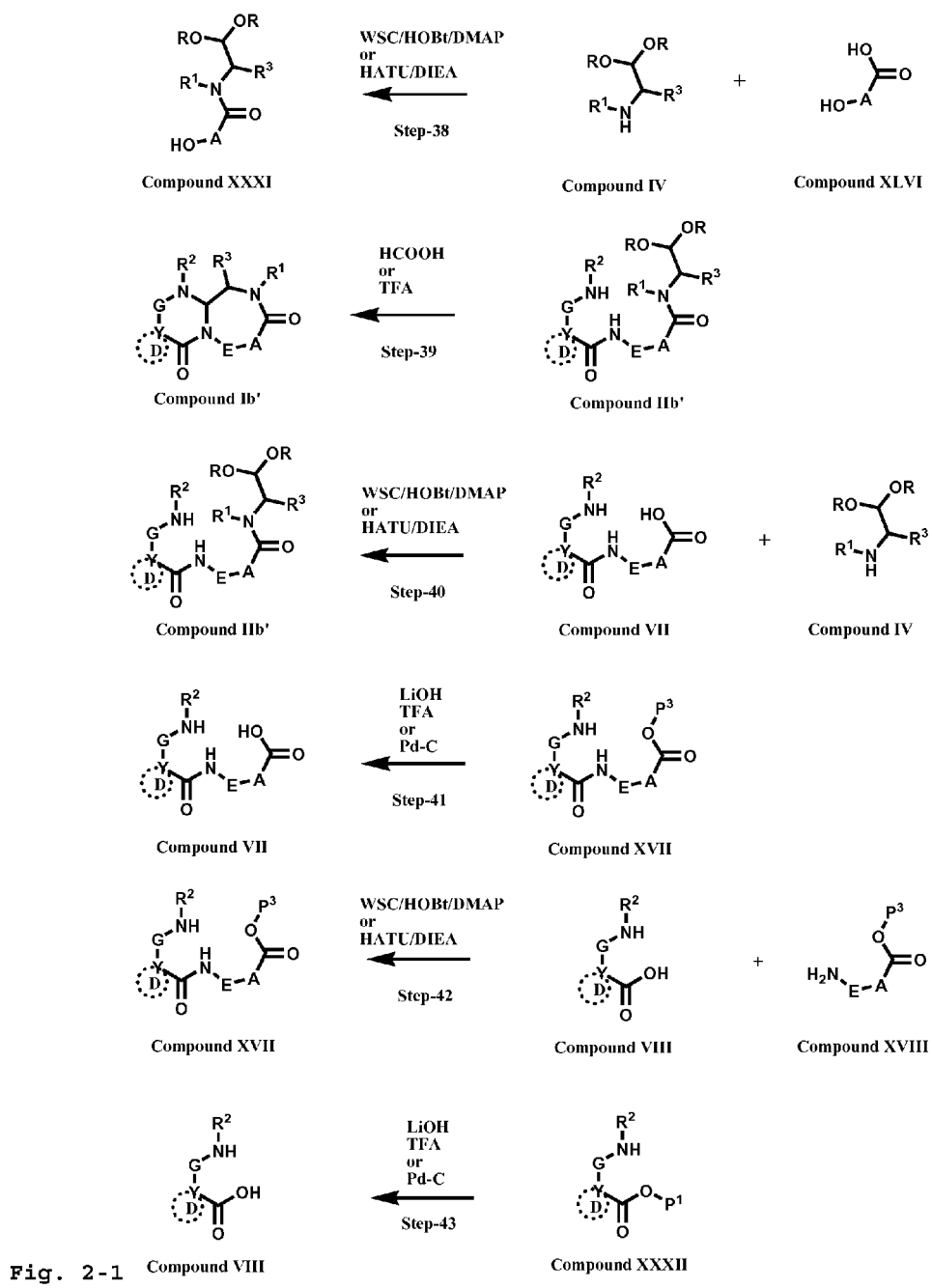
Figure 2:
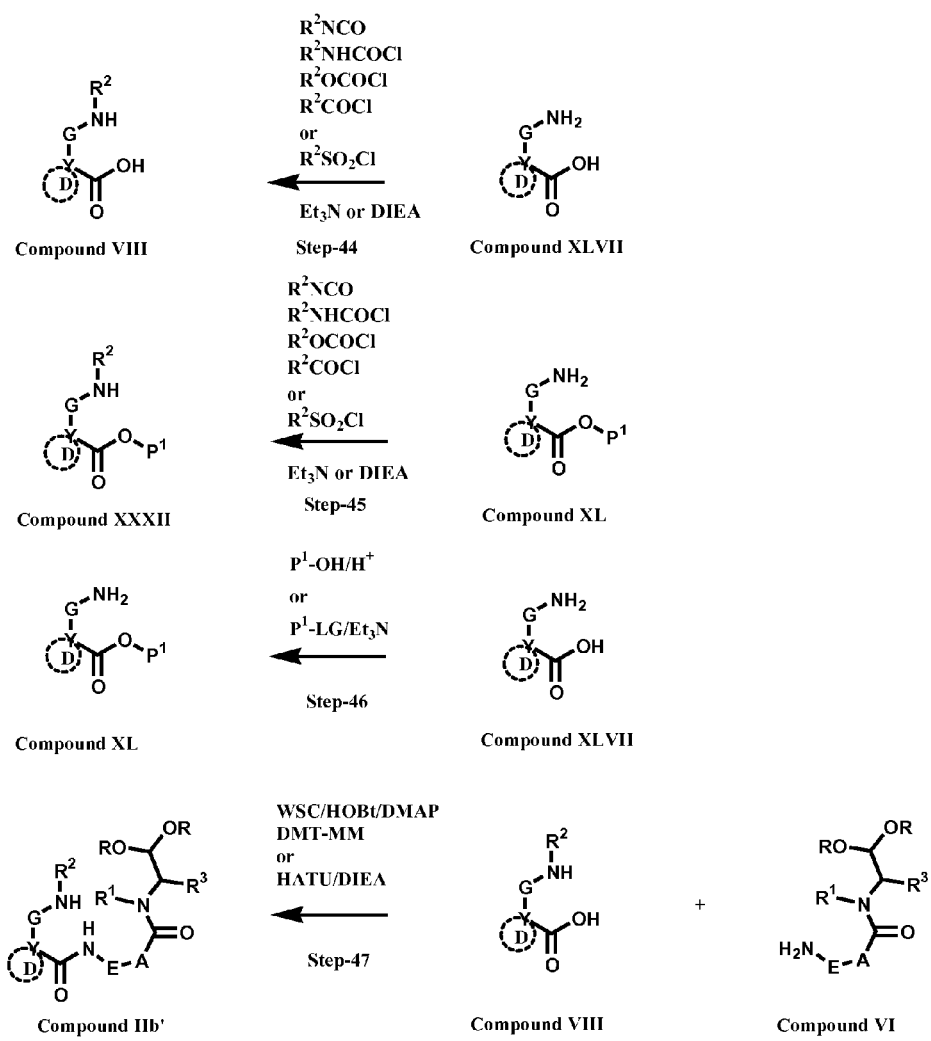

The general syntheses of the compounds in this invention are illustrated in FIG. 1 and FIG. 2, wherein Compound Ia' indicates formulas (Ia) and (Id), Compound Ib' indicates formulas (Ib) and (Ic).

The general synthesis of the compounds in this invention, represented by the formula (Ia) wherein B is present and D is void and formula (Id) wherein B is present and E is void, may be synthesized by the technique illustrated in FIG. 1.

The compounds in this invention, represented by the formula (Ib) and (Ic) wherein D is present or void and B is void can also be synthesized by the similar method illustrated in FIG. 2.

The general synthesis of the compounds in this invention, represented by the formula (IIa') wherein B is sent and D is void and may be synthesized by the technique illustrated in FIG. 1.

The compounds in this invention, represented by the formula (IIb') wherein D is present or void and B is void can also be synthesized by the similar method illustrated in FIG. 2.

R (including $R^{91}$ and $R^{92}$ in the formula (IIa') and (IIb')) illustrated in FIG. 1 and FIG. 2 is a protective group suitable for use in synthesis, where this protection group may be joined to a polymeric support to enable solid-phase synthesis. Suitable R groups include alkyl groups and, in a preferred embodiment, R is a methyl or ethyl group.

LG illustrated in FIG. 1 is a leaving group, e.g., a halogen (Hal) group, methanesulfonyloxy, trifluoromethanesulfonyloxy, toluenesufonyloxy and the like.

$P^1$ and $P^3$ illustrated in FIG. 1 and FIG. 2 are a carboxylic acid protection group. $P^2$ and $P^5$ illustrated in FIG. 1 are an amino protection group. $P^4$ illustrated in FIG. 1 is a hydroxyl protection group. Preferred protection groups include methyl, ethyl, benzyl, 9H-fluorenylmethyloxycarbonyl (Fmoc), benzyloxycarbonyl (Cbz), t-butyl dimethylsilyl (TBDMS), t-butyloxycarbonyl (BOC), methyloxycarbonyl (MOC), and allyloxycarbonyl (Alloc). For an amino protective group, also preferred is phthalimide formed together with an amino group to be protected.

Compound IV may be readily synthesized by reductive amination of $H_2N-R^1$ with $CH(OR)_2-CR^3O$, by reductive amination of $R^{1'}-CHO$ (when $R^1=CH_2R^{1'}$) with $CH(OR)_2-CHR^3NH_2$, by a displacement reaction between $H_2N-R^1$ and $CH(OR)_2-CHR^3$-LG or by a displacement reaction between LG-$R^1$ and $CH(OR)_2-CHR^3-NH_2$.

N-Protected amino acids are commercially available; for example, Fmoc amino acids are available from a variety of sources. In the case of the azido derivative of an amino acid serving as the Compound XV, such compounds may be prepared from the corresponding amino acid by the reaction disclosed by Zaloom et al. (J. Org. Chem. 46:5173-76, 1981).

A Compound VI of this invention may have the indicated structure wherein G, E, B, and $R^2$ are as defined above. Other suitable Compounds XI are commercially available from a variety of sources or can be prepared by methods well known in organic chemistry.

Compound X, XI, XII, XIII, XIV, XVIII, XIX, XX, XXIV, XXIX, XXX, XXXIII, XXXIV, XXXV, XXXIV, XXXVII, XL, XLI, XLII, XLIV, XLV, XLVI and XLVII are commercially available from a variety of sources or can be prepared by methods well known in organic chemistry.

As illustrated in FIG. 1, the alpha-helix mimetic compounds of formula (Ia') may be synthesized by reacting a Compound IV with a Compound XXI to yield a combined Compound XV, followed by treating the combined Compound XV with piperidine to provide Compound VI, reacting the Compound VI with Compound V sequentially to provide a combined Compound IIa', and then cyclizing this intermediate to yield an alpha-helix mimetic structure of formula (Ia'). Or, the alpha-helix mimetic compounds of formula (Ia') may be synthesized by reacting a Compound V with a Compound XVIII to yield a combined Compound IX, followed by treating the Compound IX with lithium hydroxide, sodium hydroxide or potassium hydroxide to provide Compound III. As illustrated in FIG. 1, the Compound III reacts with Compound IV sequentially to provide a combined Compound IIa', followed by cyclizing this intermediate to yield an alpha-helix mimetic structure of formula (Ia').

As illustrated in FIG. 2, the alpha-helix mimetic compounds of formula (Ib') may be synthesized by the methods similar to those in FIG. 1.

A compound having the following general formula (II) is a novel intermediate compound for preparing the compound of the formula (I).

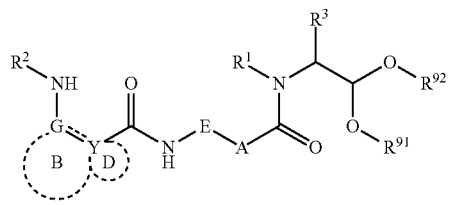

wherein
- - - - is single bond or double bond;
A is $-CHR^7-$,
  wherein
    $R^7$ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl or optionally substituted heterocycloalkylalkyl;
E is bond, $-CHR^5-$, $-O-$ or $-NR^8-$,
  wherein
    $R^5$ is hydrogen, optionally substituted alkyl, optionally substituted alkenyl, optionally substituted alkynyl, optionally substituted arylalkyl or optionally substituted heteroarylalkyl, and
    $R^8$ is hydrogen, optionally substituted alkyl, optionally substituted alkenyl or optionally substituted alkynyl;
B is void or optionally substituted monocyclic ring formed together with G and Y;
D is void or optionally substituted spiro ring formed together with Y;
with the proviso that
B and D are not both present,
when B is present, then G and Y are independently carbon atom or nitrogen atom, when D is present, then Y is carbon atom and G is —$NR^6$—, —O—, —$CHR^6$— or —$C(R^6)_2$—,
when both B and D are void, then G and Y are the same or different and each is —$NR^6$—, —O—, —$CHR^6$— or —$C(R^6)_2$—,
  wherein
    each $R^6$ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl, and
when E is bond, then D is void, B is optionally substituted monocyclic ring, and G and Y are independently carbon atom or nitrogen atom;
$R^1$ is optionally substituted alkyl, optionally substituted alkenyl, optionally substituted alkynyl, optionally substituted arylalkyl, optionally substituted heteroarylalkyl, optionally substituted cycloalkylalkyl or optionally substituted heterocycloalkylalkyl;
$R^2$ is —$W^{21}$—$W^{22}$—Rb—$R^{20}$,
  wherein
    $W^{21}$ is —(CO)— or —(SO$_2$)—,
    $W^{22}$ is bond, —O—, —NH— or optionally substituted lower alkylene,
    Rb is bond or optionally substituted alkylene, and
    $R^{20}$ is optionally substituted alkyl, optionally substituted alkenyl, optionally substituted alkynyl, optionally substituted aryl, optionally substituted heteroaryl, optionally substituted cycloalkyl or optionally substituted heterocycloalkyl;
$R^3$ is hydrogen, optionally substituted alkyl, optionally substituted alkenyl or optionally substituted alkynyl;
$R^{91}$ is selected from optionally substituted alkyl, linker and solid support; and
$R^{92}$ is selected from optionally substituted alkyl, linker and solid support;
with the proviso that
when D is void, E is bond, B is benzene, and $R^2$ is —$W^{21}$—$W^{22}$—Rb—$R^{20}$, wherein $W^{21}$ is —(CO)—, $W^{22}$ is —NH—, and Rb is bond, then $R^{20}$ should not be optionally substituted phenyl.

Examples and preferable embodiments of A, E, D, B, G, Y, $R^1$, $R^2$, and $R^3$ in the formula (II) are the same as those for the formula (I).

Examples of optionally substituted alkyl for $R^{91}$ and $R^{92}$ include those as defined for $R^7$ and the like.

Examples of linker and solid support for $R^{91}$ and $R^{92}$ include those for preparing the libraries as explained below.

The cyclization reaction of Compound II for preparing Compound (I) is explained in detail in the following.

This cyclization reaction can be carried out by reacting the Compound II with an acid.

The order of addition of the reagents is not particularly limited, and, for example, an acid may be added to Compound II or vice versa.

The acid to be used in the cyclization reaction is not particularly limited, and examples thereof include inorganic acids such as hydrochloric acid, nitric acid, sulfuric acid, phosphoric acid and the like; organic acids such as formic acid, acetic acid, trifluoroacetic acid, propionic acid, methanesulfonic acid, p-toluenesulfonic acid, trifluoromethanesulfonic acid; hydrogen chloride solution; hydrogen bromide solution; hydrogen fluoride and the like In addition, water, anisole, m-cresol, ethanedithiol, thioanisole or triisopropylsilane can be used with along the acid.

The amount of the acid to be used in the cyclization reaction is generally 0.001 mol to 1000 mol, preferably 1 mol to 100 mol, more preferably 5 mol to 50 mol, relative to 1 mol of Compound II.

The cyclization reaction may be performed with or without solvent. The solvent to be used in the cyclization reaction may be any as long as it does not inhibit the reaction. Examples thereof include ethers such as tetrahydrofuran (THF), methyl tert-butyl ether, 1,4-dioxane, diethylene glycol dimethyl ether (diglyme), ethylene glycol dimethyl ether, 1,3-dioxolane, 2-methyltetrahydrofuran and the like; aprotic polar solvents such as N,N-dimethylformamide (DMF), N,N-dimethylacetamide (DMAc), dimethyl sulfoxide (DMSO), sulfolane, N-methyl-2-pyrrolidinone (NMP), 1,3-dimethyl-2-imidazolidinone (DMI), hexamethyl phosphoramide (HMPA), acetonitrile, propionitrile and the like; halogenated solvents such as methylene chloride, 1,2-dichloroethane, carbon tetrachloride, monochlorobenzene and the like; aromatic hydrocarbon such as benzene, toluene, xylene and the like; water and the like, and a mixed solvent thereof. When a mixed solvent is used, the solvents may be mixed at optional ratios.

While the reaction temperature in the cyclization reaction depends on the reagent to be used and the like, it is generally from −40° C. to 120° C., preferably from −20° C. to 60° C., more preferably from −10° C. to 40° C. The reaction time is generally 0.5 hr to 96 hr, preferably 1 hr to 48 hr.

The compound (I) to be obtained in the cyclization reaction can be isolated and purified by a conventional method such as extraction, water-washing, acid washing, alkali washing, crystallization, recrystallization, silica gel column chromatography.

Furthermore continuing the explanation, the compounds of the present invention, salts thereof and derivatives thereof useful as prodrugs are excellent in pharmacological action selectivity, safety (various toxicities and safety pharmacology), pharmacokinetic performance, physicochemical property and the like, and therefore the usefulness as active ingredients of medicaments can be confirmed.

Examples of tests concerning pharmacological action selectivity include, but not be limited to, the following list including inhibition or activation assays on various pharmacological target receptors, inhibition assays on various pharmacological target enzymes, ion channels or transporters, cell tests to be used for the evaluation for various pharmacological action, and the like.

Examples of tests concerning safety include, but not be limited to, the following list including cytotoxic tests (e.g., tests using HL60 cells, hepatocytes, etc., and the like), genotoxicity tests (e.g., Ames test, mouse lymphoma TK test, chromosomal aberration test, micronucleus test and the like), skin sensitization tests (e.g., Buehler method, GPMT method, APT method, LLNA test and the like), skin photosensitization tests (e.g., Adjuvant and Strip method and the like), eye irritation tests (e.g., single instillation, short-term continuation instillation, repetitive instillation and the like), safety pharmacology tests for the cardiovascular system (e.g., telemetry method, APD method, hERG inhibition assay and the like), safety pharmacology tests for the central nervous system (e.g., FOB method, modified version of Irwin method and the like), safety pharmacology tests for the respiratory system (e.g., measurement method using a respiratory function measuring apparatus, measurement method using a blood gas analyzer and the like), general toxicity tests, and the like.

Examples of tests concerning pharmacokinetic performance include, but not be limited to, the following list including cytochrome P450 enzyme inhibition or induction tests, cell permeability tests (e.g., tests using CaCO-2 cells, MDCK cells etc., and the like), drug transporter ATPase assay, oral absorption tests, blood concentration transition measurement tests, metabolism tests (e.g., stability test, metabolite molecular species test, reactivity test and the like), solubility tests (e.g., solubility test based on turbidity method and the like), and the like.

Examples of tests concerning physicochemical property include, but not be limited to, the following list including chemical stability test (e.g., stability test using HPLC etc., and the like), partition coefficient (e.g., partition test using octanol phase/water phase and the like), ionization constant test, crystallization test, and the like.

The compound of the present invention are useful as bioactive agents, such as diagnostic, prophylactic, and therapeutic agents. For example, the alpha-helix mimetic structures of the present invention may be used for modulating a cell signaling transcription factor related peptides in a warm-blooded animal, by a method comprising administering to the animal an effective amount of the compound of formula (I), (Ia), (Ib), (Ic) or (Id).

In another embodiment, there is a method of treating a cancerous condition or fibrosis by administering the compound of formula (I), (Ia), (Ib), (Ic) or (Id). The compounds of the formula (I), (Ia), (Ib), (Ic) or (Id) can be used for inhibiting or treating disorders modulated by Wnt-signaling pathway, such as cancer, such as colorectal cancer, and so forth.

In another embodiment, a pharmaceutical composition comprises the compound of formula (I), (Ia), (Ib), (Ic) or (Id) or a pharmaceutically acceptable salt thereof, and, if desired or necessary, together with a pharmaceutical acceptable carrier. In another aspect, it is an object of the present invention to provide a pharmaceutical composition comprising an effective amount of the compound having general formula (I), (Ia), (Ib), (Ic) or (Id) and pharmaceutically acceptable carrier, which can be used for treatment of disorders modulated by Wnt signaling pathway, especially by TCF4-β-catenin-CBP complex.

Further, the present invention is to provide a method for inhibiting the growth of tumor cells by using the above-described composition of the present invention; a method for inducing apoptosis of tumor cells by using the above-described composition of the present invention; a method for treating a disorder modulated by TCF4-β-catenin-CBP complex by using the above-described composition of the present invention; and a method of treating cancer such as colorectal cancer by administering the composition of the present invention together with other anti-cancer agent such as 5-fluorouracil (5-FU), taxol, cisplatin, mitomycin C, tegafur, raltitrexed, capecitabine, and irinotecan, etc.

In another aspect of this invention, libraries containing alpha-helix mimetic structures of the present invention are disclosed. Once assembled, the libraries of the present invention may be screened to identify individual members having bioactivity. Such screening of the libraries for bioactive members may involve; for example, evaluating the binding activity of the members of the library or evaluating the effect the library members have on a functional assay. Screening is normally accomplished by contacting the library members (or a subset of library members) with a target of interest, such as, for example, an antibody, enzyme, receptor or cell line. Library members which are capable of interacting with the target of interest, are referred to herein as "bioactive library members" or "bioactive mimetics". For example, a bioactive mimetic may be a library member which is capable of binding to an antibody or receptor, or which is capable of inhibiting an enzyme, or which is capable of eliciting or antagonizing a functional response associated, for example, with a cell line. In other words, the screening of the libraries of the present invention determines which library members are capable of interacting with one or more biological targets of interest. Furthermore, when interaction does occur, the bioactive mimetic (or mimetics) may then be identified from the library members. The identification of a single (or limited number) of bioactive mimetic(s) from the library yields alpha-helix mimetic structures which are themselves biologically active, and thus are useful as diagnostic, prophylactic or therapeutic agents, and may further be used to significantly advance identification of lead compounds in these fields.

Synthesis of the peptide mimetics of the library of the present invention may be accomplished using known peptide synthesis techniques, in combination with the first, second and third component pieces of this invention. More specifically, any amino acid sequence may be added to the N-terminal and/or C-terminal of the conformationally constrained alpha-helix mimetic. To this end, the mimetics may be synthesized on a solid support (such as PAM resin) by known techniques (see, e.g., John M. Stewart and Janis D. Young, Solid Phase Peptide Synthesis, 1984, Pierce Chemical Comp., Rockford, Ill.) or on a silyl-linked resin by alcohol attachment (see Randolph et al., J. Am Chem. Soc. 117:5712-14, 1995).

In addition, a combination of both solution and solid phase synthesis techniques may be utilized to synthesize the peptide mimetics of this invention. For example, a solid support may be utilized to synthesize the linear peptide sequence up to the point that the conformationally constrained alpha-helix is added to the sequence. A suitable conformationally constrained alpha-helix mimetic structure which has been previously synthesized by solution synthesis techniques may then be added as the next "amino acid" to the solid phase synthesis (i.e., the conformationally constrained alpha-helix mimetic, which has both an N-terminus and a C-terminus, may be utilized as the next amino acid to be added to the linear peptide). Upon incorporation of the conformationally constrained alpha-helix mimetic structures into the sequence, additional amino acids may then be added to complete the peptide bound to the solid support. Alternatively, the linear N-terminus and C-terminus protected peptide sequences may be synthesized on a solid support, removed from the support, and then coupled to the conformationally constrained alpha-helix mimetic structures in solution using known solution coupling techniques.

As to methods for constructing the libraries, traditional combinatorial chemistry techniques (see, e.g., Gallop et al., J. Med. Chem. 37:1233-1251, 1994) permit a vast number of compounds to be rapidly prepared by the sequential combination of reagents to a basic molecular scaffold. Combinatorial techniques can be used to construct peptide libraries derived from the naturally occurring amino acids. For example, by taking 20 mixtures of 20 suitably protected and different amino acids and coupling each with one of the 20 amino acids, a library of 400 (i.e., $20^2$) dipeptides is created. Repeating the procedure seven times results in the preparation of a peptide library comprised of about 26 billion (i.e., $20^8$) octapeptides.

Specifically, synthesis of the peptide mimetics of the library of the present invention may be accomplished using known peptide synthesis techniques, such as those disclosed, for example, in WO 2005/116032, which is incorporated herein by reference.

In a further aspect of this invention, the present invention provides methods for screening the libraries for bioactivity and isolating bioactive library members.

In one embodiment, data of biological activity is determined in the following manner. Compounds are assayed by using a method of the following reporter gene assay.

Reporter Gene Assay

Screening for inhibitory action of the Wnt signaling pathway can be carried out according to the following procedure using the stably transfected cell line Hek-293, STF1.1.

Growth Medium: DMEM, 10% FBS, Pen-Strep, supplemented with 400 µg/mL G418 to maintain selection of SuperTOPFLASH driven Luciferase gene 1. On the day prior to assay, split cells into a white opaque 96-well plate at 20,000 cells per well in 200 µl of complete growth medium
2. Incubate the plate overnight at 37° C., 5% $CO_2$ and allow the cells to attach
3. Next day, prepare the inhibitors to be tested in complete growth medium, without G418, at 2× the desired final concentration (all conditions are done in duplicates)
4. Carefully remove the old medium from each well using a multiple pipettor
5. Add 50 µl of fresh growth medium (without G148) containing the inhibitor to each well
6. Be sure to include 2 wells containing medium only, 2 wells for stimulation control, 2 wells for DMSO control, and wells for the positive control ICG-001 (2, 5, and 10 micromolar)
7. Once all inhibitors and controls are added, incubate the plate for 1 hour at 37° C., 5% $CO_2$
8. While plate is incubating, prepare fresh 20 mM LiCl in complete growth medium (without G418)
9. After 1 hour, remove plate from incubator and add 50 µl of the medium containing 20 mM LiCl to each well, except for the two wells of the unstimulated control (add 50 µl of just complete medium)
10. Incubate the plate for 24 hours at 37° C., 5% $CO_2$
11. After 24 hours, add 100 µl of BrightGlo (Promega, Cat. #: G7573) to each well
12. Shake plate for 5 minutes to ensure complete lysis
13. Read plate on the Packard TopCount The libraries of the present invention also can be screened for bioactivity by other various techniques and methods. For example, the screening assay may be performed by (1) contacting the mimetics of a library with a biological target of interest, such as a receptor, to allow binding between the mimetics of the library and the target to occur, and (2) detecting the binding event by an appropriate assay, such as the calorimetric assay disclosed by Lam et al. (Nature 354:82-84, 1991) or Griminski et al. (Biotechnology 12:1008-1011, 1994) (both of which are incorporated herein by reference). In a preferred embodiment, the library members are in solution and the target is immobilized on a solid phase. Alternatively, the library may be immobilized on a solid phase and may be probed by contacting it with the target in solution.

A method for carrying out a binding assay also can be applied as follows. The method can include providing a composition that includes a first co-activator, an interacting protein, and a test compound. The amino acid structure of the first co-activator includes a binding motif of LXXLL, LXXLI or FxxFF wherein X is any amino acid. The method further includes detecting an alteration in binding between the first co-activator and the interacting protein due to the presence of the compound, and then characterizing the test compound in terms of its effect on the binding. The assay may be carried out by any means that can measure the effect of a test compound on the binding between two proteins. Many such assays are known in the art and can be utilized in the method of the present invention, including the so-called Two-Hybrid and Split-Hybrid systems. The Two-Hybrid system, and various means to carry out an assay using this system, are described in, e.g., U.S. Pat. No. 6,410,245. The Split-Hybrid system has been described by, e.g., Hsiu-Ming Shiu et al. Proc. Natl. Acad. Sci. USA, 93:13896-13901, November 1996; and John D. Crispino, et al. Molecular Cell, 3:1-20, February 1999. In the Split-Hybrid system, a fusion protein is utilized where protein X is fused to the lexA DNA binding domains (pLexA) and protein Y is fused to the transcription activator VP16 (pSHM.1-LacZ). Interaction between lexA-X and VP16-Y leads to the expression of the Tetracycline repressor protein (TetR). TetR prevents transcription of the HIS3 reporter gene, making the cells unable to grow on media lacking histidine. Disruption of protein-protein interaction will restore the ability of the cells to grow on such media by shutting down expression of the tetracycline repressor. Accordingly, compounds of the present invention may be added to the growing cells, and if the addition of the compound restores the ability of the cells to grow on the media, the compound may be seen as an effective disrupter of the protein-protein interaction. The yeast strains required to make the Split-Hybrid system work can be employed with two hybrid LexA/VP16 constructs such as those described by Stanley M. Hollenberg, et al. Molecular and Cellular Biology 15(7):3813-3822, July 1995. A useful modification of the Split-Hybrid system was utilized by Takemaru, K. I. and Moon, R. T. J. of Cell Biol. 149:249-254, 2000.

Other assay formats can also be suitable. For example, reporter gene assays for AP-1, ELISA, for example, blocking the production of IL-2 by a T-cell line after stimulation with CD3 and CD28 to look for inhibitors of IL-2 transcription. Direct binding assays (between coactivators and their partners) can be performed by surface plasmon resonance spectroscopy (Biacore, Sweden, manufactures suitable instruments) or ELISA.

Exemplary transcriptional regulators include, without limitation, VP16, VP64, p300, CBP, PCAF.SRC1 PvALF, AtHD2A and ERF-2. See, for example, Robyr et al. (2000) Mol. Endocrinol. 14:329-347; Collingwood et al. (1999) J. Mol. Endocrinol. 23:255-275; Leo et al. (2000) Gene 245: 1-11; Manteuffel-Cymborowska (1999) Acta Biochim. Pol. 46:77-89; McKenna et al. (1999) J. Steroid Biochem. Mol. Biol. 69:3-12; Malik et al. (2000) Trends Biochem. Sci. 25:277-283; and Lemon et al. (1999) Curr. Opin. Genet. Dev. 9:499-504. Other exemplary transcription factors include, without limitation, OsGAI, HALF-1, C1, AP1, ARF-5, -6, -7, and -8, CPRF1, CPRF4, MYC-RP/GP, and TRAB1. See, for example, Ogawa et al. (2000) Gene 245:21-29; 5 Okanami et al. (1996) Genes Cells 1:87-99; Goff et al. (1991) Genes Dev. 5:298-309; Cho et al. (1999) Plant Mol. Biol. 40:419-429; Ulmason et al. (1999) Proc. Natl. Acad. Sci. USA 96:5844-5849; Sprenger-Haussels et al. (2000) Plant J. 22:1-8; Gong et al. (1999) Plant Mol. Biol. 41:33-44; and Hobo et al. (1999) Proc. Natl. Acad. Sci. USA 96:15,348-15,353.

The transcriptional coactivator can be a human transcriptional coactivator. In another embodiment, the transcriptional coactivator is a member of the p300/CBP family of co-activators which have histone acetyltransferase activity. p300 is described for example by Eckner et al., 1994 and CBP by Bannister and Kouzarides, 1996. For the 5 purposes of the present invention, reference to p300/CBP refers to human allelic and synthetic variants of p300, and to other mammalian variants and allelic and synthetic variants thereof, as well as fragments of said human and mammalian forms of p300. In one aspect of the assay, the interacting protein is a transcription factor or a second co-activator. In one aspect of the assay, the interacting protein is any one of RIP140; SRC-1 (NCoA-1); TIF2 (GRIP-1; SRC-2); p (CIP; RAC3; ACTR; AIB-1; TRAM-1; SRC-3); CBP (p300); TRAPs (DRIPs); PGC-1; CARM-1; PRIP (ASC-2; AIB3; RAP250; NRC); GT-198; and SHARP (CoAA; p68; p72). In another aspect of the assay, the interacting protein is any one of TAL 1; p73; MDm2; TBP; HIF-1; Ets-1; RXR; p65; AP-1; Pit-1; HNF-4; Stat2; HPV E2; BRCA1; p45 (NF-E2); c-Jun; c-myb; Tax; Sap 1; YY1; SREBP; ATF-1; ATF-4; Cubitus; Interruptus; Gli3; MRF; AFT-2; JMY; dMad; PyLT: HPV E6; CITTA; Tat; SF-1; E2F; junB; RNA helicase A; C/EBP β; GATA-1; Neuro D; Microphthalimia; E1A; TFIIB; p53; P/CAF; Twist; Myo D; pp9O RSK; c-Fos; and SV40 Large T. In another aspect of the assay, the interacting protein is any one of ERAP140; RIP140; RIP160; Trip1; SWI1 (SNF); ARA70; RAP46; TIF1; TIF2; GRIP1; and TRAP. In another aspect of the invention, the interacting protein is any one of VP16; VP64; p300; CBP; PCAF; SRC1 PvALF; AtHD2A; ERF-2; OsGAI; HALF-1; C1; AP-1; ARF-5; ARF-6; ARF-7; ARF-8; CPRF1; CPRF4; MYC-RP/GP; and TRAB1. In another aspect of the invention, the first co-activator is CBP or p300.

The test compound is selected from compounds as described herein. For example, compounds having the formula (I), (Ia), (Ib), (Ic) or (Id). Typically, a test compound can be evaluated at several different concentrations, where these concentrations will be selected, in part, based on the conditions of the assay, e.g., the concentrations of the first co-activator and the interacting protein. Concentrations in the range of about 0.1 to 10 µM may be used. In one aspect, the assay evaluates the relative efficacy of two compounds to affect the binding interaction between two proteins, where at least one of those two compounds is a compound of the present invention. The more effective compound can than serve as a reference compound in a study of the relationship between compound structure and compound activity.

Compounds of general formula (I), (Ia), (Ib), (Ic) or (Id) may inhibit CBP-mediated transcriptional activation in cancer cells due to their specific binding to CBP. The compounds of the present invention may also inhibit the survivin expression in SW480 cells, and therefore, inhibit the oncogenic activity in cancer cells.

The compounds of the present invention can be used for inhibiting cancer cells, and thus, would be useful for the regulation of cell growth. The compounds of the present invention can be also advantageously used for inducing apoptosis in cells.

The present invention is also related to prodrugs using the libraries containing one or more compounds of formula (I), (Ia), (Ib), (Ic) or (Id). A prodrug is typically designed to release the active drug in the body during or after absorption by enzymatic and/or chemical hydrolysis. The prodrug approach is an effective means of improving the oral bioavailability or i.v. administration of poorly water-soluble drugs by chemical derivatization to more water-soluble compounds. The most commonly used prodrug approach for increasing aqueous solubility of drugs containing a hydroxyl group is to produce esters containing an ionizable group; e.g., phosphate group, carboxylate group, alkylamino group (Fleisher et al., Advanced Drug Delivery Reviews, 115-130, 1996; Davis et al., Cancer Res., 7247-7253).

In other aspects, the present invention provides pharmaceutical compositions containing a compound having the general formula (I), (Ia), (Ib), (Ic) or (Id). These compositions may be used in various methods (e.g., treating cancer, fibrosis or Alzheimer's disease) of the present invention as described in detail below.

The pharmaceutical composition of the present invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. In addition, pH may be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound, e.g., a compound having general formula (I), (Ia), (Ib), (Ic) or (Id) in the required amount, in an appropriate solvent with one or a combination of ingredients enumerated above, as required, followed by filtered sterilization. Generally, dispersions are prepared by incorporating the active compound into a sterile vehicle that contains a dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules.

Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It can be advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For instance, in certain embodiments, a pharmaceutical composition of the present invention is one suitable for oral administration in unit dosage form such as a tablet or capsule that contains from about 1 mg to about 1 g of the compound of this invention. In some other embodiments, a pharmaceutical composition of the present invention is one suitable for intravenous, subcutaneous or intramuscular injection. A patient may receive, for example, an intravenous, subcutaneous or intramuscular dose of about 1 µg/kg to about 1 g/kg of the compound of the present invention. The intravenous, subcutaneous and intramuscular dose may be given by means of a bolus injection or by continuous infusion over a period of time. Alternatively a patient will receive a daily oral dose approximately equivalent to the daily parenteral dose, the composition being administered 1 to 4 times per day.

Preferably, the compound of the formula (I), (Ia), (Ib), (Ic) or (Id) of the present invention can be administered intravenously (particularly preferably, by continuous drip infusion or rapid intravenous administration) to mammals inclusive of human.

In the case, the dose is selected appropriately depending on various factors such as the body weight and/or age of patients, and/or the degree of the symptom and an administration route. For example, the dose of the compound of the formula (I), (Ia), (Ib), (Ic) or (Id) for intravenous administration is generally in the range of 1 to 10000 mg/day/m$^2$ human body surface area, preferably in the range of 1 to 5000 mg/day/m$^2$ human body surface area, and more preferably 10 to 5000 mg/day/m$^2$ human body surface area by continuous drip infusion administration.

The pharmaceutical composition containing the compound of general formula (I), (Ia), (Ib), (Ic) or (Id) can be used for treatment of disorders modulated by Wnt signaling pathway, especially cancer, more especially colorectal cancer.

In one aspect, the present invention provides methods for inhibiting tumor growth. Such methods comprise the step of administering to a subject (e.g., a mammalian subject) having a tumor a compound with general formula (I), (Ia), (Ib), (Ic) or (Id) in an amount effective to inhibit tumor growth. A compound or composition inhibits tumor growth if the tumor sizes are statistically significantly smaller in subjects with the treatment of the compound or composition than those without the treatment.

The inhibitory effect of a particular compound or composition of the present invention on tumor growth may be characterized by any appropriate methods known in the art. For instance, the effect of the compound or composition on survivin expression may be measured. Compounds or compositions down-regulate survivin expression are likely to have inhibitory effects on tumor growth. In addition, assays using tumor cell lines (e.g., soft agar assays using SW480 cells) and animal models for tumor growth (e.g., nude mice grafted with tumor cells and Min mouse model) may also be used to evaluate the inhibitory effect on tumor growth of a given compound or composition as described in detail in the examples. Other exemplary animal models or xenografts for tumor growth include those for breast cancer (Guo et al., Cancer Res. 62: 4678-84, 2002; Lu et al., Breast Cancer Res. Treat. 57: 183-92, 1999), pancreatic cancer (Bouvet et al., Cancer Res. 62: 1534-40, 2002), ovarian tumor (Nilsson et al., Cancer Chemother. Pharmacol. 49: 93-100, 2002; Bao et al., Gynecol. Oncol. 78: 373-9, 2000), melanoma (Demidem et al., Cancer Res. 61: 2294-300, 2001), colorectal cancer (Brown et al., Dig. Dis. Sci. 45: 1578-84, 2000; Tsunoda et al., Anticancer Res. 19: 1149-52, 1999; Cao et al., Clin. Cancer Res. 5: 267-74, 1999; Shawler et al., J. Immunother. Emphasis Tumor Immunol. 17: 201-8, 1995; McGregor et al., Dis. Colon. Rectum. 36: 834-9, 1993; Verstijnen et al., Anticancer Res. 8: 1193-200, 1988), hepatocellular cancer (Labonte et al., Hepatol. Res. 18: 72-85, 2000), and gastric cancer (Takahashi et al., Int. J. Cancer 85: 243-7, 2000).

The compound or composition that inhibits tumor growth may be administered into a subject with a tumor via an appropriate route depending on, for example, the tissue in which the tumor resides. The appropriate dosage may be determined using knowledge and techniques known in the art as described above. The effect of the treatment of the compound or composition on tumor growth may also be monitored using methods known in the art. For instance, various methods may be used for monitoring the progression and/or growth of colorectal cancer, including colonoscopy, sigmoidoscopy, biopsy, computed tomograph, ultrasound, magnetic resonance imaging, and positron emission tomography. Methods for monitoring the progression and/or growth of ovarian cancer include, for example, ultrasound, computed tomography, magnetic resonance imaging, chest X-ray, laparoscopy, and tissue sampling.

In a related aspect, the present invention provides a method for treating or preventing cancer or fibrosis. Such methods comprise the step of administering to a subject in need thereof a compound or composition having general formula (I), (Ia), (Ib), (Ic) or (Id) in an amount effective to treat or prevent cancer or fibrosis in the subject. Treating cancer (or fibrosis) is understood to encompass reducing or eliminating cancer progression, e.g., cancer growth and metastasis (or fibrosis, as applicable). Preventing cancer (or fibrosis) is understood to encompass preventing or delaying the onset of cancer (or fibrosis, as applicable). Various types of cancer may be treated or prevented by the present invention. They include, but are not limited to, lung cancer, breast cancer, colorectal cancer, stomach cancer, pancreatic cancer, liver cancer, uterus cancer, ovarian cancer, gliomas, melanoma, lymphoma, and leukemia. A subject in need of treatment may be a human or non-human primate or other animal with various types of cancer.

A subject in need of prevention may be a human or non-human primate or other animal that is at risk for developing cancer or fibrosis. Methods for diagnosing cancer (or fibrosis) and screening for individuals with high risk of cancer (or fibrosis) are known in the art and may be used in the present invention. For instance, colorectal cancer may be diagnosized by fecal occult blood test, sigmoidoscopy, colonoscopy, barium enema with air contrast, and virtual colonoscopy. An individual with high risk of colorectal cancer may have one or more colorectal cancer risk factors such as a strong family history of colorectal cancer or polyps, a known family history of hereditary colorectal cancer syndromes, a personal history of adenomatous polyps, and a personal history of chronic inflammatory bowel disease.

A compound with general formula (I), (Ia), (Ib), (Ic) or (Id) useful in cancer (or fibrosis) treatment or prevention may be identified by appropriate methods known in the art. Methods that may be used to select compounds for inhibitory effect on tumor growth as described above may also be used. The route of administration, the dosage of a given compound, the effectiveness of the treatment may be determined using knowledge and techniques known in the art. Factors that may be considered in making such a determination include, for example, type and stage of the cancer (or fibrosis) to be treated.

The compound with general formula (I), (Ia), (Ib), (Ic) or (Id) useful in cancer treatment and prevention may be administered in combination with an other anti-neoplastic agent. The anti-neoplastic agent refers to a compound that inhibits tumor growth.

Specific examples of the other anti-neoplastic agent include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma 11 and calicheamicin omega 11 (see, e.g., Agnew, Chem Intl. Ed. Engl. 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRLAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU), tegafur, raltitrexed; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhne-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; and pharmaceutically acceptable salts, acids or derivatives of any of the above.

In addition, examples of the other anti-neoplastic agent also include anti-hormonal agents that act to regulate or inhibit hormone action on tumors such as anti-estrogens and selective estrogen receptor modulators (SERMs), including, for example, tamoxifen (including NOLVADEX™ tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestane, fadrozole, RIVISOR® vorozole, FEMARA® letrozole, and ARIMIDEX®. anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

Moreover, examples of the other anti-neoplastic agent also include a "growth inhibitory agent" referring to a compound or composition which inhibits growth of a cell in vitro and/or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

Furthermore, examples of the other anti-neoplastic agent also include a "molecular target drug" that blocks the proliferation and metastasis of cancer by interfering with specific molecules involved in carcinogenesis (the process by which normal cells become cancer cells), tumor growth, or tumor spread. Specific examples of the "molecular target drug" include kinase inhibitors that inhibit kinase activity on tumors, including, for example, imatinib, erlotinib, gefitinib, sunitinib, sorafenib, dasatinib, nilotinib; antibodies that bind to the cell surface molecule on tumor cells or to the growth factor and the like such as, for example, ibritumomab, cetuximab, trastuzumab, panitumumab, bevacizumab, rituximab; and proteasome inhibitors that inhibit the proteasome which regulates protein expression and function by degradation of ubiquitinylated proteins, such as bortezomib; and pharmaceutically acceptable salts, acids or derivatives of any of above.

Further information can be found in The Molecular Basis of Cancer, Mendelsohn and Israel, eds., Chapter 1, entitled "Cell cycle regulation, oncogenes, and antineoplastic drugs" by Murakami et al. (W B Saunders: Philadelphia, 1995), especially p. 13.

A compound with general formula (I), (Ia), (Ib), (Ic) or (Id) administered in combination with an anti-neoplastic agent does not necessarily require that the compound and the anti-neoplastic agent be administered concurrently. The compound and the agent may be administered separately as long as at a time point, they both have effects on same cancer cells.

For example, the administration mode may be exemplified by (1) administration of a single preparation obtained by simultaneously formulating the compound of formula (I), (Ia), (Ib), (Ic) or (Id) and the other anti-neoplastic agent, (2) simultaneous administration through the same administration route of two preparations obtained by separately formulating the compound of formula (I), (Ia), (Ib), (Ic) or (Id) and the other anti-neoplastic agent, (3) administration with a time interval through the same administration route of two preparations obtained by separately formulating the compound of formula (I), (Ia), (Ib), (Ic) or (Id) and the other anti-neoplastic agent, (4) simultaneous administration through different administration routes of two preparations obtained by separately formulating the compound of formula (I) and the other anti-neoplastic agent, (5) administration with a time interval through different administration routes of two preparations obtained by separately formulating the compound of formula (I), (Ia), (Ib), (Ic) or (Id) and the other anti-neoplastic agent (e.g., administration in order of the compound of formula (I), (Ia), (Ib), (Ic) or (Id) and then the other anti-neoplastic agent, or administration in the reverse order), or the like. The amount of the other anti-neoplastic agent to be administered can be appropriately selected with reference to the clinically used dosage. The mixing ratio of the compound of formula (I), (Ia), (Ib), (Ic) or (Id) and the other anti-neoplastic agent can be appropriately selected in accordance with the subject of administration, administration route, disease to be treated, symptoms, combination, and the like.

In addition, the compound of the present invention can be also used in combination with, for example, gene therapy involving VEGF, TNFa or the like, or therapeutic methods involving various antibody medicines or the like.

In a further related aspect, the present invention provides methods for promoting apoptosis in cancer cells. Such methods comprise the step of contacting cancer cells with a compound having general formula (I), (Ia), (Ib), (Ic) or (Id) in an amount effective to promote apoptosis in these cells. A compound promotes apoptosis if the number of cancer cells undergoing apoptosis is statistically significantly larger in the presence of the compound than that in the absence of the compound. Such compounds may be identified by methods known in the art (e.g., measuring caspase activities and/or cell death) using cultured cancer cell lines, xenografts, or animal cancer models. Preferably, the compound is more active in promoting apoptosis in cancer cells than in normal cells. Cancer cells treatable by the present method may be from various tissue origins.

In another aspect of the present invention, a method for treating a disorder modulated by Wnt signaling pathway in which the method comprises administering to a patient a safe and effective amount of the compounds having general formula (I), (Ia), (Ib), (Ic) or (Id) is disclosed. Pharmaceutical composition containing the compound of the present invention can be also used for this purpose. In this connection, it is found in the present invention that the compounds having general formula (I), (Ia), (Ib), (Ic) or (Id) or the pharmaceutical composition containing thereof can be useful for the treatment of disorder modulated by TCF4/β-catenin/CBP complex, which is believed to be responsible for initiating the overexpression of cancer cells related to Wnt signaling pathway. Thus, it is another aspect of the present invention to provide a method for the treatment of disorder modulated by TCF4/β-catenin/CBP complex, using the compounds having the general formula (I), (Ia), (Ib), (Ic) or (Id).

The present invention also provides compounds and methods for inhibiting survivin expression. Survivin is a target gene of the TCF/β-catenin pathway, and more specifically is a target gene of the TCF/β-catenin/CBP pathway. It is a member of the IAP (Inhibitor of Apoptosis Protein) family of proteins. Biological activity associated with survivin includes: highly expressed at G2/M, regulating cell cycle entry and exit; associated with microtubule, centrosomes, centromeres and midbody depending upon the phases of the cell cycle; and anti-apoptosis via interacting directly or indirectly with caspases (e.g., caspase 3, 7 and 9). In connection with cancer, survivin is widely and highly expressed in tumor cells, but expressed to little or no extent in normal tissue cells. Also, it has been observed that cancer patients whose tumors expressed survivin had a decreased overall survival. Furthermore, the degree of survivin expression has been correlated with other cancer markers, e.g., Ki67, PNCA, p53, APC, etc.

The effect of a particular compound of the present invention on survivin expression may be characterized by methods known in the art. Such methods include methods for characterizing survivin expression at the transcriptional or translational level. Exemplary methods for characterizing survivin expression at the transcriptional level are: cDNA microarry, reverse transcription-polymerase chain reaction (RT-PCR), chromatin immunoprecipitation (ChIP), and assays for reporter activities driven by survivin promoter. Exemplary methods for characterizing survivin expression at the translational level are: Western blot analysis, immunochemistry and caspase activities. Detailed descriptions of the above exemplary methods may be found in the examples below.

As described above, the present invention provides methods for inhibiting survivin expression. Such methods comprise the step of contacting a survivin-expressing cell with a compound of the present invention in an amount effective to inhibit survivin expression. A compound inhibits survivin expression if survivin expression in a cell is decreased in the presence of the compound compared to survivin expression in the absence of the compound. Survivin-expressing cells include tumor cells that express, such as cells in or from lung cancer, breast cancer, stomach cancer, pancreatic cancer, liver cancer, uterus cancer, ovarian cancer, gliomas, melanoma, colorectal cancer, lymphoma and leukemia. The step of contacting the survivin-expressing cells with the compound may be performed in vitro, ex vivo, or in vivo. A compound useful in inhibiting survivin expression may be identified, and the effects of a particular compound of the present invention may be characterized, by appropriate methods known in the art, as described in detail above.

Compounds of the present invention also may inhibit the expression of survivin. Blanc-Brude et al., Nat. Medicine 8:987 (2002), have shown that survivin is a critical regulator of smooth muscle cell apoptosis which is important in pathological vessel-wall remodeling. Accordingly, another aspect of the present invention provides a method of treating or preventing restenosis associated with angioplasty comprising administering to a subject in need thereof a safe and effective amount of an alpha-helix mimetic of the present invention. In one embodiment the invention treats the restenosis, i.e., administration of an alpha-helix mimetic of the present invention to a subject having restenosis achieves a reduction in the severity, extent, or degree, etc. of the restenosis. In another embodiment the invention prevents the restenosis, i.e., administration of an alpha-helix mimetic of the present invention to a subject that is anticipated to develop new or additional restenosis achieves a reduction in the anticipated severity, extent, or degree, etc. of the restenosis. Optionally, the subject is a mammalian subject.

Compounds of the present invention also may inhibit TCF/β-catenin transcription. Rodova et al., J. Biol. Chem. 277:29577 (2002), have shown that PKD-1 promoter is a target of the TCF/β-catenin pathway. Accordingly, another aspect of the present invention provides a method of treating or preventing polycystic kidney disease comprising administering to a subject in need thereof a safe and effective amount of an alpha-helix mimetic of the present invention. In one embodiment the invention treats the polycystic kidney disease, i.e., administration of an alpha-helix mimetic of the present invention to a subject having polycystic kidney disease achieves a reduction in the severity, extent, or degree, etc. of the polycystic kidney disease. In another embodiment the invention prevents polycystic kidney disease, i.e., administration of an alpha-helix mimetic of the present invention to a subject that is anticipated to develop new or additional polycystic kidney disease achieves a reduction in the anticipated severity, extent, or degree, etc. of the polycystic kidney disease. Optionally, the subject is a mammalian subject.

Compounds of the present invention also may inhibit the expression of Wnt signaling. Hanai et al., J. Cell Bio. 158:529 (2002), have shown that endostatin, a known anti-angiogenic factor, inhibits Wnt signaling. Accordingly, another aspect of the present invention provides a method of treating or preventing aberrant angiogenesis disease comprising administering to a subject in need thereof a safe and effective amount of an alpha-helix mimetic of the present invention. In one embodiment the invention treats the aberrant angiogenesis disease, i.e., administration of an alpha-helix mimetic of the present invention to a subject having aberrant angiogenesis disease achieves a reduction in the severity, extent, or degree, etc. of the aberrant angiogenesis disease. In another embodiment the invention prevents aberrant angiogenesis disease, i.e., administration of an alpha-helix mimetic of the present invention to a subject that is anticipated to develop new or additional aberrant angiogenesis disease achieves a reduction in the anticipated severity, extent, or degree, etc. of the aberrant angiogenesis disease. Optionally, the subject is a mammalian subject.

Compounds of the present invention also may inhibit Wnt TCF/β-catenin signalling. Accordingly, another aspect of the invention provides a method of treating or preventing tuberous sclerosis complex (TSC) comprising administering to a subject in need thereof a safe and effective amount of an alpha-helix mimetic the present invention. Subjects having TSC typically develop multiple focal lesions in the brain, heart, kidney and other tissues (see, e.g., Gomez, M. R. Brain Dev. 17(suppl): 55-57 (1995)). Studies in mammalian cells have shown that overexpression of TSC1 (which expresses hamartin) and TSC2 (which expresses tuberin) negatively regulates cell proliferation and induces G1/S arrest (see, e.g., Miloloza, A. et al., Hum. Mol. Genet. 9: 1721-1727 (2000)). Other studies have shown that hamartin and tuberin function at the level of the β-catenin degradation complex, and more specifically that these proteins negatively regulate β-catenin stability and activity by participating in the β-catenin degradation complex (see, e.g., Mak, B. C., et al. J. Biol. Chem. 278(8): 5947-5951, (2003)). β-catenin is a 95-kDa protein that participates in cell adhesion through its association with members of the membrane-bound cadherin family, and in cell proliferation and differentiation as a key component of the Wnt/Wingless pathway (see, e.g., Daniels, D. L., et al., Trends Biochem. Sci 26: 672-678 (2001)). Misregulation of this pathway has been shown to be oncogenic in humans and rodents. The present invention provides compounds that modulate β-catenin activity, and particularly its interactions with other proteins, and accordingly may be used in the treatment of TSC. Thus, in one embodiment the invention treats TSC, i.e., administration of an alpha-helix mimetic of the present invention to a subject having TSC achieves a reduction in the severity, extent, or degree, etc. of the TSC. In another embodiment the invention prevents TSC, i.e., administration of an alpha-helix mimetic of the present invention to a subject that is anticipated to develop new or additional TSC achieves a reduction in the anticipated severity, extent, or degree, etc. of the TSC. Optionally, the subject is a mammalian subject.

Compounds of the present invention also may inhibit the expression of Wnt signalling. The Kaposi's sarcoma-associated herpesvirus (KSHV) latency-associated nuclear antigen (LANA) is expressed in all KSHV-associated tumors, including Kaposi's sarcoma (KS) and β-cell malignancies such as primary effusion lymphoma (PEL) and multicentric Castleman's disease. Fujimuro, M. et al., Nature Medicine 9(3):300-306 (2003), have shown that LANA acts to stabilize β-catenin, apparently by redistribtution of the negative regular GSK-3β. The present invention provides compounds and methods for inhibiting β-catenin protein interactions, e.g., β-catenin/TCF complex formation. Thus, the compounds of the present invention thwart the LANA-induced accumulation of β-catenin/TCF complex and, at least in part, the consequences of KSHV infection. Accordingly, another aspect of the present invention provides a method of treating or preventing conditions due to infection by Karposi's sarcoma-associated herpesvirus (KSHV). Such conditions include KSHV-associated tumors, including Kaposi's sarcoma (KS) and primary effusion lymphoma (PEL). The method comprises administering to a subject in need thereof a safe and effective amount of an alpha-helix mimetic the present invention. In one embodiment the invention treats the KSHV-associated tumor, i.e., administration of an alpha-helix mimetic of the present invention to a subject having a KSHV-associated tumor achieves a reduction in the severity, extent, or degree, etc. of the tumor. In another embodiment the invention prevents a KSHV-associated tumor, i.e., administration of an alpha-helix mimetic of the present invention to a subject that is anticipated to develop new or additional KSHV-associated tumors achieves a reduction in the anticipated severity, extent, or degree, etc. of the tumor. Optionally, the subject is a mammalian subject.

LEF/TCF DNA-binding proteins act in concert with activated β-catenin (the product of Wnt signaling) to transactivate downstream target genes. DasGupta, R. and Fuchs, E. Development 126(20):4557-68 (1999) demonstrated the importance of activated LEF/TCF complexes at distinct times in hair development and cycling when changes in cell fate and differentiation commitments take place. Furthermore, in skin morphogenesis, β-catenin has been shown to be essential for hair follicle formation, its overexpression causing the "furry" phenotype in mice (Gat, U., et al. Cell 95:605-614 (1998) and Fuchs, E. Harvey Lect. 94:47-48 (1999). See also Xia, X. et al. Proc. Natl. Acad. Sci. USA 98:10863-10868 (2001). Compounds of the present invention have been shown to inhibit the expression of Wnt signaling, and interfere with formation of β-catenin complexes. Accordingly, the present invention provides a method for modulating hair growth comprising administering to a subject in need thereof a safe and effective amount of an alpha-helix mimetic the present invention, where the amount is effective to modulate hair growth in the subject. Optionally, the subject is a mammalian subject.

The present invention also provides compounds that may be useful in treating or preventing Alzheimer's disease. Alzheimer's disease (AD) is a neurodegenerative disease with progressive dementia. This disease is accompanied by three main structural changes in the brain, namely, i) intracellular protein deposits (also known as neurofibrillary tangles, or NFT), ii) extracellular protein deposits termed amyloid plaques that are surrounded by dystrophic neuritis, and iii) diffuse loss of neurons.

The compounds or compositions of the present invention may rescue defects in neuronal differentiation caused by a presenilin-1 mutation and may decrease the number, or rate at which neuronal precursor populations differentiate to neurons in Alzheimer's brains. Presenilins are transmembrane proteins whose functions are related to trafficking, turnover and cleavage of Notch and Amyloid Precursor Protein. Missense mutations in presenilin-1 (PS-1) are associated with early-onset familial Alzheimer's disease (Fraser et al., Biochem. Soc. Symp. 67, 89 (2001)). The compounds of the present invention may be applicable not only to individuals with PS-1 familial Alzheimer's mutations, but also to general Alzheimer's patients.

In addition, the present invention can provide a method for treating or preventing Alzheimer's disease comprising administering to a subject in need thereof a safe and effective amount of an alpha-helix mimetic of the present invention, where the amount is effective to treat or prevent Alzheimer's disease in the subject. Treating Alzheimer's disease is understood to encompass reducing or eliminating the manifestation of symptoms characteristic of Alzheimer's disease, or delaying the progression of this disease. Preventing Alzheimer's disease is understood to encompass preventing or delaying the onset of this disease.

A subject in need of treatment may be a human or non-human primate or other animal that is at various stages of Alzheimer's disease. Methods for diagnosing Alzheimer's disease are known in the art (see, e.g., Dinsmore, J. Am. Osteopath. Assoc. 99.9, Suppl. p:S1-6, 1999; Kurz et al., J. Neural Transm. Suppl. 62: 127-33, 2002; Storey et al., Front Viosci. 7: e155-84, 2002; Marin et al., Geriatrics 57: 36-40, 2002; Kril and Halliday, Int. Rev. Neurobiol. 48: 167-217, 2001; Gurwitz, Trends Neurosci. 23: 386, 2000; Muller- Spahn and Hock, Eur. Arch. Psychiatry Clin. Neurosci. 249 Suppl. 3: 37-42; Fox and Rossor, Rev. Neuro. (Paris) 155 Suppl. 4: S33-7, 1999), including the use of neuropsychological measures, functional imaging measures, biological markers, and autopsy of brain tissue. A subject in need of prevention may be a human or non-human primate or other animal that is at risk for developing Alzheimer's disease, such as an individual having a mutation of certain genes responsible for this disease (e.g., genes encoding amyloid precursor protein, presenilin-1, and presenilin-2), and/or a gene involved in the pathogenesis of this disease (e.g., apolipoprotein E gene) (Rocchi et al., Brain Res. Bull. 61: 1-24, 2003).

Compounds with structures as set forth in formula (I), (Ia), (Ib), (Ic) or (Id) may be screened for their activities in treating or preventing Alzheimer's disease by any appropriate methods known in the art. Such screening may be initially performed using in vitro cultured cells (e.g, PC-12 cells). Compounds capable of rescuing defects in neuronal differentiation caused by a presenilin-1 mutation may be further screened using various animal models for Alzheimer's disease. Alternatively, compounds with structures as set forth in formula (I), (Ia), (Ib), (Ic) or (Id) may be directly tested in animal models for Alzheimer's disease. Many model systems are known in the art and may be used in the present invention (see, e.g., Rowan et al., Philos. Trans. R. Soc. Lond. B. Biol. Sci. 358: 821-8, 2003; Lemere et al., Neurochem. Res. 28: 1017-27, 2003; Sant'Angelo et al., Neurochem. Res. 28: 1009-15, 2003; Weiner Harv. Rev. Psychiatry 4: 306-16, 1997). The effects of the selected compounds on treating or preventing Alzheimer's disease may be characterized or monitored by methods known in the art for evaluating the progress of Alzheimer's disease, including those described above for diagnosing this disease.

The present invention also provides methods for promoting neurite outgrowth. Such methods comprise the step of contacting a neuron with a compound according to formula (I), (Ia), (Ib), (Ic) or (Id) in an amount effective to promote neurite outgrowth. These methods are useful in treating neurodegenerative diseases (e.g., glaucoma, macular degeneration, Parkinson's Disease, and Alzheimer's disease) and injuries to nervous system. A compound promotes neurite outgrowth if the neurite lengths of neurons are statistically significantly longer in the presence of the compound than those in the absence of the compound. Such a compound may be identified using in vitro cultured cells (e.g, PC-12 cells, neuroblastoma B104 cell) (Bitar et al., Cell Tissue Res. 298: 233-42, 1999; Pellitteri et al., Eur. J. Histochem. 45: 367-76, 2001; Satoh et al., Biochem. Biophys. Res. Commun. 258: 50-3, 1999; Hirata and Fujisawa, J. Neurobiol. 32:415-25, 1997; Chauvet et al., Glia 18: 211-23, 1996; Vetter and Bishop, Curr. Biol. 5: 168-78, 1994; Koo et al., Proc. Natl. Acad. Sci. USA 90: 4748-52, 1993; Skubitz et al., J. Cell Biol. 115: 1137-48, 1991; O'Shea et al., Neuron 7: 231-7, 1991; Rydel and Greene, Proc. Natl. Acad. Sci. USA 85: 1257-61, 1988) or using explants (Kato et al., Brain Res. 31: 143-7, 1983; Vanhems et al., Eur. J. Neurosci. 2: 776-82, 1990; Carri et al., Int. J. Dev. Neurosci. 12: 567-78, 1994). Contacting a neuron with a compound according to the present invention may be carried out in vitro or in vivo. The resulting treated neuron, if generated in vitro, may be transplanted into a tissue in need thereof (Lacza et al., Brain Res. Protoc. 11: 145-54, 2003; Chu et al., Neurosci. Lett 343: 129-33, 2003; Fukunaga et al., Cell Transplant 8: 435-41, 1999).

The present invention also provides methods for promoting differentiation of a neural stem cell comprising contacting a neural stem cell with a compound according to formula (I), (Ia), (Ib), (Ic) or (Id) in an amount effective to promote differentiation of a neural stem cell. Such methods are also useful in treating neurodegenerative diseases (e.g., glaucoma, macular degeneration, Parkinson's Disease, and Alzheimer's disease) and injuries to nervous system. "Neural stem cell" refers to a clonogenic, undifferentiated, multipotent cell capable of differentiating into a neuron, an astrocyte or an oligodendrocyte under appropriate conditions. A compound promotes differentiation of neural stem cells if neural stem cells exhibit a statistically significantly higher degree of differentiation in the presence of the compound than in the absence of the compound. Such a compound may be identified using assays involving in vitro cultured stem cells or animal models (Albranches et al., Biotechnol. Lett. 25: 725-30, 2003; Deng et al., Exp. Neurol. 182: 373-82, 2003; Munoz-Elias et al., Stem Cells 21: 437-48, 2003; Kudo et al., Biochem. Pharmacol. 66: 289-95, 2003; Wan et al., Chin. Med. J. 116: 428-31, 2003; Kawamorita et al., Hum. Cell 15: 178-82, 2002; Stavridis and Smith, Biochem. Soc. Trans. 31: 45-9, 2003; Pachenik et al., Reprod. Nutr. Dev. 42: 317-26, 2002; Fukunaga et al., supra). The neural stem cell may be a cultured stem cell, a stem cell freshly isolated from its source tissue, or a stem cell within its source organism. Thus, contacting the neural stem cell with a compound according to the present invention may be carried out either in vitro (for a cultured or freshly isolated stem cell) or in vivo (for a stem cell within its source organism). The resulting differentiated neural cell, if generated in vitro, may be transplanted into a tissue in need thereof (Lacza et al., supra; Chu et al., supra; Fukunaga et al., supra). Such a tissue includes a brain tissue or other nervous tissue that suffers from a trauma or a neurodegenerative disease.

In an embodiment of the present invention, the compound(s) of the present invention or pharmaceutical formulations containing one or more compounds of the present invention are useful in the treatment and/or prevention of fibrosis in general. Below is a further description of examples of various types/forms of fibrosis that are treatable with the compounds of the present invention.

Transforming growth factor β (TGF-β), a key mediator in the development of fibrosis, is important in cell proliferation and differentiation, apoptosis, and deposition of extracellular matrix (ECM). TGF-β signaling activates both the Smad and AP-1 transcription pathways. TGF-β in the airways of patients with pulmonary fibrosis (PF) may function initially as a "healing molecule" involved in the diminution of initial airway inflammation and in tissue repair. However, with continued inflammatory response such as may occur in PF, the balance may be shifted, to excessive ECM deposition and development of airway fibrosis.

Fibroproliferative diseases are generally caused by the activation of resident stellate cells which are found in most organs. This activation of stellate cells leads to their conversion to myofibroblasts which display characteristics of muscle and non-muscle cells. Activated stellate cells initiate inflammatory signals, principally mediated through TGF-β. Inflammatory cytokines and mediators in addition to TGF-β, lead to proliferation of myofibroblasts. Stellate-derived myofibroblasts proliferate and replace healthy, functional organ cells with extra-cellular matrix that exhibit muscle and connective tissue traits. Ultimately, organ failure results when the nonfunctional fibrotic honeycomb matrix replaces a critical number of healthy cells.

The initial cause of fibrosis is believed to be the result of injury or insult to organ tissues. This cellular injury to organ tissues can often be traced to toxic or infectious agents. Pulmonary fibrosis, or interstitial lung disease, is often the result of smoking, chronic asthma, chronic obstructive pulmonary disease (COPD) or pneumonia. Fibrosis affects nearly all tissues and organ systems. Non-limiting examples of disorders in which fibrosis is a major cause of morbidity and mortality are listed below.

Major-Organ Fibrosis

Interstitial lung disease (ILD) includes a wide range of distinct disorders in which pulmonary inflammation and fibrosis are the final common pathway of pathology. There are more than 150 causes of ILD, including sarcoidosis, silicosis, adverse drug reactions, infections and collagen vascular diseases and systemic sclerosis (scleroderma).

Idiopathic pulmonary fibrosis (IPF) is the most common type of ILD. Liver cirrhosis has similar causes to ILD, with viral hepatitis, schistosomiasis and chronic alcoholism being the major causes worldwide.

Kidney disease including diabetes can damage and scar the kidneys, which leads to progressive loss of function. Untreated hypertension can also contribute to the fibroproliferation of the kidneys.

Heart disease associated with scar tissue can impair the heart's pumping ability.

Eye disease includes macular degeneration and retinal and vitreal retinopathy can impair vision.

Chronic pancreatitis is an irreversible disease of the pancreas characterized by chronic inflammation and fibrosis which leads to the loss of endocrine and exocrine function.

Fibroproliferative disorders include systemic and local scleroderma. Scleroderma is a chronic connective tissue disease that may be localized or systemic, and may have an affect in many organs and tissues of the body.

Keloids and hypertrophic scars, which can occur after surgery, traumatic wounds, burns, or even scratches. They manifest as an overgrowth of scar tissue at the site of injury.

Atherosclerosis and restenosis. Restenosis refers to the re-narrowing of a coronary artery after angioplasty to treat atherosclerosis. Scarring associated with trauma can be associated with overgrowth of scar tissue at the site of the trauma-related injury. Surgical complications can lead to fibrosis in any organ in which scar tissue and fibroproliferation result from the surgical procedures.

Chemotherapy induced fibrosis can occur in, for example, the lungs following chemotherapy, manifests as pulmonary fibrosis, and can be severe enough to require lung transplant, even in cases where the underlying malignancy did not affect the lungs.

Radiation-induced fibrosis (RIF) is a serious and common complication of radiation therapy that may cause chronic pain, neuropathy, limited movement of joints, and swelling of the lymph nodes. It occurs most often in breast, head, neck, and connective tissues. RIF may develop from 4-6 months to 1-2 years following exposure to radiation therapy, and it becomes more severe over time. Risk factors for developing RIF include high radiation dose, large volumes of tissue exposed to radiation, and radiation combined with surgery, chemotherapy, or both.

Burns can lead to fibrosis when there is an overproduction of ECM proteins. Excessive ECM deposition causes the tissue to become fibrotic.

Pulmonary Fibrosis

Pulmonary fibrosis destroys the lung's ability to transport oxygen and other gases into or out of the blood. This disease modifies the delicate and elastic tissues of the lung, changing these tissues into thicker, stiff fibrous tissue. This change or replacement of the original tissue is similar to the permanent scarring that can occur to other damaged tissues. Scarring of the lung reduces the lung's ability to allow gases to pass (i.e. oxygen, carbon dioxide) into or out of the blood. Gradually, the air sacs of the lungs become replaced by fibrotic tissue. When the scar forms, the tissue becomes thicker causing an irreversible loss of the tissue's ability to transfer oxygen into the bloodstream. Symptoms include shortness of breath, particularly with exertion; chronic dry, hacking cough; fatigue and weakness; discomfort in the chest; loss of appetite; and rapid weight loss.

Several causes of pulmonary fibrosis are known and they include occupational and environmental exposures. Many jobs, particularly those that involve mining or that expose workers to asbestos or metal dusts, can cause pulmonary fibrosis. Workers doing these kinds of jobs may inhale small particles (like silica dusts or asbestos fibers) that can damage the lungs, especially the small airways and air sacs, and cause the scarring associated with fibrosis. Agricultural workers also can be affected. Some organic substances, such as moldy hay, cause an allergic reaction in the lung. This reaction is called Farmer's Lung and can cause pulmonary fibrosis. Other fumes found on farms are directly toxic to the lungs.

Another cause is Sarcoidosis, a disease characterized by the formation of granulomas (areas of inflammatory cells), which can attack any area of the body but most frequently affects the lungs.

Certain medicines may have the undesirable side effect of causing pulmonary fibrosis, as can radiation, such as treatment for breast cancer. Connective tissue or collagen diseases such as systemic sclerosis are also associated with pulmonary fibrosis. Although genetic and familial factors may be involved, this cause is not as common as the other causes listed above.

In Chronic Obstructive Pulmonary Disease (COPD), connective tissue proliferation and fibrosis can characterize severe COPD. COPD can develop as a result of smoking or chronic asthma.

Idiopathic Pulmonary Fibrosis (IPF)

When all known causes of interstitial lung disease have been ruled out, the condition is called "idiopathic" (of unknown origin) pulmonary fibrosis (IPF). Over 83,000 Americans are living with IPF, and more than 31,000 new cases develop each year. This debilitating condition involves scarring of the lungs. The lungs' air sacs develop scar, or fibrotic tissue, which gradually interferes with the body's ability to transfer the oxygen into the bloodstream, preventing vital organs and tissue from obtaining enough oxygen to function normally.

There are several theories as to what may cause IPF, including viral illness and allergic or environmental exposure (including tobacco smoke). These theories are still being researched. Bacteria and other microorganisms are not thought to be the cause of IPF. There is also a familial form of the disease, known as familial idiopathic pulmonary fibrosis. Additional research is being done to determine whether there is a genetic tendency to develop the disease, as well as to determine other causes of IPF.

Patients with IPF suffer similar symptoms to those with pulmonary fibrosis when their lungs lose the ability to transfer oxygen into the bloodstream. The symptoms include shortness of breath, particularly during or after physical activity; spasmodic, dry cough; gradual, unintended weight loss; fatigue and weakness;

chest discomfort; clubbing, or enlargement of the ends of the fingers (or sometimes the toes) due to a buildup of tissue. These symptoms can greatly reduce IPF patients' quality of life. Pulmonary rehabilitation, and oxygen therapy can reduce the lifestyle-altering effects of IPF, but do not provide a cure.

In order to develop a treatment for fibrotic disease, it is important to focus on the common pathway to the ultimate pathology that is shared by the disease states, regardless of cause or of tissue in which it is manifested. Several components of the causative pathway are discussed below, particularly in relation to the role of β-catenin.

Other Pathological Conditions

Survivin, an inhibitor of apoptosis, is implicated in pulmonary hypertension. CK2 kinase activity has been shown to promote cell survival by increasing survivin expression via β-catenin TCF/LEF-mediated transcription. Tapia, lC. et al., Proc. Nat. Acad. Sci. U.S.A. 103: 15079-84 (2006). This pathway therefore provides another opportunity to utilize the present compounds to alter the β-catenin-mediated gene transcription processes.

McMurtry, M. S. et al., J. Clin. Invest. 115:1461-1463 (2005) reported that survivin was expressed in the pulmonary arteries of patients with pulmonary arterial hypertension, but not in the pulmonary arteries of patients without pulmonary arterial hypertension. Comparable results were found in rats treated with monocrotaline to induce pulmonary arterial hypertension. In the rats, survival was prolonged and the pulmonary arterial hypertension was reversed by gene therapy with inhalation of an adenovirus carrying a survivin mutant with dominant-negative properties.

Survivin expression is upregulated in hyperproliferative neovasculature (Simosa, H. F. et al., J. Vase. Surg. 41:682-690, 2005). Survivin was specifically expressed in human other sclerotic plaque and stenotic vein grafts. In a rabbit model of hyperplasia after balloon injury of iliofemoral arteries, treatment with a phosphorylation-defective survivin mutant vector reduced the neointimal area. The correlation between survinin expression and regulation of a smooth muscle cell phenotype after vascular injury points to survivin as a target for therapy in treating vascular disease.

Survivin is amenable to targeting by administration of a compound disclosed herein via one or more of the routes as described herein. Without being bound by a particular mode of action, the compounds disclosed herein can be administered in the form of coated stents, for example in connection with angioplasty. The methods for preparing coated stents are described in the art and would be modified as needed for use with the compounds of the invention. For example, U.S. Pat. No. 7,097,850 discloses and teaches methods of coating a stent with a variety of bioactive compounds. U.S. Pat. No. 7,087,078 discloses methods of preparing a stent with at least one active ingredient. Both coronary and peripheral stents are amenable to incorporating one or more compounds disclosed herein. Further teachings regarding drug-coated stents is available in Grube, E. et al., Herz 29:162-6 (2004) and W. L. Hunter, Adv Drug Deliv Rev. 58:347-9 (2006).

Bone marrow cells contribute to transplant-associated atherosclerosis (Sata, M., Trends Cardiovasc. Med. 13:249-253, 2003). Bone marrow cells also contribute to the pathogenesis of lesion formation after mechanical vascular injury (Sata, M. et al., Nat. Med. 8:403-409, 2002). Thus, by treating atherosclerosis and vascular damage with one of more compounds of the invention, reduction in vascular lesion formation can be accomplished.

Survivin also plays a role in vein graft hyperplasia (Wang, G. J. et al., Arterioscler. Thromb. Vase. Biol. 25:2091-2087, 2005). Bypass grafts often develop intimal hyperplasia, a fibroproliferative lesion characterized by intimal thickening. Rabbit vein grafts were treated with adenoviral survivin constructs. Transgene expression was demonstrated in all the adenovirus-treated grafts. Treatment with a dominant negative mutant adenovirus decreased cellular proliferation in the early phase of graft remodeling. The data provide evidence for an important role of survivin in the regulation of vein graft remodeling in this system as well, and further support a role for the compounds of the invention in conjunction with bypass grafts.

Lymphangioleiomyomatosis (LAM) is a disease that occurs in some patients with tuberous sclerosis complex (Moss, J. et al., Am. J. Respir. Crit Care Med. 163:669-671, 2001).

Cystic lung disease in LAM is characterized by abnormal smooth muscle cell proliferation. Compounds disclosed herein are expected to find use in regulating and alleviating the cell proliferation, thus moderating the clinical symptoms.

The Role of TGF-β

In pulmonary fibrosis, the normally thin lung tissue is replaced with thick, coarse scar tissue that impairs the flow of oxygen into the blood and leads to a loss of lung function. A growing body of research suggests that excess TGF-β is the immediate cause of the fibrosis. This over-expression of TGF-β has been shown to cause pulmonary fibrosis in mice. An abnormally high TGF-β signal causes healthy epithelial cells in the lung to die via apoptosis. Cell death leads to the replacement of healthy lung tissue by thick, poor functioning scar tissue. Apoptosis of healthy epithelial cells is required prior to the development of pulmonary fibrosis (Elias et al). One form of treatment of fibrotic lung disorders involves administering drugs that specifically inhibit TGF-β, which in turn blocks apoptosis, preventing the formation of fibrotic tissue in the lung. However, for reasons discussed below, TGF-β itself may not be an ideal therapeutic target.

TGF-β is a member of the transforming growth factor-superfamily which consists of secreted polypeptide signaling molecules involved in cell proliferation and differentiation, apoptosis, deposition of extracellular matrix (ECM) and cell adhesion. TGF-β is a potent inhibitor of cell growth, and has immunosuppressive properties. However, TGF-β also causes the deposition of ECM components leading to fibrosis. A role for TGF-β as a key mediator in the development of fibrosis relates to its ability to act as a chemoattractant for fibroblasts, stimulate fibroblast procollagen gene expression/collagen protein synthesis, and inhibit collagen breakdown. TGF-β further stabilizes the ECM by inhibiting the expression of ECM proteases and stimulating the expression of ECM protease inhibitors. The fibrinolysis system is essential in ECM accumulation and fibrosis. Inhibition of fibrinolysis results in the accumulation of fibrin and ECM. Plasminogen activator inhibitor-1 (PAI-1) is the key inhibitor of fibrinolysis. The PAI-promoter contains several transcription factor binding sites including an AP-1 and Smad binding elements that promote PAI-1 induction by TGF-β. PAI-1 is the primary inhibitor of both tissue-type (TPA) and urokinase-type plasminogen (uPA) activator. Thus, TGF-β and PAI-1 work in tandem to produce the characteristic tissue of fibrosis.

In the bleomycin-induced model of pulmonary fibrosis (PF), mice in which the PAI-1 gene is deleted are protected from developing PF. Additionally, adenovirus-mediated transfer of the uPA gene to the lung significantly reduces the production of lung hydroxyproline and attenuated the bleomycin-induced increase in lung collagen, both hallmarks of fibrosis. The TGF-β signaling pathway is complex. TGF-β family members bind to specific pairs of receptor serine/threonine kinases. Upon binding, the ligand acts to assemble two type I and two type II receptors into a complex. The type II receptor phosphorylates the type I receptor that subsequently phosphorylates the intracellular substrates Smad 2 and Smad 3. This complex then binds Smad 4 and translocates to the nucleus for signal propagation. TGF-β can also activate AP-1 transcription via the MAPK pathway. TGF-β may originally act as a "healing molecule" in the lung or liver after initial inflammation and injury to the tissue. However, with continued inflammation/injury the balance may be shifted to excessive fibroproliferation and ECM deposition, leading to an "endless healing" process and development of fibrosis. Thus, complete inhibition of TGF-β could initially undermine the healing process.

TGF-β is highly expressed in airway epithelium and macrophages of small airways in patients with COPD. Using anti-inflammatory therapies, such as corticosteroids and interferon-γ, to treat PF has been disappointing due to variable efficacy and significant adverse effects. Therefore, an important goal is to identify small molecules that interact with previously identified molecular pathways (i.e. TGF-β signaling) involved in the development of fibrosis to prevent the progression or reverse the fibrosis seen in patients.

Wnt Signaling and Human Disease

Vertebrate Wnt proteins are homologues of the *Drosophila* wingless gene and have been shown to play important roles in regulating cell differentiation, proliferation, and polarity. Cadijan, K. M. et al., Genes Dev. 11:3286-3305 (1997); Parr, B. A. et al., Curr. Opin. Genet. Dev. 4:523-528 (1994); Smalley, M. J. et al., Cancer Met. Rev. 18:215-230 (1999); and Willert, K. et al., Curr. Opin. Genet. Dev. 8:95-102 (1998). Wnt proteins are cysteine-rich secreted glycoproteins that signal through at least three known pathways. The best understood of these, commonly called the canonical pathway, involves binding of Wnt proteins to frizzled cell surface receptors and low-density lipoprotein cell surface co-receptors, thereby inhibiting glycogensynthase kinase 3β (GSK-3β) phosphorylation of the cytoskeletal protein β-catenin. This hypophosphorylated β-catenin is then translocated to the nucleus, where it binds to members of the LEF/TCF family of transcription factors. Binding of β-catenin converts LEF/TCF factors from repressors to activators, thereby switching on cell-specific gene transcription. The other two pathways that Wnt proteins can signal through either activate calmodulin kinase II and protein kinase C (known as the Wnt/Ca++ pathway) or jun N-terminal kinase (also known as the planar cell polarity pathway).

Several components of the Wnt pathway have been implicated in tumorigenesis in humans and mice, and studies of those have in turn identified a role for β-catenin. Wnt1 was first identified from a retroviral integration in mice that caused mammary tumors. Tsukamoto, A. S. et al., Cell 55:619-625 (1988); and Jue, S. F. et al., Mol. Cell. Biol. 12:321-328 (1992). Overexpression of protein kinase CK2 in the mammary gland, which potentiates β-catenin-dependent Wnt signaling, also increases the incidence of mammary tumors in transgenic mice. Landesman-Bollag, E. et al., Oncogene 20:3247-3257 (2001); and Song, D. H. et al., J. Biol. Chem. 275:23790-23797 (2000). Gut epithelia has revealed the most extensive correlation between Wnt signaling and tumorigenesis. Several reports have described mutations in β-catenin itself in some colon tumors and these mutations occur in or near the GSK-3β phosphorylation sites. Polakis, P. et al., Adv. Exp. Med. Biol. 470:23-32 (1999); and Morin, P. J. et al., Science 275:1787-1790 (1997). Chilosi and colleagues (Chilosi, M. et al., Am. J. Pathol. 162:1497-1502, 2003) investigated β-catenin mutations in IPF patients but did not identify any. This is consistent with a mechanism in which the aberrant activation of the Wnt pathway is a response and not a cause of IPF.

Lung Development and Wnt Signaling

In the mouse, the lung arises from the primitive foregut endoderm starting at approximately E9.5 during mouse development. (Warburton, D. et al., Mech. Dev. 92:55-81, 2000). This primitive epithelium is surrounded by mesodermally derived multipotent mesenchymal cells, which in time will differentiate into several cell lineages including bronchial and vascular smooth muscle, pulmonary fibroblasts, and endothelial cells of the vasculature. During gestation, the airway epithelium evolves and grows through a process termed branching morphogenesis. This process results in the three-dimensional arborized network of airways required to generate sufficient surface area for postnatal respiration. Mouse embryonic lung development can be divided into at least four stages: embryonic (E9.5 to E12.5), pseudoglandular (E12.5 to E16.0), canalicular (E16.0 to E17.5), and saccular/alveolar (E17.5 to postnatal).

During development, epithelial-mesenchymal signaling plays an important role in the regulation of both epithelial and mesenchymal cell differentiation and development. Several important signaling molecules are expressed in the airway epithelium and signal to the adjacent mesenchyme including members of the bone morphogenetic family (BMP-4), transforming growth factor family (TGF-β1, -2), and sonic hedgehog (SHH). In turn, the mesenchyme expresses several signaling molecules such as FGF-7, -9, and -10, important for lung epithelial development and proliferation. Gain of function and loss of function experiments in mice have demonstrated an important role for each of these factors in regulating lung epithelial and mesenchymal proliferation and differentiation. Bellusci, S., et al., Development 1997, 124:4867-4878; Simonet, W. S., et al., Proc. Natl. Acad. Sci. USA 1995, 92:12461-12465; Clark, J C., et al., Am. J. Physiol. 2001, 280:L705-L715; Min, R., et al., Genes Dev. 1998, 12:3156-3161; Motoyama, I., et al., Nat. Genet. 1998, 20:54-57; Litingtung, Y, et al., Nat. Genet. 1998, 20:58-61; Pepicelli, C. V., et al., Curr. Biol. 1998, 8:1083-1086; Weaver, M., et al., Development 1999, 126: 4005-4015.

Wnt signaling also plays a role during lung development. Several Wnt genes are expressed in the developing and adult lung including Wnt2, Wnt2b/13, Wnt7b, Wnt5a, and Wnt11. Kispert, A., et al., Development 1996, 122:3627-3637; Lin, Y., et al., Dev. Dyn. 2001, 222:26-39; Monkley, S. l., et al., Development 1996, 122:3343-3353; Yamaguchi, T. P., et al., Development 1999, 126:1211-1223; Weidenfeld, J., et al., J. Biol. Chem. 2002, 277:21061-21070. Of these, Wnt5a and Wnt7b are expressed at high levels exclusively in the developing airway epithelium during lung development. Wnt2, Wnt5a, and Wnt7b have been inactivated through homologous recombination in mice. Wnt2-null mice do not display an overt lung phenotype and Wnt5a null mice have late-stage lung maturation defects, corresponding to expression of Wnt5a later in lung development. (Monkley, (1996); Li, C. et al., Dev. Biol. 248:68-81 (2000). Inactivation of Wnt7b results in either early embryo demise because of defects in extra-embryonic tissues or perinatal demise because of defects in lung development. Parr, B. A., et al., Dev. Biol. 237:324-332 (2001); Shu, W. et al., Development 129:4831-4842 (2002)). These lung defects include decreased mesenchymal proliferation, lung hypoplasia caused by reduced branching, and pulmonary vascular smooth muscle defects leading to blood vessel hemorrhage in the lung (Shu, W. (2002)). Thus, Wnt signaling regulates important aspects of both epithelial and mesenchymal development during gestation, likely through both autocrine and paracrine signaling mechanisms.

Accumulation of nuclear β-catenin has been observed in both epithelial and mesenchymal (myofibroblasts) cell lineages in adult human lung. Other reports support these observations during mouse lung development. (Tebar, R., et al., Mech. Dev. 109:437-440 (2001)). Type 2 pneumocytes appear to express high levels of β-catenin both in the embryo and in the adult. (Tebar, 2001). Type 2 cells are precursors of type 1 cells, which form the thin diffusible stratum important for gas exchange in the lung. Type 2 cells have been shown to re-enter the cell cycle, grow, and differentiate into type 1 cells in some models of lung re-epithelialization. (Borok, Z. et al., Am. J. Respir. Cell Mol. Biol. 12:50-55 (1995); Danto, S. l. et al., Am. J. Respir. Cell Mol. Biol. 12:497-502 (1995)).

Importantly, type 2 cells proliferate excessively during idiopathic fibrosis (IPF) and other proliferative lung diseases, and increased nuclear β-catenin in these cells suggests that Wnt signaling regulates this proliferation. (Kawanami, O., et al., Lab. Invest. 46:39-53 (1982); Kasper, M. et al., Histol. Histopathol. 11:463-483 (1996)). Increased proliferation of type 2 cells in IPF may also inhibit their differentiation into type 1 cells because excessive proliferation is often antagonistic to cellular differentiation. In this context, it is important to note that expression of certain important transcriptional and signaling regulators in the lung decreases with gestational age. Forced overexpression of some of these such as BMP-4, GATA6, and Foxa2 results in aberrant lung development that exhibits many aspects of arrested lung epithelial maturity. (Weaver, 1999; Koutsourakis, M. et al., Mech. Dev. 105: 105-114, 2001; Zhou, L. et al., Dev. Dyn. 210:305-314, 1997). Thus, a careful balance of the correct spatial and temporal expression of certain regulatory genes is required for normal lung development, and improper activation of these pathways can result in severe defects in epithelial differentiation.

Nuclear β-catenin is found in the mesenchyme adjacent to the airway epithelium (Chilosi, 2003), and this is significant especially because these cells appear to be myofibroblastic in nature and may contribute to bronchial and vascular smooth muscle in the lung. Although Wnt signals in these mesenchymal cells could be autocrine in nature, it is just as likely that the mesenchymal cells are responding to a paracrine signal from the airway epithelium where Wnts such as Wnt5a and Wnt7b are expressed. In this way, the epithelium may be responsible for causing the aberrant activation of Wnt signaling in adjacent mesenchyme, leading to increased fibrosis and damage to the lung. This is particularly relevant because of the increase in the number of type 2 cells in the airways of IPF patients. This may also be reflective of a switch to an embryonic phenotype in the alveolus, where type 1 cells are rare. In turn, this would result in an increase in expression of several genes, including Wnts such as Wnt7b, whose expression is dramatically down-regulated in postnatal development. (Weidenfeld, 2002; Shu, 2002.) The increased level of Wnts may inhibit the proper differentiation of more mature alveolar cells such as type 1 cells, impairing the repair process.

Because nuclear translocation of β-catenin is a result of Wnt signaling activity, its presence in cells such as distal airway epithelium, and in mesenchyme adjacent to airway epithelium suggests that epithelial-mesenchymal Wnt signaling is active and likely plays an important role during both lung development and disease states such as IPF.

Regulation of Cell-Matrix Interactions by Wnt Signaling

A link has been shown between Wnt signaling and regulation of cell-matrix interactions including cell adhesion and migration. In particular, Wnt signaling has been shown to affect cell motility and invasiveness of melanoma cells. (Weeraratna, A. T. et al., Cancer Cell 1:279-288 (2002)). In this system, melanoma cells overexpressing Wnt5a displayed increased adhesiveness, which correlated to a reorganized actin cytoskeleton (Weer, 2002). These data suggest that Wnt5a expression correlates directly with the metastatic ability of melanoma tumors. In IPF lung tissue (Chilosi, 2003), the important extracellular matrix metalloproteinase matrilysin was overexpressed in some of the cells containing high levels of nuclear β-catenin. This is supported by previous studies showing that matrilysin is a molecular target of Wnt signaling. (Crawford, H. C., Oncogene 18:2883-2891, 1999). Matrilysin has been linked to a role in carcinogenesis both in intestinal and endometrial tumors. Increased matrilysin expression strongly correlates with increased nuclear β-catenin expression and inhibition of this nuclear translocation results in decreased matrilysin expression. (Crawford, 1999). Without being bound by a specific hypothesis, the mechanism may involve increased degradation of the extracellular matrix from increased matrilysin expression, leading to decreased cell adhesion and increased cell motility. In IPF, this might reduce the ability of both epithelial and mesenchymal cells to properly restructure the alveolar architecture after injury. In addition, extracellular matrix integrity may be required for type 1 cell differentiation, because of their flattened morphology and the very large surface area that they cover in the alveolus. This process may contribute to an increase in type 2 cell proliferation, which in turn could decrease type 1 cell differentiation.

Wnt Signaling and IPF

Without being bound by a specific hypothesis, several models could explain the finding that Wnt signaling is aberrantly activated in IPF. First, unregulated activation of the Wnt signaling pathway could be a physiological response to either lung injury or the repair process, possibly because of the requirement of the Wnt pathway for proliferation in cells such as type 2 alveolar epithelium and adjoining myofibroblasts. In this model, Wnt signaling should deactivate once the repair process is complete, leading to a return to normal proliferation. In the second model, aberrant Wnt signaling is the initiating event leading to increased cell proliferation in type 2 cells, which may inhibit their ability to differentiate into type 1 cells and restructure the alveolar architecture properly. Either injury-induced or spontaneous mutations in certain components of the canonical Wnt pathway or in regulatory molecules that regulate this pathway may result in this dysregulation of cell proliferation. The fact that nuclear β-catenin is up-regulated in other lung proliferative diseases suggests that the previous data (Chilosi, 2003) may be a response and not a primary causative event in IPF. Moreover, the unregulated proliferation in type 2 cells and mesenchymal fibroblasts along with the increased presence of nuclear β-catenin suggests that the Wnt pathway is continuously stimulated in lung diseases such as IPF and that inhibitors of Wnt signaling may provide a means to control this proliferation. Increased nuclear β-catenin was detected in the mesenchyme adjacent to the airway epithelium, described as myofibroblasts (Chilosi, 2003). These myofibroblasts can induce apoptosis in neighboring epithelial cells in vitro and in vivo, probably through degradation of the extracellular matrix (Ubal, B. D. et al., Am. J. Physiol. 275:L1192-L1199, 1998; Dhal, B. D. et al., Am. J. Physiol. 269:L819-L822, 1995; Selman, M. et al., Am. J. Physiol. 279:L562-L574, 2000). In addition, in IPF there appears to be either a lack of re-epithelialization or an increase in type 2 cells with little if any maturation of type 1 cells, leading to injured areas with exposed mesodermal components or re-epithelialized with immature type 2 cells. Since it has been demonstrated that type 2 cells express high levels of TGF-β1, which is a profibrotic cytokine, in IPF either scenario would inhibit the proper re-epithelialization of these injured areas, causing more fibrosis (Kapanci, Y., et al., Am. J. Respir. Crit. Care Med. 152:2163-2169, 1995; Khalil, N., et al., Am. 1. Respir. Cell Mol. Biol. 5: 155-162, 1991). This process could go unchecked and eventually lead to massive changes in tissue architecture, eventual tissue destruction, and loss of lung function.

Connective tissue growth factor (CTGF) is a 36 to 38 kD cysteine-rich peptide containing 349 amino acids. It belongs to the CCN (CTGF, cyr 61/cef 10, nov) family of growth factors. The gene for CTGF was originally cloned from a human umbilical endothelial cell cDNA library. CTGF has been detected in endothelial cells, fibroblasts, cartilaginous cells, smooth muscle cells, and some cancer cell lines. Earlier studies revealed that TGF-β1 increases CTGF mRNA markedly in human foreskin fibroblasts. PDGF, EGF, and FGF were also shown to induce CTGF expression, but their effects were only transient and weak.

Connective tissue growth factor has diverse bioactivities. Depending on cell types, CTGF was shown to trigger mitogenesis, chemotaxis, ECM production, apoptosis, and angiogenesis. In earlier studies, CTGF was noted to have mitogenic and chemotactic effects on fibroblasts. CTGF was also reported to enhance the mRNA expression of α1(I) collagen, fibronectin, and as integrin in fibroblasts. The finding that TGF-β increases CTGF synthesis and that TGF-β and CTGF share many functions is consistent with the hypothesis that CTGF is a downstream mediator of TGF-β.

The mechanism by which CTGF exerts its effects on cells, especially its signal transduction, is still unclear. CTGF was reported to bind to the surface of fibroblasts with high affinity, and this binding was competed with recombinant PDGF BB. This suggests that CTGF binds to a certain class of PDGF receptors, or that there is some cross reactivity of PDGF BB with CTGF receptors.

Connective tissue growth factor mRNA has been detected in fibroblasts of sclerotic lesions of patients with systemic sclerosis. In patients with localized scleroderma, CTGF mRNA was detected in fibroblasts in tissues from sclerotic stage more than the inflammatory stage, which suggests a close correlation between CTGF and fibrosis. Similar results were also obtained in keloid and other fibrotic diseases. Subsequently, expression of CTGF has been reported in a variety of fibrosis, such as liver fibrosis, pulmonary fibrosis, and heart fibrosis.

CTGF is also implicated in dermal fibrosis of scleroderma. However, the detailed role of CTGF in fibrosis is still unclear. Further studies are needed to clarify this point.

The CCN family comprises cysteine-rich 61 (CYR61/CCN1), connective tissue growth factor (CTGF/CCN2), nephroblastoma overexpressed (NOV/CCN3), and Wnt-induced secreted proteins-1 (WISP-1/CCN4), -2 (WISP-2/CCN5) and -3 (WISP-3/CCN6). These proteins stimulate mitosis, adhesion, apoptosis, extracellular matrix production, growth arrest and migration of multiple cell types. Many of these activities probably occur through the ability of CCN proteins to bind and activate cell surface integrins.

Connective tissue growth factor (CTGF) has been identified as a potential target of Wnt and BMP signaling. It has been confirmed by microarray results, and demonstrated that CTGF was up-regulated at the early stage of B:MP9 and Wnt3A stimulations and that Wnt3A-regulated CTGF expression was β-catenin-dependent.

Each of the above conditions can benefit from treatment with one or more compounds of the present invention. Each of the types of fibrosis described above can be treated with one or more compounds of the present invention.

The following non-limiting examples illustrate the compounds, compositions, and methods of use of this invention.

EXAMPLES

The present invention will be further specifically explained with reference to examples. However, the scope of the present invention is not limited to the following examples. In the examples, for thin layer chromatography (TLC), Precoated Silica Gel 60 F254 (produced by Merck, product number: 5715-1M) was used. After development with chloroform:methanol (1:0 to 1:1) or ethyl acetate:hexane (1:0 to 0:1), spots were observed by UV irradiation (254 nm) or color development with ninhydrine or phosphomoribdic acid solution in ethanol. For drying organic solvent, anhydrous magnesium sulfate or anhydrous sodium sulfate was used. As for column chromatography, the indication of "Buch" means use of Buch sepacore preparative chromatography system (produced by Buch), and one or several columns selected from cartridge columns Si6M-12× 75 mm, 12×150 mm, 40×75 mm and 40×150 mm produced by the same manufacturer depending on the amount of sample. As for column chromatography, the indication of "Purif" means use of Moritex Purif preparative chromatography system (produced by Moritex), and one or several columns selected from cartridge columns 20, 35, 60, 200 and 400 produced by the same manufacturer were used depending on the amount of sample. For flash column chromatography, Silica gel 60N (spherical shape, neutral, 40 to 100 μm, produced by Kanto Chemicals) was used. Preparative thin layer chromatography (hereinafter abbreviated as "PTLC") was performed by using one or several plates of PLC Plate Silica Gel 60 F254 (20×20 cm, thickness: 2 mm, concentration zone: 4 cm, produced by Merck, product number: 13793-1M) were used depending on the amount of sample.

The indication of "LCMS" means that mass spectrum was measured by liquid chromatography-mass spectrometry (LC/MS). Platform-LC type mass spectrometry apparatus ZQ2000 (produced by Micromass) was used as the mass spectrometer, and the measurement was performed by the electrospray ionization (ESI) method. As a liquid chromatography apparatus, an apparatus produced by waters was used. As a separation column, Develosil C30-UG-5 (50×4.6 mm, Nomura Kagaku Co., Ltd.) for method "A" or Agilent ZOBAX SB-C (2.1×50 mm, Agilent) in the tables mentioned below was used. Elution was performed at a flow rate of 1 ml/minute, and Solution A=water [containing 0.1% (v/v) formic acid] and Solution B=acetonitrile [containing 0.1% (v/v) formic acid] for method "A" were used as solvents.

In the tables mentioned below, data indicated by "RT" mean data of liquid chromatography retention time. In the columns of "Mass", data of mass spectrometry were shown (the indication "N.D" means that no molecular ion peak was detected). In the columns of "method", elution conditions of the liquid chromatography are described. For the indication of retention time in the liquid chromatography, the indication "A" for elution condition means that measurement was performed by elution with a linear gradient of 5 to 100% (v/v) Solution B from 0 minute to 5 minutes and then with 100% Solution B until 6 minutes.

In the tables, the compounds having inhibitory activity more than 50% at the concentration of 10 microM (μM) determined by reporter gene assay are shown below.

Reporter Gene Assay

Screening for inhibitory action of the Wnt signaling pathway was carried out according to the following procedure using the stably transfected cell line Hek-293, STF1.1
Growth Medium: DMEM, 10% FBS, Pen-Strep, supplemented with 400 μg/mL G418 to maintain selection of SuperTOPFLASH driven Luciferase gene
1. On the day prior to assay, split cells into a white opaque 96-well plate at 20,000 cells per well in 200 μl of complete growth medium
2. Incubate the plate overnight at 37° C., 5% $CO_2$ and allow the cells to attach
3. Next day, prepare the inhibitors to be tested in complete growth medium, without G418, at 2× the desired final concentration (all conditions are done in duplicates)
4. Carefully remove the old medium from each well using a multiple pipettor
5. Add 50 μl of fresh growth medium (without G148) containing the inhibitor to each well
6. Be sure to include 2 wells containing medium only, 2 wells for stimulation control, 2 wells for DMSO control, and wells for the positive control ICG-001 (2, 5, and 10 micromolar)
7. Once all inhibitors and controls are added, incubate the plate for 1 hour at 37° C., 5% $CO_2$
8. While plate is incubating, prepare fresh 20 mM LiCl in complete growth medium (without G418)
9. After 1 hour, remove plate from incubator and add 50 μl of the medium containing 20 mM LiCl to each well, except for the two wells of the unstimulated control (add 50 μl of just complete medium)
10. Incubate the plate for 24 hours at 37° C., 5% $CO_2$
11. After 24 hours, add 100 μl of BrightGlo (Promega, Cat. #: G7573) to each well
12. Shake plate for 5 minutes to ensure complete lysis
13. Read plate on the Packard TopCount Many compounds of the Examples showed inhibitory activity. For example, the compounds of Examples I-2, I-253, I-254, I-255, I-257, I-259 and I-260 showed inhibitory activity of not less than 1% not more than 50% less than 50% at the concentration of 10 μM. In addition, the compounds of Examples I-4, I-250, I-251, I-252, I-261, I-262, I-268, I-270 and I-271 showed excellent inhibitory activity of not less than 50% at the concentration of 10 μM.

Example XXXVIII-1

Synthesis of (S)-benzyl 1-(methoxy(methyl)amino)-1-oxopropan-2-ylcarbamate (Compound XXXVIII-1)

To a solution of N-methoxy-N-methylamine hydrochloride 21.95 g (225 mmol) in 1N sodium hydroxide 225 ml, a solution of (S)-2-(benzyloxycarbonylamino)propanoic acid 33.48 g (150 mmol) and 4-(4,6-dimethoxy-1,3,5-triazin-2-yl)-4-methylmorpholinium chloride 62.26 g (225 mmol) in acetonitrile 225 ml was added and the mixture was stirred at room temperature for 2 hours. The reaction mixture was concentrated in vacuo and the residue was diluted with ethyl acetate 600 ml and washed with water 300 ml and brine 300 ml. The organic phase was dried over magnesium sulfate and filtered and the mother solution was concentrated in vacuo to obtain the title compound 42 g (93%).

Example XX-1

Synthesis of (S)-benzyl 1,1-diethoxypropan-2-ylcarbamate (Compound XX-1)

To a solution of (S)-benzyl 1-(methoxy(methyl)amino)-1-oxopropan-2-ylcarbamate (Compound XXXVIII-1) 5.33 g (20.0 mmol) in tetrahydrofuran 40 ml, a 2M solution of lithium aluminum hydride in tetrahydrofuran 10 ml was added at 0° C. for 0.5 hr. The resulting solution was stirred at room temperature for 2 hours. The reaction mixture was cooled to 0° C. and saturated ammonium chloride aq. 10 ml was added drop wisely. The precipitate was filtered on celite and washed with methanol 50 ml. The mother solution was concentrated in vacuo and the residue was diluted with ethyl acetate 200 ml and washed with water 100 ml and brine 100 ml. The organic phase was dried over magnesium sulfate and filtered and the mother solution was concentrated in vacuo. The residue was diluted in ethanol 50 ml and the mixture was added to 4N hydrochloric acid in dioxane 0.25 ml. The reaction mixture was refluxed for 18 hours and concentrated in vacuo. The residue was diluted with ethyl acetate 200 ml and washed with saturated sodium bicarbonate 200 ml and brine 200 ml. The organic phase was dried over magnesium sulfate and filtered and the mother solution was concentrated in vacuo. The residue was purified on silica gel column chromatography (n-hexane:ethyl acetate=100:0 to 80:20) to obtain the title compound 3.55 g (63%, 2 steps).

Example XIV-1

Synthesis of (S)-1,1-diethoxypropan-2-amine (Compound XIV-1)

To a solution of (S)-benzyl 1,1-diethoxypropan-2-ylcarbamate (Compound XX-1) 844 mg (3.00 mmol) in methanol 50 ml, 5% palladium on carbon 30 mg was added and the mixture was stirred at room temperature for 2 hours under hydrogen atmosphere. The reaction mixture was filtered on celite and washed with methanol 200 ml and the mother solution was concentrated in vacuo to obtain the title compound 442 mg (100%).

Example IV-1

Synthesis of N-benzyl-2,2-diethoxyethanamine (Compound IV-1)

A solution of benzaldehyde 5.1 ml (50.0 mmol) in 2,2-diethoxyethanamine 10.9 ml (75.0 mmol) was stirred at room temperature for 0.5 hour. The reaction mixture was diluted with tetrahydrofuran 450 ml and triacetoxyborohydride 32.0 g (150 mmol) was added and the mixture was stirred overnight. The reaction mixture was diluted with ethyl acetate 500 ml and washed with saturated sodium bicarbonate 500 ml, water 500 ml and brine 500 ml. The organic phase was dried over magnesium sulfate and filtered. The filtrate was concentrated in vacuo and the residue was purified on silica gel column chromatography (n-hexane:ethyl acetate=70:30 to 50:50) to obtain the title compound 7.8 g (yield 70%).

The following compounds shown in Table I were obtained by a similar method to described above.

TABLE I

| Example No. | structure | chemical name | yield (%) |
|---|---|---|---|
| IV-2 | EtO-CH(OEt)-CH2-NH-CH2-(naphthalen-1-yl) | 2,2-diethoxy-N-(naphthalen-1-ylmethyl)ethanamine | 68 |
| IV-3 | EtO-CH(OEt)-CH2-NH-CH2-(quinolin-8-yl) | 2,2-diethoxy-N-(quinolin-8-ylmethyl)ethanamine | 100 |
| IV-4 | EtO-CH(OEt)-CH2-NH-CH2-(benzo[b]thiophen-3-yl) | N-(benzo[b]thiophen-3-ylmethyl)-2,2-diethoxyethanamine | 86 |
| IV-5 | EtO-CH(OEt)-CH2-NH-CH2-(pyridin-4-yl) | 2,2-diethoxy-N-(pyridin-4-ylmethyl)ethanamine | 44 |
| IV-6 | EtO-CH(OEt)-CH2-NH-CH2-(2,4-difluorophenyl) | N-(2,4-difluorobenzyl)-2,2-diethoxyethanamine | 36 |

Example IV-7

Synthesis of N-(2,2-diethoxyethyl)-3-methylbutan-1-amine (Compound IV-7)

To a solution of 2,2-diethoxyethanamine 2.91 ml (20 mmol) in acetonitrile 50 ml, potassium carbonate 2.0 g (15 mmol) and a solution of isoamylbromide 1.26 ml (10 mmol) in acetonitrile 20 ml were added and the mixture was stirred at 65° C. overnight. The reaction mixture was concentrated in vacuo and the residue was diluted with ethyl acetate 100 ml and washed with water 100 ml and brine 100 ml. The organic phase was dried over magnesium sulfate and filtered. The filtrate was concentrated in vacuo and the residue was purified on Bach silica gel column chromatography (n-hexane:ethyl acetate=90:10 to 80:20) to obtain the title compound 1.57 g (77%).

The following compounds shown in Table II were obtained by a similar method to described above.

TABLE II

| Example No. | structure | chemical name | yield (%) |
|---|---|---|---|
| IV-8 | EtO-CH(OEt)-CH2-NH-CH2CH2-Ph | 2,2-diethoxy-N-phenethylethanamine | 94 |
| IV-9 | EtO-CH(OEt)-CH2-NH-CH2CH2CH2-Ph | N-(2,2-diethoxyethyl)-3-phenylpropan-1-amine | 27 |
| IV-10 | EtO-CH(OEt)-CH2-NH-CH2CH2-CH(Ph)2 | N-(2,2-diethoxyethyl)-3,3-diphenylpropan-1-amine | 61 |
| IV-11 | EtO-CH(OEt)-CH2-NH-CH2-(naphthalen-2-yl) | 2,2-diethoxy-N-(naphthalen-2-ylmethyl)ethanamine | 78 |
| IV-12 | EtO-CH(OEt)-CH2-NH-CH2-(2-(Boc-amino)benzo[d]thiazol-4-yl) | tert-butyl 4-((2,2-diethoxyethylamino)methyl)benzo[d]thiazol-2-ylcarbamate | 85 |

Example IV-13

Synthesis of (R)-2,2-diethoxy-N-(1-phenylethyl)ethanamine (Compound IV-13)

To a solution of (R)-(+)-1-phenylethylamine 66.6 g (550 mmol) in acetonitrile 300 ml, 2-bromo-1,1-diethoxyethane 41.3 ml (270 mmol) and potassium carbonate 70.7 g (405 mmol) were added and the mixture was stirred at room temperature overnight. The reaction mixture was concentrated in vacuo and the residue was diluted with ethyl acetate 300 ml and washed with water 500 ml and brine 500 ml. The organic phase was dried with magnesium sulfate and filtered. The filtrate was concentrated in vacuo and the residue was purified on silica gel column chromatography (n-hexane:ethyl acetate=5:1 and 1:1) to obtain the title compound 46.0 g (70%).

The following compound shown in Table III was obtained by a similar method to that described above.

TABLE III

| Example No. | structure | chemical name | yield (%) |
|---|---|---|---|
| IV-14 | EtO-CH(OEt)-CH2-NH-CH2-(pyridin-2-yl) | 2,2-diethoxy-N-(pyridin-2-ylmethyl)ethanamine | 65 |

Example IV-15

Synthesis of
(S)—N-benzyl-1,1-diethoxypropan-2-amine
(Compound IV-15)

To a solution of (S)-1,1-diethoxypropan-2-amine (Compound XIV-1) 682 mg (3.55 mmol) in tetrahydrofuran 2 ml, benzaldehyde 337 mg (3.55 mmol) was added and the mixture was stirred at room temperature for 0.5 hour. The reaction mixture was diluted with tetrahydrofuran 3 ml and sodium triacetoxyborohydride 829 mg (3.91 mmol) was added and the mixture was stirred at room temperature for 18 hours. The reaction mixture was diluted with ethyl acetate 50 ml and washed with saturated sodium bicarbonate aq. 50 ml twice, water 50 ml twice and brine 50 ml twice. The organic phase was dried over magnesium sulfate and filtered and the mother solution was concentrated in vacuo to obtain the title compound 826 mg (98%).

The following compounds shown in Table IV were obtained by a similar method to that described above.

TABLE IV

| Example No. | structure | chemical name | yield (%) |
|---|---|---|---|
| IV-16 | 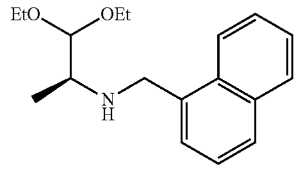 [SMILES: CCOC(OCC)[C@H](C)NCc1cccc2ccccc12] | (S)-1,1-diethoxy-N-(naphthalen-1-ylmethyl)propan-2-amine | 67 |
| IV-17 | 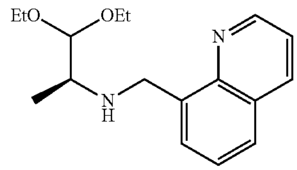 [SMILES: CCOC(OCC)[C@H](C)NCc1cccc2cccnc12] | (S)-1,1-diethoxy-N-(quinolin-8-ylmethyl)propan-2-amine | 91 |
| IV-18 | 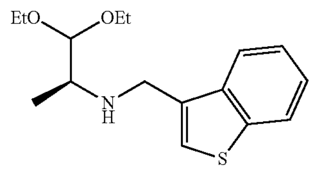 [SMILES: CCOC(OCC)[C@H](C)NCc1csc2ccccc12] | (S)-N-(benzo[b]thiophen-3-ylmethyl)-1,1-diethoxypropan-2-amine | 97 |

Example XV-1

Synthesis of (S)-(9H-fluoren-9-yl)methyl 1-(benzyl (2,2-diethoxyethyl)amino)-1-oxopropan-2-ylcarbamate (Compound XV-1)

To a solution of (S)-2-(((9H-fluoren-9-yl)methoxy)carbonylamino)propanoic acid 1.98 g (6.0 mmol), a solution of 1-hydroxybenzotriazol 1.01 g (7.5 mmol) and 1-ethyl-3-(3-dimethylaminopropyl)carbodiimide 1.44 g (7.5 mmol) in dichloromethane 20 ml, and a solution of N-benzyl-2,2-diethoxyethanamine (Compound IV-1) 1.12 g (5.0 mmol) and 4-dimethylaminopyridine 61 mg (0.5 mmol) in dichloromethane 5 ml were added and the mixture was stirred at room temperature overnight. The reaction mixture was diluted with ethyl acetate 20 ml and washed with saturated aqueous sodium bicarbonate 20 ml, water 20 ml and brine 20 ml. The organic phase was dried over magnesium sulfate and filtered. The filtrate was concentrated in vacuo and the residue was purified on silica gel column chromatography (n-hexane:ethyl acetate=90:10 to 70:30) to obtain the title compound 1.1 g (yield 42%).

The following compounds shown in Tables V-1 to V-4 were obtained by a similar method to that described above. In the Tables, "Int_1" means an intermediate compound number and "Int_X" is corresponding to carboxylic acid.

TABLE V-1

| Example No. | chemical name | yield (%) | Int_1 | Int_X |
|---|---|---|---|---|
| XV-2 | (S)-(9H-fluoren-9-yl)methyl 1-(benzyl(2,2-diethoxyethyl)amino)-3-(4-tert-butoxyphenyl)-1-oxopropan-2-ylcarbamate | 85 | IV-1 | Fmoc-Tyr(tBu)-OH |
| XV-3 | N-Benzyl-N-(2,2-dimethoxyethyl)-6-(tert-butoxycarbonylamino)-2-(S)-(9H-fluoren-9-yl)methoxycarbonylaminohexamide | 84 | IV-1 | Fmoc-Lys(Boc)-OH |
| XV-4 | (S)-(9H-fluoren-9-yl)methyl 3-(4-tert-butoxyphenyl)-1-((2,2-diethoxyethyl)(naphthalen-1-ylmethyl)amino)-1-oxopropan-2-ylcarbamate | 55 | IV-2 | Fmoc-Tyr(tBu)-OH |
| XV-5 | (S)-tert-butyl 3-(((9H-fluoren-9-yl)methoxy)carbonylamino)-4-((2,2-diethoxyethyl)(naphthalen-1-ylmethyl)amino)-4-oxobutanoate | 44 | IV-2 | Fmoc-Asp(OtBu)-OH |
| XV-6 | (S)-(9H-fluoren-9-yl)methyl 3-(4-tert-butoxyphenyl)-1-((2,2-diethoxyethyl)(quinolin-8-ylmethyl)amino)-1-oxopropan-2-ylcarbamate | 80 | IV-3 | Fmoc-Tyr(tBu)-OH |
| XV-7 | (S)-(9H-fluoren-9-yl)methyl 1-((2,2-diethoxyethyl)(quinolin-8-ylmethyl)amino)-1,4-dioxo-4-(tritylamino)butan-2-ylcarbamate | 31 | IV-3 | Fmoc-Asn(Trt)-OH |
| XV-8 | (S)-(9H-fluoren-9-yl)methyl 1-((benzo[b]thiophen-3-ylmethyl)(2,2-diethoxyethyl)amino)-1-oxopropan-2-ylcarbamate | 66 | IV-4 | Fmoc-Ala-OH |
| XV-9 | (S)-(9H-fluoren-9-yl)methyl 1-((benzo[b]thiophen-3-ylmethyl)(2,2-diethoxyethyl)amino)-3-(4-tert-butoxyphenyl)-1-oxopropan-2-ylcarbamate | 71 | IV-4 | Fmoc-Tyr(tBu)-OH |
| XV-10 | (S)-(9H-fluoren-9-yl)methyl 1-((2,2-diethoxyethyl)(isopentyl)amino)-1-oxopropan-2-ylcarbamate | 71 | IV-7 | Fmoc-Ala-OH |
| XV-11 | (S)-(9H-fluoren-9-yl)methyl 3-(4-tert-butoxyphenyl)-1-((2,2-diethoxyethyl)(isopentyl)amino)-1-oxopropan-2-ylcarbamate | 64 | IV-7 | Fmoc-Tyr(tBu)-OH |
| XV-12 | (S)-(9H-fluoren-9-yl)methyl 6-(tert-butoxycarbonylamino)-1-((2,2-diethoxyethyl)(isopentyl)amino)-1-oxohexan-2-ylcarbamate | 65 | IV-7 | Fmoc-Lys(Boc)-OH |
| XV-13 | (S)-tert-butyl 3-(((9H-fluoren-9-yl)methyl9H-fluoren-9-yl)methoxy)carbonylamino)-4-((2,2-diethoxyethyl)(isopentyl)amino)-4-oxobutanoate | 65 | IV-7 | Fmoc-Asp(OtBu)-OH |
| XV-14 | (S)-(9H-fluoren-9-yl)methyl 1-((2,2-diethoxyethyl)(isopentyl)amino)-1,4-dioxo-4-(tritylamino)butan-2-ylcarbamate | 65 | IV-7 | Fmoc-Asn(Trt)-OH |
| XV-15 | (S)-(9H-fluoren-9-yl)methyl 3-tert-butoxy-1-((2,2-diethoxyethyl)(isopentyl)amino)-1-oxopropan-2-ylcarbamate | 75 | IV-7 | Fmoc-Ser(tBu)-OH |
| XV-16 | (S)-(9H-fluoren-9-yl)methyl 1-((2,2-diethoxyethyl)(isopentyl)amino)-4-methyl-1-oxopentan-2-ylcarbamate | 69 | IV-7 | Fmoc-Leu-OH |

TABLE V-2

| Example No. | chemical name | yield (%) | Int_1 | Int_X |
|---|---|---|---|---|
| XV-17 | (S)-(9H-fluoren-9-yl)methyl 2-((2,2-diethoxyethyl)(isopentyl)amino)-2-oxo-1-phenylethylcarbamate | 62 | IV-7 | Fmoc-Phg-OH |
| XV-18 | (S)-(9H-fluoren-9-yl)methyl 1-((2,2-diethoxyethyl)(isopentyl)amino)-1-oxo-3-phenylpropan-2-ylcarbamate | 76 | IV-7 | Fmoc-Phe-OH |
| XV-19 | (S)-(9H-fluoren-9-yl)methyl 1-((2,2-diethoxyethyl)(isopentyl)amino)-1-oxo-4-phenylbutan-2-ylcarbamate | 75 | IV-7 | Fmoc-Hph-OH |
| XV-20 | (S)-(9H-fluoren-9-yl)methyl 3-(benzyloxy)-1-((2,2-diethoxyethyl)(isopentyl)amino)-1-oxopropan-2-ylcarbamate | 57 | IV-7 | Fmoc-Ser(Bzl)-OH |
| XV-21 | (S)-(9H-fluoren-9-yl)methyl 1-((2,2-diethoxyethyl)(isopentyl)amino)-3-(naphthalen-1-yl)-1-oxopropan-2-ylcarbamate | 61 | IV-7 | Fmoc-Ala(1-Naph)-OH |
| XV-22 | (S)-(9H-fluoren-9-yl)methyl 1-((2,2-diethoxyethyl)(isopentyl)amino)-3-(naphthalen-2-yl)-1-oxopropan-2-ylcarbamate | 53 | IV-7 | Fmoc-Ala(2-Naph)-OH |
| XV-23 | (S)-(9H-fluoren-9-yl)methyl 1-((2,2-diethoxyethyl)(phenethyl)amino)-1-oxopropan-2-ylcarbamate | 45 | IV-8 | Fmoc-Ala-OH |
| XV-24 | (S)-(9H-fluoren-9-yl)methyl 3-(4-tert-butoxyphenyl)-1-((2,2-diethoxyethyl)(phenethyl)amino)-1-oxopropan-2-ylcarbamate | 68 | IV-8 | Fmoc-Tyr(tBu)-OH |
| XV-25 | (S)-(9H-fluoren-9-yl)methyl 6-(tert-butoxycarbonylamino)-1-((2,2-diethoxyethyl)(phenethyl)amino)-1-oxohexan-2-ylcarbamate | 72 | IV-8 | Fmoc-Lys(Boc)-OH |
| XV-26 | (S)-tert-butyl 3-((((9H-fluoren-9-yl)methyl9H-fluoren-9-yl)methoxy)carbonylamino)-4-((2,2-diethoxyethyl)(phenethyl)amino)-4-oxobutanoate | 57 | IV-8 | Fmoc-Asp(OtBu)-OH |

TABLE V-2-continued

| Example No. | chemical name | yield (%) | Int_1 | Int_X |
|---|---|---|---|---|
| XV-27 | (S)-(9H-fluoren-9-yl)methyl 1-((2,2-diethoxyethyl)(phenethyl)amino)-1,4-dioxo-4-(tritylamino)butan-2-ylcarbamate | 50 | IV-8 | Fmoc-Asn(Trt)-OH |
| XV-28 | (S)-(9H-fluoren-9-yl)methyl 3-tert-butoxy-1-((2,2-diethoxyethyl)(phenethyl)amino)-1-oxopropan-2-ylcarbamate | 79 | IV-8 | Fmoc-Ser(tBu)-OH |
| XV-29 | (S)-(9H-fluoren-9-yl)methyl 1-((2,2-diethoxyethyl)(phenethyl)amino)-4-methyl-1-oxopentan-2-ylcarbamate | 79 | IV-8 | Fmoc-Leu-OH |
| XV-30 | (S)-(9H-fluoren-9-yl)methyl 1-((2,2-diethoxyethyl)(phenethyl)amino)-1-oxo-4-phenylbutan-2-ylcarbamate | 65 | IV-8 | Fmoc-Hph-OH |
| XV-31 | (S)-(9H-fluoren-9-yl)methyl 3-(benzyloxy)-1-((2,2-diethoxyethyl)(3-phenylpropyl)amino)-1-oxopropan-2-ylcarbamate | 61 | IV-9 | Fmoc-Ser(Bzl)-OH |

TABLE V-3

| Example No. | chemical name | yield (%) | Int_1 | Int_X |
|---|---|---|---|---|
| XV-32 | (S)-(9H-fluoren-9-yl)methyl 1-((2,2-diethoxyethyl)(3-phenylpropyl)amino)-3-(naphthalen-1-yl)-1-oxopropan-2-ylcarbamate | 65 | IV-9 | Cbz-Ala(1-Naph)-OH |
| XV-33 | (S)-(9H-fluoren-9-yl)methyl 1-((2,2-diethoxyethyl)(3-phenylpropyl)amino)-3-(naphthalen-2-yl)-1-oxopropan-2-ylcarbamate | 84 | IV-9 | Cbz-Ala(2-Naph)-OH |
| XV-34 | (S)-(9H-fluoren-9-yl)methyl 1-((2,2-diethoxyethyl)(3,3-diphenylpropyl)amino)-1-oxopropan-2-ylcarbamate | 82 | IV-10 | Fmoc-Ala-OH |
| XV-35 | (S)-(9H-fluoren-9-yl)methyl 3-(4-tert-butoxyphenyl)-1-((2,2-diethoxyethyl)(3,3-diphenylpropyl)amino)-1-oxopropan-2-ylcarbamate | 77 | IV-10 | Fmoc-Tyr(tBu)-OH |
| XV-36 | (S)-(9H-fluoren-9-yl)methyl 6-(tert-butoxycarbonylamino)-1-((2,2-diethoxyethyl)(3,3-diphenylpropyl)amino)-1-oxohexan-2-ylcarbamate | 63 | IV-10 | Fmoc-Lys(Boc)-OH |
| XV-37 | (S)-tert-butyl 3-((((9H-fluoren-9-yl)methyl9H-fluoren-9-yl)methoxy)carbonylamino)-4-((2,2-diethoxyethyl)(3,3-diphenylpropyl)amino)-4-oxobutanoate | 71 | IV-10 | Fmoc-Asp(OtBu)-OH |
| XV-38 | (S)-(9H-fluoren-9-yl)methyl 1-((2,2-diethoxyethyl)(3,3-diphenylpropyl)amino)-1,4-dioxo-4-(tritylamino)butan-2-ylcarbamate | 68 | IV-10 | Fmoc-Asn(Trt)-OH |
| XV-39 | (S)-(9H-fluoren-9-yl)methyl 1-((2,2-diethoxyethyl)(3,3-diphenylpropyl)amino)-4-methyl-1-oxopentan-2-ylcarbamate | 84 | IV-10 | Fmoc-Leu-OH |
| XV-40 | (S)-(9H-fluoren-9-yl)methyl 2((2,2-diethoxyethyl)(3,3-diphenylpropyl)amino)-2-oxo-1-phenylethylcarbamate | 90 | IV-10 | Fmoc-Phg-OH |
| XV-41 | (S)-(9H-fluoren-9-yl)methyl 1-((2,2-diethoxyethyl)(3,3-diphenylpropyl)amino)-1-oxo-3-phenylpropan-2-ylcarbamate | 88 | IV-10 | Fmoc-Phe-OH |
| XV-42 | (S)-(9H-fluoren-9-yl)methyl 3-(benzyloxy)-1-((2,2-diethoxyethyl)(3,3-diphenylpropyl)amino)-1-oxopropan-2-ylcarbamate | 89 | IV-10 | Fmoc-Ser(Bzl)-OH |
| XV-43 | (S)-(9H-fluoren-9-yl)methyl 1-((2,2-diethoxyethyl)(3,3-diphenylpropyl)amino)-3-(naphthalen-1-yl)-1-oxopropan-2-ylcarbamate | 89 | IV-10 | Fmoc-Ala(1-Naph)-OH |
| XV-44 | (S)-(9H-fluoren-9-yl)methyl 1-((2,2-diethoxyethyl)(3,3-diphenylpropyl)amino)-3-(naphthalen-2-yl)-1-oxopropan-2-ylcarbamate | 91 | IV-10 | Fmoc-Ala(2-Naph)-OH |
| XV-45 | (S)-(9H-fluoren-9-yl)methyl 1-((2,2-diethoxyethyl)(naphthalen-2-ylmethyl)amino)-1-oxopropan-2-ylcarbamate | 92 | IV-11 | Fmoc-Ala-OH |
| XV-46 | (S)-(9H-fluoren-9-yl)methyl 3-(4-tert-butoxyphenyl)-1((2,2-diethoxyethyl)(naphthalen-2-ylmethyl)amino)-1-oxopropan-2-ylcarbamate | 85 | IV-11 | Fmoc-Tyr(tBu)-OH |

TABLE V-4

| Example No. | chemical name | yield (%) | Int_1 | Int_X |
|---|---|---|---|---|
| XV-47 | (S)-(9H-fluoren-9-yl)methyl 6-(tert-butoxycarbonylamino)-1-((2,2-diethoxyethyl)(naphthalen-2-ylmethyl)amino)-1-oxohexan-2-ylcarbamate | 76 | IV-11 | Fmoc-Lys(Boc)-OH |

TABLE V-4-continued

| Example No. | chemical name | yield (%) | Int_1 | Int_X |
|---|---|---|---|---|
| XV-48 | (S)-tert-butyl 3-((((9H-fluoren-9-yl)methyl9H-fluoren-9-yl)methoxy)carbonylamino)-4-((2,2-diethoxyethyl)(naphthalen-2-ylmethyl)amino)-4-oxobutanoate | 74 | IV-11 | Fmoc-Asp(OtBu)-OH |
| XV-49 | (S)-(9H-fluoren-9-yl)methyl 1-((2,2-diethoxyethyl)(naphthalen-2-ylmethyl)amino)-1,4-dioxo-4-(tritylamino)butan-2-ylcarbamate | 67 | IV-11 | Fmoc-Asn(Trt)-OH |
| XV-50 | (S)-(9H-fluoren-9-yl)methyl 3-tert-butoxy-1-((2,2-diethoxyethyl)(naphthalen-2-ylmethyl)amino)-1-oxopropan-2-ylcarbamate | 75 | IV-11 | Fmoc-Ser(tBu)-OH |
| XV-51 | (S)-(9H-fluoren-9-yl)methyl 1-((2,2-diethoxyethyl)(naphthalen-2-ylmethyl)amino)-4-methyl-1-oxopentan-2-ylcarbamate | 77 | IV-11 | Fmoc-Leu-OH |
| XV-52 | (S)-(9H-fluoren-9-yl)methyl 2-((2,2-diethoxyethyl)(naphthalen-2-ylmethyl)amino)-2-oxo-1-phenylethylcarbamate | 82 | IV-11 | Fmoc-Phg-OH |
| XV-53 | (S)-(9H-fluoren-9-yl)methyl 1-((2,2-diethoxyethyl)(naphthalen-2-ylmethyl)amino)-1-oxo-3-phenylpropan-2-ylcarbamate | 86 | IV-11 | Fmoc-Phe-OH |
| XV-54 | (S)-(9H-fluoren-9-yl)methyl 1-((2,2-diethoxyethyl)(naphthalen-2-ylmethyl)amino)-1-oxo-4-phenylbutan-2-ylcarbamate | 79 | IV-11 | Fmoc-Hph-OH |
| XV-55 | (S)-tert-butyl 4-((2-(9H-fluoren-9-yl) methoxycarbonylamino-3-(4-tert-butoxyphenyl)-N-(2,2-diethoxyethyl)propanamido)methyl)benzo[d]thiazol-2-ylcarbamate | 100 | IV 12 | Fmoc-Tyr(tBu)-OH |
| XV-56 | (9H-fluoren-9-yl)methyl (S)-3-(4-tert-butoxyphenyl)-1-((2,2-diethoxyethyl)((R)-1-phenylethyl)amino)-1-oxopropan-2-ylcarbamate | 87 | IV-13 | Fmoc-Tyr(tBu)-OH |
| XV-57 | (S)-(9H-fluoren-9-yl)methyl 3-(4-tert-butoxyphenyl)-1-((2,2-diethoxyethyl)(pyridin-4-ylmethyl)amino)-1-oxopropan-2-ylcarbamate | 76 | IV-5 | Fmoc-Tyr(tBu)-OH |
| XV-58 | (S)-(9H-fluoren-9-yl)methyl 3-(4-tert-butoxyphenyl)-1-((2,2-diethoxyethyl)(pyridin-2-ylmethyl)amino)-1-oxopropan-2-ylcarbamate | 90 | IV-14 | Fmoc-Tyr(tBu)-OH |
| XV-59 | (S)-(9H-fluoren-9-yl)methyl 3-(4-tert-butoxyphenyl)-1-((2,2-diethoxyethyl)(2,4-difluorobenzyl)amino)-1-oxopropan-2-ylcarbamate | 36 | IV-6 | Fmoc-Tyr(tBu)-OH |

Example XV-60

Synthesis of (9H-fluoren-9-yl)methyl (S)-1-((S)-(1,1-diethoxypropan-2-yl)(benzyl)amino)-1-oxopropan-2-ylcarbamate (Compound XV-60)

To a solution of (S)-2-(((9H-fluoren-9-yl)methoxy)carbonylamino)propanoic acid 68 mg (0.22 mmol) and O-(7-azabenzotriazol-1-yl)-1,1,3,3-tetramethyluronium hexafluorophosphate 84 mg (0.22 mmol) in dichloromethane 1 ml, a solution of (S)—N-benzyl-1,1-diethoxypropan-2-amine (Compound IV-15) 47 mg (0.2 mmol) and N,N'-diisopropylethylamine 38 ml (0.22 mmol) in dichloromethane 1 ml was added and the mixture was stirred at room temperature overnight. The reaction mixture was diluted with ethyl acetate 50 ml and washed with saturated aqueous sodium bicarbonate 50 ml, water 50 ml and brine 50 ml. The organic phase was dried over magnesium sulfate and filtered. The filtrate was concentrated in vacuo and the residue was purified on silica gel column chromatography (n-hexane: ethyl acetate=9:1 to 7:3) to obtain the title compound 48 mg (45%).

The following compounds shown in Table VI were obtained by a similar method to that described above. In the Table, "Int_1" means an intermediate compound number and "Int_X" is corresponding to carboxylic acid.

TABLE VI

| Example No. | chemical name | yield (%) | Int_1 | Int_X |
|---|---|---|---|---|
| XV-61 | (9H-fluoren-9-yl)methyl (S)-1-(benzyl((S)-1,1-diethoxypropan-2-yl)amino)-3-(4-tert-butoxyphenyl)-1-oxopropan-2-ylcarbamate | 77 | IV-15 | Fmoc-Tyr(tBu)-OH |
| XV-62 | (S)-tert-butyl 3-(((9H-fluoren-9-yl)methoxy)carbonylamino)-4-(benzyl((S)-1,1-diethoxypropan-2-yl)amino)-4-oxobutanoate | 52 | IV-15 | Fmoc-Asp(OtBu)-OH |
| XV-63 | (9H-fluoren-9-yl)methyl (S)-1-(((S)-1,1-diethoxypropan-2-yl)(naphthalen-1-ylmethyl)amino)-1-oxopropan-2-ylcarbamate | 32 | IV-16 | Fmoc-Ala-OH |
| XV-64 | (9H-fluoren-9-yl)methyl (S)-3-(4-tert-butoxyphenyl)-1-(((S)-1,1-diethoxypropan-2-yl)(naphthalen-1-ylmethyl)amino)-1-oxopropan-2-ylcarbamate | 79 | IV-16 | Fmoc-Tyr(tBu)-OH |
| XV-65 | (9H-fluoren-9-yl)methyl (S)-6-(tert-butoxycarbonylamino)-1-(((S)-1,1-diethoxypropan-2-yl)(naphthalen-1-ylmethyl)amino)-1-oxohexan-2-ylcarbamate | 22 | IV-16 | Fmoc-Lys(Boc)-OH |
| XV-66 | (S)-tert-butyl 3-(((9H-fluoren-9-yl)methoxy)carbonylamino)-4-(((S)-1,1-diethoxypropan-2-yl)(naphthalen-1-ylmethyl)amino)-4-oxobutanoate | 35 | IV-16 | Fmoc-Asp(OtBu)-OH |
| XV-67 | (9H-fluoren-9-yl)methyl (S)-1-(((S)-1,1-diethoxypropan-2-yl)(quinolin-8-ylmethyl)amino)-1-oxopropan-2-ylcarbamate | 42 | IV-17 | Fmoc-Ala-OH |
| XV-68 | (9H-fluoren-9-yl)methyl (S)-3-(4-tert-butoxyphenyl)-1-(((S)-1,1-diethoxypropan-2-yl)(quinolin-8-ylmethyl)amino)-1-oxopropan-2-ylcarbamate | 68 | IV-17 | Fmoc-Tyr(tBu)-OH |

TABLE VI-continued

| Example No. | chemical name | yield (%) | Int_1 | Int_X |
|---|---|---|---|---|
| XV-69 | (9H-fluoren-9-yl)methyl (S)-6-(tert-butoxycarbonylamino)-1-(((S)-1,1-diethoxypropan-2-yl)(quinolin-8-ylmethyl)amino)-1-oxohexan-2-ylcarbamate | 65 | IV-17 | Fmoc-Lys(Boc)-OH |
| XV-70 | (9H-fluoren-9-yl)methyl (S)-1-(((S)-1,1-diethoxypropan-2-yl)(quinolin-8-ylmethyl)amino)-1,4-dioxo-4-(tritylamino)butan-2-ylcarbamate | 44 | IV-17 | Fmoc-Asn(Trt)-OH |
| XV-71 | (9H-fluoren-9-yl)methyl (S)-1-((benzo[b]thiophen-3-ylmethyl)((S)-1,1-diethoxypropan-2-yl)amino)-3-(4-tert-butoxyphenyl)-1-oxopropan-2-ylcarbamate | 61 | IV-18 | Fmoc-Tyr(tBu)-OH |
| XV-72 | (9H-fluoren-9-yl)methyl (S)-6-(tert-butoxycarbonylamino)-1-((benzo[b]thiophen-3-ylmethyl)((S)-1,1-diethoxypropan-2-yl)amino)-1-oxohexan-2-ylcarbamate | 59 | IV-18 | Fmoc-Lys(Boc)-OH |
| XV-73 | (S)-tert-butyl 3-(((9H-fluoren-9-yl)methoxy)carbonylamino)-4-((benzo[b]thiophen-3-ylmethyl)((S)-1,1-diethoxypropan-2-yl)amino)-4-oxobutanoate | 40 | IV-18 | Fmoc-Asp(OtBu)-OH |
| XV-74 | (9H-fluoren-9-yl)methyl (S)-1-((benzo[b]thiophen-3-ylmethyl)((S)-1,1-diethoxypropan-2-yl)amino)-1,4-dioxo-4-(tritylamino)butan-2-ylcarbamate | 35 | IV-18 | Fmoc-Asn(Trt)-OH |

Example VI-1

Synthesis of (S)-2-amino-N-benzyl-N-(2,2-diethoxyethyl)propanamide (Compound VI-1)

To (S)-(9H-fluoren-9-yl)methyl 1-(benzyl(2,2-diethoxyethyl)amino)-1-oxopropan-2-ylcarbamate (Compound XV-1) 1.12 g (2.1 mmol), 25%-piperidine/dichloromethane 16 ml was added and the mixture was stirred at room temperature for 1 hour. The reaction mixture was concentrated in vacuo and the residue was purified on silica gel column chromatography (n-hexane:ethyl acetate=100:0 to 70:30, chloroform:methanol=100:0 to 80:20) to obtain the title compound 640 mg (yield 100%).

The following compounds shown in Tables VII-1 to VII-4 were obtained by a similar method to that described above. In the Tables, "Int_1" means an intermediate compound number.

TABLE VII-1

| Example No. | chemical name | yield (%) | Int _1 |
|---|---|---|---|
| VI-2 | (S)-2-amino-N-benzyl-3-(4-tert-butoxyphenyl)-N-(2,2-diethoxyethyl)propanamide | 91 | XV-2 |
| VI-3 | (S)-tert-butyl 5-amino-6-(benzyl(2,2-diethoxyethyl)amino)-6-oxohexylcarbamate | 100 | XV-3 |
| VI-4 | (S)-2-amino-3-(4-tert-butoxyphenyl)-N-(2,2-diethoxyethyl)-N-(naphthalen-1-ylmethyl)propanamide | 100 | XV-4 |
| VI-5 | (S)-tert-butyl 3-amino-4-((2,2-diethoxyethyl)(naphthalen-1-ylmethyl)amino)-4-oxobutanoate | 87 | XV-5 |
| VI-6 | (S)-2-amino-3-(4-tert-butoxyphenyl)-N-(2,2-diethoxyethyl)-N-(quinolin-8-ylmethyl)propanamide | 20 | XV-6 |
| VI-7 | (S)-2-amino-N1-(2,2-diethoxyethyl)-N1-(quinolin-8-ylmethyl)-N4-tritylsuccinamide | 77 | XV-7 |
| VI-8 | (S)-2-amino-N-(benzo[b]thiophen-3-ylmethyl)-N-(2,2-diethoxyethyl)propanamide | 81 | XV-8 |
| VI-9 | (S)-2-amino-N-(benzo[b]thiophen-3-ylmethyl)-3-(4-tert-butoxyphenyl)-N-(2,2-diethoxyethyl)propanamide | 60 | XV-9 |
| VI-10 | (S)-2-amino-N-(2,2-diethoxyethyl)-N-isopentylpropanamide | 86 | XV-10 |
| VI-11 | (S)-2-amino-3-(4-tert-butoxyphenyl)-N-(2,2-diethoxyethyl)-N-isopentylpropanamide | 98 | XV-11 |
| VI-12 | (S)-tert-butyl 5-amino-6-((2,2-diethoxyethyl)(isopentyl)amino)-6-oxohexylcarbamate | 98 | XV-12 |
| VI-13 | (S)-tert-butyl 3-amino-4-((2,2-diethoxyethyl)(isopentyl)amino)-4-oxobutanoate | 83 | XV-13 |
| VI-14 | (S)-2-amino-N1-(2,2-diethoxyethyl)-N1-isopentyl-N4-tritylsuccinamide | 85 | XV-14 |
| VI-15 | (S)-2-amino-3-tert-butoxy-N-(2,2-diethoxyethyl)-N-isopentylpropanamide | 72 | XV-15 |
| VI-16 | (S)-2-amino-N-(2,2-diethoxyethyl)-N-isopentyl-4-methylpentanamide | 74 | XV-16 |
| VI-17 | (S)-2-amino-N-(2,2-diethoxyethyl)-N-isopentyl-2-phenylacetamide | 88 | XV-17 |
| VI-18 | (S)-2-amino-N-(2,2-diethoxyethyl)-N-isopentyl-3-phenylpropanamide | 85 | XV-18 |
| VI-19 | (S)-2-amino-N-(2,2-diethoxyethyl)-N-isopentyl-4-phenylbutanamide | 83 | XV-19 |
| VI-20 | (S)-2-amino-3-(benzyloxy)-N-(2,2-diethoxyethyl)-N-isopentylpropanamide | 76 | XV-20 |

TABLE VII-2

| Example No. | chemical name | yield (%) | Int_1 |
|---|---|---|---|
| VI-21 | (S)-2-amino-N-(2,2-diethoxyethyl)-N-isopentyl-3-(naphthalen-1-yl)propanamide | 90 | XV-21 |
| VI-22 | (S)-2-amino-N-(2,2-diethoxyethyl)-N-isopentyl-3-(naphthalen-2-yl)propanamide | 90 | XV-22 |
| VI-23 | (S)-2-amino-N-(2,2-diethoxyethyl)-N-phenethylpropanamide | 83 | XV-23 |
| VI-24 | (S)-2-amino-3-(4-tert-butoxyphenyl)-N-(2,2-diethoxyethyl)-N-phenethylpropanamide | 86 | XV-24 |
| VI-25 | (S)-tert-butyl 5-amino-6-((2,2-diethoxyethyl)(phenethyl)amino)-6-oxohexylcarbamate | 91 | XV-25 |
| VI-26 | (S)-tert-butyl 3-amino-4-((2,2-diethoxyethyl)(phenethyl)amino)-4-oxobutanoate | 73 | XV-26 |
| VI-27 | (S)-2-amino-N1-(2,2-diethoxyethyl)-N1-phenethyl-N4-tritylsuccinamide | 60 | XV-27 |
| VI-28 | (S)-2-amino-3-tert-butoxy-N-(2,2-diethoxyethyl)-N-phenethylpropanamide | 79 | XV-28 |
| VI-29 | (S)-2-amino-N-(2,2-diethoxyethyl)-4-methyl-N-phenethylpentanamide | 88 | XV-29 |
| VI-30 | (S)-2-amino-N-(2,2-diethoxyethyl)-N-phenethyl-4-phenylbutanamide | 83 | XV-30 |
| VI-31 | (S)-2-amino-3-(benzyloxy)-N-(2,2-diethoxyethyl)-N-(3-phenylpropyl)propanamide | 75 | XV-31 |
| VI-34 | (S)-2-amino-N-(2,2-diethoxyethyl)-N-(3,3-diphenylpropyl)propanamide | 89 | XV-34 |
| VI-35 | (S)-2-amino-3-(4-tert-butoxyphenyl)-N-(2,2-diethoxyethyl)-N-(3,3-diphenylpropyl)propanamide | 85 | XV-35 |
| VI-36 | (S)-tert-butyl 5-amino-6-((2,2-diethoxyethyl)(3,3-diphenylpropyl)amino)-6-oxohexylcarbamate | 78 | XV-36 |
| VI-37 | (S)-tert-butyl 3-amino-4-((2,2-diethoxyethyl)(3,3-diphenylpropyl)amino)-4-oxobutanoate | 66 | XV-37 |
| VI-38 | (S)-2-amino-N1-(2,2-diethoxyethyl)-N1-(3,3-diphenylpropyl)-N4-tritylsuccinamide | 65 | XV-38 |
| VI-39 | (S)-2-amino-N-(2,2-diethoxyethyl)-N-(3,3-diphenylpropyl)-4-methylpentanamide | 87 | XV-39 |
| VI-40 | (S)-2-amino-N-(2,2-diethoxyethyl)-N-(3,3-diphenylpropyl)-2-phenylacetamide | 85 | XV-40 |
| VI-41 | (S)-2-amino-N-(2,2-diethoxyethyl)-N-(3,3-diphenylpropyl)-3-phenylpropanamide | 79 | XV-41 |

TABLE VII-3

| Example No. | chemical name | yield (%) | Int_1 |
|---|---|---|---|
| VI-42 | (S)-2-amino-3-(benzyloxy)-N-(2,2-diethoxyethyl)-N-(3,3-diphenylpropyl)propanamide | 78 | XV-42 |
| VI-43 | (S)-2-amino-N-(2,2-diethoxyethyl)-N-(3,3-diphenylpropyl)-3-(naphthalen-1-yl)propanamide | 98 | XV-43 |
| VI-44 | (S)-2-amino-N-(2,2-diethoxyethyl)-N-(3,3-diphenylpropyl)-3-(naphthalen-2-yl)propanamide | 92 | XV-44 |
| VI-45 | (S)-2-amino-N-(2,2-diethoxyethyl)-N-(naphthalen-2-ylmethyl)propanamide | 85 | XV-45 |
| VI-46 | (S)-2-amino-3-(4-tert-butoxyphenyl)-N-(2,2-diethoxyethyl)-N-(naphthalen-2-ylmethyl)propanamide | 72 | XV-46 |
| VI-47 | (S)-tert-butyl 5-amino-6-((2,2-diethoxyethyl)(naphthalen-2-ylmethyl)amino)-6-oxohexylcarbamate | 68 | XV-47 |
| VI-48 | (S)-tert-butyl 3-amino-4-((2,2-diethoxyethyl)(naphthalen-2-ylmethyl)amino)-4-oxobutanoate | 65 | XV-48 |
| VI-49 | (S)-2-amino-N1-(2,2-diethoxyethyl)-N1-(naphthalen-2-ylmethyl)-N4-tritylsuccinamide | 58 | XV-49 |
| VI-50 | (S)-2-amino-3-tert-butoxy-N-(2,2-diethoxyethyl)-N-(naphthalen-2-ylmethyl)propanamide | 67 | XV-50 |
| VI-51 | (S)-2-amino-N-(2,2-diethoxyethyl)-4-methyl-N-(naphthalen-2-ylmethyl)pentanamide | 79 | XV-51 |
| VI-52 | (S)-2-amino-N-(2,2-diethoxyethyl)-N-(naphthalen-2-ylmethyl)-2-phenylacetamide | 81 | XV-52 |
| VI-53 | (S)-2-amino-N-(2,2-diethoxyethyl)-N-(naphthalen-2-ylmethyl)-3-phenylpropanamide | 74 | XV-53 |
| VI-54 | (S)-2-amino-N-(2,2-diethoxyethyl)-N-(naphthalen-2-ylmethyl)-4-phenylbutanamide | 74 | XV-54 |
| VI-55 | (S)-tert-butyl 44(2-amino-3-(4-tert-butoxyphenyl)-N-(2,2-diethoxyethyl)propanamido)methyl)benzo[d]thiazol-2-ylcarbamate | 99 | XV-55 |
| VI-56 | (S)-2-amino-3-(4-tert-butoxyphenyl)-N-(2,2-diethoxyethyl)-N-((R)-1-phenylethyl)propanamide | 97 | XV-56 |

TABLE VII-3-continued

| Example No. | chemical name | yield (%) | Int_1 |
|---|---|---|---|
| VI-57 | (S)-2-amino-3-(4-tert-butoxyphenyl)-N-(2,2-diethoxyethyl)-N-(pyridin-4-ylmethyl)propanamide | 97 | XV-57 |
| VI-58 | (S)-2-amino-3-(4-tert-butoxyphenyl)-N-(2,2-diethoxyethyl)-N-(pyridin-2-ylmethyl)propanamide | 97 | XV-58 |
| VI-59 | (S)-2-amino-3-(4-tert-butoxyphenyl)-N-(2,2-diethoxyethyl)-N-(2,4-difluorobenzyl)propanamide | 100 | XV-59 |
| VI-60 | (S)-2-amino-N-benzyl-N-((R)-1,1-diethoxypropan-2-yl)propanamide | 84 | XV-60 |

TABLE VII-4

| Example No. | chemical name | yield (%) | Int_1 |
|---|---|---|---|
| VI-61 | (S)-2-amino-N-benzyl-3-(4-tert-butoxyphenyl)-N-((R)-1,1-diethoxypropan-2-yl)propanamide | 82 | XV-61 |
| VI-62 | (S)-tert-butyl 3-amino-4-(benzyl((R)-1,1-diethoxypropan-2-yl)amino)-4-oxobutanoate | 87 | XV-62 |
| VI-63 | (S)-2-amino-N-((R)-1,1-diethoxypropan-2-yl)-N-(naphthalen-1-ylmethyl)propanamide | 83 | XV-63 |
| VI-64 | (S)-2-amino-3-(4-tert-butoxyphenyl)-N-((R)-1,1-diethoxypropan-2-yl)-N-(naphthalen-1-ylmethyl)propanamide | 68 | XV-64 |
| VI 65 | tert-butyl (S)-5-amino-6-(((R)-1,1-diethoxypropan-2-yl)(naphthalen-1-ylmethyl)amino)-6-oxohexylcarbamate | 100 | XV-65 |
| VI 66 | (S)-tert-butyl 3-amino-4-(((R)-1,1-diethoxypropan-2-yl)(naphthalen-1-ylmethyl)amino)-4-oxobutanoate | 100 | XV-66 |
| VI-67 | (S)-2-amino-N-((R)-1,1-diethoxypropan-2-yl)-N-(quinolin-8-ylmethyl)propanamide | 86 | XV-67 |
| VI-68 | (S)-2-amino-3-(4-tert-butoxyphenyl)-N-((S)-1,1-diethoxypropan-2-yl)-N-(quinolin-8-ylmethyl)propanamide | 100 | XV-68 |
| VI-69 | tert-butyl (S)-5-amino-6-(((R)-1,1-diethoxypropan-2-yl)(quinolin-8-ylmethyl)amino)-6-oxohexylcarbamate | 87 | XV-69 |
| VI-70 | (S)-2-amino-N1-((R)-1,1-diethoxypropan-2-yl)-N1-(quinolin-8-ylmethyl)-N4-tritylsuccinamide | 68 | XV-70 |
| VI-71 | (S)-2-amino-N-(benzo[b]thiophen-3-ylmethyl)-3-(4-tert-butoxyphenyl)-N-((R)-1,1-diethoxypropan-2-yl)propanamide | 72 | XV-71 |
| VI-72 | tert-butyl (S)-5-amino-6-((benzo[b]thiophen-3-ylmethyl)((R)-1,1-diethoxypropan-2-yl)amino)-6-oxohexylcarbamate | 74 | XV-72 |
| VI-73 | (S)-tert-butyl 3-amino-4-((benzo[b]thiophen-3-ylmethyl)((R)-1,1-diethoxypropan-2-yl)amino)-4-oxobutanoate | 69 | XV-73 |
| VI-74 | (S)-2-amino-N1-(benzo[b]thiophen-3-ylmethyl)-N1-((S)-1,1-diethoxypropan-2-yl)-N4-tritylsuccinamide | 57 | XV-74 |

Example VI-32

Synthesis of (S)-2-amino-N-(2,2-diethoxyethyl)-3-(naphthalen-1-yl)-N-(3-phenylpropyl)propanamide (Compound VI-32)

To a solution of (S)-benzyl 1-((2,2-diethoxyethyl)(3-phenylpropyl)amino)-3-(naphthalen-1-yl)-1-oxopropan-2-yl-carbamate (Compound XV-32) 21.4 g (36.8 mmol) in methanol 200 ml, 10% of palladium on carbon (8 g) was added, then the mixture was stirred at H$_2$ atmosphere overnight. The mixture was filtered and the filtrate was evaporated to obtain the title compound 14.5 g (yield 88%).

The following compound shown in Table VIII was obtained by a similar method to that described above. In the Table, "Int_1" means an intermediate compound number.

TABLE VIII

| Example No. | chemical name | yield (%) | Int_1 |
|---|---|---|---|
| VI-33 | (S)-2-amino-N-(2,2-diethoxyethyl)-3-(naphthalen-2-yl)-N-(3-phenylpropyl)propanamide | 85 | XV-33 |

Example V-1

Synthesis of 3-(3-benzylureido)thiophene-2-carboxylic acid (Compound V-1)

To a solution of methyl 3-amino-thiophene-2-carboxylate 9.43 g (60 mmol) in acetonitrile 12 ml, 2N-sodium hydroxide 36 ml (72 mmol) was added and the mixture was stirred for 5 hrs. at 85° C. The reaction mixture was neutralized with 2N-hydrochloric acid 36 ml (72 mmol), then saturated sodium bicarbonate solution 50 ml and a solution of benzyl isocyanate 7.41 ml (60 mmol) in acetonitrile 36 ml were added and the mixture was stirred overnight. The reaction mixture was basified with 2N-sodium hydroxide 60 ml and washed with ether 100 ml. The aqueous phase was acidified with 2N-hydochloric acid 85 ml. The aqueous phase was filtered and washed with H$_2$O. The solid was dried in vacuo to obtain the title compound 6.46 g (yield 39%)

The following compounds shown in Table IX were obtained by a similar method to that described above.

TABLE IX

| Example No. | structure | chemical name | yield (%) |
|---|---|---|---|
| V-2 | 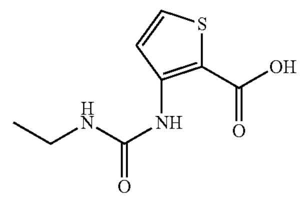 | 3-(3-ethylureido)thiophene-2-carboxylic acid | 15 |
| V-17 | 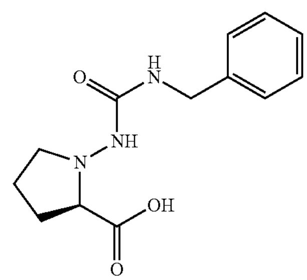 [SMILES: O=C(NCc1ccccc1)NN1CCC[C@@H]1C(=O)O] | (R)-1-(3-benzylureido)pyrrolidine-2-carboxylic acid | 23 |
| V-18 | 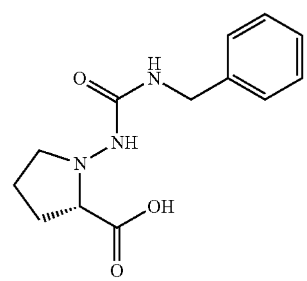 [SMILES: O=C(NCc1ccccc1)NN1CCC[C@H]1C(=O)O] | (S)-1-(3-benzylureido)pyrrolidine-2-carboxylic acid | 27 |
| V-19 | 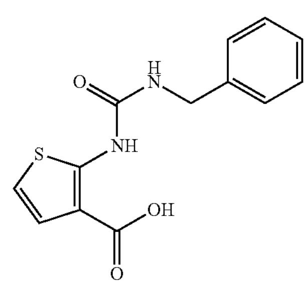 [SMILES: O=C(NCc1ccccc1)Nc1sccc1C(=O)O] | 2-(3-benzylureido)thiophene-3-carboxylic acid | 64 |
| V-20 | 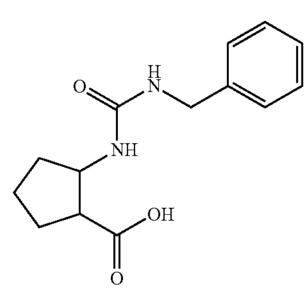 [SMILES: O=C(NCc1ccccc1)NC1CCCC1C(=O)O] | 2-(3-benzylureido)cyclopentanecarboxylic acid | 32 |

TABLE IX-continued

| Example No. | structure | chemical name | yield (%) |
|---|---|---|---|
| V-21 | 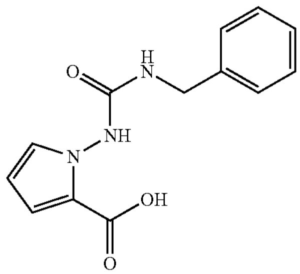 [SMILES: O=C(NCc1ccccc1)Nn1cccc1C(=O)O] | 1-(3-benzylureido)-1H-pyrrole-2-carboxylic acid | 92 |
| V-22 | 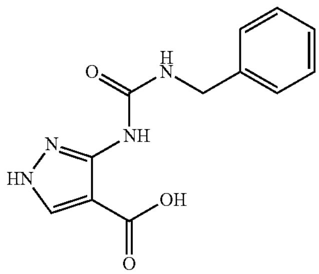 [SMILES: O=C(NCc1ccccc1)Nc1n[nH]cc1C(=O)O] | 3-(3-benzylureido)-1H-pyrazole-4-carboxylic acid | 29 |
| V-23 | 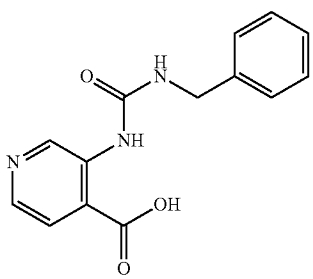 [SMILES: O=C(NCc1ccccc1)Nc1cnccc1C(=O)O] | 3-(3-benzylureido)isonicotinic acid | 25 |

Example V-3

Synthesis of 3-(3-(pyridin-4-ylmethyl)ureido)thiophene-2-carboxylic acid (Compound V-3)

To a solution of methyl 3-aminothiophene-2-carboxylate 20.0 g (0.127 mol) in water 150 ml was added the aqueous solution of potassium hydroxide 10.7 g (0.191 mol). The resulting solution wad heated to 90° C. for 2 hrs. After being checked by TLC till the starting material was consumed, the reaction solution was cooled to 0° C. Then a solution of triphosgene 18.9 g (0.064 mol) in toluene 150 ml was added dropwise. The resulting solution was stirred at room temperature for 2 hrs. The residue was filtered, and the solid was recrystallized from tetrahydrofuran to obtain 1H-thieno[3,2-d][1,3]oxazine-2,4-dione 8.5 g (yield 40%).

A solution of the above compound 1.01 g (6.0 mmol) and 4-picolylamine 731 μl (7.2 mmol) in tetrahydrofuran 20 ml was stirred at room temperature for 18 hrs. After being checked by TLC, the precipitate was filtered, and washed with tetrahydrofuran 20 ml to obtain the title compound 1.47 g (yield 88%).

The following compounds shown in Table X were obtained by a similar method to that described above. In the Table, "Int_1" means an intermediate compound number.

TABLE X

| Example No. | structure | chemical name | yield (%) | Int_1 |
|---|---|---|---|---|
| V-4 | 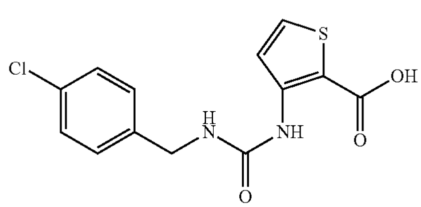 [SMILES: O=C(NCc1ccc(Cl)cc1)Nc1ccsc1C(=O)O] | 3-(3-(4-chlorobenzyl)ureido)thiophene-2-carboxylic acid | 66 | XLVIII-1 |

TABLE X-continued

| Example No. | structure | chemical name | yield (%) | Int_1 |
|---|---|---|---|---|
| V-5 | 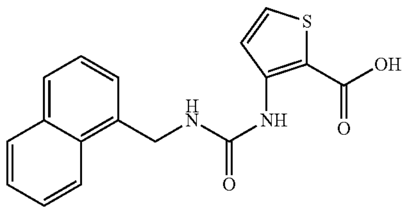 [SMILES: O=C(NCc1cccc2ccccc12)Nc1ccsc1C(=O)O] | 3-(3-(naphthalen-1-ylmethyl)ureido)thiophene-2-carboxylic acid | 60 | XLVIII-1 |
| V-6 | 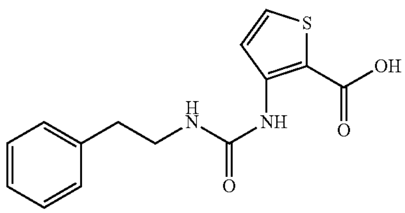 [SMILES: O=C(NCCc1ccccc1)Nc1ccsc1C(=O)O] | 3-(3-phenethylureido)thiophene-2-carboxylic acid | 62 | XLVIII-1 |
| V-7 | 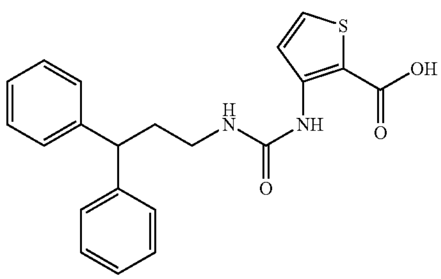 [SMILES: O=C(NCCC(c1ccccc1)c1ccccc1)Nc1ccsc1C(=O)O] | 3-(3-(3,3-diphenylpropyl)ureido)thiophene-2-carboxylic acid | 65 | XLVIII-1 |
| V-8 | 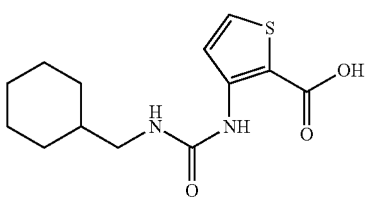 [SMILES: O=C(NCC1CCCCC1)Nc1ccsc1C(=O)O] | 3-(3-(cyclohexylmethyl)ureido)thiophene-2-carboxylic acid | 66 | XLVIII-1 |
| V-9 | 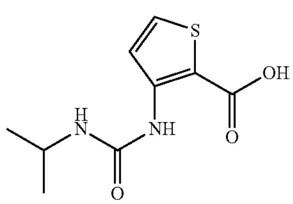 | 3-(3-isopropylureido)thiophene-2-carboxylic acid | 70 | XLVIII-1 |
| V-10 | 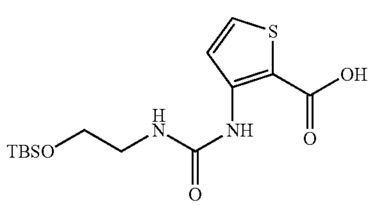 [SMILES: CC(C)(C)[Si](C)(C)OCCNC(=O)Nc1ccsc1C(=O)O] | 3-(3-(2-(tert-butyldimethylsilyloxy)ethyl)ureido)thiophene-2-carboxylic acid | 56 | XLVIII-1 |
| V-11 | 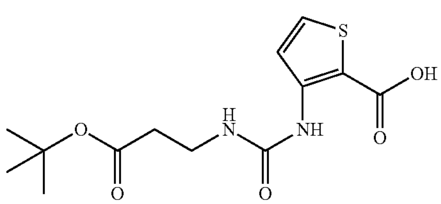 [SMILES: CC(C)(C)OC(=O)CCNC(=O)Nc1ccsc1C(=O)O] | 3-(3-(3-tert-butoxy-3-oxopropyl)ureido)thiophene-2-carboxylic acid | 55 | XLVIII-1 |

TABLE X-continued

| Example No. | structure | chemical name | yield (%) | Int_1 |
|---|---|---|---|---|
| V-12 | 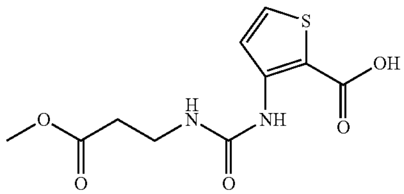 [SMILES: COC(=O)CCNC(=O)Nc1ccsc1C(=O)O] | 3-(3-(3-methoxy-3-oxopropyl)ureido)thiophene-2-carboxylic acid | 52 | XLVIII-1 |
| V-13 | 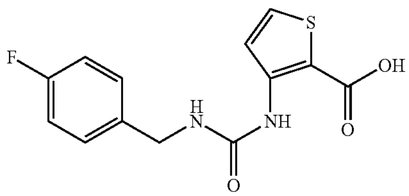 [SMILES: O=C(NCc1ccc(F)cc1)Nc1ccsc1C(=O)O] | 3-(3-(4-fluorobenzyl)ureido)thiophene-2-carboxylic acid | 68 | XLVIII-1 |
| V-14 | 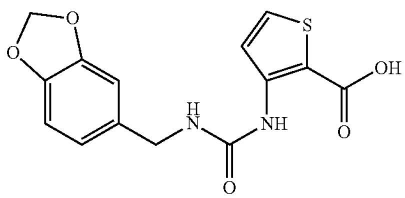 [SMILES: O=C(NCc1ccc2c(c1)OCO2)Nc1ccsc1C(=O)O] | 3-(3-(benzo[d][1,3]dioxol-5-ylmethyl)ureido)thiophene-2-carboxylic acid | 63 | XLVIII-1 |
| V-15 | 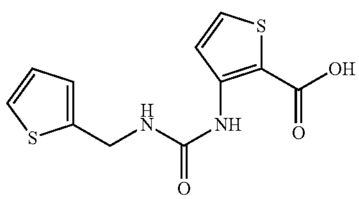 [SMILES: O=C(NCc1cccs1)Nc1ccsc1C(=O)O] | 3-(3-(thiophen-2-ylmethyl)ureido)thiophene-2-carboxylic acid | 71 | XLVIII-1 |
| V-16 | 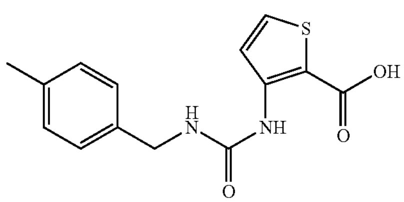 [SMILES: Cc1ccc(CNC(=O)Nc2ccsc2C(=O)O)cc1] | 3-(3-(4-methylbenzyl)ureido)thiophene-2-carboxylic acid | 75 | XLVIII-1 |

Example XL-1

Synthesis of ethyl 2-(1-methylhydrazinyl)acetate (Compound XL-1)

To a solution of methylhydrazine 7.13 ml (150 mmol) and triethylamine 16.7 ml (120 mmol), ethyl 2-bromoacetate 16.7 g (100 mmol) in dichloromethane 50 ml was added and the mixture was stirred at room temperature overnight. The reaction mixture was diluted with ethyl acetate 300 ml and washed with brine 200 ml. The organic phase was dried over magnesium sulfate and filtered and the mother solution was concentrated in vacuo to obtain the title compound 10.2 g (77%).

Example XXXII-1

Synthesis of ethyl 2-(1-methyl-2-(benzylcarbamoyl) hydrazinyl)acetate (Compound XXXII-1)

To a solution of ethyl 2-(1-methylhydrazinyl)acetate (Compound XL-1) 10 ml (76 mmol) in tetrahydrofuran 40 ml, benzyl isocyanate 11.1 g (83.3 mmol) was added at 0° C. and the mixture was stirred at room temperature overnight. The reaction mixture was diluted with ethyl acetate 150 ml and washed with water 75 ml and brine 75 ml. The organic phase was dried over magnesium sulfate and filtered. The filtrate was concentrated in vacuo to obtain the title compound 15.2 g (76%).

Example VIII-1

Synthesis of 3-(3-benzylureido)propanoic acid (Compound VIII-1)

To a solution of β-alanine 5.0 g (56 mmol) in dichloromethane 56 ml and tetrahydrofuran 56 ml was added benzyl isocyanate 6.6 ml (53 mmol) at 0° C. After stirring at room temperature overnight, the reaction mixture was diluted with ethyl acetate 200 ml and washed with water 200 ml and brine 200 ml. The residual solution was concentrated to about 100 ml in vacuo. To the mixture was added 1N sodium hydroxide solution 60 ml at 0° C. The aqueous phase was acidified with 3N HCl aq. 20 ml and then extracted with ethyl acetate 100 ml twice. The extract was washed with brine 50 ml and dried over magnesium sulfate and filtered. The filtrate was concentrated in vacuo. To the residue was added ether:n-hexane=1:1 30 ml and the precipitate was corrected by filtration to obtain the title compound 7.05 g (59%).

Example VIII-2

Synthesis of 2-(2-(benzylcarbamoyl)-1-methylhydrazinyl)acetic acid (Compound VIII-2)

To a solution of ethyl 2-(1-methyl-2-(benzylcarbamoyl) hydrazinyl)acetate (Compound XXXII-1) 1.33 g (5.0 mmol) in tetrahydrofuran/methanol/water (2:3:1) 24 ml, lithium hydroxide monohydrate 420 mg (10.0 mmol) was added and the mixture was stirred at room temperature overnight. The reaction mixture was diluted with water 25 ml and washed with ether 25 ml. The aqueous phase was acidified with 10%-citric acid 25 ml and extracted with chloroform 30 ml. The organic phase was washed with brine 25 ml and dried with magnesium sulfate and then filtered. The filtrate was concentrated in vacuo to obtain the title compound 1.05 g (88%).

Example XXXIV-1

Synthesis of N-methyl-N'-tert-butoxycarbonylhydrazine (Compound XXXIV-1)

To a solution of N-methylhydrazine 5.27 ml (100 mmol) and triethylamine 8.36 ml (60.0 mmol) in dichloromethane 200 ml, 300 benzoxyloxycarbonyl chloride in toluene 11.37 ml (20.0 mmol) was added and the mixture was stirred at 0° C. for 1 hr. The reaction mixture was diluted with chloroform 200 ml and washed with brine 200 ml. The organic phase was dried over magnesium sulfate and filtered. The mother solution was concentrated in vacuo to give N-benzoxyloxycarbonyl-N-methylhydrazine. The product was used without further purification.

To a solution of the above compound 3.60 g (20.0 mmol) and potassium carbonate 11.1 g (80.0 mmol) in water 42 ml, a solution of di-tert-butyl dicarbonate 9.19 ml (40.0 mmol) in acetonitrile 18 ml was added and the mixture was stirred at room temperature overnight. The reaction mixture was diluted with ethyl acetate 200 ml and washed with water 200 ml and brine 200 ml. The organic phase was dried over magnesium sulfate and filtered. The mother solution was concentrated in vacuo. The residue was purified on silica gel column chromatography (Merck 60N spherical, neutral elution by chloroform) to give N-benzoxyloxycarbonyl-N-methyl-N'-(tert-butyoxycarbonyl)hydrazine 4.08 g (72.8%).

To a solution of the above compound 5.61 g (20.0 mmol) in methanol 80 ml, 5% palladium on carbon 400 mg was added and the mixture was stirred at room temperature under hydrogen atmosphere overnight. The reaction mixture was filtered on celite and washed with methanol 400 ml. The mother solution was concentrated in vacuo to obtain the title compound 3.05 g (80.10).

Example XLIII-1

Synthesis of (R)-benzyl 3-(4-(benzyloxy)phenyl)-2-hydroxypropanoate (Compound XLIII-1)

To a solution of 4-hydroxyphenylpyruvic acid 9.01 g (50.0 mmol) in tetrahydrofuran 120 ml, triethylamine 7.0 ml (50.0 mmol) was added and the mixture was stirred at −20° C. for 0.5 hr. A solution of (−)-B-chlorodiisopinocamphenylborane in 60% hexane 41.2 ml (70.0 mmol) was added to the reaction mixture dropwisely and the mixture was warmed to room temperature and stirred for 6 hrs. 1N sodium hydroxide solution 200 ml was added to the reaction mixture and the mixture was washed with ethyl ether 200 ml. 3N hydrochloride aq. 80 ml was added to the aqueous phase and the mixture was extracted with ethyl acetate 200 ml. The organic phase was washed with brine 200 ml and dried over magnesium sulfate and filtered. The filtrate was concentrated in vacuo and n-hexane:ethyl acetate=60:40 50 ml was added to the residue and the precipitate was corrected by filtration to obtain (R)-2-hydroxy-3-(4-hydroxyphenyl)propanoic acid 5.53 g (yield 61%).

To a solution of the above compound 2.73 g (15.0 mmol) in N,N-dimethyl formamide 100 ml, potassium carbonate 5.18 g (37.5 mmol) was added and the mixture was stirred at 0° C. for 10 min. Benzyl bromide 3.92 ml (33.0 mmol) was added dropwisely and the mixture was stirred at room temperature overnight. The reaction mixture was diluted with ethyl acetate 300 ml and washed with water 300 ml and brine 300 ml. The organic phase was dried over magnesium sulfate and filtered. The filtrate was concentrated in vacuo and n-hexane:ethyl acetate=90:10 40 ml was added to the residue and the precipitate was corrected by filtration to obtain the title compound 3.78 g (yield 69%).

Example XXVII-1

Synthesis of (S)-benzyl 3-(4-(benzyloxy)phenyl)-2-hydroxypropanoate (Compound XXVIII-1)

To a solution of (R)-benzyl 3-(4-(benzyloxy)phenyl)-2-hydroxypropanoate (Compound XLIII-1) 1.81 g (5.00 mmol) and 2,6-lutidine 874 µl (7.50 mmol) in dichloromethane 15 ml, trifluoromethanesulfonic anhydride 1.26 ml (7.50 mmol) was added and the mixture was stirred at 0° C. for 0.5 hr. N-tert-butoxycarbonyl-N'-methylhydrazine (Compound XXXIV-1) 1.46 g (10.0 mol) was added to the solution mixture and the mixture was stirred at room temperature overnight. The reaction mixture was diluted with ethyl acetate 100 ml and washed with water 100 ml. The organic phase was washed with brine 100 ml and dried over magnesium sulfate and filtered. The mother solution was concentrated in vacuo and the residue was purified on silica gel column chromatography (Merck 60N spherical, neutral elution by chloroform) to obtain the title compound 0.97 g (17.3%).

Example XXVIII-1

Synthesis of (S)-benzyl 3-(4-(benzyloxy)phenyl)-2-(1,3-dioxoisoindolin-2-yloxy)propanoate (Compound XXVIII-2)

To a solution of (R)-benzyl 3-(4-(benzyloxy)phenyl)-2-hydroxypropanoate (Compound XLIII-1) 18.1 g (50.0 mmol) in dichloromethane 80 ml, trifluoromethanesulfonic anhydride 10.1 ml (60.0 mmol) and 2,6-lutidine 8.74 ml (75.0 mmol) were added and the mixture was stirred at room temperature for 0.5 hr. N-hydroxyphthalimide 8.16 g (50.0 mmol) and triethylamine 10.5 ml (75.0 mmol) were added to the reaction mixture and the mixture was stirred at room temperature overnight. The reaction mixture was concentrated in vacuo and diluted with ethyl acetate 500 ml and washed with saturated sodium bicarbonate solution 500 ml, water 500 ml and brine 500 ml. The organic phase was dried over magnesium sulfate and filtered. The filtrate was concentrated in vacuo and the residue was purified on silica gel column chromatography (Merck 60N spherical, neutral elution by n-hexane:ethyl acetate=90:10 to 70:30) to obtain the title compound 15.0 g (yield 59%).

Example XVIII-1

Synthesis of (S)-benzyl 3-(4-(benzyloxy)phenyl)-2-(1-methylhydrazinyl)propanoate (Compound XVIII-1)

To a solution of (S)-benzyl 3-(4-(benzyloxy)phenyl)-2-(N-(tert-butoxycarbonyl)-N'-methylhydrazinyl)propanoate (Compound XXVII-1) 491 mg (1.00 mmol) in dichloromethane 1 ml, trifluoroacetic acid 743 µl (10.0 mmol) was added and the mixture was stirred at room temperature for 0.5 hr. The reaction mixture was concentrated in vacuo and the residue was diluted with ethyl acetate 50 ml and washed with saturated sodium bicarbonate solution 50 ml. The organic phase was washed with water 50 ml and brine 50 ml. The organic phase was dried over magnesium sulfate and filtered. The mother solution was concentrated in vacuo to give the title compound, which was used without further purification.

Example XVIII-2

Synthesis of (S)-benzyl 2-(aminooxy)-3-(4-(benzyloxy)phenyl)propanoate (Compound XVIII-2)

To a mixed solution of (S)-benzyl 3-(4-(benzyloxy)phenyl)-2-(1,3-dioxoisoindolin-2-yloxy)propanoate (Compound XXVIII-1) 15.02 g (29.6 mmol) in tetrahydrofuran 60 ml and methanol 60 ml, hydrazine monohydrate 4.31 ml (88.8 mmol) was added and the mixture was stirred at room temperature for 1 hr. The reaction mixture was diluted with ethyl acetate 500 ml and washed with saturated sodium bicarbonate solution 200 ml, water 200 ml and brine 200 ml. The organic phase was dried over magnesium sulfate and filtered. The filtrate was concentrated in vacuo to give the title compound, which was used without further purification.

Example XVII-1

Synthesis of (S)-benzyl 3-(4-(benzyloxy)phenyl)-2-(2-(3-(3-benzylureido)propanoyl)-1-methylhydrazinyl)propanoate (Compound XVII-1)

To a solution of 3-(3-benzylureido)propanoic acid (Compound VIII-1) 267 mg (1.20 mmol) in dichloromethane 5 ml, N-hydroxybenztriazole 203 mg (1.50 mmol) and 1-ethyl-3-(3-dimethylaminopropyl)carbodiimide hydrochloride 288 mg (1.50 mmol) were added and the mixture was stirred at room temperature for 0.5 hr. (S)-benzyl 3-(4-(benzyloxy)phenyl)-2-(1-methylhydrazinyl)propanoate (Compound XVIII-1) 390 mg (1.00 mmol) and a solution of dimethylaminopyridine 61 mg (0.50 mmol) in dichloromethane 1 ml were added to the reaction mixture and the mixture was stirred at room temperature for 3 hrs. The reaction mixture was diluted with ethyl acetate 50 ml and washed with saturated sodium bicarbonate solution 50 ml twice, water 50 ml twice and brine 50 ml and the organic phase was dried over magnesium sulfate and filtered. The mother solution was concentrated in vacuo and the residue was purified on silica gel column chromatography (Merck 60N spherical, neutral elution by chloroform:methanol=100:0 to 95:5) to obtain the title compound 0.31 g (52.0%).

The following compounds shown in Table XI were obtained by a similar method to that described above. In the Table, "Int_1" and "Int_2" mean an intermediate compound number.

TABLE XI

| Example No. | structure | chemical name | yield (%) | Int_1 | Int_2 |
|---|---|---|---|---|---|
| XVII-2 | 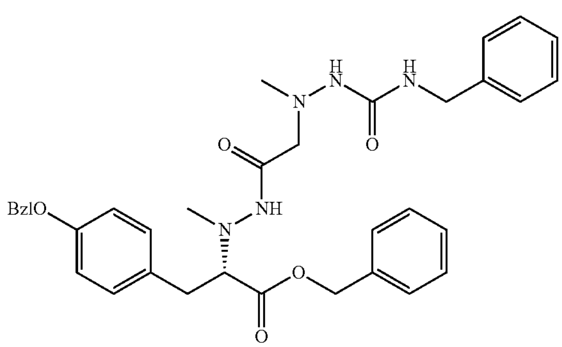 | (S)-benzyl 3-(4-(benzyloxy)phenyl)-2-(2-(3-(3-benzylureido)propanoyl)-1-methylhydrazinyl)propanoate | 55 | VIII-2 | XVIII-1 |

| Example No. | structure | chemical name | yield (%) | Int_1 | Int_2 |
|---|---|---|---|---|---|
| XVII-3 | 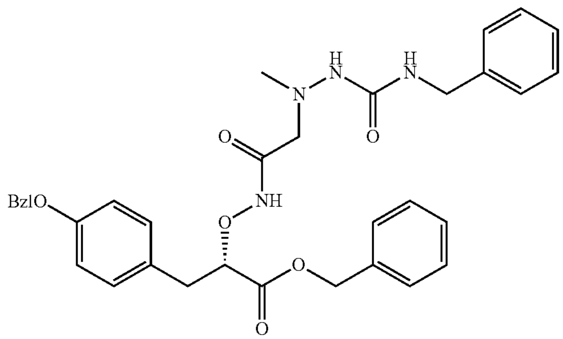 | (S)-benzyl 10-(4-(benzyloxy)benzyl)-5-methyl-3,7-dioxo-1-phenyl-9-oxa-2,4,5,8-tetraazaundecan-11-oate | 73 | VIII-2 | XVIII-2 |

Example XVII-4

Synthesis of (S)-benzyl 3-(4-(benzyloxy)phenyl)-2-(1-((3-benzylureido)methyl)cyclohexanecarboxamidooxy)propanoate (Compound XVII-4)

To a solution of Fmoc-1-aminomethyl-cyclohexane carboxylic acid 2.41 g (6.36 mmol), N-hydroxybenzotriazol 1.07 g (7.95 mmol) and 1-ethyl-3-(3-dimethylaminopropyl) carbodiimide hydrochloride 1.52 g (7.95 mmol) in dichloromethane 20 ml, a solution of (S)-benzyl 2-(aminooxy)-3-(4-(benzyloxy)phenyl)propanoate (Compound XVIII-2) 2.0 g (5.3 mmol) and 4-dimethylaminopyridine 65 mg (0.53 mmol) in dichloromethane 15 ml was added and the mixture was stirred at room temperature overnight. The reaction mixture was washed with saturated sodium bicarbonate solution 40 ml, water 40 ml and brine 40 ml. The organic phase was dried over magnesium sulfate and filtered. The filtrate was concentrated in vacuo and the residue was purified on silica gel column chromatography (Merck 60N spherical, neutral elution by n-hexanae:ethylacetate=100:0 to 70:30) to obtain (S)-benzyl 2-(1-((((9H-fluoren-9-yl)methoxy)carbonylamino)methyl)cyclohexanecarboxamidooxy)-3-(4-(benzyloxy)phenyl)propanoate 1.25 g (32%).

To the above compound 1.25 g (1.69 mmol), 25%-piperidine/dichloromethane 20 ml was added and the mixture was stirred at room temperature for 1 hour. The reaction mixture was concentrated in vacuo and the residue was purified on silica gel column chromatography (Merck 60N spherical, neutral elution by n-hexane:ethyl acetate=100:0 to 70:30 and chloroform:methanol=100:0 to 80:20) to obtain (S)-benzyl 2-(1-(aminomethyl)cyclohexanecarboxamidooxy)-3-(4-(benzyloxy)phenyl)propanoate 528 mg (60%).

To a solution of (S)-benzyl 2-(1-(aminomethyl)cyclohexanecarboxamidooxy)-3-(4-(benzyloxy)phenyl)propanoate in dichloromethane 9 ml, benzyl isocyanate 143 μl (1.16 mmol) and triethylamine 271 al (1.94 mmol) were added and the mixture was stirred at room temperature overnight. The reaction mixture was washed with water 10 ml and brine 10 ml. Then the organic phase was dried over magnesium sulfate, filtered and concentrated. The crude residue was purified on silica gel column chromatography (Merck 60N spherical, neutral elution by n-hexane:ethylacetate=100:0 to 70:30) to obtain the title compound 257 mg (41%).

Example VII-1

Synthesis of (S)-3-(4-(benzyloxy)phenyl)-2-(2-(3-(3-benzylureido)propanoyl)-1-methylhydrazinyl) propanoic acid (Compound VII-1)

To a solution of (S)-benzyl 3-(4-(benzyloxy)phenyl)-2-(2-(3-(3-benzylureido)propanoyl)-1-methylhydrazinyl)propanoate (Compound XVII-1) 149 mg (0.25 mmol) in tetrahydrofuran:methanol=1:1.5 1.5 ml, a solution of lithium hydroxide monohydrate 16 mg in water 0.3 ml was added and the mixture was stirred at room temperature for 1.5 hr. The reaction mixture was cooled to 0° C. and 1N HCl aq. 10 ml was added and the mixture was extracted with ethyl acetate 20 ml. The organic phase was washed with water 20 ml and brine 20 ml and dried over magnesium sulfate and filtered. The mother solution was concentrated in vacuo to obtain the title compound. The residue was used without further purification.

The following compounds shown in Table XII were obtained by a similar method to that described above. In the Table, "Int_1" means an intermediate compound number.

TABLE XII

| Example No. | structure | chemical name | Int_1 |
|---|---|---|---|
| VII-2 | 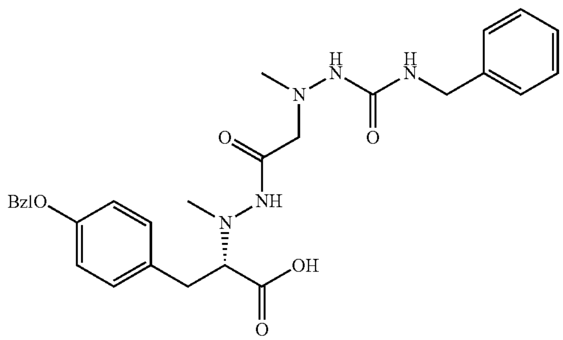 | (S)-2-(2-(2-(2-(benzylcarbamoyl)-1-methylhydrazinyl)acetyl)-1-methylhydrazinyl)-3-(4-(benzyloxy)phenyl)propanoic acid | XVII-2 |
| VII-3 | 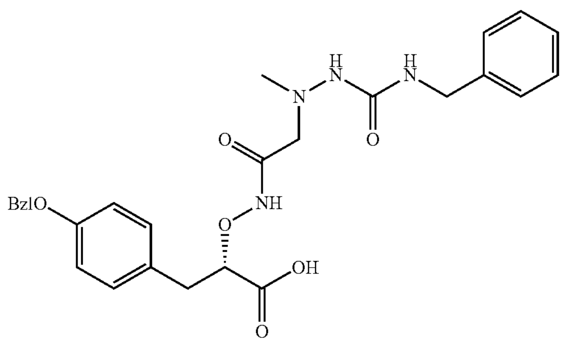 | (S)-10-(4-(benzyloxy)benzyl)-5-methyl-3,7-dioxo-1-phenyl-9-oxa-2,4,5,8-tetraazaundecan-11-oic acid | XVII-3 |
| VII-4 | 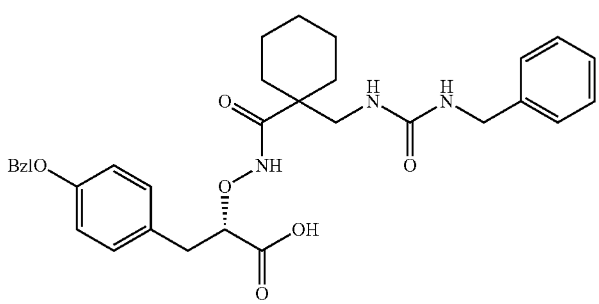 | (S)-3-(4-(benzyloxy)phenyl)-2-(1-((3-benzylureido)methyl)cyclohexanecarboxamidooxy)propanoic acid | XVII-4 |

[Example II-1] (Syn. II-1)

Synthesis of (S)—N-(1-(benzyl(2,2-diethoxyethyl)amino)-1-oxopropan-2-yl)-3-(3-benzylureido)thiophene-2-carboxamide (Compound II-1)

To a solution of 3-(3-benzylureido)thiophene-2-carboxylic acid (Compound V-1) 49.7 mg (0.18 mmol) and N-hydroxybenzotriazol 6.1 mg (0.045 mmol) in dichloromethane 1 ml, 1-ethyl-3-(3-dimethylaminopropyl)carbodiimide 43.1 mg (0.225 mmol) was added and the mixture was stirred at room temperature for 0.5 hr. A solution of (S)-2-amino-N-benzyl-N-(2,2-diethoxyethyl)propanamide (Compound VI-1) 44.2 mg (0.15 mmol) in dichloromethane 1 ml was added to the reaction mixture and the mixture was stirred at room temperature for 18 hrs. The reaction mixture was washed with sat. NaHCO₃ aq. 1 ml, water 1 ml and brine 1 ml. The organic phase was filtered on celite 1 g and magnesium sulfate 150 mg. The mother solution was concentrated in vacuo and the residue was purified with PTLC (development solvent: chloroform:methanol=98:2) to obtain the titled compound 44.7 mg (54%).

[Example 11-262] (Syn. 11-2)

Synthesis of (S)-3-(4-(benzyloxy)phenyl)-2-(2-(3-(3-benzylureido)propanoyl)-1-methylhydrazinyl)-N-(2,2-diethoxyethyl)-N-(naphthalen-1-ylmethyl)propanamide (Compound II-262)

To a solution of (S)-3-(4-(benzyloxy)phenyl)-2-(2-(3-(3-benzylureido)propanoyl)-1-methylhydrazinyl)propanoic acid (Compound VII-1) 126 mg (0.25 mmol) in dichloromethane 1.5 ml, 2,2-diethoxy-N-(naphthalen-1-ylmethyl)ethanamine (Compound IV-2) 85 mg (0.31 mmol) and DMT-MM 173 mg (0.63 mmol) were added and the mixture was stirred at room temperature for 3 hr. The reaction mixture was diluted with chloroform 50 ml and washed with water 50 ml twice and brine 50 ml twice and dried over magnesium sulfate and filtered. The mother solution was concentrated in vacuo and the residue was purified on silica gel column chromatography (Merck 60N spherical, neutral 10 ml elution by chloroform:methanol=100:0 to 90:10, each elution 50 ml) to give the desired product as pale yellow oil 85.0 mg (35.8%).

Typical examples of the compound having general formula II of the present invention that can be obtained by reacting and treating corresponding intermediates using any of the methods described in the present specification including the examples described above are shown in Tables XIII-1 to XIII-25. The compounds were prepared according to the preparation methods of the compound numbers (e.g., "II-1") shown in the columns of "Syn" in the Tables, "Int_1" and "Int_2" indicate intermediate compound numbers. "n.d." in the columns of "yield" means not determined in this step and was used to further reaction. In the column of "R", "$R^1$", "$R^2$" and "$R^3$" were indicated as chemical groups in the general formula II.

General formula (II)

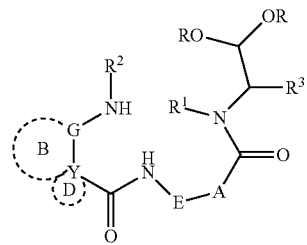

TABLE XIII-1

| Example No. | R1 | R2 | R3 | (structure) |
|---|---|---|---|---|
| II-2 | benzyl | benzyl-NH-C(=O)- | H | 4-tert-butoxybenzyl ketone |
| II-3 | benzyl | benzyl-NH-C(=O)- | H | Boc-aminobutyl ketone |
| II-4 | naphthalen-1-ylmethyl | benzyl-NH-C(=O)- | H | 4-tert-butoxybenzyl ketone |
| II-5 | naphthalen-1-ylmethyl | benzyl-NH-C(=O)- | H | tert-butyl ester ketone |

TABLE XIII-1-continued
| | | | | |
|---|---|---|---|---|
| II-6 | 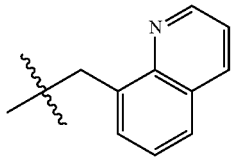 [SMILES: *Cc1cccc2cccnc12] | 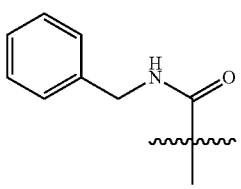 [SMILES: *C(=O)NCc1ccccc1] | H | 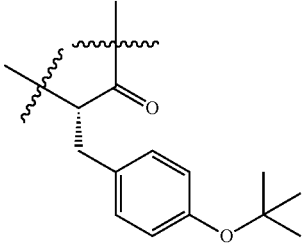 [SMILES: *C(=O)[C@@H](*)Cc1ccc(OC(C)(C)C)cc1] |
| II-7 | 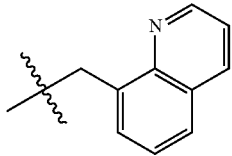 [SMILES: *Cc1cccc2cccnc12] | 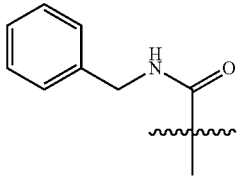 [SMILES: *C(=O)NCc1ccccc1] | H | 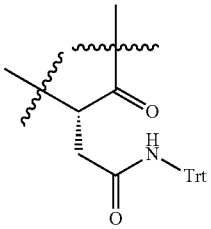 |
| II-8 | 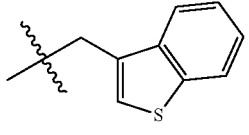 [SMILES: *Cc1csc2ccccc12] | 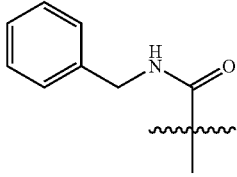 [SMILES: *C(=O)NCc1ccccc1] | H | 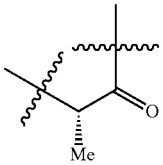 |
| II-9 | 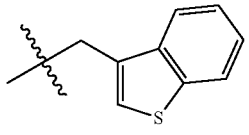 [SMILES: *Cc1csc2ccccc12] | 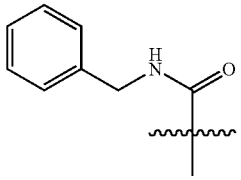 [SMILES: *C(=O)NCc1ccccc1] | H | 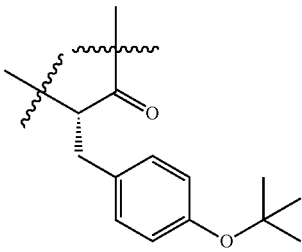 [SMILES: *C(=O)[C@@H](*)Cc1ccc(OC(C)(C)C)cc1] |
| II-10 | 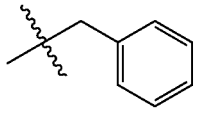 [SMILES: *Cc1ccccc1] | 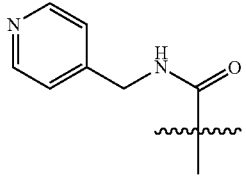 [SMILES: *C(=O)NCc1ccncc1] | H | 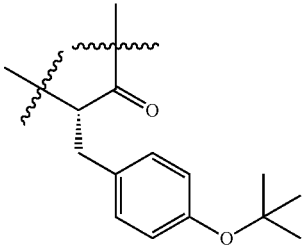 [SMILES: *C(=O)[C@@H](*)Cc1ccc(OC(C)(C)C)cc1] |
| II-11 | 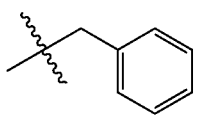 [SMILES: *Cc1ccccc1] | 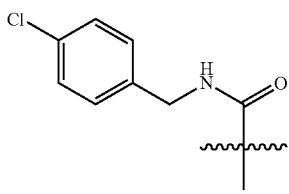 [SMILES: *C(=O)NCc1ccc(Cl)cc1] | H | 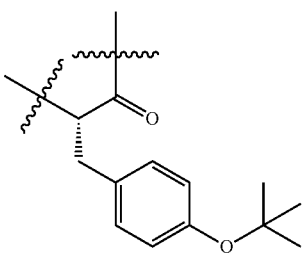 [SMILES: *C(=O)[C@@H](*)Cc1ccc(OC(C)(C)C)cc1] |

TABLE XIII-1-continued
| Example No. | (B-G=Y structure) | R | Int_1 | Int_2 | syn. | yield (%) |
|---|---|---|---|---|---|---|
| II-12 | 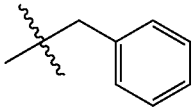 [SMILES: *Cc1ccccc1] phenylmethyl; 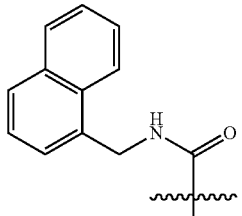 naphthylmethyl amide; H; 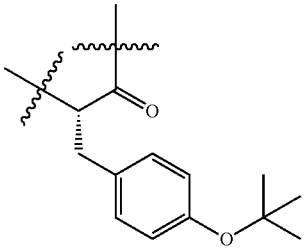 [SMILES: *C(=O)[C@@H](*)Cc1ccc(OC(C)(C)C)cc1] 4-tert-butoxybenzyl ketone | | | | | |
| II-2 | 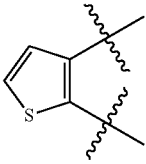 [SMILES: *c1ccsc1*] | Ethyl | VI-2 | V-1 | II-1 | 74 |
| II-3 | 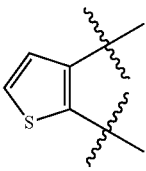 [SMILES: *c1ccsc1*] | Ethyl | Vi-3 | V-1 | II-1 | 82 |
| II-4 | 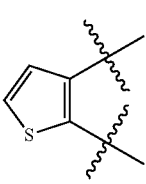 | Ethyl | VI-4 | V-1 | II-1 | 63 |
| II-5 | 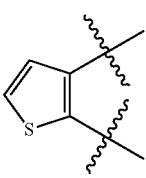 [SMILES: *c1ccsc1*] | Ethyl | VI-5 | V-1 | II-1 | 82 |
| II-6 | 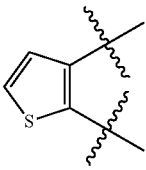 [SMILES: *c1ccsc1*] | Ethyl | VI-6 | V-1 | II-1 | 38 |
| II-7 | 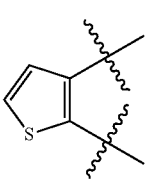 [SMILES: *c1ccsc1*] | Ethyl | VI-7 | V-1 | II-1 | 9 |

TABLE XIII-1-continued

| | | | | | | | |
|---|---|---|---|---|---|---|---|
| II-8 | (thiophene) | Ethyl | VI-8 | V-1 | II-1 | 100 | |
| II-9 | (thiophene) | Ethyl | VI-9 | V-1 | II-1 | 100 | |
| II-10 | (thiophene) | Ethyl | VI-2 | V-3 | II-1 | 64 | |
| II-11 | (thiophene) | Ethyl | VI-2 | V-4 | II-1 | 67 | |
| II-12 | (thiophene) | Ethyl | VI-2 | V-5 | II-1 | 39 | |

TABLE XIII-2

| Example No. | R1 | R2 | R3 | E—A | B/G/Y ring | R | Int_1 | Int_2 | syn. | yield (%) |
|---|---|---|---|---|---|---|---|---|---|---|
| II-13 | benzyl | N-ethylamide | H | (CH2-Ar-OtBu ketone) | (thiophene) | Ethyl | VI-2 | V-2 | II-1 | 61 |
| II-14 | naphthylmethyl | pyridin-4-ylmethylamide | H | (CH2-Ar-OtBu ketone) | (thiophene) | Ethyl | VI-4 | V-3 | II-1 | 58 |

TABLE XIII-2-continued
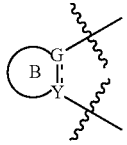

TABLE XIII-2-continued

| Example No. | R1 | R2 | R3 | E-A (structure) | B/Y (structure) | R | Int_1 | Int_2 | syn. | yield (%) |
|---|---|---|---|---|---|---|---|---|---|---|
| II-22 | benzothiophen-3-ylmethyl | pyridin-4-ylmethyl-NH-C(O)- | H | benzyl with 4-OtBu ketone | thiophene | Ethyl | VI-9 | V-3 | II-1 | 56 |
| II-23 | benzothiophen-3-ylmethyl | 4-chlorobenzyl-NH-C(O)- | H | benzyl with 4-OtBu ketone | thiophene | Ethyl | VI-9 | V-4 | II-1 | 59 |

TABLE XIII-3

| Example No. | R1 | R2 | R3 | E-A (structure) | B/Y (structure) | R | Int_1 | Int_2 | syn. | yield (%) |
|---|---|---|---|---|---|---|---|---|---|---|
| II-24 | benzothiophen-3-ylmethyl | naphthalen-1-ylmethyl-NH-C(O)- | H | benzyl with 4-OtBu ketone | thiophene | Ethyl | VI-9 | V-5 | II-1 | 37 |
| II-25 | benzothiophen-3-ylmethyl | ethyl-NH-C(O)- | H | benzyl with 4-OtBu ketone | thiophene | Ethyl | VI-9 | V-2 | II-1 | 57 |
| II-26 | isohexyl | naphthalen-1-ylmethyl-NH-C(O)- | H | Me-substituted ketone | thiophene | Ethyl | VI-10 | V-5 | II-1 | n.d. |
| II-27 | isohexyl | benzyl-NH-C(O)- | H | benzyl with 4-OtBu ketone | thiophene | Ethyl | VI-11 | V-1 | II-1 | n.d. |

TABLE XIII-3-continued

| Example No. | R1 | R2 | R3 | ⟨E-A-C(=O)⟩ | ⟨B=G/Y⟩ | R | Int_1 | Int_2 | syn. | yield (%) |
|---|---|---|---|---|---|---|---|---|---|---|
| II-28 | isohexyl | pyridin-4-ylmethyl-NHC(O)- | H | 4-tBuO-benzyl ketone | thiophene | Ethyl | VI-11 | V-3 | II-1 | n.d. |
| II-29 | isohexyl | phenethyl-NHC(O)- | H | 4-tBuO-benzyl ketone | thiophene | Ethyl | VI-11 | V-6 | II-1 | n.d. |
| II-30 | isohexyl | naphth-1-ylmethyl-NHC(O)- | H | 4-tBuO-benzyl ketone | thiophene | Ethyl | VI-11 | V-5 | II-1 | n.d. |
| II-31 | isohexyl | 3,3-diphenylpropyl-NHC(O)- | H | 4-tBuO-benzyl ketone | thiophene | Ethyl | VI-11 | V-7 | II-1 | n.d. |
| II-32 | isohexyl | cyclohexylmethyl-NHC(O)- | H | 4-tBuO-benzyl ketone | thiophene | Ethyl | VI-11 | V-8 | II-1 | n.d. |
| II-33 | isohexyl | isopropyl-NHC(O)- | H | 4-tBuO-benzyl ketone | thiophene | Ethyl | VI-11 | V-9 | II-1 | n.d. |
| II-34 | isohexyl | naphth-1-ylmethyl-NHC(O)- | H | NHBoc-alkyl ketone | thiophene | Ethyl | VI-12 | V-5 | II-1 | n.d. |

TABLE XIII-4

| Example No. | R1 | R2 | R3 | E-A (group) | R (ring) | R | Int_1 | Int_2 | syn. | yield (%) |
|---|---|---|---|---|---|---|---|---|---|---|
| II-35 | isopentyl | naphthylmethyl-NHC(O)- | H | CH(CH2C(O)OtBu)C(O) | thiophene | Ethyl | VI-13 | V-5 | II-1 | n.d. |
| II-36 | isopentyl | naphthylmethyl-NHC(O)- | H | CH(CH2C(O)NHTrt)C(O) | thiophene | Ethyl | VI-14 | V-5 | II-1 | n.d. |
| II-37 | isopentyl | naphthylmethyl-NHC(O)- | H | CH(CH2OtBu)C(O) | thiophene | Ethyl | VI-15 | V-5 | II-1 | n.d. |
| II-38 | isopentyl | naphthylmethyl-NHC(O)- | H | CH(iBu)C(O) | thiophene | Ethyl | VI-16 | V-5 | II-1 | n.d. |
| II-39 | isopentyl | naphthylmethyl-NHC(O)- | H | CH(Ph)C(O) | thiophene | Ethyl | VI-17 | V-5 | II-1 | n.d. |
| II-40 | isopentyl | naphthylmethyl-NHC(O)- | H | CH(CH2Ph)C(O) | thiophene | Ethyl | VI-18 | V-5 | II-1 | n.d. |
| II-41 | isopentyl | naphthylmethyl-NHC(O)- | H | CH(CH2OPh)C(O) | thiophene | Ethyl | VI-19 | V-5 | II-1 | n.d. |

TABLE XIII-4-continued

| Example No. | R1 | R2 | R3 | E-A(=O)- | B/G/Y ring | R | Int_1 | Int_2 | syn. | yield (%) |
|---|---|---|---|---|---|---|---|---|---|---|
| II-42 | isohexyl | naphthylmethyl-NHC(O)- | H | benzyloxymethyl-CH-C(O)- | thienyl | Ethyl | VI-20 | V-5 | II-1 | n.d. |
| II-43 | isohexyl | 3,3-diphenylpropyl-NHC(O)- | H | benzyloxymethyl-CH-C(O)- | thienyl | Ethyl | VI-20 | V-7 | II-1 | n.d. |
| II-44 | isohexyl | cyclohexylmethyl-NHC(O)- | H | benzyloxymethyl-CH-C(O)- | thienyl | Ethyl | VI-20 | V-8 | II-1 | n.d. |
| II-45 | isohexyl | isopropyl-NHC(O)- | H | benzyloxymethyl-CH-C(O)- | thienyl | Ethyl | VI-20 | V-9 | II-1 | n.d. |

TABLE XIII-5

| Example No. | R1 | R2 | R3 | E-A(=O)- | B/G/Y ring | R | Int_1 | Int_2 | syn. | yield (%) |
|---|---|---|---|---|---|---|---|---|---|---|
| II-46 | isohexyl | naphthylmethyl-NHC(O)- | H | naphthylmethyl-CH-C(O)- | thienyl | Ethyl | VI-21 | V-5 | II-1 | n.d. |

TABLE XIII-5-continued
| Example No. | R1 | R2 | R3 | E-A / B-G-Y | R | Int_1 | Int_2 | syn. | yield (%) |
|---|---|---|---|---|---|---|---|---|---|
| II-47 | 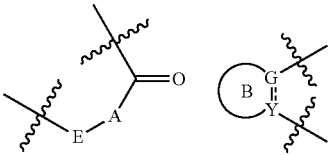 |  | H |  | 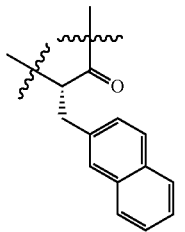 | Ethyl | VI-22 | V-1 | II-1 | n.d. |
| II-48 | 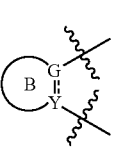 | 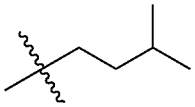 [SMILES: *CCC(C)C] | H | 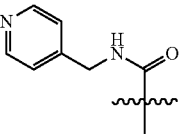 [SMILES: *C(=O)NCc1ccncc1] | 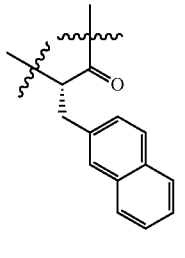 [SMILES: *C(=O)[C@@H](*)Cc1ccc2ccccc2c1] | Ethyl | VI-22 | V-3 | II-1 | n.d. |
| II-49 | 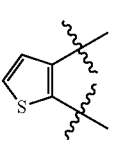 [SMILES: *c1ccsc1*] |  | H |  | 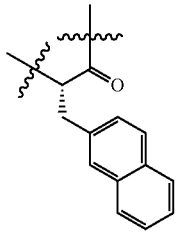 [SMILES: *C(=O)[C@@H](*)Cc1ccc2ccccc2c1] | Ethyl | VI-22 | V-6 | II-1 | n.d. |
| II-50 | 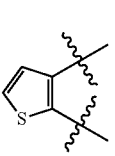 [SMILES: *c1ccsc1*] |  | H |  | 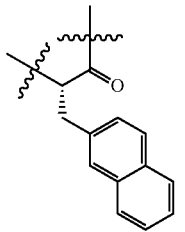 [SMILES: *C(=O)[C@@H](*)Cc1ccc2ccccc2c1] | Ethyl | VI-22 | V-5 | II-1 | n.d. |
| II-51 | 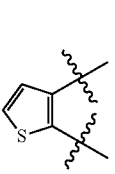 |  | H |  | 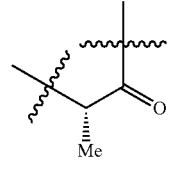 | Ethyl | VI-10 | V-10 | II-1 | n.d. |
| II-52 | 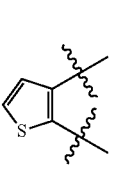 [SMILES: *c1ccsc1*] |  | H |  | 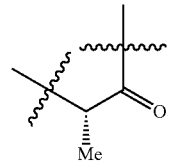 | Ethyl | VI-10 | V-11 | II-1 | n.d. |

TABLE XIII-5-continued

| Example No. | R1 | R2 | R3 | [E-A-C(=O)] | [B-G=Y ring] | R | Int_1 | Int_2 | syn. | yield (%) |
|---|---|---|---|---|---|---|---|---|---|---|
| II-53 | isohexyl | methyl β-amido propanoate | H | CH(Me)-C(=O) | thiophene | Ethyl | VI-10 | V-12 | II-1 | n.d. |
| II-54 | isohexyl | benzodioxol-CH2-NH-C(=O) | H | CH(Me)-C(=O) | thiophene | Ethyl | VI-10 | V-14 | II-1 | n.d. |
| II-55 | isohexyl | thiophen-2-yl-CH2-NH-C(=O) | H | CH(Me)-C(=O) | thiophene | Ethyl | VI-10 | V-15 | II-1 | n.d. |
| II-56 | isohexyl | thiophen-2-yl-CH2-NH-C(=O) | H | CH(CH2-C6H4-OtBu)-C(=O) | thiophene | Ethyl | VI-11 | V-15 | II-1 | n.d. |

TABLE XIII-6

| Example No. | R1 | R2 | R3 | [E-A-C(=O)] | [B-G=Y ring] | R | Int_1 | Int_2 | syn. | yield (%) |
|---|---|---|---|---|---|---|---|---|---|---|
| II-57 | isohexyl | 4-methylbenzyl-NH-C(=O) | H | CH(CH2-C6H4-OtBu)-C(=O) | thiophene | Ethyl | VI-11 | V-16 | II-1 | n.d. |
| II-58 | isohexyl | thiophen-2-yl-CH2-NH-C(=O) | H | CH(CH2CH2CH2-NHBoc)-C(=O) | thiophene | Ethyl | VI-12 | V-15 | II-1 | n.d. |

TABLE XIII-6-continued

| Example No. | R1 | R2 | R3 | E-A structure | Ring | R | Int_1 | Int_2 | syn. | yield (%) |
|---|---|---|---|---|---|---|---|---|---|---|
| II-59 | isohexyl | thiophene-CH2-NH-C(=O)- | H | CH(CH2-C(=O)-O-tBu)-C(=O)- | thiophene | Ethyl | VI-13 | V-15 | II-1 | n.d. |
| II-60 | isohexyl | thiophene-CH2-NH-C(=O)- | H | CH(CH2-C(=O)-NH-Trt)-C(=O)- | thiophene | Ethyl | VI-14 | V-15 | II-1 | n.d. |
| II-61 | isohexyl | thiophene-CH2-NH-C(=O)- | H | CH(CH2-O-tBu)-C(=O)- | thiophene | Ethyl | VI-15 | V-15 | II-1 | n.d. |
| II-62 | isohexyl | thiophene-CH2-NH-C(=O)- | H | CH(iBu)-C(=O)- | thiophene | Ethyl | VI-16 | V-15 | II-1 | n.d. |
| II-63 | isohexyl | thiophene-CH2-NH-C(=O)- | H | CH(Ph)-C(=O)- | thiophene | Ethyl | VI-17 | V-15 | II-1 | n.d. |
| II-64 | isohexyl | TBSO-CH2CH2-NH-C(=O)- | H | CH(Bn)-C(=O)- | thiophene | Ethyl | VI-18 | V-10 | II-1 | n.d. |

TABLE XIII-6-continued
| Example No. | R1 | R2 | R3 | 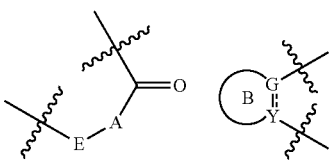 | | R | Int_1 | Int_2 | syn. | yield (%) |
|---|---|---|---|---|---|---|---|---|---|---|
| II-65 | 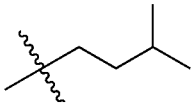 [SMILES: *CCC(C)C] | 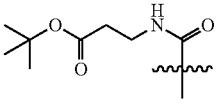 | H | 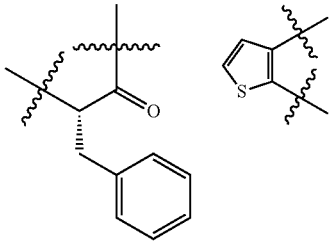 | 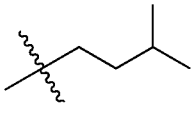 [SMILES: *CCC(C)C] | Ethyl | VI-18 | V-11 | II-1 | n.d. |
| II-66 | 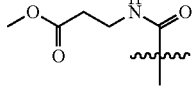 | 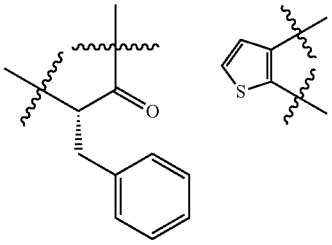 | H | 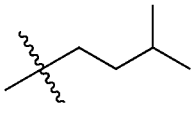 [SMILES: *CCC(C)C] | 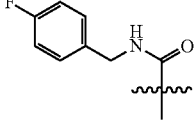 | Ethyl | VI-18 | V-12 | II-1 | n.d. |
| II-67 | 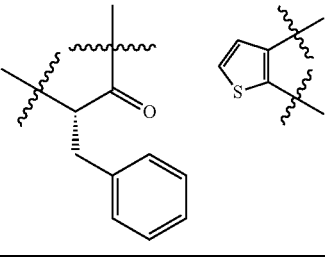 | 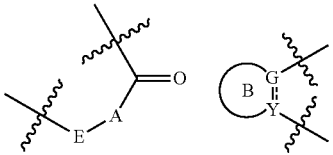 | H | 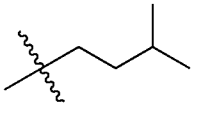 [SMILES: *CCC(C)C] | 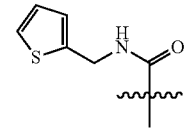 [SMILES: *C(=O)NCc1cccs1] | Ethyl | VI-18 | V-13 | II-1 | n.d. |
TABLE XIII-7
| Example No. | R1 | R2 | R3 | | | R | Int_1 | Int_2 | syn. | yield (%) |
|---|---|---|---|---|---|---|---|---|---|---|
| II-68 | 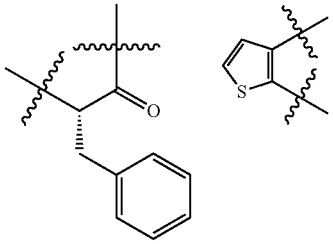 | | H | | | Ethyl | VI-18 | V-15 | II-1 | n.d. |

TABLE XIII-7-continued

| Example No. | R1 | R2 | R3 | E-A | G/B/Y | R | Int_1 | Int_2 | syn. | yield (%) |
|---|---|---|---|---|---|---|---|---|---|---|
| II-69 | isohexyl | 4-fluorobenzyl-NH-C(O)- | H | naphthalen-1-ylmethyl-CH-C(O)- | thiophene | Ethyl | VI-21 | V-13 | II-1 | n.d. |
| II-70 | isohexyl | benzo[1,3]dioxol-5-ylmethyl-NH-C(O)- | H | naphthalen-1-ylmethyl-CH-C(O)- | thiophene | Ethyl | VI-21 | V-14 | II-1 | n.d. |
| II-71 | isohexyl | thiophen-2-ylmethyl-NH-C(O)- | H | naphthalen-1-ylmethyl-CH-C(O)- | thiophene | Ethyl | VI-21 | V-15 | II-1 | n.d. |
| II-72 | isohexyl | 4-methylbenzyl-NH-C(O)- | H | naphthalen-1-ylmethyl-CH-C(O)- | thiophene | Ethyl | VI-21 | V-16 | II-1 | n.d. |
| II-73 | 2-phenylethyl | 2-phenylethyl-NH-C(O)- | H | Me-CH-C(O)- | thiophene | Ethyl | VI-23 | V-6 | II-1 | n.d. |

TABLE XIII-7-continued
| Example No. | R1 | R2 | R3 | E-A (center structure) | B-G-Y ring | R | Int_1 | Int_2 | syn. | yield (%) |
|---|---|---|---|---|---|---|---|---|---|---|
| II-74 | 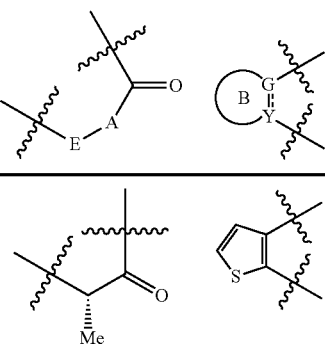 | 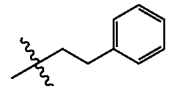 [SMILES: *CCc1ccccc1] | H | 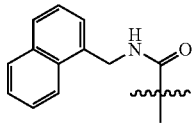 [SMILES: *C(=O)NCc1cccc2ccccc12] | 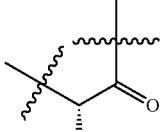 | Ethyl | VI-23 | V-5 | II-1 | n.d. |
| II-75 | 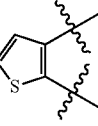 | 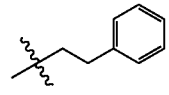 [SMILES: *CCc1ccccc1] | H | 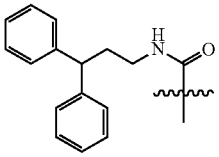 [SMILES: *C(=O)NCCC(c1ccccc1)c1ccccc1] | 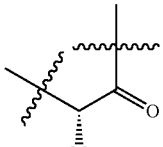 | Ethyl | VI-23 | V-7 | II-1 | n.d. |
| II-76 | 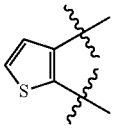 [SMILES: *c1ccsc1*] | 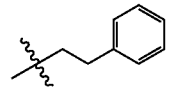 [SMILES: *CCc1ccccc1] | H | 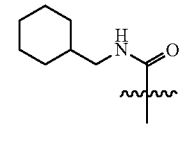 | 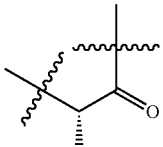 | Ethyl | VI-23 | V-8 | II-1 | n.d. |
| II-77 | 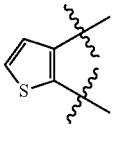 [SMILES: *c1ccsc1*] | 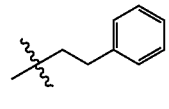 [SMILES: *CCc1ccccc1] | H | 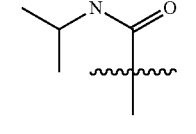 | 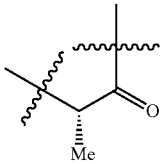 | Ethyl | VI-23 | V-9 | II-1 | n.d. |
| II-78 | 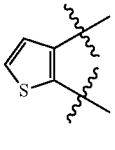 [SMILES: *c1ccsc1*] | 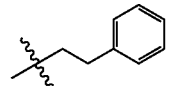 [SMILES: *CCc1ccccc1] | H | 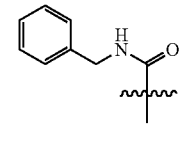 [SMILES: *C(=O)NCc1ccccc1] | 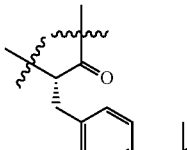 | Ethyl | VI-24 | V-1 | II-1 | n.d. |
TABLE XIII-8
| Example No. | R1 | R2 | R3 | E-A | B-G-Y | R | Int_1 | Int_2 | syn. | yield (%) |
|---|---|---|---|---|---|---|---|---|---|---|
| II-79 | 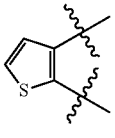 [SMILES: *c1ccsc1*] | 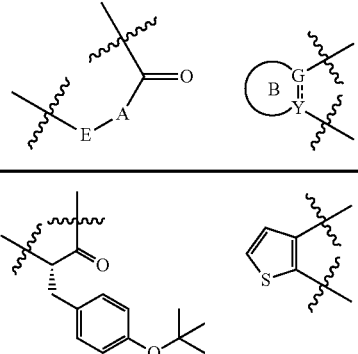 | H | 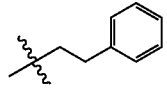 [SMILES: *CCc1ccccc1] | 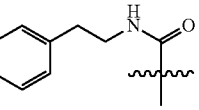 | Ethyl | VI-24 | V-6 | II-1 | n.d. |

TABLE XIII-8-continued
| Example No. | R1 | R2 | R3 | 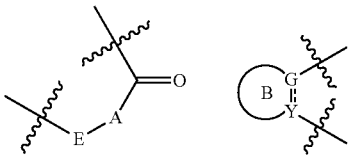 | 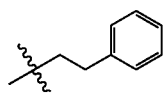 [SMILES: *CCc1ccccc1] | R | Int_1 | Int_2 | syn. | yield (%) |
|---|---|---|---|---|---|---|---|---|---|---|
| II-80 |  |  | H | 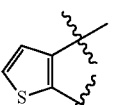 | 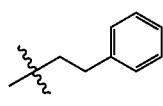 [SMILES: *CCc1ccccc1] | Ethyl | VI-24 | V-5 | II-1 | n.d. |
| II-81 |  |  | H | 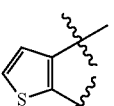 | 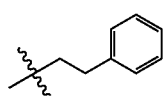 [SMILES: *CCc1ccccc1] | Ethyl | VI-24 | V-7 | II-1 | n.d. |
| II-82 | 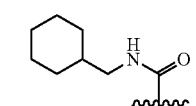 | 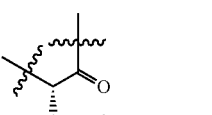 | H | 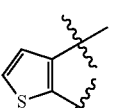 | 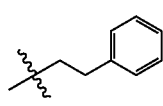 [SMILES: *CCc1ccccc1] | Ethyl | VI-24 | V-8 | II-1 | n.d. |
| II-83 | 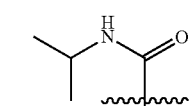 | 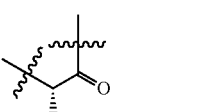 | H | 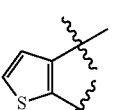 | 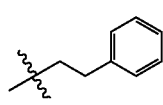 | Ethyl | VI-24 | V-9 | II-1 | n.d. |
| II-84 | 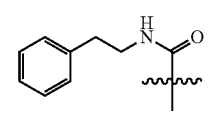 [SMILES: *C(=O)NCCc1ccccc1] | 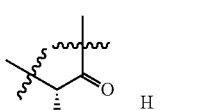 | H | 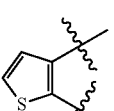 | 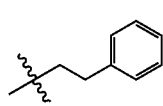 [SMILES: *CCc1ccccc1] | Ethyl | VI-25 | V-6 | II-1 | n.d. |
| II-85 | 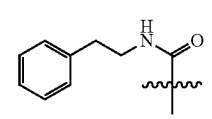 [SMILES: *C(=O)NCCc1ccccc1] | 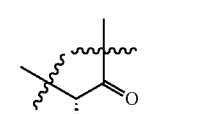 | H | 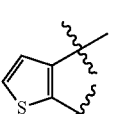 | 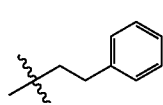 [SMILES: *CCc1ccccc1] | Ethyl | VI-26 | V-6 | II-1 | n.d. |
| II-86 | 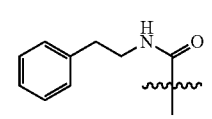 [SMILES: *C(=O)NCCc1ccccc1] | 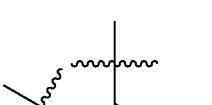 | H | 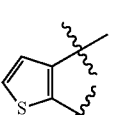 | | Ethyl | VI-27 | V-6 | II-1 | n.d. |

TABLE XIII-8-continued

| Example No. | R1 | R2 | R3 | [E-A-C(O)] | [B-Y-G ring] | R | Int_1 | Int_2 | syn. | yield (%) |
|---|---|---|---|---|---|---|---|---|---|---|
| II-87 | phenethyl | phenethyl-NH-C(O)-C(CH₃)₂- | H | CH(CH₂-O-tBu)-C(O)- | thiophene | Ethyl | VI-28 | V-6 | II-1 | n.d. |
| II-88 | phenethyl | phenethyl-NH-C(O)-C(CH₃)₂- | H | CH(iBu)-C(O)- | thiophene | Ethyl | VI-29 | V-6 | II-1 | n.d. |
| II-89 | phenethyl | phenethyl-NH-C(O)-C(CH₃)₂- | H | CH(CH₂CH₂Ph)-C(O)- | thiophene | Ethyl | VI-30 | V-1 | II-1 | n.d. |

TABLE XIII-9

| Example No. | R1 | R2 | R3 | [E-A-C(O)] |
|---|---|---|---|---|
| II-90 | phenethyl | phenethyl-NH-C(O)-C(CH₃)₂- | H | CH(CH₂CH₂Ph)-C(O)- |

TABLE XIII-9-continued
| | | | | |
|---|---|---|---|---|
| II-91 | 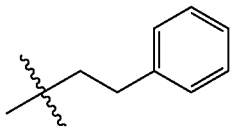 [SMILES: *CCc1ccccc1] | 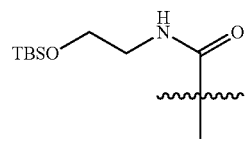 [SMILES: *C(=O)NCCO[Si](C)(C)C(C)(C)C] | H | 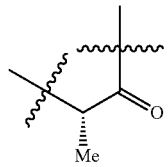 [SMILES: *C(=O)[C@@H](*)C] |
| II-92 | 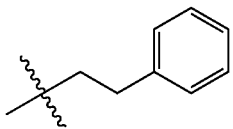 [SMILES: *CCc1ccccc1] | 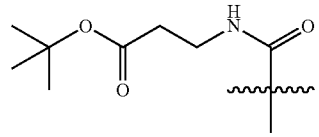 [SMILES: *C(=O)NCCC(=O)OC(C)(C)C] | H | 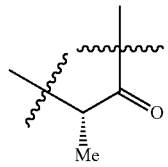 |
| II-93 | 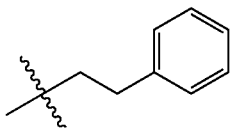 [SMILES: *CCc1ccccc1] | 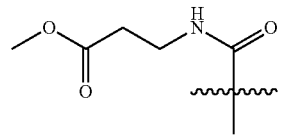 [SMILES: *C(=O)NCCC(=O)OC] | H | 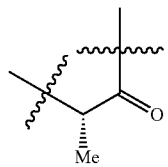 [SMILES: *C(=O)[C@@H](*)C] |
| II-94 | 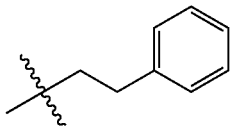 [SMILES: *CCc1ccccc1] | 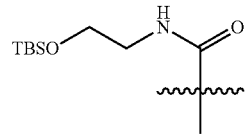 [SMILES: *C(=O)NCCO[Si](C)(C)C(C)(C)C] | H | 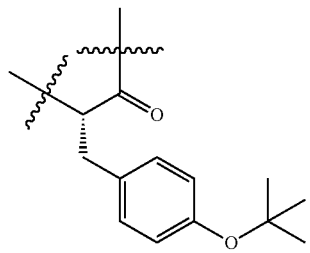 [SMILES: *C(=O)[C@@H](*)Cc1ccc(OC(C)(C)C)cc1] |
| II-95 | 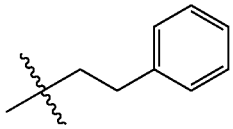 [SMILES: *CCc1ccccc1] | 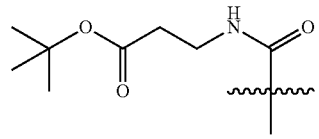 [SMILES: *C(=O)NCCC(=O)OC(C)(C)C] | H | 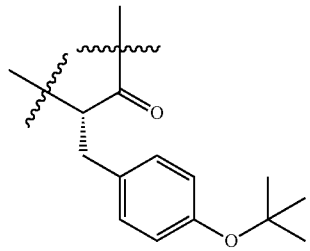 [SMILES: *C(=O)[C@@H](*)Cc1ccc(OC(C)(C)C)cc1] |
| II-96 | 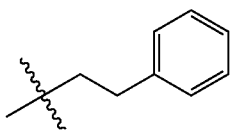 [SMILES: *CCc1ccccc1] | 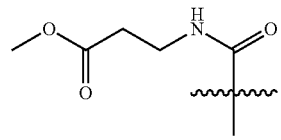 [SMILES: *C(=O)NCCC(=O)OC] | H | 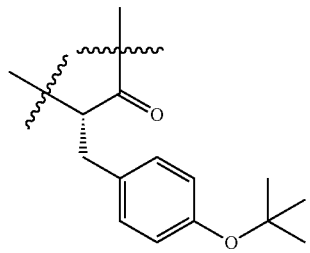 [SMILES: *C(=O)[C@@H](*)Cc1ccc(OC(C)(C)C)cc1] |
| II-97 | 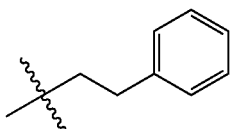 [SMILES: *CCc1ccccc1] | 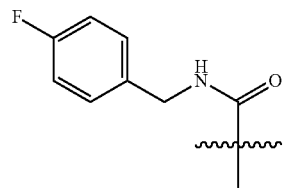 [SMILES: *C(=O)NCc1ccc(F)cc1] | H | 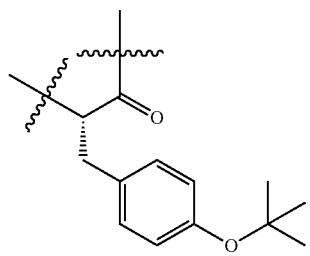 [SMILES: *C(=O)[C@@H](*)Cc1ccc(OC(C)(C)C)cc1] |

TABLE XIII-9-continued
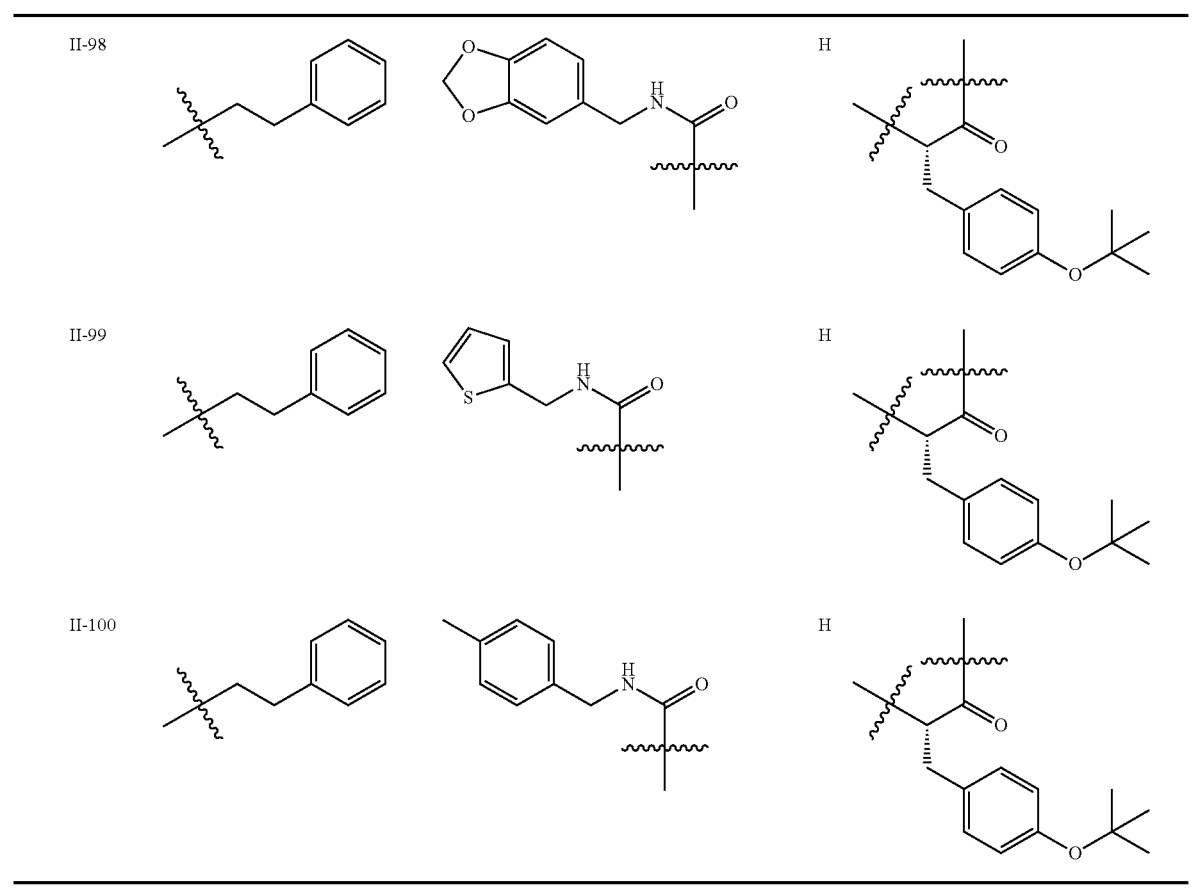
| Example No. | 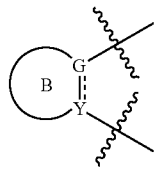 | R | Int_1 | Int_2 | syn. | yield (%) |
|---|---|---|---|---|---|---|
| II-90 | | Ethyl | VI-30 | V-6 | II-1 | n.d. |
| II-91 | | Ethyl | VI-23 | V-10 | II-1 | n.d. |
| II-92 | | Ethyl | VI-23 | V-11 | II-1 | n.d. |

TABLE XIII-9-continued

| | | | | | | |
|---|---|---|---|---|---|---|
| II-93 | (thiophene) | Ethyl | VI-23 | V-12 | II-1 | n.d. |
| II-94 | (thiophene) | Ethyl | VI-24 | V-10 | II-1 | n.d. |
| II-95 | (thiophene) | Ethyl | VI-24 | V-11 | II-1 | n.d. |
| II-96 | (thiophene) | Ethyl | VI-24 | V-12 | II-1 | n.d. |
| II-97 | (thiophene) | Ethyl | VI-24 | V-13 | II-1 | n.d. |
| II-98 | (thiophene) | Ethyl | VI-24 | V-14 | II-1 | n.d. |
| II-99 | (thiophene) | Ethyl | VI-24 | V-15 | II-1 | n.d. |
| II-100 | (thiophene) | Ethyl | VI-24 | V-16 | II-1 | n.d. |

TABLE XIII-10
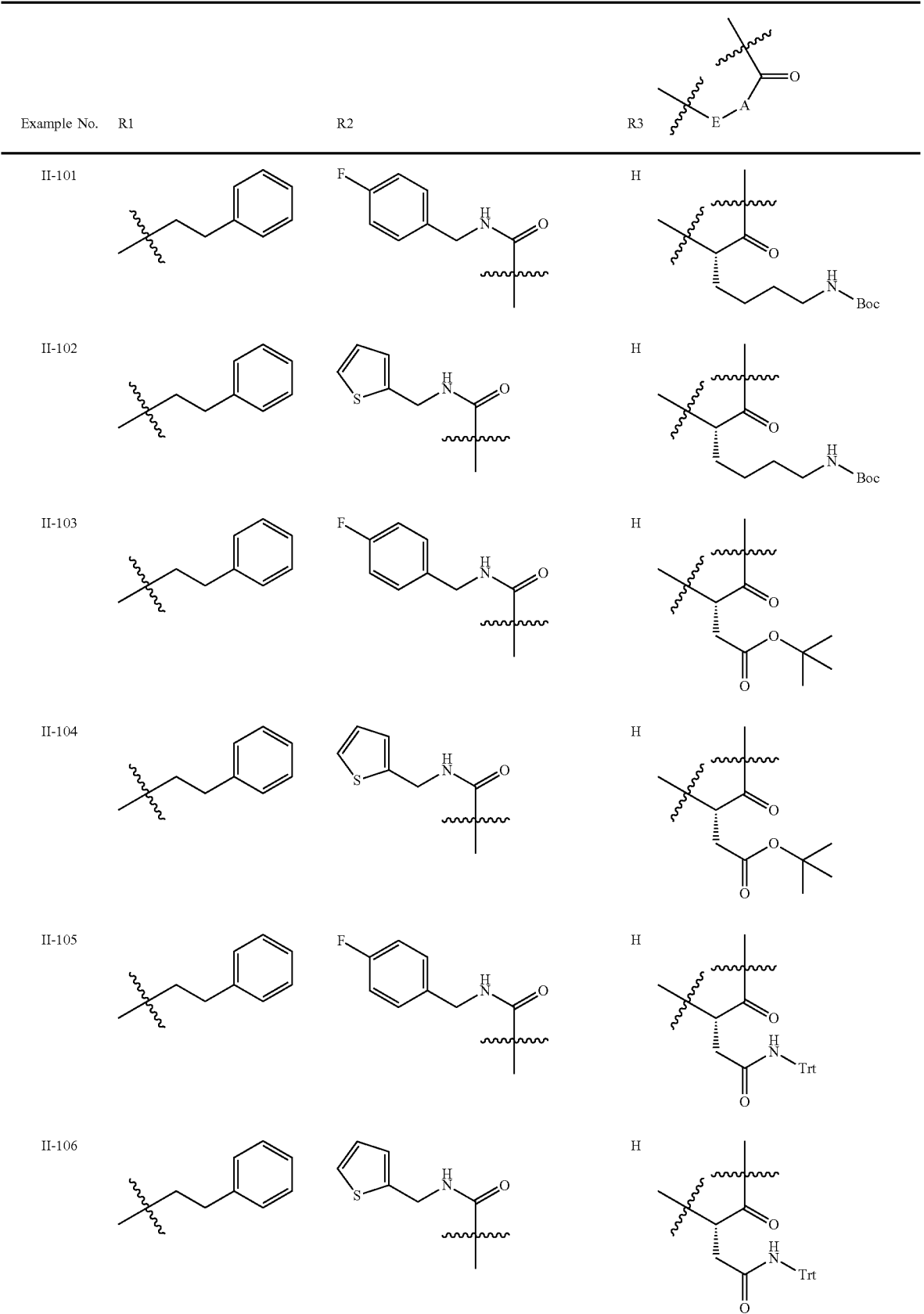

TABLE XIII-10-continued
| | | | |
|---|---|---|---|
| II-107 | 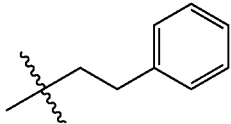 [SMILES: *CCc1ccccc1] | 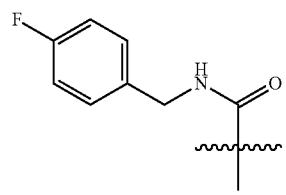 [SMILES: *C(=O)NCc1ccc(F)cc1] | H 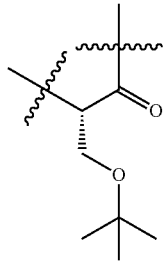 [SMILES: *C(=O)[C@@H](*)COC(C)(C)C] |
| II-108 | 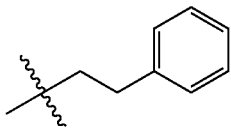 [SMILES: *CCc1ccccc1] | 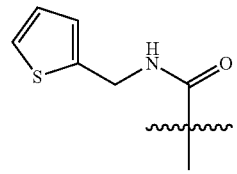 [SMILES: *C(=O)NCc1cccs1] | H 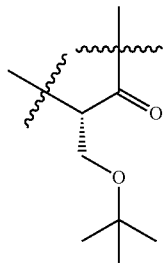 [SMILES: *C(=O)[C@@H](*)COC(C)(C)C] |
| II-109 | 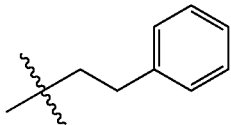 [SMILES: *CCc1ccccc1] | 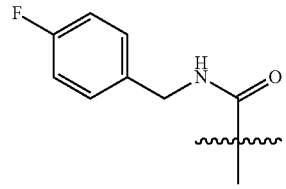 [SMILES: *C(=O)NCc1ccc(F)cc1] | H 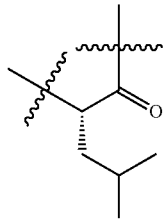 [SMILES: *C(=O)[C@@H](*)CC(C)C] |
| II-110 | 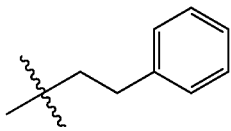 [SMILES: *CCc1ccccc1] | 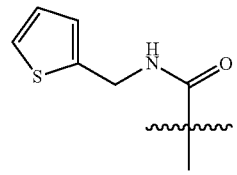 [SMILES: *C(=O)NCc1cccs1] | H 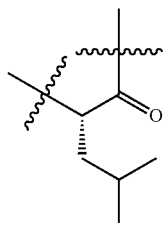 [SMILES: *C(=O)[C@@H](*)CC(C)C] |
| II-111 | 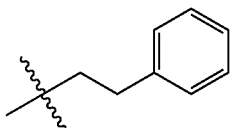 [SMILES: *CCc1ccccc1] | 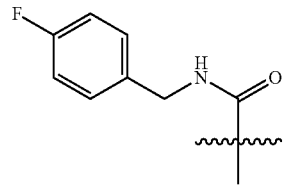 [SMILES: *C(=O)NCc1ccc(F)cc1] | H 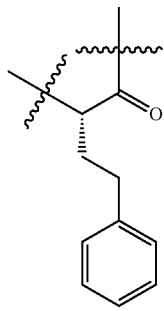 [SMILES: *C(=O)[C@@H](*)CCc1ccccc1] |

TABLE XIII-10-continued
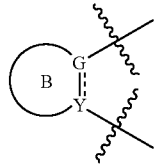
| Example No. | | R | Int_1 | Int_2 | syn. | yield (%) |
|---|---|---|---|---|---|---|
| II-101 | 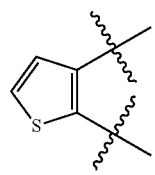 [SMILES: *c1ccsc1*] | Ethyl | VI-25 | V-13 | II-1 | n.d. |
| II-102 | 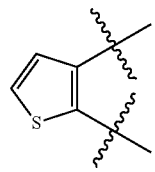 [SMILES: *c1ccsc1*] | Ethyl | VI-25 | V-15 | II-1 | n.d. |
| II-103 | 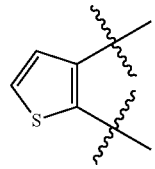 [SMILES: *c1ccsc1*] | Ethyl | VI-26 | V-13 | II-1 | n.d. |
| II-104 | 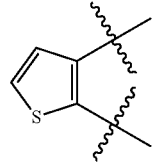 [SMILES: *c1ccsc1*] | Ethyl | VI-26 | V-15 | II-1 | n.d. |
| II-105 | 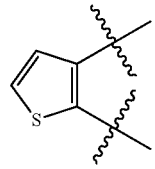 [SMILES: *c1ccsc1*] | Ethyl | VI-27 | V-13 | II-1 | n.d. |
| II-106 | 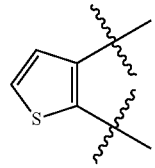 [SMILES: *c1ccsc1*] | Ethyl | VI-27 | V-15 | II-1 | n.d. |
| II-107 | 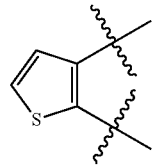 [SMILES: *c1ccsc1*] | Ethyl | VI-28 | V-13 | II-1 | n.d. |

TABLE XIII-10-continued

| Example No. | | | | | | | |
|---|---|---|---|---|---|---|---|
| II-108 | (thiophene) | Ethyl | VI-28 | V-15 | II-1 | n.d. | |
| II-109 | (thiophene) | Ethyl | VI-29 | V-13 | II-1 | n.d. | |
| II-110 | (thiophene) | Ethyl | VI-29 | V-15 | II-1 | n.d. | |
| II-111 | (thiophene) | Ethyl | VI-30 | V-13 | II-1 | n.d. | |

TABLE XIII-11

| Example No. | R1 | R2 | R3 | E—A |
|---|---|---|---|---|
| II-112 | phenethyl | benzo[d][1,3]dioxol-5-ylmethyl-NH-C(O)- | H | (2-phenethyl-substituted C(O)) |
| II-113 | phenethyl | thiophen-2-ylmethyl-NH-C(O)- | H | (2-phenethyl-substituted C(O)) |

TABLE XIII-11-continued
| | | | | |
|---|---|---|---|---|
| II-114 | 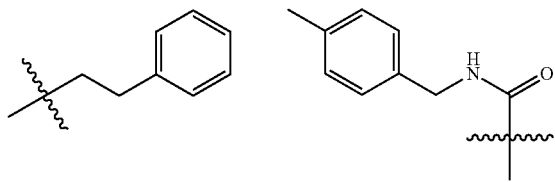 | | H | 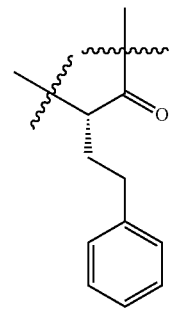 [SMILES: *C(=O)[C@@H](*)CCc1ccccc1] |
| II-115 | 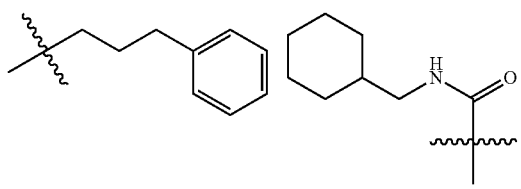 | | H | 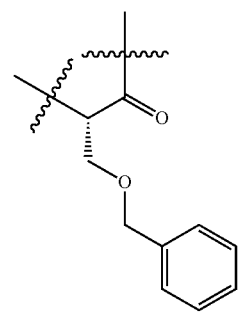 [SMILES: *C(=O)[C@@H](*)COCc1ccccc1] |
| II-116 | 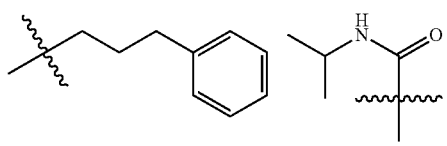 | | H | 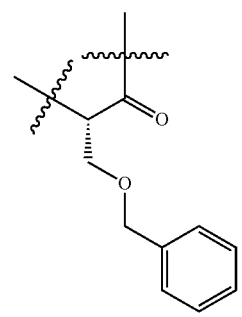 [SMILES: *C(=O)[C@@H](*)COCc1ccccc1] |
| II-117 | 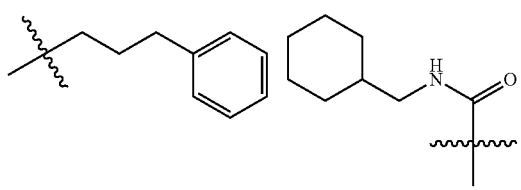 | | H | 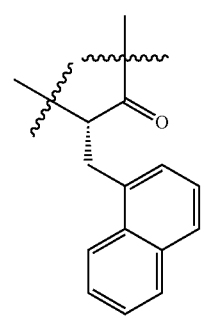 [SMILES: *C(=O)[C@@H](*)Cc1cccc2ccccc12] |
| II-118 | 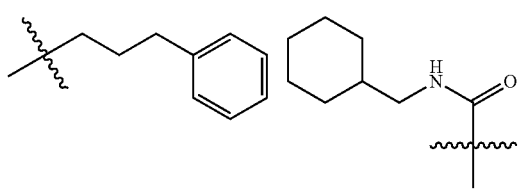 | | H | 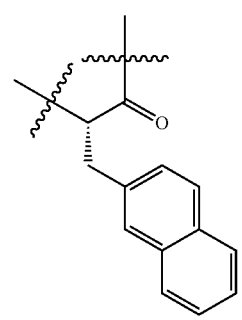 [SMILES: *C(=O)[C@@H](*)Cc1ccc2ccccc2c1] |

TABLE XIII-11-continued
| | | | |
|---|---|---|---|
| II-119 | 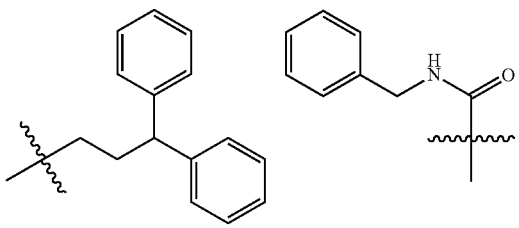 | H | 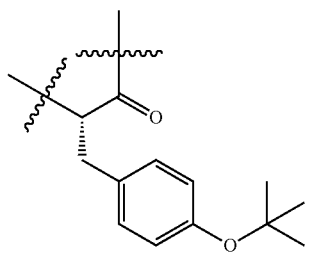 [SMILES: *C(=O)[C@@H](*)Cc1ccc(OC(C)(C)C)cc1] |
| II-120 | 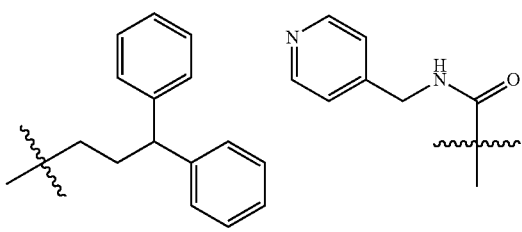 | H | 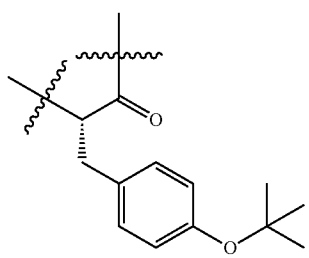 [SMILES: *C(=O)[C@@H](*)Cc1ccc(OC(C)(C)C)cc1] |
| II-121 | 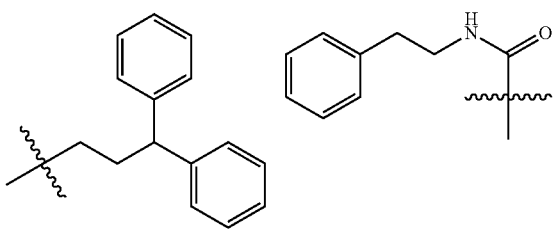 | H | 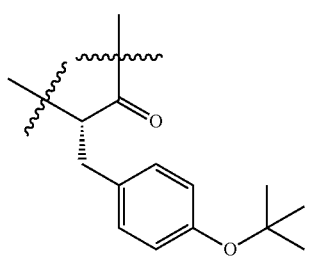 [SMILES: *C(=O)[C@@H](*)Cc1ccc(OC(C)(C)C)cc1] |
| II-122 | 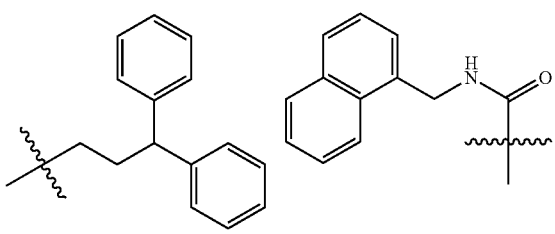 | H | 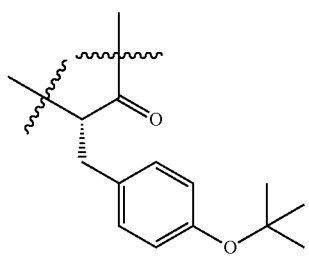 [SMILES: *C(=O)[C@@H](*)Cc1ccc(OC(C)(C)C)cc1] |
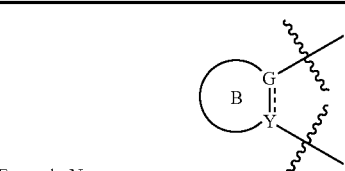
| Example No. | | R | Int_1 | Int_2 | syn. | yield (%) |
|---|---|---|---|---|---|---|
| II-112 | 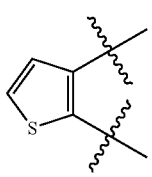 [SMILES: *c1ccsc1*] | Ethyl | VI-30 | V-14 | II-1 | n.d. |
| II-113 | 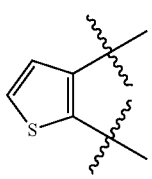 [SMILES: *c1ccsc1*] | Ethyl | VI-30 | V-15 | II-1 | n.d. |

TABLE XIII-11-continued

| | | | | | | |
|---|---|---|---|---|---|---|
| II-114 | (thiophene) | Ethyl | VI-30 | V-16 | II-1 | n.d. |
| II-115 | (thiophene) | Ethyl | VI-31 | V-8 | II-1 | n.d. |
| II-116 | (thiophene) | Ethyl | VI-31 | V-9 | II-1 | n.d. |
| II-117 | (thiophene) | Ethyl | VI-32 | V-8 | II-1 | n.d. |
| II-118 | (thiophene) | Ethyl | VI-33 | V-8 | II-1 | n.d. |
| II-119 | (thiophene) | Ethyl | VI-35 | V-1 | II-1 | n.d. |
| II-120 | (thiophene) | Ethyl | VI-35 | V-3 | II-1 | n.d. |
| II-121 | (thiophene) | Ethyl | VI-35 | V-6 | II-1 | n.d. |

TABLE XIII-11-continued
| | | | | | | | |
|---|---|---|---|---|---|---|---|
| II-122 | 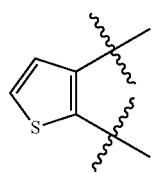 [SMILES: *c1ccsc1*] | | Ethyl | VI-35 | V-5 | II-1 | n.d. |
TABLE XIII-12
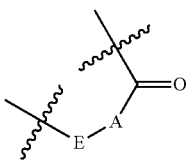
| Example No. | R1 | R2 | R3 | |
|---|---|---|---|---|
| II-123 | 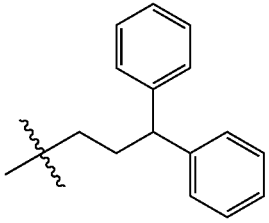 [SMILES: *CCC(c1ccccc1)c1ccccc1] | 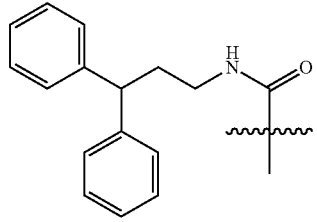 [SMILES: *C(=O)NCCC(c1ccccc1)c1ccccc1] | H | 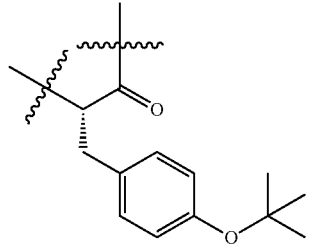 [SMILES: *C(=O)[C@@H](*)Cc1ccc(OC(C)(C)C)cc1] |
| II-124 | 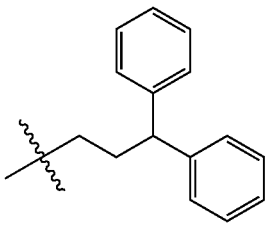 [SMILES: *CCC(c1ccccc1)c1ccccc1] | 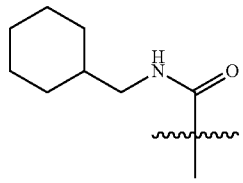 [SMILES: *C(=O)NCC1CCCCC1] | H | 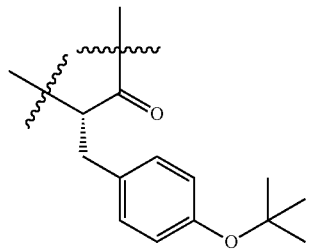 [SMILES: *C(=O)[C@@H](*)Cc1ccc(OC(C)(C)C)cc1] |
| II-125 | 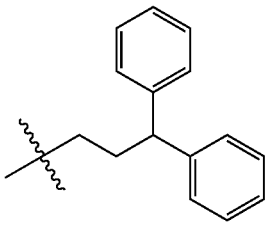 [SMILES: *CCC(c1ccccc1)c1ccccc1] | 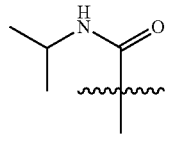 [SMILES: *C(=O)NC(C)C] | H | 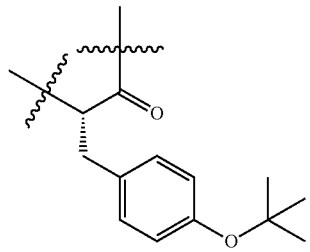 [SMILES: *C(=O)[C@@H](*)Cc1ccc(OC(C)(C)C)cc1] |
| II-126 | 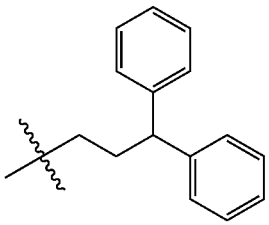 [SMILES: *CCC(c1ccccc1)c1ccccc1] | 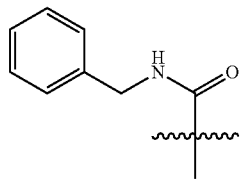 [SMILES: *C(=O)NCc1ccccc1] | H | 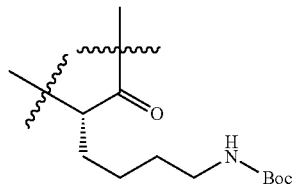 [SMILES: *C(=O)[C@@H](*)CCCCNC(=O)OC(C)(C)C] |

TABLE XIII-12-continued
| | | | |
|---|---|---|---|
| II-127 | 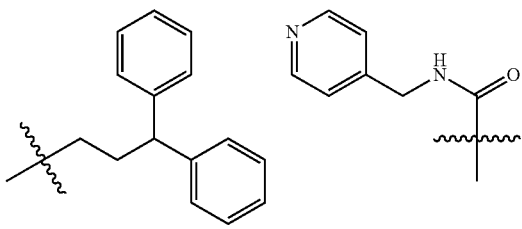 | H | 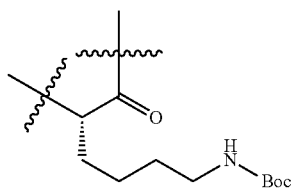 [SMILES: *C(=O)[C@@H](*)CCCCNC(=O)OC(C)(C)C] |
| II-128 | 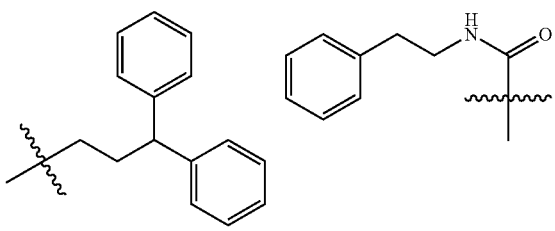 | H | 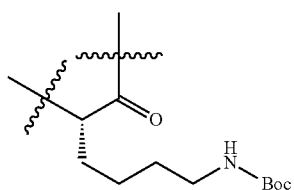 [SMILES: *C(=O)[C@@H](*)CCCCNC(=O)OC(C)(C)C] |
| II-129 | 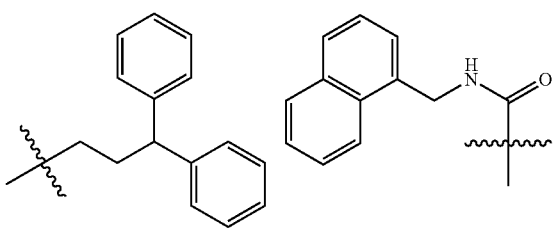 | H | 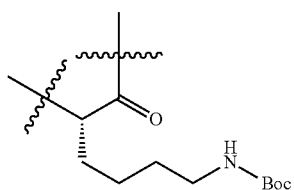 [SMILES: *C(=O)[C@@H](*)CCCCNC(=O)OC(C)(C)C] |
| II-130 | 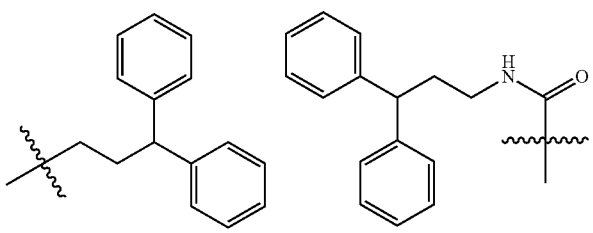 | H | 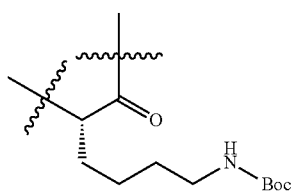 [SMILES: *C(=O)[C@@H](*)CCCCNC(=O)OC(C)(C)C] |
| II-131 | 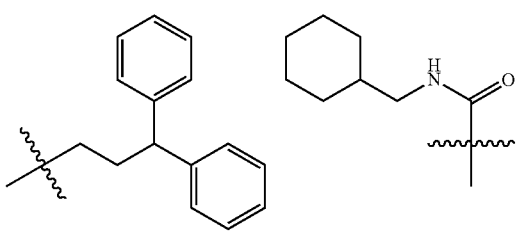 | H | 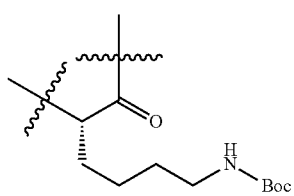 [SMILES: *C(=O)[C@@H](*)CCCCNC(=O)OC(C)(C)C] |
| II-132 | 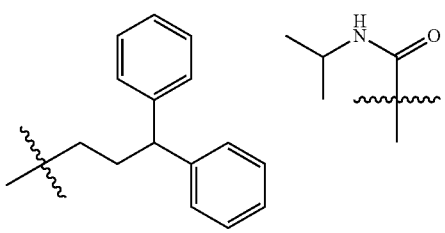 | H | 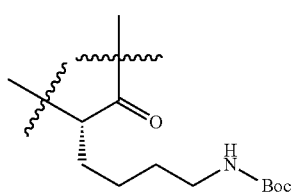 [SMILES: *C(=O)[C@@H](*)CCCCNC(=O)OC(C)(C)C] |
| II-133 | 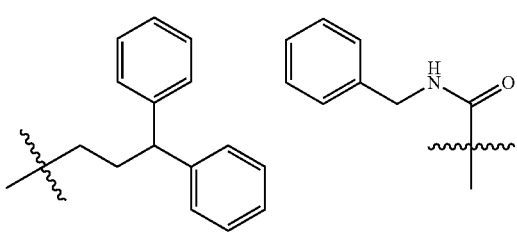 | H | 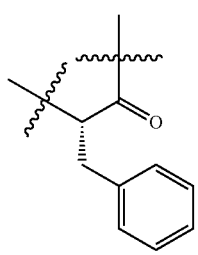 [SMILES: *C(=O)[C@@H](*)Cc1ccccc1] |

TABLE XIII-12-continued

| Example No. | | R | Int_1 | Int_2 | syn. | yield (%) |
|---|---|---|---|---|---|---|
| II-123 | thiophene | Ethyl | VI-35 | V-7 | II-1 | n.d. |
| II-124 | thiophene | Ethyl | VI-35 | V-8 | II-1 | n.d. |
| II-125 | thiophene | Ethyl | VI-35 | V-9 | II-1 | n.d. |
| II-126 | thiophene | Ethyl | VI-36 | V-1 | II-1 | n.d. |
| II-127 | thiophene | Ethyl | VI-36 | V-3 | II-1 | n.d. |
| II-128 | thiophene | Ethyl | VI-36 | V-6 | II-1 | n.d. |
| II-129 | thiophene | Ethyl | VI-36 | V-5 | II-1 | n.d. |

TABLE XIII-12-continued

| | | | | | | | |
|---|---|---|---|---|---|---|---|
| II-130 | [thiophene] | Ethyl | VI-36 | V-7 | II-1 | n.d. | |
| II-131 | [thiophene] | Ethyl | VI-36 | V-8 | II-1 | n.d. | |
| II-132 | [thiophene] | Ethyl | VI-36 | V-9 | II-1 | n.d. | |
| II-133 | [thiophene] | Ethyl | VI-41 | V-1 | II-1 | n.d. | |

TABLE XIII-13

| Example No. | R1 | R2 | R3 | E–A |
|---|---|---|---|---|
| II-134 | [1,1-diphenylpropyl] | [pyridin-4-ylmethyl-NH-C(O)-] | H | [benzyl-substituted acyl] |
| II-135 | [1,1-diphenylpropyl] | [phenethyl-NH-C(O)-] | H | [benzyl-substituted acyl] |

TABLE XIII-13-continued
| | | | |
|---|---|---|---|
| II-136 | 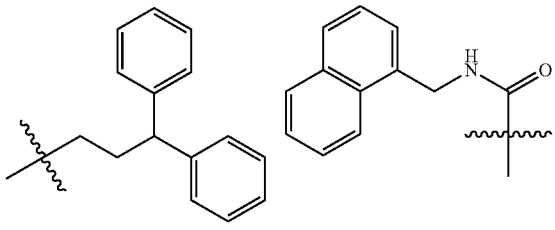 | 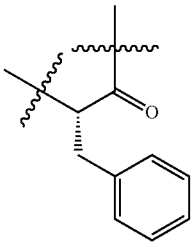 [SMILES: *C(=O)[C@@H](*)Cc1ccccc1] | H |
| II-137 | 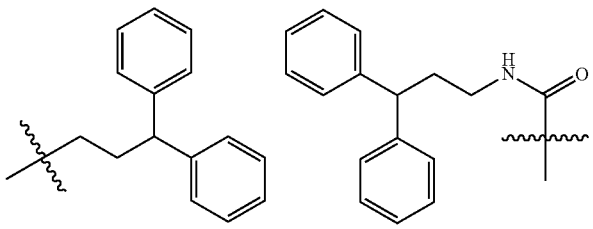 | 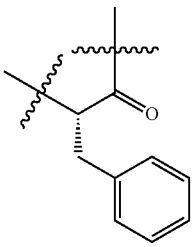 [SMILES: *C(=O)[C@@H](*)Cc1ccccc1] | H |
| II-138 | 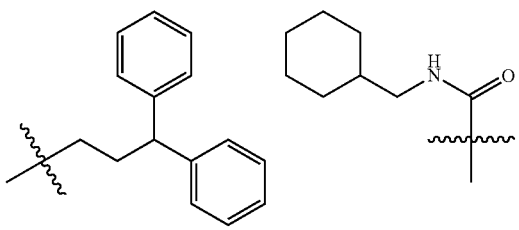 | 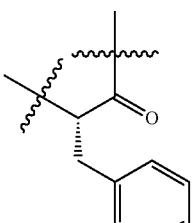 | H |
| II-139 | 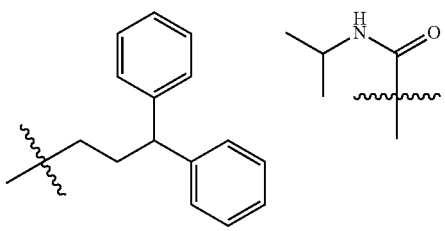 | 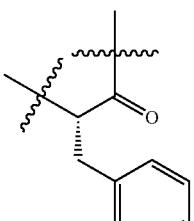 | H |
| II-140 | 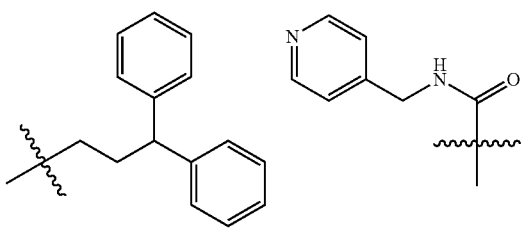 | 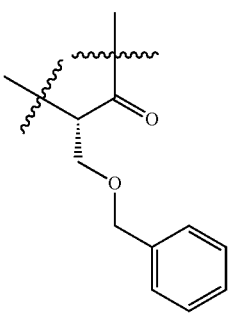 [SMILES: *C(=O)[C@@H](*)COCc1ccccc1] | H |
| II-141 | 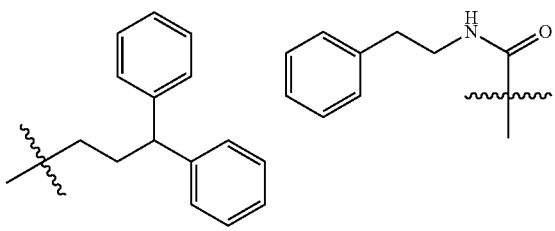 | 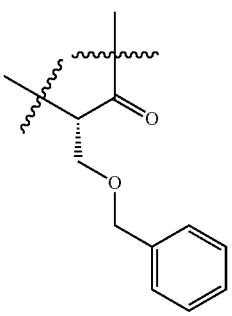 [SMILES: *C(=O)[C@@H](*)COCc1ccccc1] | H |

TABLE XIII-13-continued
| | | | | |
|---|---|---|---|---|
| II-142 | 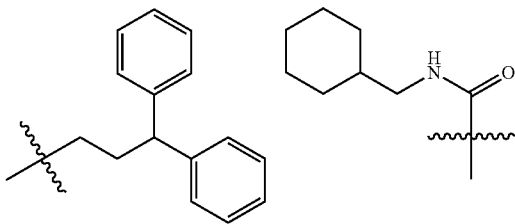 | H | 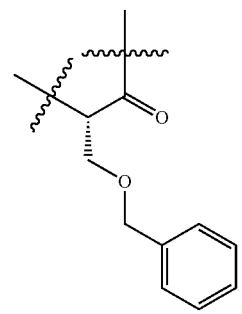 [SMILES: *C(=O)[C@@H](*)COCc1ccccc1] | |
| II-143 | 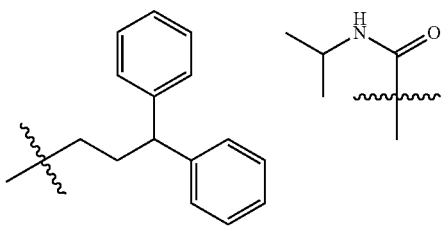 | H | 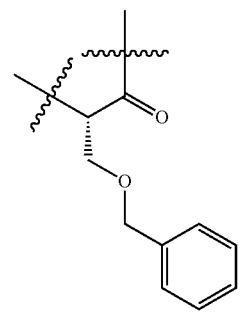 [SMILES: *C(=O)[C@@H](*)COCc1ccccc1] | |
| II-144 | 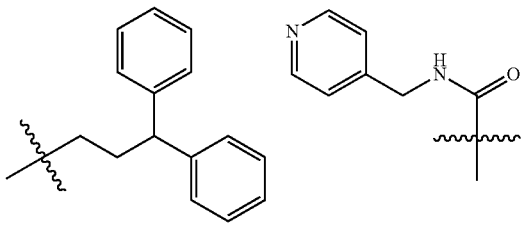 | H | 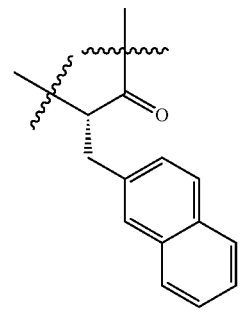 [SMILES: *C(=O)[C@@H](*)Cc1ccc2ccccc2c1] | |
| Example No. | | R | Int_1 | Int_2 | syn. | yield (%) |
|---|---|---|---|---|---|---|
| II-134 | 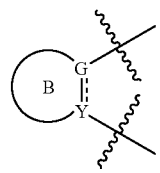 | Ethyl | VI-41 | V-3 | II-1 | n.d. |
| II-135 | 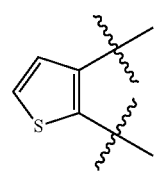 [SMILES: *c1ccsc1*] | Ethyl | VI-41 | V-6 | II-1 | n.d. |

TABLE XIII-13-continued

| II-136 | (thiophene) | Ethyl | VI-41 | V-5 | II-1 | n.d. |
| II-137 | (thiophene) | Ethyl | VI-41 | V-7 | II-1 | n.d. |
| II-138 | (thiophene) | Ethyl | VI-41 | V-8 | II-1 | n.d. |
| II-139 | (thiophene) | Ethyl | VI-41 | V-9 | II-1 | n.d. |
| II-140 | (thiophene) | Ethyl | VI-42 | V-3 | II-1 | n.d. |
| II-141 | (thiophene) | Ethyl | VI-42 | V-6 | II-1 | n.d. |
| II-142 | (thiophene) | Ethyl | VI-42 | V-8 | II-1 | n.d. |
| II-143 | (thiophene) | Ethyl | VI-42 | V-9 | II-1 | n.d. |

TABLE XIII-13-continued
| II-144 | 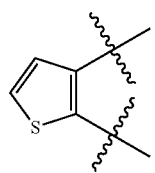 [SMILES: *c1ccsc1*] | Ethyl | VI-44 | V-3 | II-1 | n.d. |
TABLE XIII-14
| Example No. | R1 | R2 | R3 | 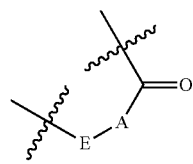 |
|---|---|---|---|---|
| II-145 | 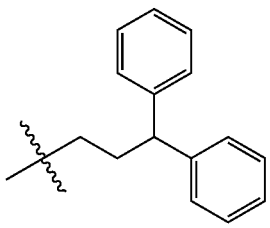 [SMILES: *CCC(c1ccccc1)c1ccccc1] | 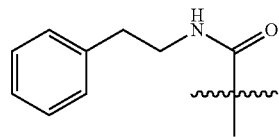 [SMILES: *C(=O)NCCc1ccccc1] | H | 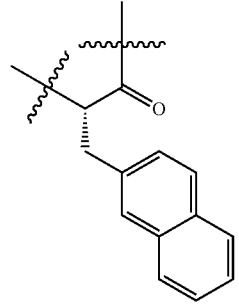 [SMILES: *C(=O)[C@@H](*)Cc1ccc2ccccc2c1] |
| II-146 | 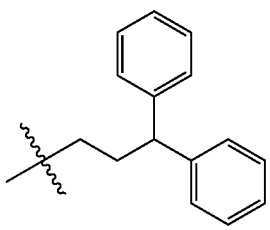 [SMILES: *CCC(c1ccccc1)c1ccccc1] | 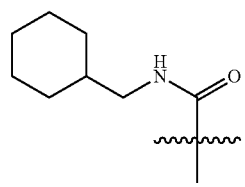 [SMILES: *C(=O)NCC1CCCCC1] | H | 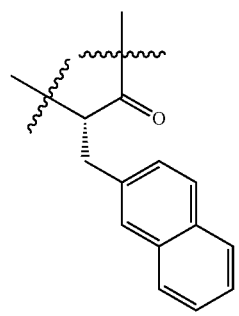 [SMILES: *C(=O)[C@@H](*)Cc1ccc2ccccc2c1] |
| II-147 | 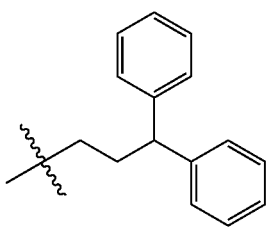 [SMILES: *CCC(c1ccccc1)c1ccccc1] | 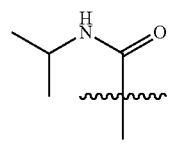 [SMILES: *C(=O)NC(C)C] | H | 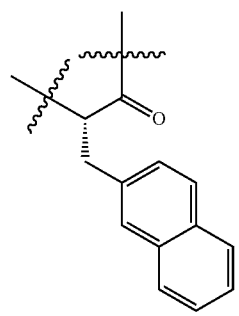 [SMILES: *C(=O)[C@@H](*)Cc1ccc2ccccc2c1] |

TABLE XIII-14-continued
| | | | | |
|---|---|---|---|---|
| II-148 | 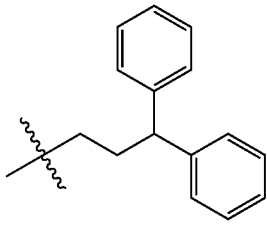 [SMILES: *CCC(c1ccccc1)c1ccccc1] | 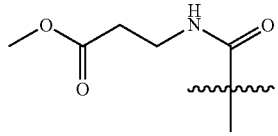 [SMILES: *C(=O)NCCC(=O)OC] | H | 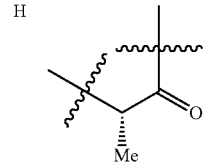 |
| II-149 | 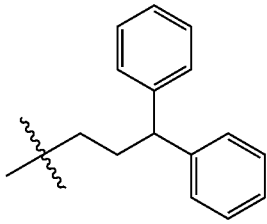 [SMILES: *CCC(c1ccccc1)c1ccccc1] | 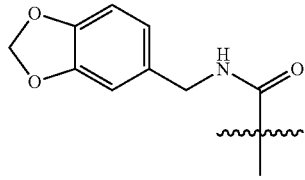 [SMILES: *C(=O)NCc1ccc2c(c1)OCO2] | H | 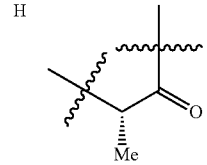 |
| II-150 | 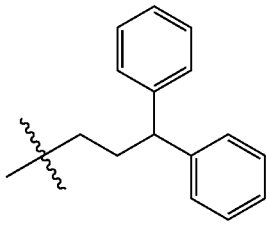 [SMILES: *CCC(c1ccccc1)c1ccccc1] | 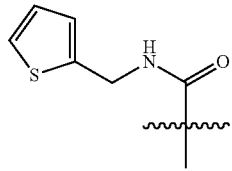 [SMILES: *C(=O)NCc1cccs1] | H | 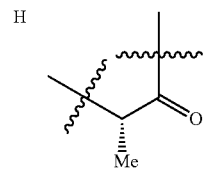 |
| II-151 | 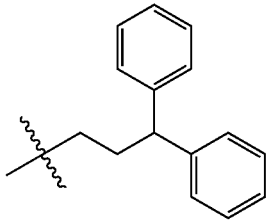 [SMILES: *CCC(c1ccccc1)c1ccccc1] | 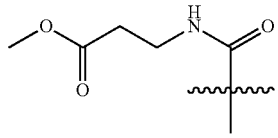 [SMILES: *C(=O)NCCC(=O)OC] | H | 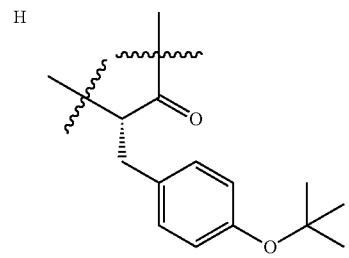 |
| II-152 | 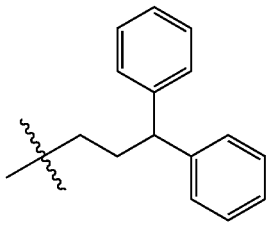 [SMILES: *CCC(c1ccccc1)c1ccccc1] | 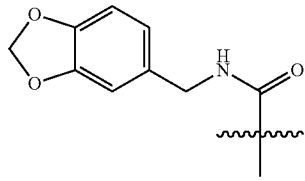 [SMILES: *C(=O)NCc1ccc2c(c1)OCO2] | H | 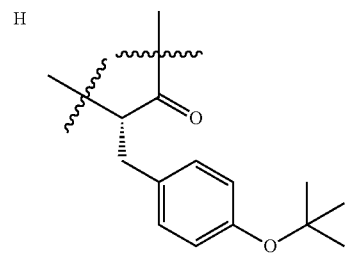 |
| II-153 | 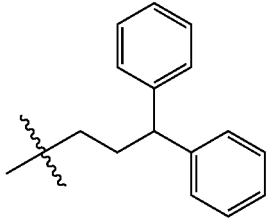 [SMILES: *CCC(c1ccccc1)c1ccccc1] | 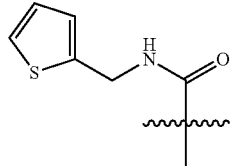 [SMILES: *C(=O)NCc1cccs1] | H | 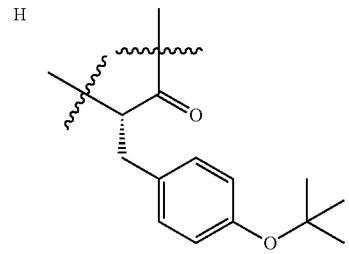 |

TABLE XIII-14-continued

| Example No. | (structure) | R | Int_1 | Int_2 | syn. | yield (%) |
|---|---|---|---|---|---|---|
| II-145 | thiophene | Ethyl | VI-44 | V-6 | II-1 | n.d. |
| II-146 | thiophene | Ethyl | VI-44 | V-8 | II-1 | n.d. |
| II-147 | thiophene | Ethyl | VI-44 | V-9 | II-1 | n.d. |
| II-148 | thiophene | Ethyl | VI-34 | V-12 | II-1 | n.d. |
| II-149 | thiophene | Ethyl | VI-34 | V-14 | II-1 | n.d. |

TABLE XIII-14-continued

| | | | | | | | |
|---|---|---|---|---|---|---|---|
| II-150 | (thiophene) | Ethyl | VI-34 | V-15 | II-1 | n.d. | |
| II-151 | (thiophene) | Ethyl | VI-35 | V-12 | II-1 | n.d. | |
| II-152 | (thiophene) | Ethyl | VI-35 | V-14 | II-1 | n.d. | |
| II-153 | (thiophene) | Ethyl | VI-35 | V-15 | II-1 | n.d. | |
| II-154 | (thiophene) | Ethyl | VI-36 | V-12 | II-1 | n.d. | |
| II-155 | (thiophene) | Ethyl | VI-36 | V-14 | II-1 | n.d. | |

TABLE XIII-15

| Example No. | R1 | R2 | R3 |
|---|---|---|---|
| II-156 | 1,1-diphenylbutyl | thiophen-2-ylmethyl-NH-C(O)- | H |

TABLE XIII-15-continued
| | | | | |
|---|---|---|---|---|
| II-157 | 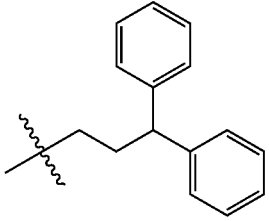 [SMILES: *CCC(c1ccccc1)c1ccccc1] | 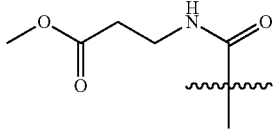 [SMILES: *C(=O)NCCC(=O)OC] | H | 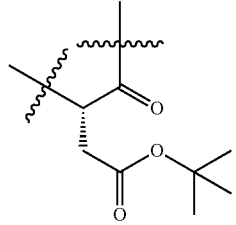 [SMILES: *C(=O)[C@@H](*)CC(=O)OC(C)(C)C] |
| II-158 | 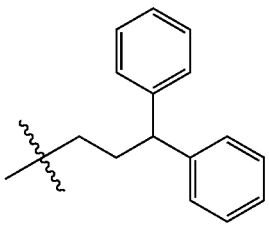 [SMILES: *CCC(c1ccccc1)c1ccccc1] | 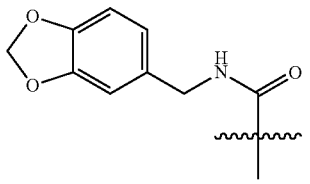 [SMILES: *C(=O)NCc1ccc2c(c1)OCO2] | H | 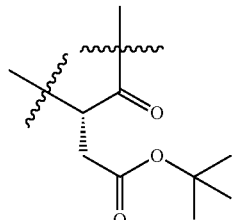 |
| II-159 | 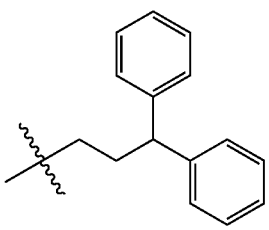 [SMILES: *CCC(c1ccccc1)c1ccccc1] | 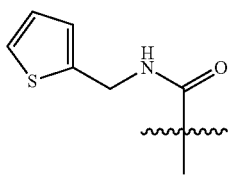 [SMILES: *C(=O)NCc1cccs1] | H | 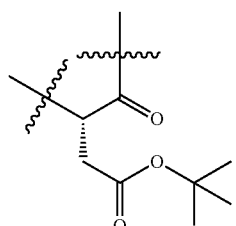 |
| II-160 | 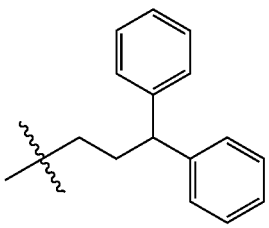 [SMILES: *CCC(c1ccccc1)c1ccccc1] | 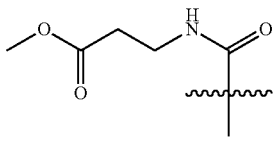 [SMILES: *C(=O)NCCC(=O)OC] | H | 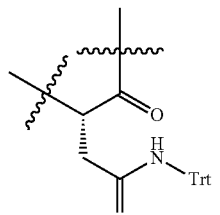 |
| II-161 | 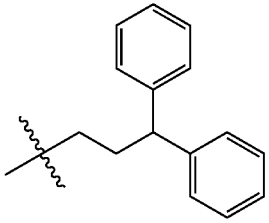 [SMILES: *CCC(c1ccccc1)c1ccccc1] | 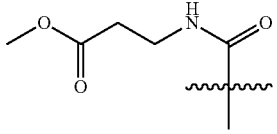 [SMILES: *C(=O)NCCC(=O)OC] | H | 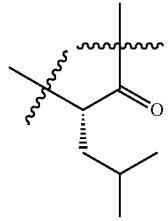 [SMILES: *C(=O)[C@@H](*)CC(C)C] |
| II-162 | 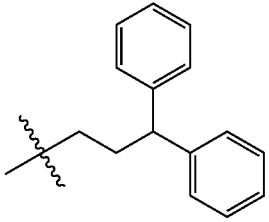 [SMILES: *CCC(c1ccccc1)c1ccccc1] | 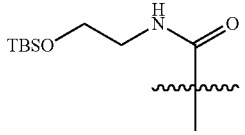 [SMILES: *C(=O)NCCO[Si](C)(C)C(C)(C)C] | H | 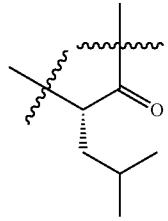 [SMILES: *C(=O)[C@@H](*)CC(C)C] |
| II-163 | 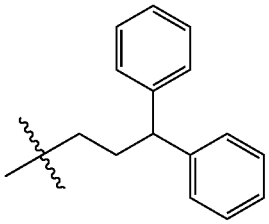 [SMILES: *CCC(c1ccccc1)c1ccccc1] | 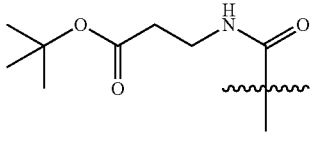 [SMILES: *C(=O)NCCC(=O)OC(C)(C)C] | H | 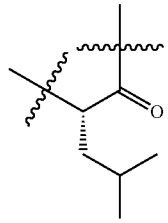 [SMILES: *C(=O)[C@@H](*)CC(C)C] |

TABLE XIII-15-continued

| Example No. | | R | Int_1 | Int_2 | syn. | yield (%) |
|---|---|---|---|---|---|---|
| II-156 | (thiophene) | Ethyl | VI-36 | V-15 | II-1 | n.d. |
| II-157 | (thiophene) | Ethyl | VI-37 | V-12 | II-1 | n.d. |
| II-158 | (thiophene) | Ethyl | VI-37 | V-14 | II-1 | n.d. |
| II-159 | (thiophene) | Ethyl | VI-37 | V-15 | II-1 | n.d. |

Entries II-164, II-165, II-166 depicted with structural formulas (diphenylpropyl group; methyl β-alaninate amide / piperonylamide / thiophen-2-ylmethylamide substituents; H; and leucyl ketone fragment).

TABLE XIII-15-continued

| | | | | | | |
|---|---|---|---|---|---|---|
| II-160 | (thiophene) | Ethyl | VI-38 | V-12 | II-1 | n.d. |
| II-161 | (thiophene) | Ethyl | VI-39 | V-12 | II-1 | n.d. |
| II-162 | (thiophene) | Ethyl | VI-39 | V-10 | II-1 | n.d. |
| II-163 | (thiophene) | Ethyl | VI-39 | V-11 | II-1 | n.d. |
| II-164 | (thiophene) | Ethyl | VI-39 | V-12 | II-1 | n.d. |
| II-165 | (thiophene) | Ethyl | VI-39 | V-14 | II-1 | n.d. |
| II-166 | (thiophene) | Ethyl | VI-39 | V-15 | II-1 | n.d. |

TABLE XIII-16

| Example No. | R1 | R2 | R3 | |
|---|---|---|---|---|
| II-167 | (diphenylpropyl) | TBSO-CH2CH2-NH-C(O)- | H | (phenyl-CH-C(O)-) |
| II-168 | (diphenylpropyl) | tBuO-C(O)-CH2CH2-NH-C(O)- | H | (phenyl-CH-C(O)-) |
| II-169 | (diphenylpropyl) | MeO-C(O)-CH2CH2-NH-C(O)- | H | (phenyl-CH-C(O)-) |
| II-170 | (diphenylpropyl) | (benzo[d][1,3]dioxol-5-yl)-CH2-NH-C(O)- | H | (phenyl-CH-C(O)-) |
| II-171 | (diphenylpropyl) | (thiophen-2-yl)-CH2-NH-C(O)- | H | (phenyl-CH-C(O)-) |

TABLE XIII-16-continued
| | | | | |
|---|---|---|---|---|
| II-172 | 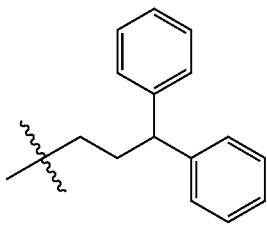 [SMILES: *CCC(c1ccccc1)c1ccccc1] | 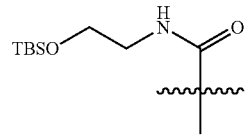 [SMILES: *C(=O)NCCO[Si](C)(C)C(C)(C)C] | H | 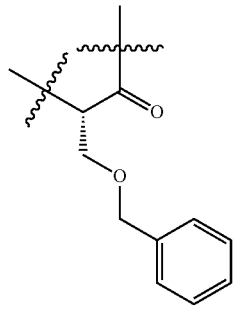 [SMILES: *C(=O)[C@@H](*)COCc1ccccc1] |
| II-173 | 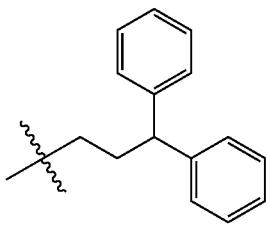 [SMILES: *CCC(c1ccccc1)c1ccccc1] | 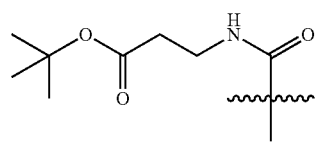 [SMILES: *C(=O)NCCC(=O)OC(C)(C)C] | H | 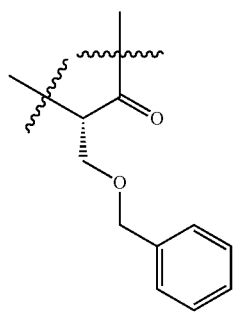 [SMILES: *C(=O)[C@@H](*)COCc1ccccc1] |
| II-174 | 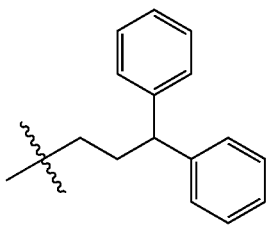 [SMILES: *CCC(c1ccccc1)c1ccccc1] | 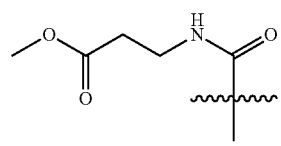 [SMILES: *C(=O)NCCC(=O)OC] | H | 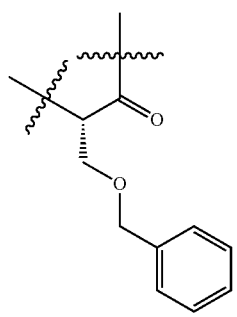 [SMILES: *C(=O)[C@@H](*)COCc1ccccc1] |
| II-175 | 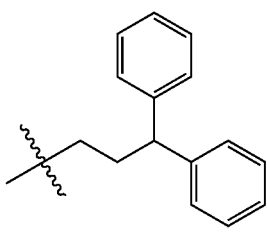 [SMILES: *CCC(c1ccccc1)c1ccccc1] | 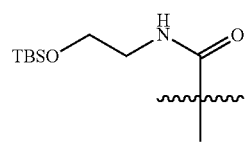 [SMILES: *C(=O)NCCO[Si](C)(C)C(C)(C)C] | H | 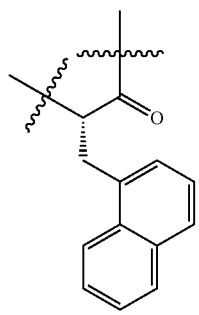 [SMILES: *C(=O)[C@@H](*)Cc1cccc2ccccc12] |
| II-176 | 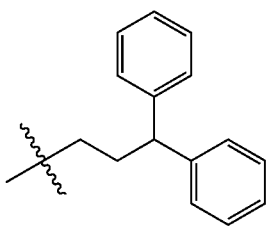 [SMILES: *CCC(c1ccccc1)c1ccccc1] | 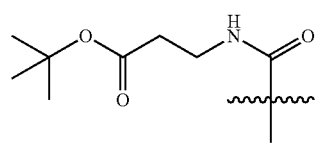 [SMILES: *C(=O)NCCC(=O)OC(C)(C)C] | H | 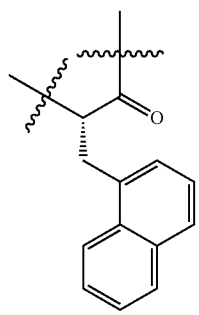 [SMILES: *C(=O)[C@@H](*)Cc1cccc2ccccc12] |

TABLE XIII-16-continued

| II-177 | (diphenylpropyl group) | (methyl 3-aminopropanoate amide group) | H | (naphthalen-1-ylmethyl ketone group) |

| Example No. | B-G=Y structure | R | Int_1 | Int_2 | syn. | yield (%) |
|---|---|---|---|---|---|---|
| II-167 | thiophene | Ethyl | VI-40 | V-10 | II-1 | n.d. |
| II-168 | thiophene | Ethyl | VI-40 | V-11 | II-1 | n.d. |
| II-169 | thiophene | Ethyl | VI-40 | V-12 | II-1 | n.d. |
| II-170 | thiophene | Ethyl | VI-40 | V-14 | II-1 | n.d. |
| II-171 | thiophene | Ethyl | VI-40 | V-15 | II-1 | n.d. |
| II-172 | thiophene | Ethyl | VI-42 | V-10 | II-1 | n.d. |

TABLE XIII-16-continued

| | | | | | | | |
|---|---|---|---|---|---|---|---|
| II-173 | [thiophene structure] | Ethyl | VI-42 | V-11 | II-1 | n.d. | |
| II-174 | [thiophene structure] | Ethyl | VI-42 | V-12 | II-1 | n.d. | |
| II-175 | [thiophene structure] | Ethyl | VI-43 | V-10 | II-1 | n.d. | |
| II-176 | [thiophene structure] | Ethyl | VI-43 | V-11 | II-1 | n.d. | |
| II-177 | [thiophene structure] | Ethyl | VI-43 | V-12 | II-1 | n.d. | |

TABLE XIII-17

| Example No. | R1 | R2 | R3 | E–A structure |
|---|---|---|---|---|
| II-178 | [naphthylmethyl] | [benzyl-NH-C(O)-] | H | [CH(Me)C(O)] |
| II-179 | [naphthylmethyl] | [cyclohexylmethyl-NH-C(O)-] | H | [CH(Me)C(O)] |

TABLE XIII-17-continued
| | | | |
|---|---|---|---|
| II-180 | 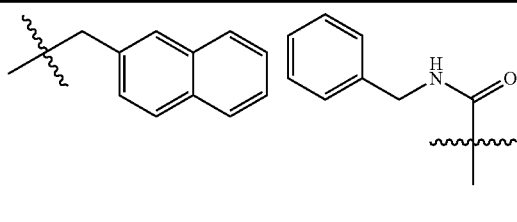 | H | 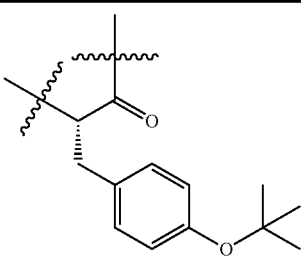 |
| II-181 | 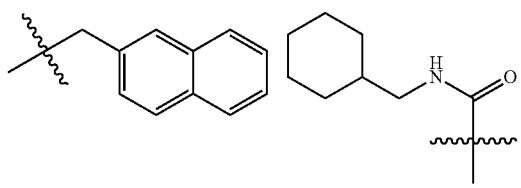 | H | 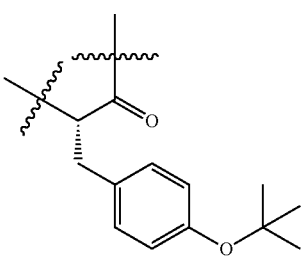 [SMILES: *C(=O)[C@@H](*)Cc1ccc(OC(C)(C)C)cc1] |
| II-182 | 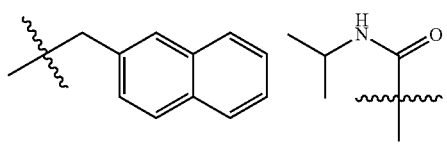 | H | 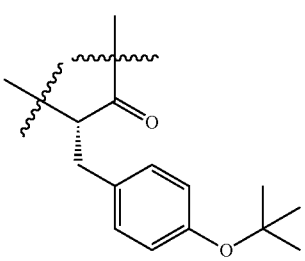 [SMILES: *C(=O)[C@@H](*)Cc1ccc(OC(C)(C)C)cc1] |
| II-183 | 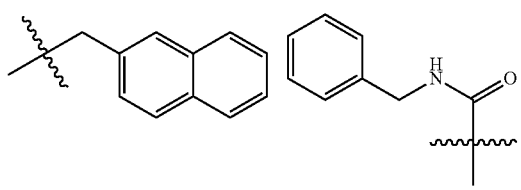 | H | 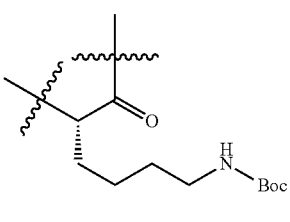 [SMILES: *C(=O)[C@@H](*)CCCCNC(=O)OC(C)(C)C] |
| II-184 | 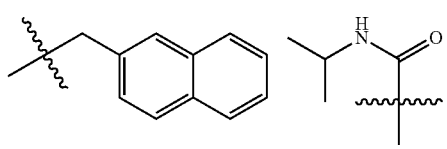 | H | 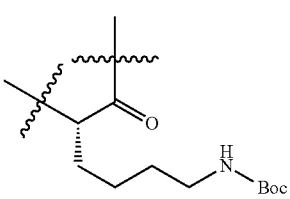 [SMILES: *C(=O)[C@@H](*)CCCCNC(=O)OC(C)(C)C] |
| II-185 | 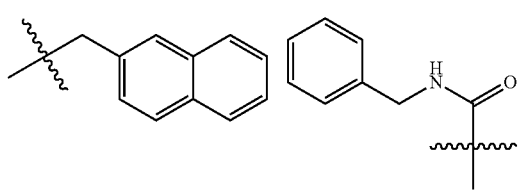 | H | 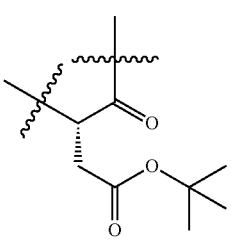 [SMILES: *C(=O)[C@@H](*)CC(=O)OC(C)(C)C] |
| II-186 | 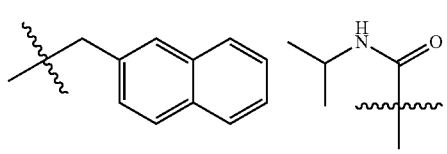 | H | 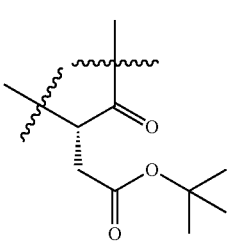 [SMILES: *C(=O)[C@@H](*)CC(=O)OC(C)(C)C] |

TABLE XIII-17-continued
| | | | |
|---|---|---|---|
| II-187 | 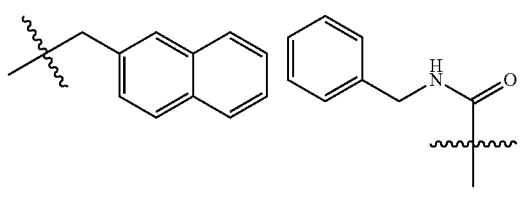 | H | 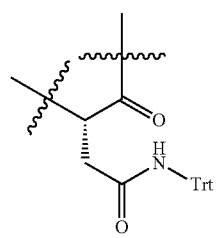 |
| II-188 | 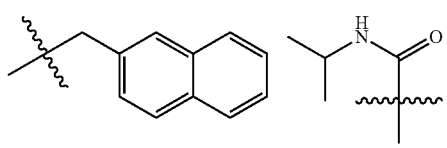 | H | 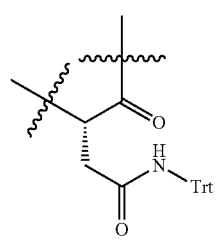 |
| Example No. | B-G/Y | R | Int_1 | Int_2 | syn. | yield (%) |
|---|---|---|---|---|---|---|
| II-178 | 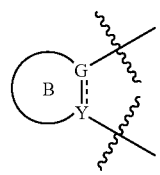 | Ethyl | VI-45 | V-1 | II-1 | n.d. |
| II-179 | 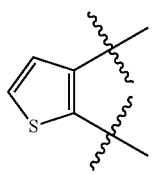 [SMILES: *c1ccsc1*] | Ethyl | VI-45 | V-8 | II-1 | n.d. |
| II-180 | 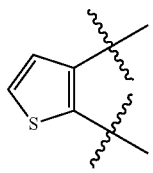 [SMILES: *c1ccsc1*] | Ethyl | VI-46 | V-1 | II-1 | n.d. |
| II-181 | 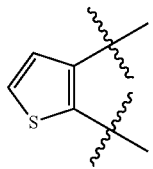 [SMILES: *c1ccsc1*] | Ethyl | VI-46 | V-8 | II-1 | n.d. |
| II-182 | 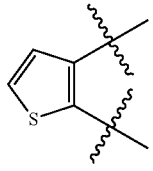 [SMILES: *c1ccsc1*] | Ethyl | VI-46 | V-9 | II-1 | n.d. |

TABLE XIII-17-continued

| | | | | | | | |
|---|---|---|---|---|---|---|---|
| II-183 | | | Ethyl | VI-47 | V-1 | II-1 | n.d. |
| II-184 | | | Ethyl | VI-47 | V-9 | II-1 | n.d. |
| II-185 | | | Ethyl | VI-48 | V-1 | II-1 | n.d. |
| II-186 | | | Ethyl | VI-48 | V-9 | II-1 | n.d. |
| II-187 | | | Ethyl | VI-49 | V-1 | II-1 | n.d. |
| II-188 | | | Ethyl | VI-49 | V-9 | II-1 | n.d. |

TABLE XIII-18

| Example No. | R1 | R2 | R3 | (structure) |
|---|---|---|---|---|
| II-189 | naphthyl-CH< | benzyl-NHC(O)-C(CH3)< | H | -C(=O)-CH(CH2-O-tBu)- |
| II-190 | naphthyl-CH< | iPr-NHC(O)-C(CH3)< | H | -C(=O)-CH(CH2-O-tBu)- |
| II-191 | naphthyl-CH< | benzyl-NHC(O)-C(CH3)< | H | -C(=O)-CH(iBu)- |
| II-192 | naphthyl-CH< | iPr-NHC(O)-C(CH3)< | H | -C(=O)-CH(iBu)- |
| II-193 | naphthyl-CH< | benzyl-NHC(O)-C(CH3)< | H | -C(=O)-CH(Ph)- |

TABLE XIII-18-continued
| | 211 | | 212 |
|---|---|---|---|
| II-194 | 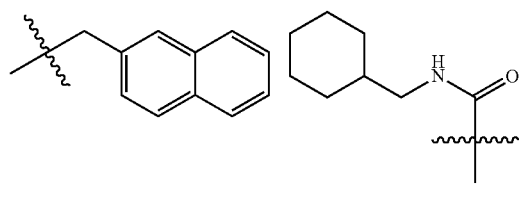 | H | 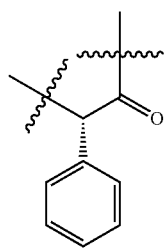 [SMILES: *C(=O)[C@@H](*)c1ccccc1] |
| II-195 | 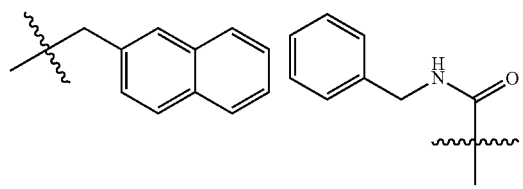 | H | 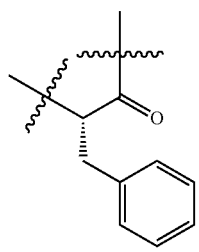 [SMILES: *C(=O)[C@@H](*)Cc1ccccc1] |
| II-196 | 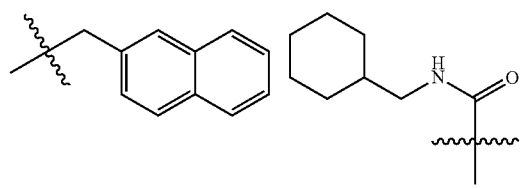 | H | 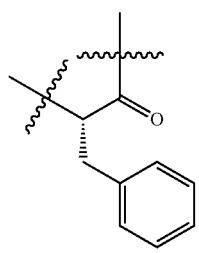 [SMILES: *C(=O)[C@@H](*)Cc1ccccc1] |
| II-197 | 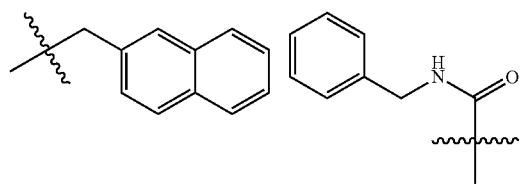 | H | 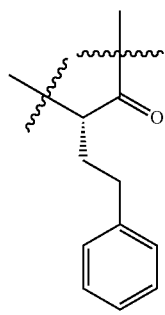 [SMILES: *C(=O)[C@@H](*)CCc1ccccc1] |
| II-198 | 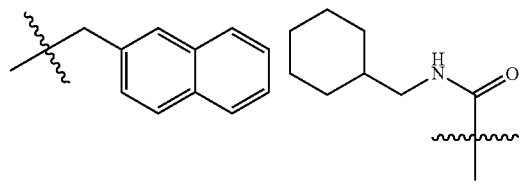 | H | 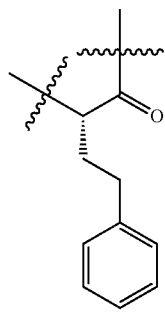 [SMILES: *C(=O)[C@@H](*)CCc1ccccc1] |
| II-199 | 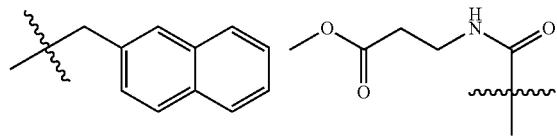 | H | 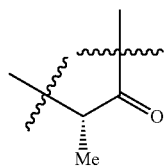 |

TABLE XIII-18-continued
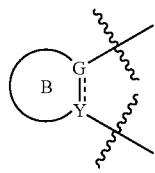
| Example No. | | R | Int_1 | Int_2 | syn. | yield (%) |
|---|---|---|---|---|---|---|
| II-189 | 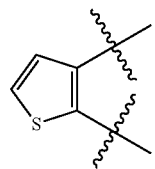 [SMILES: *c1ccsc1*] | Ethyl | VI-50 | V-1 | II-1 | n.d. |
| II-190 | 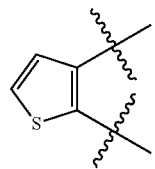 [SMILES: *c1ccsc1*] | Ethyl | VI-50 | V-9 | II-1 | n.d. |
| II-191 | 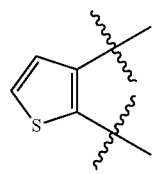 [SMILES: *c1ccsc1*] | Ethyl | VI-51 | V-1 | II-1 | n.d. |
| II-192 | 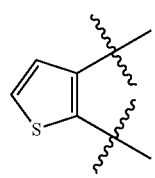 [SMILES: *c1ccsc1*] | Ethyl | VI-51 | V-9 | II-1 | n.d. |
| II-193 | 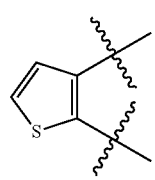 [SMILES: *c1ccsc1*] | Ethyl | VI-52 | V-1 | II-1 | n.d. |
| II-194 | 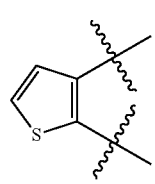 [SMILES: *c1ccsc1*] | Ethyl | VI-52 | V-8 | II-1 | n.d. |
| II-195 | 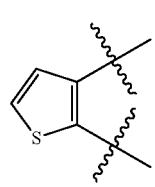 [SMILES: *c1ccsc1*] | Ethyl | VI-53 | V-1 | II-1 | n.d. |
| II-196 | 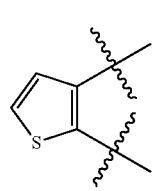 [SMILES: *c1ccsc1*] | Ethyl | VI-53 | V-8 | II-1 | n.d. |

TABLE XIII-18-continued

| Ex. No. | (structure) | | VI | V | II | |
|---|---|---|---|---|---|---|
| II-197 | (thiophene) | Ethyl | VI-54 | V-1 | II-1 | n.d. |
| II-198 | (thiophene) | Ethyl | VI-54 | V-8 | II-1 | n.d. |
| II-199 | (thiophene) | Ethyl | VI-45 | V-12 | II-1 | n.d. |

TABLE XIII-19

| Example No. | R1 | R2 | R3 | E–A |
|---|---|---|---|---|
| II-200 | 2-naphthylmethyl | benzo[1,3]dioxol-5-ylmethyl-NH-C(O)- | H | -CH(Me)-C(O)- |
| II-201 | 2-naphthylmethyl | 4-methylbenzyl-NH-C(O)- | H | -CH(Me)-C(O)- |
| II-202 | 2-naphthylmethyl | MeO-C(O)-CH2CH2-NH-C(O)- | H | -CH(CH2-C6H4-O-tBu)-C(O)- |

TABLE XIII-19-continued
| | | | | |
|---|---|---|---|---|
| II-203 | 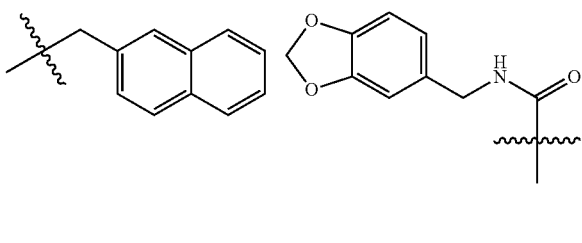 | | H | 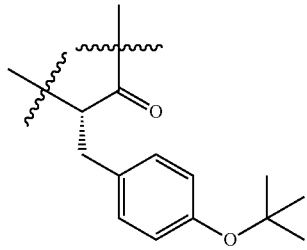 [SMILES: *C(=O)[C@@H](*)Cc1ccc(OC(C)(C)C)cc1] |
| II-204 | 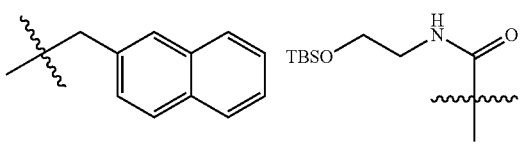 | | H | 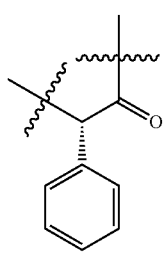 [SMILES: *C(=O)[C@@H](*)c1ccccc1] |
| II-205 | 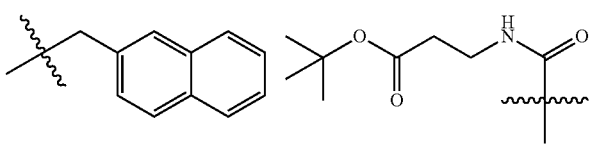 | | H | 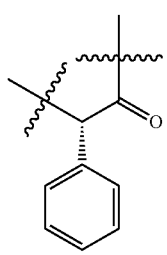 [SMILES: *C(=O)[C@@H](*)c1ccccc1] |
| II-206 | 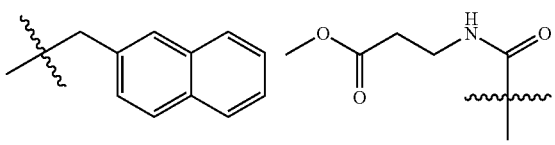 | | H | 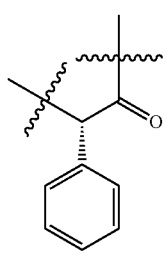 [SMILES: *C(=O)[C@@H](*)c1ccccc1] |
| II-207 | 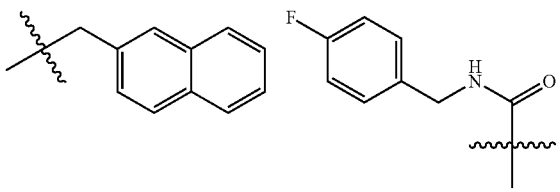 | | H | 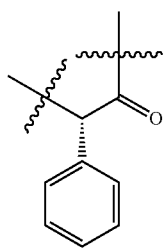 [SMILES: *C(=O)[C@@H](*)c1ccccc1] |
| II-208 | 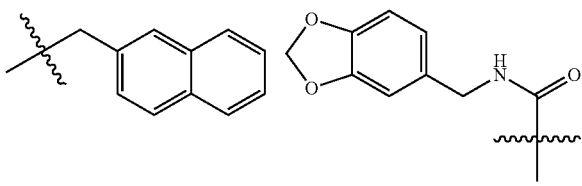 | | H | 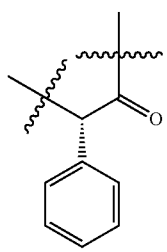 [SMILES: *C(=O)[C@@H](*)c1ccccc1] |

TABLE XIII-19-continued
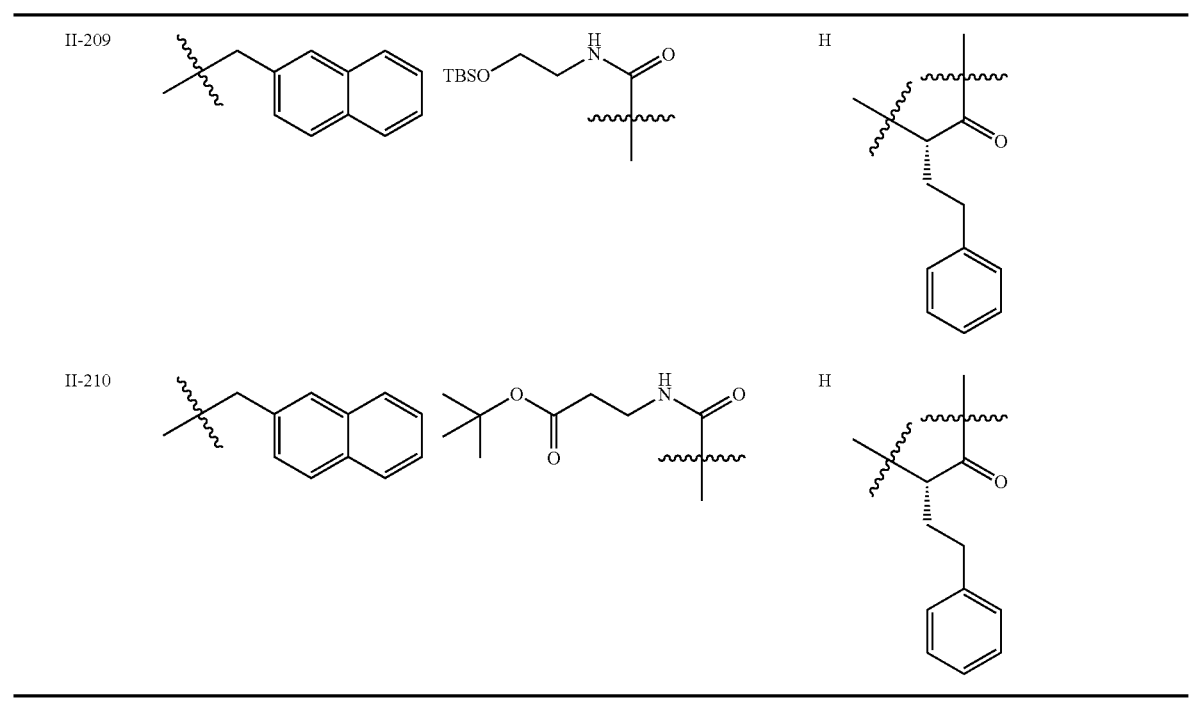
| Example No. | 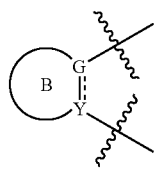 | R | Int_1 | Int_2 | syn. | yield (%) |
|---|---|---|---|---|---|---|
| II-200 | | Ethyl | VI-45 | V-14 | II-1 | n.d. |
| II-201 | | Ethyl | VI-45 | V-16 | II-1 | n.d. |
| II-202 | | Ethyl | VI-46 | V-12 | II-1 | n.d. |
| II-203 | | Ethyl | VI-46 | V-14 | II-1 | n.d. |

TABLE XIII-19-continued

| | | | | | | |
|---|---|---|---|---|---|---|
| II-204 | (thiophene) | Ethyl | VI-52 | V-10 | II-1 | n.d. |
| II-205 | (thiophene) | Ethyl | VI-52 | V-11 | II-1 | n.d. |
| II-206 | (thiophene) | Ethyl | VI-52 | V-12 | II-1 | n.d. |
| II-207 | (thiophene) | Ethyl | VI-52 | V-13 | II-1 | n.d. |
| II-208 | (thiophene) | Ethyl | VI-52 | V-14 | II-1 | n.d. |
| II-209 | (thiophene) | Ethyl | VI-54 | V-10 | II-1 | n.d. |
| II-210 | (thiophene) | Ethyl | VI-54 | V-11 | II-1 | n.d. |

TABLE XIII-20

| Example No. | R1 | R2 | R3 | E-A-C(O)- | B-G-Y | R | Int_1 | Int_2 | syn. | yield (%) |
|---|---|---|---|---|---|---|---|---|---|---|
| II-211 | 2-naphthylmethyl | methyl 3-(amido)propanoate | H | CH(CH2CH2Ph)C(O)- | thiophene | Ethyl | VI-54 | V-12 | II-1 | n.d. |
| II-212 | 2-naphthylmethyl | 4-fluorobenzylamide | H | CH(CH2CH2Ph)C(O)- | thiophene | Ethyl | VI-54 | V-13 | II-1 | n.d. |
| II-213 | 2-naphthylmethyl | benzo[1,3]dioxol-5-ylmethylamide | H | CH(CH2CH2Ph)C(O)- | thiophene | Ethyl | VI-54 | V-14 | II-1 | n.d. |
| II-214 | benzyl | pyridin-4-ylmethylamide | Me | CH(Me)C(O)- | thiophene | Ethyl | VI-60 | V-3 | II-1 | n.d. |
| II-215 | benzyl | 4-chlorobenzylamide | Me | CH(Me)C(O)- | thiophene | Ethyl | VI-60 | V-4 | II-1 | n.d. |
| II-216 | benzyl | naphthalen-1-ylmethylamide | Me | CH(Me)C(O)- | thiophene | Ethyl | VI-60 | V-5 | II-1 | n.d. |
| II-217 | benzyl | pyridin-4-ylmethylamide | Me | CH(CH2-4-OtBu-C6H4)C(O)- | thiophene | Ethyl | VI-61 | V-3 | II-1 | n.d. |

TABLE XIII-20-continued

| Example No. | R1 | R2 | R3 | (E-A-C(O)) | (B-G-Y ring) | R | Int_1 | Int_2 | syn. | yield (%) |
|---|---|---|---|---|---|---|---|---|---|---|
| II-218 | benzyl | 4-Cl-benzyl-NHC(O)- | Me | CH2-(4-OtBu-phenyl) substituted ketone | thiophene | Ethyl | VI-61 | V-4 | II-1 | n.d. |
| II-219 | benzyl | naphthyl-CH2-NHC(O)- | Me | CH2-(4-OtBu-phenyl) substituted ketone | thiophene | Ethyl | VI-61 | V-5 | II-1 | n.d. |
| II-220 | benzyl | pyridin-4-yl-CH2-NHC(O)- | Me | CH2-C(O)OtBu substituted ketone | thiophene | Ethyl | VI-62 | V-3 | II-1 | n.d. |
| II-221 | benzyl | 4-Cl-benzyl-NHC(O)- | Me | CH2-C(O)OtBu substituted ketone | thiophene | Ethyl | VI-62 | V-4 | II-1 | n.d. |

TABLE XIII-21

| Example No. | R1 | R2 | R3 | (E-A-C(O)) | (B-G-Y ring) | R | Int_1 | Int_2 | syn. | yield (%) |
|---|---|---|---|---|---|---|---|---|---|---|
| II-222 | benzyl | naphthyl-CH2-NHC(O)- | Me | CH2-C(O)OtBu substituted ketone | thiophene | Ethyl | VI-62 | V-5 | II-1 | n.d. |
| II-223 | naphthylmethyl | pyridin-4-yl-CH2-NHC(O)- | Me | Me-substituted ketone | thiophene | Ethyl | VI-63 | V-3 | II-1 | n.d. |

TABLE XIII-21-continued
| Example No. | R1 | R2 | R3 | 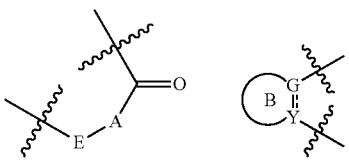 | 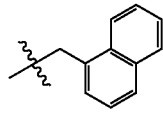 [SMILES: *Cc1cccc2ccccc12] | R | Int_1 | Int_2 | syn. | yield (%) |
|---|---|---|---|---|---|---|---|---|---|---|
| II-224 | 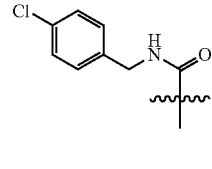 [SMILES: *C(=O)NCc1ccc(Cl)cc1] | 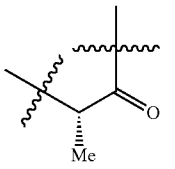 | Me | 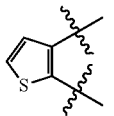 [SMILES: *c1ccsc1*] | 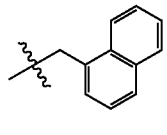 [SMILES: *Cc1cccc2ccccc12] | Ethyl | VI-63 | V-4 | II-1 | n.d. |
| II-225 | 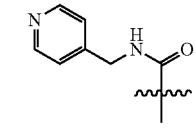 [SMILES: *C(=O)NCc1ccncc1] | 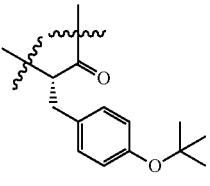 [SMILES: *C(=O)[C@@H](*)Cc1ccc(OC(C)(C)C)cc1] | Me | 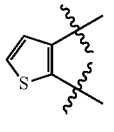 [SMILES: *c1ccsc1*] | 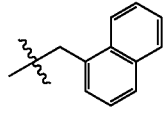 [SMILES: *Cc1cccc2ccccc12] | Ethyl | VI-64 | V-3 | II-1 | n.d. |
| II-226 | 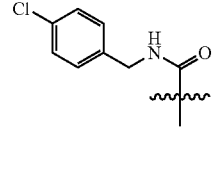 [SMILES: *C(=O)NCc1ccc(Cl)cc1] | 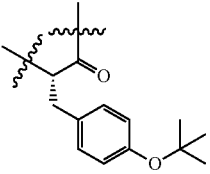 [SMILES: *C(=O)[C@@H](*)Cc1ccc(OC(C)(C)C)cc1] | Me | 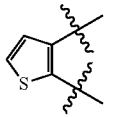 [SMILES: *c1ccsc1*] | 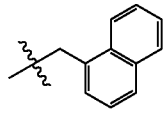 [SMILES: *Cc1cccc2ccccc12] | Ethyl | VI-64 | V-4 | II-1 | n.d. |
| II-227 | 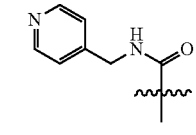 [SMILES: *C(=O)NCc1ccncc1] | 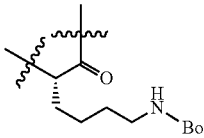 | Me | 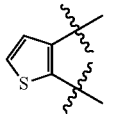 [SMILES: *c1ccsc1*] | 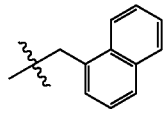 [SMILES: *Cc1cccc2ccccc12] | Ethyl | VI-65 | V-3 | II-1 | n.d. |
| II-228 | 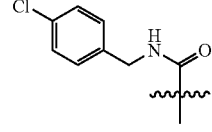 [SMILES: *C(=O)NCc1ccc(Cl)cc1] | 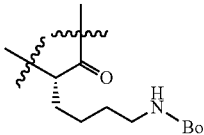 | Me | 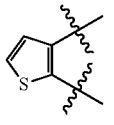 | 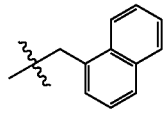 [SMILES: *Cc1cccc2ccccc12] | Ethyl | VI-65 | V-4 | II-1 | n.d. |
| II-229 | 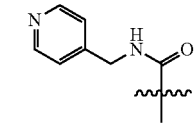 [SMILES: *C(=O)NCc1ccncc1] | 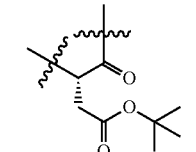 | Me | 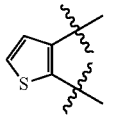 [SMILES: *c1ccsc1*] | 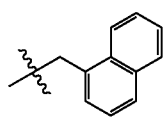 [SMILES: *Cc1cccc2ccccc12] | Ethyl | VI-66 | V-3 | II-1 | n.d. |
| II-230 | 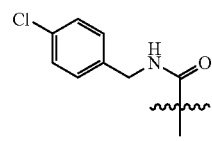 [SMILES: *C(=O)NCc1ccc(Cl)cc1] | 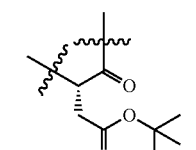 | Me | 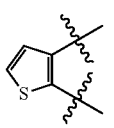 [SMILES: *c1ccsc1*] | 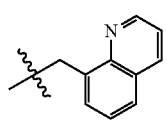 | Ethyl | VI-66 | V-4 | II-1 | n.d. |
| II-231 | 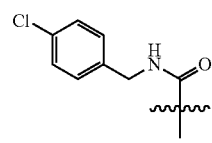 [SMILES: *C(=O)NCc1ccc(Cl)cc1] | 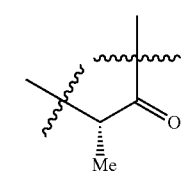 | Me | 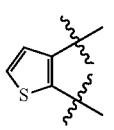 | | Ethyl | VI-67 | V-4 | II-1 | n.d. |

TABLE XIII-21-continued

| Example No. | R1 | R2 | R3 | E-A-C(O)- | B/G/Y ring | R | Int_1 | Int_2 | syn. | yield (%) |
|---|---|---|---|---|---|---|---|---|---|---|
| II-232 | 8-quinolinyl-CH2- | naphthyl-CH2-NH-C(O)- | Me | -C(Me)(H)-C(O)- | thiophene | Ethyl | VI-67 | V-5 | II-1 | n.d. |

TABLE XIII-22

| Example No. | R1 | R2 | R3 | E-A-C(O)- | B/G/Y ring | R | Int_1 | Int_2 | syn. | yield (%) |
|---|---|---|---|---|---|---|---|---|---|---|
| II-233 | 8-quinolinyl-CH2- | 4-Cl-C6H3-CH2-NH-C(O)- | Me | -CH(CH2-C6H4-O-tBu)-C(O)- | thiophene | Ethyl | VI-68 | V-4 | II-1 | n.d. |
| II-234 | 8-quinolinyl-CH2- | 4-Cl-C6H3-CH2-NH-C(O)- | Me | -CH((CH2)3-NHBoc)-C(O)- | thiophene | Ethyl | VI-69 | V-4 | II-1 | n.d. |
| II-235 | 8-quinolinyl-CH2- | naphthyl-CH2-NH-C(O)- | Me | -CH((CH2)3-NHBoc)-C(O)- | thiophene | Ethyl | VI-69 | V-5 | II-1 | n.d. |
| II-236 | 8-quinolinyl-CH2- | 4-Cl-C6H3-CH2-NH-C(O)- | Me | -CH(CH2-C(O)-NHTrt)-C(O)- | thiophene | Ethyl | VI-70 | V-4 | II-1 | n.d. |
| II-237 | 8-quinolinyl-CH2- | naphthyl-CH2-NH-C(O)- | Me | -CH(CH2-C(O)-NHTrt)-C(O)- | thiophene | Ethyl | VI-70 | V-5 | II-1 | n.d. |

TABLE XIII-22-continued

| Example No. | R1 | R2 | R3 | (E-A structure) | (B-Y structure) | R | Int_1 | Int_2 | syn. | yield (%) |
|---|---|---|---|---|---|---|---|---|---|---|
| II-238 | benzothiophene-CH2- | pyridin-4-yl-CH2-NH-C(O)- | Me | -CH(CH2-C6H4-O-tBu)-C(O)- | thiophene | Ethyl | VI-71 | V-3 | II-1 | n.d. |
| II-239 | benzothiophene-CH2- | naphthalen-1-yl-CH2-NH-C(O)- | Me | -CH(CH2-C6H4-O-tBu)-C(O)- | thiophene | Ethyl | VI-71 | V-5 | II-1 | n.d. |
| II-240 | benzothiophene-CH2- | pyridin-4-yl-CH2-NH-C(O)- | Me | -CH((CH2)4-NHBoc)-C(O)- | thiophene | Ethyl | VI-72 | V-3 | II-1 | n.d. |
| II-241 | benzothiophene-CH2- | naphthalen-1-yl-CH2-NH-C(O)- | Me | -CH((CH2)4-NHBoc)-C(O)- | thiophene | Ethyl | VI-72 | V-5 | II-1 | n.d. |
| II-242 | benzothiophene-CH2- | pyridin-4-yl-CH2-NH-C(O)- | Me | -CH(CH2-C(O)-O-tBu)-C(O)- | thiophene | Ethyl | VI-73 | V-3 | II-1 | n.d. |
| II-243 | benzothiophene-CH2- | naphthalen-1-yl-CH2-NH-C(O)- | Me | -CH(CH2-C(O)-O-tBu)-C(O)- | thiophene | Ethyl | VI-73 | V-5 | II-1 | n.d. |

TABLE XIII-23

| Example No. | R1 | R2 | R3 | (E-A structure) | (B-Y structure) | R | Int_1 | Int_2 | syn. | yield (%) |
|---|---|---|---|---|---|---|---|---|---|---|
| II-244 | benzothiophene-CH2- | pyridin-4-yl-CH2-NH-C(O)- | Me | -CH(CH2-C(O)-NH-Trt)-C(O)- | thiophene | Ethyl | VI-74 | V-3 | II-1 | n.d. |

TABLE XIII-23-continued

| Example No. | R1 | R2 | R3 | E-A (C=O) | B-G=Y ring | R | Int_1 | Int_2 | syn. | yield (%) |
|---|---|---|---|---|---|---|---|---|---|---|
| II-245 | benzothiophene-CH2- | naphthyl-CH2-NH-C(O)- | Me | -CH(CH2C(O)NHTrt)-C(O)- | thiophene | Ethyl | VI-74 | V-5 | II-1 | n.d. |
| II-246 | 1-naphthyl-CH2- | Ph-CH2-NH-C(O)- | H | -CH(CH2-C6H4-O-tBu)-C(O)- | pyrrolidine | Ethyl | VI-4 | V-17 | II-1 | 79 |
| II-247 | (2-NHBoc-benzothiazol-4-yl)-CH2- | Ph-CH2-NH-C(O)- | H | -CH(CH2-C6H4-O-tBu)-C(O)- | pyrrolidine | Ethyl | VI-55 | V-17 | II-1 | 77 |
| II-248 | 1-naphthyl-CH2- | Ph-CH2-NH-C(O)- | H | -CH(CH2-C6H4-O-tBu)-C(O)- | pyrrolidine | Ethyl | VI-4 | V-18 | II-1 | 88 |
| II-249 | (2-NHBoc-benzothiazol-4-yl)-CH2- | Ph-CH2-NH-C(O)- | H | -CH(CH2-C6H4-O-tBu)-C(O)- | pyrrolidine | Ethyl | VI-55 | V-18 | II-1 | 72 |
| II-250 | 1-naphthyl-CH2- | Ph-CH2-NH-C(O)- | H | -CH(CH2-C6H4-O-tBu)-C(O)- | thiophene | Ethyl | VI-4 | V-19 | II-1 | 90 |
| II-251 | (2-NHBoc-benzothiazol-4-yl)-CH2- | Ph-CH2-NH-C(O)- | H | -CH(CH2-C6H4-O-tBu)-C(O)- | thiophene | Ethyl | VI-55 | V-1 | II-1 | 62 |

TABLE XIII-23-continued

| Example No. | R1 | R2 | R3 | E-A(C=O) | B/G/Y ring | R | Int_1 | Int_2 | syn. | yield (%) |
|---|---|---|---|---|---|---|---|---|---|---|
| II-252 | benzothiazol-4-yl-CH2 with HN-Boc | benzyl-NH-C(=O)-CH2 | H | CH2-C6H4-O-tBu with α-methyl ketone | thiophene-2,3-diyl | Ethyl | VI-55 | V-19 | II-1 | 37 |

TABLE XIII-24

| Example No. | R1 | R2 | R3 | E-A(C=O) | B/G/Y ring | R | Int_1 | Int_2 | syn. | yield (%) |
|---|---|---|---|---|---|---|---|---|---|---|
| II-253 | naphthalen-1-yl-CH2 | benzyl-NH-C(=O)-CH2 | H | CH2-C6H4-O-tBu ketone | pyridin-3,4-diyl | Ethyl | VI-4 | V-23 | II-1 | 25 |
| II-254 | naphthalen-1-yl-CH2 | benzyl-NH-C(=O)-CH2 | H | CH2-C6H4-O-tBu ketone | pyrrol-1,2-diyl | Ethyl | VI-4 | V-21 | II-1 | 11 |
| II-255 | naphthalen-1-yl-CH2 | benzyl-NH-C(=O)-CH2 | H | CH2-C6H4-O-tBu ketone | 1H-pyrazol-3,4-diyl | Ethyl | VI-4 | V-22 | II-1 | 42 |
| II-256 | 1-phenylethyl | benzyl-NH-C(=O)-CH2 | H | CH2-C6H4-O-tBu ketone | thiophene-2,3-diyl | Ethyl | VI-56 | V-1 | II-1 | 18 |
| II-257 | pyridin-4-yl-CH2 | benzyl-NH-C(=O)-CH2 | H | CH2-C6H4-O-tBu ketone | thiophene-2,3-diyl | Ethyl | VI-57 | V-1 | II-1 | 22 |

TABLE XIII-24-continued

| Example No. | R1 | R2 | R3 | (E-A-C(O)) | (B-G-Y ring) | R | Int_1 | Int_2 | syn. | yield (%) |
|---|---|---|---|---|---|---|---|---|---|---|
| II-258 | 2-pyridylmethyl | benzylamide | H | CH(CH2-C6H4-O-tBu)-C(O) | thiophene | Ethyl | VI-58 | V-1 | II-1 | 20 |
| II-259 | 2,4-difluorobenzyl | benzylamide | H | CH(CH2-C6H4-O-tBu)-C(O) | thiophene | Ethyl | VI-59 | V-1 | II-1 | 31 |
| II-260 | 1-naphthylmethyl | benzylamide | H | CH(CH2-C6H4-O-tBu)-C(O) | cyclopentane | Ethyl | VI-4 | V-20 | II-1 | 76 |
| II-261 | 8-quinolylmethyl | benzylamide | H | CH(CH2-C6H4-O-tBu)-C(O) | pyridine | Ethyl | VI-6 | V-23 | II-1 | 22 |

TABLE XIII-25

| Example No. | R1 | R2 | R3 | (E-A-C(O)) | (G-Y-D ring) |
|---|---|---|---|---|---|
| II-262 | 1-naphthylmethyl | benzylamide | H | N(CH3)2-CH(CH2-C6H4-O-CH2-C6H5)-C(O) | cyclopentane |

TABLE XIII-25-continued
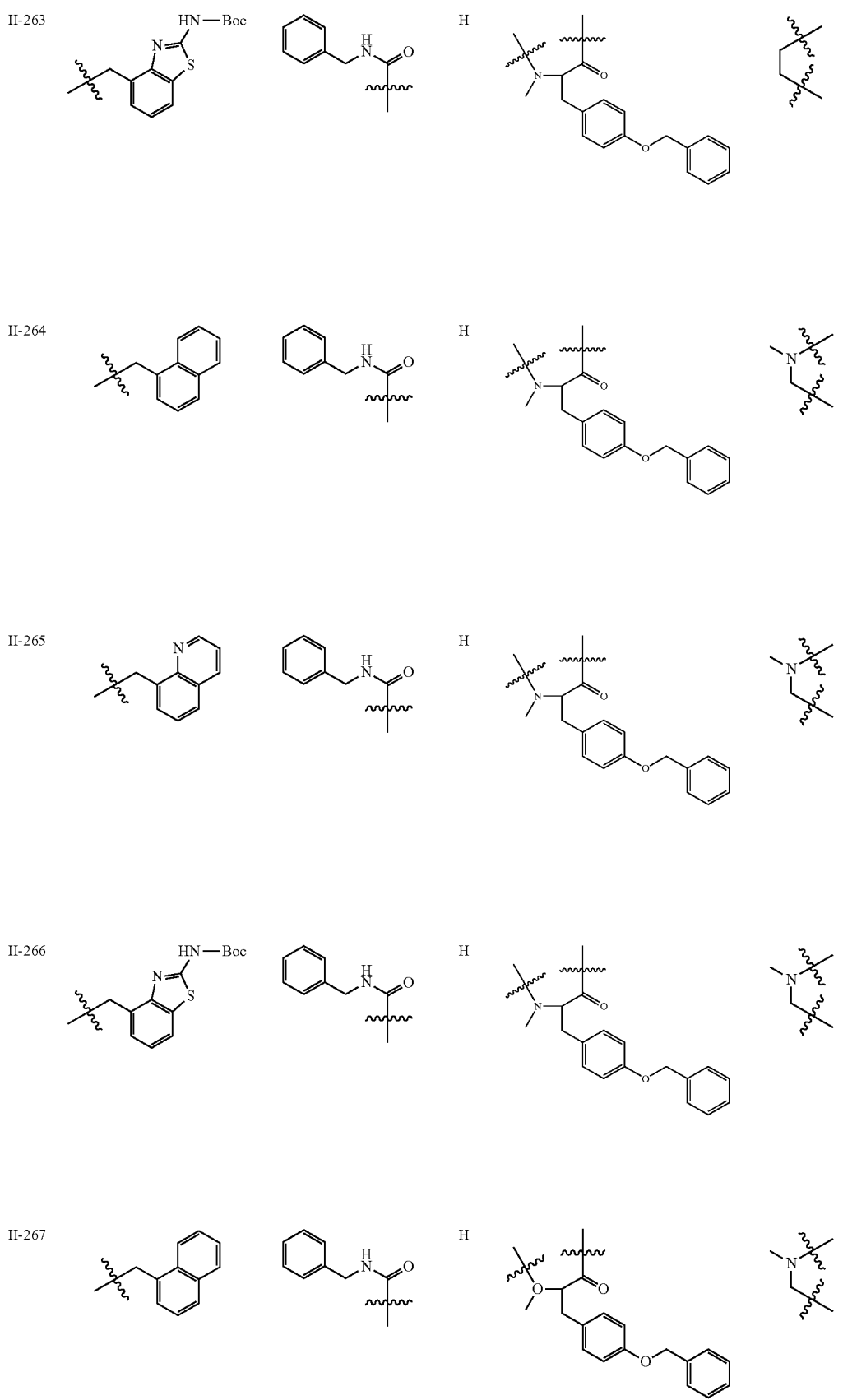

TABLE XIII-25-continued

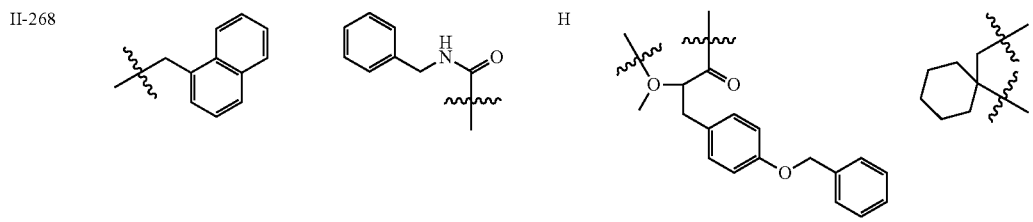

| Example No. | R | Int_1 | Int_2 | syn. | yield (%) |
|---|---|---|---|---|---|
| II-262 | Ethyl | VII-1 | IV-2 | II-2 | 36 |
| II-263 | Ethyl | VII-1 | IV-12 | II-2 | 26 |
| II-264 | Ethyl | VII-2 | IV-2 | II-2 | 56 |
| II-265 | Ethyl | VII-2 | IV-3 | II-2 | 77 |
| II-266 | Ethyl | VII-2 | IV-12 | II-2 | 62 |
| II-267 | Ethyl | VII-3 | IV-2 | II-2 | 71 |
| II-268 | Ethyl | VII-4 | IV-2 | II-2 | 46 |

[Example I-1] (Syn. I-1)

Synthesis of (8S)—N,6-dibenzyl-8-methyl-7,10-dioxo-4a,5,6,7,8,10-hexahydro-4H-pyradino[1,2-a]thieno[3,2-d]pyrimidine-4-carboxamide (Compound I-1)

To (S)—N-(1-(benzyl(2,2-diethoxyethyl)amino)-1-oxopropan-2-yl)-3-(3-benzylureido)thiophene-2-carboxamide (Compound II-1) 44.7 mg (0.08 mmol), formic acid 2 ml was added and the mixture was stirred at room temperature overnight. The reaction mixture was concentrated in vacuo and the residue was purified with PTLC (development solvent chloroform:methanol=95:5) to obtain the titled compound 28 mg (76%).

[Example 1-268] (Syn. 1-2)

Synthesis of (2S)—N-benzyl-2-(4-hydroxybenzyl)-1-methyl-4-(naphthalen-1-ylmethyl)-3,9-dioxooctahydropyrimido[1,2-b][1,2,5]triazepine-6(7H)-carboxamide (Compound I-268)

(2S)—N-benzyl-2-(4-(benzyloxy)benzyl)-1-methyl-4-(naphthalen-1-ylmethyl)-3,9-dioxooctahydropyrimido[1,2-b][1,2,5]triazepine-6(7H)-carboxamide (Compound I-267) 33 mg (0.05 mmol) was dissolved in 25% HBr acetic acid solution 0.2 ml and the mixture was stirred at room temperature for 5 hr. Ether 1.2 ml and n-hexane 0.8 ml were added to the reaction mixture and the mixture was concentrated in vacuo. The precipitation was purified on silica gel column chromatography (chloroform:methanol=100:0 to 95:5) to obtain the title compound 7.3 mg (yield 25%).

Typical examples of the compound I of the present invention that can be given by reacting and treating corresponding starting compounds using any of the methods described in the present specification are shown in Tables XIV-1 to XIV-25. The compounds were prepared according to the preparation methods of the compound numbers (e.g., "I-1") shown in the columns of "Syn" in the Tables. "Int" means an intermediate compound number. In the Tables mentioned below, data indicated by "RT" mean data of liquid chromatography retention time. In the columns of "Mass", data of mass spectrometry were shown. In the columns of "method", elution conditions of the liquid chromatography are described. For the indication of retention time in the liquid chromatography, the indication "A" for elution condition means that measurement was performed by elution with a linear gradient of 5 to 100% (v/v) Solution B from 0 minute to 5 minutes and then with 100% Solution B until 6 minutes.

General formula (I)

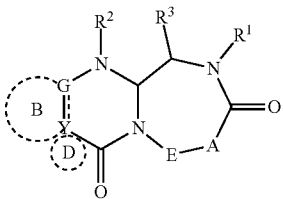

TABLE XIV-1

| Example No. | R1 | R2 | R3 | E-A | B/G/Y | Syn. | Int | method | RT | Mass |
|---|---|---|---|---|---|---|---|---|---|---|
| I-2 | benzyl | benzylamide | H | CH2-C6H4-OH ketone | thiophene | I-1 | II-2 | A | 4.61 | 553 |
| I-3 | benzyl | benzylamide | H | (CH2)3NH2 ketone | thiophene | I-1 | II-3 | A | 3.24 | 518 |
| I-4 | 1-naphthylmethyl | benzylamide | H | CH2-C6H4-OH ketone | thiophene | I-1 | II-4 | A | 5 | 603 |
| I-5 | 1-naphthylmethyl | benzylamide | H | CH2COOH ketone | thiophene | I-1 | II-5 | A | 4.67 | 555 |
| I-6 | 8-quinolinylmethyl | benzylamide | H | CH2-C6H4-OH ketone | thiophene | I-1 | II-6 | A | 4.31 | 604 |
| I-7 | 8-quinolinylmethyl | benzylamide | H | CH2CONH2 ketone | thiophene | I-1 | II-7 | A | 3.85 | 555 |
| I-8 | 3-benzothienylmethyl | benzylamide | H | CH(Me) ketone | thiophene | I-1 | II-8 | A | 4.95 | 517 |
| I-9 | 3-benzothienylmethyl | benzylamide | H | CH2-C6H4-OH ketone | thiophene | I-1 | II-9 | A | 4.98 | 609 |

TABLE XIV-1-continued

| Example No. | R1 | R2 | R3 | ![E-A structure] | ![B-G-Y structure] | Syn. | Int | method | RT | Mass |
|---|---|---|---|---|---|---|---|---|---|---|
| I-10 | benzyl | (pyridin-4-yl)methyl-NH-C(=O)- | H | 4-hydroxybenzyl-CH-C(=O)- | thiophene | I-1 | II-10 | A | 2.94 | 554 |
| I-11 | benzyl | (4-chlorobenzyl)-NH-C(=O)- | H | 4-hydroxybenzyl-CH-C(=O)- | thiophene | I-1 | II-11 | A | 4.95 | 587 |
| I-12 | benzyl | (naphthalen-1-yl)methyl-NH-C(=O)- | H | 4-hydroxybenzyl-CH-C(=O)- | thiophene | I-1 | II-12 | A | 5 | 603 |

TABLE XIV-2

| Example No. | R1 | R2 | R3 | E-A |
|---|---|---|---|---|
| I-13 | benzyl | ethyl-NH-C(=O)- | H | 4-hydroxybenzyl-CH-C(=O)- |
| I-14 | (naphthalen-1-yl)methyl | (pyridin-4-yl)methyl-NH-C(=O)- | H | 4-hydroxybenzyl-CH-C(=O)- |

TABLE XIV-2-continued
| | | | | |
|---|---|---|---|---|
| I-15 | 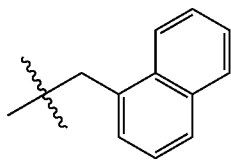 | 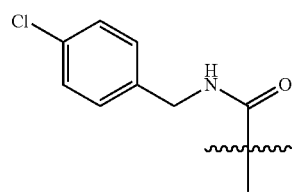 [SMILES: *C(=O)NCc1ccc(Cl)cc1] | H | 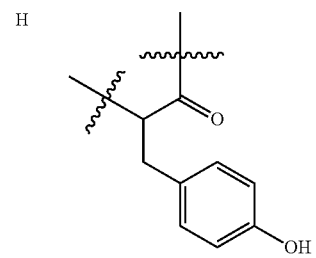 |
| I-16 | 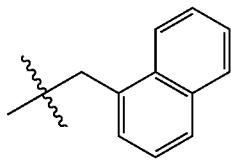 [SMILES: *Cc1cccc2ccccc12] | 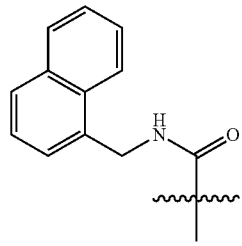 [SMILES: *C(=O)NCc1cccc2ccccc12] | H | 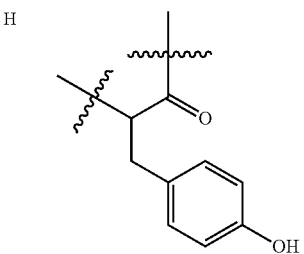 |
| I-17 | 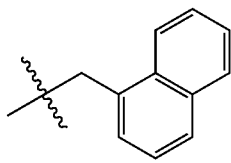 | 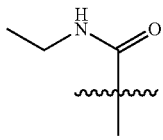 [SMILES: *C(=O)NCC] | H | 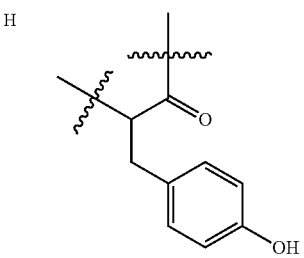 |
| I-18 | 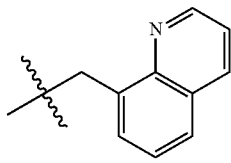 [SMILES: *Cc1cccc2cccnc12] | 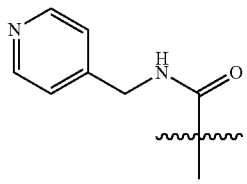 [SMILES: *C(=O)NCc1ccncc1] | H | 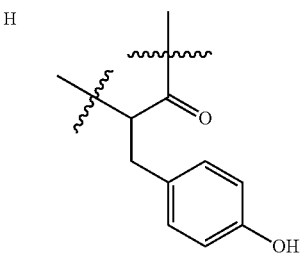 |
| I-19 | 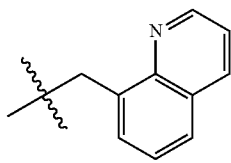 [SMILES: *Cc1cccc2cccnc12] | 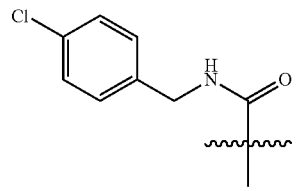 [SMILES: *C(=O)NCc1ccc(Cl)cc1] | H | 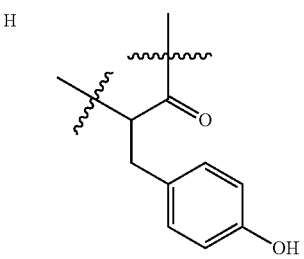 |
| I-20 | 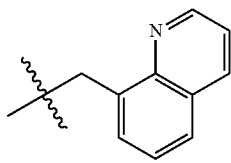 | 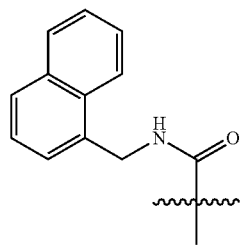 [SMILES: *C(=O)NCc1cccc2ccccc12] | H | 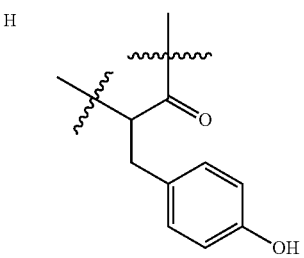 |

TABLE XIV-2-continued
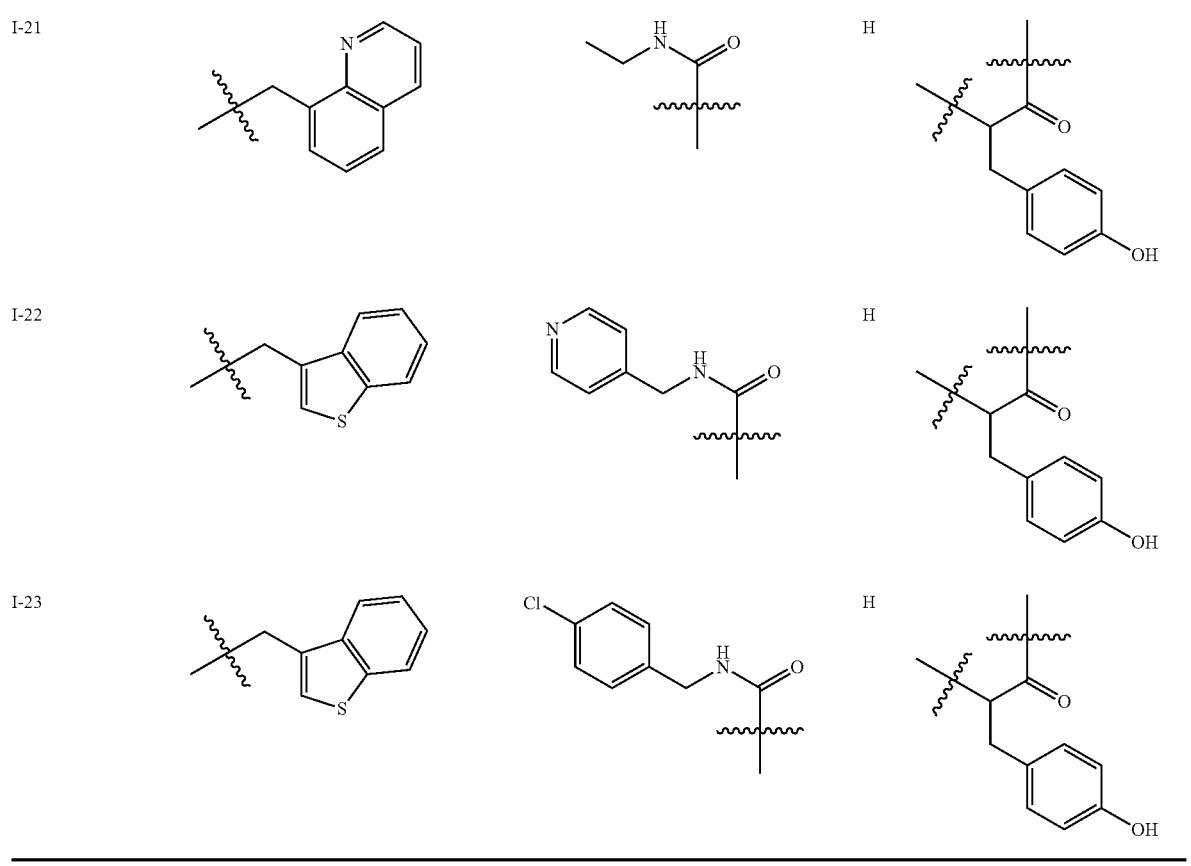
| Example No. | 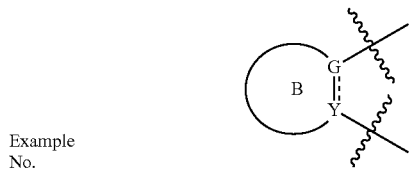 | Syn. | Int | method | RT | Mass |
|---|---|---|---|---|---|---|
| I-13 | | I-1 | II-13 | A | 4.13 | 491 |
| I-14 | | I-1 | II-14 | A | 3.32 | 604 |
| I-15 | | I-1 | II-15 | A | 5.3 | 637 |

TABLE XIV-2-continued

| | | | | | | |
|---|---|---|---|---|---|---|
| I-16 | (thiophene) | I-1 | II-16 | A | 5.42 | 653 |
| I-17 | (thiophene) | I-1 | II-17 | A | 4.57 | 541 |
| I-18 | (thiophene) | I-1 | II-18 | A | 2.75 | 605 |
| I-19 | (thiophene) | I-1 | II-19 | A | 4.61 | 638 |
| I-20 | (thiophene) | I-1 | II-20 | A | 4.77 | 654 |
| I-21 | (thiophene) | I-1 | II-21 | A | 3.68 | 542 |
| I-22 | (thiophene) | I-1 | II-22 | A | 3.28 | 610 |
| I-23 | (thiophene) | I-1 | II-23 | A | 5.26 | 643 |

TABLE XIV-3
| Example No. | R1 | R2 | R3 | 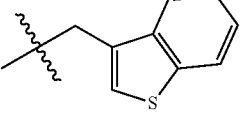 |
|---|---|---|---|---|
| I-24 | 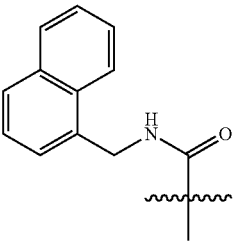 [SMILES: *C(=O)NCc1cccc2ccccc12] | 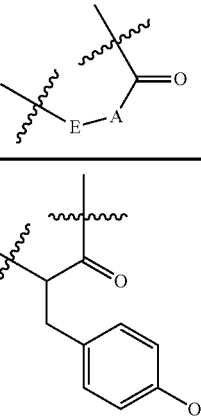 | H | 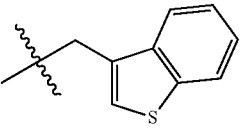 [SMILES: *Cc1csc2ccccc12] |
| I-25 | 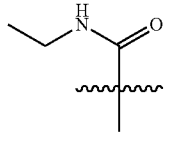 [SMILES: *C(=O)NCC] | 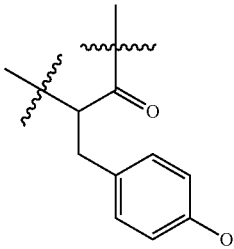 | H | 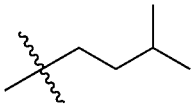 [SMILES: *CCC(C)C] |
| I-26 | 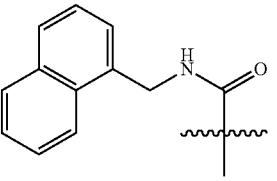 [SMILES: *C(=O)NCc1cccc2ccccc12] | 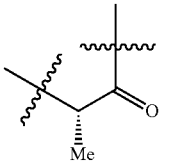 [SMILES: *C(=O)[C@@H](*)C] | H | 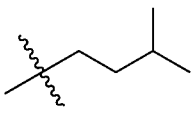 [SMILES: *CCC(C)C] |
| I-27 | 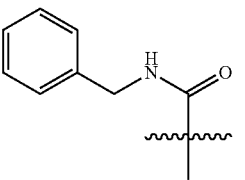 [SMILES: *C(=O)NCc1ccccc1] | 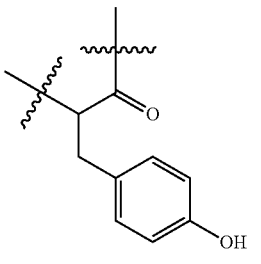 [SMILES: *C(=O)C(*)Cc1ccc(O)cc1] | H | 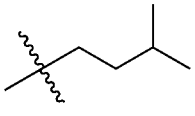 [SMILES: *CCC(C)C] |
| I-28 | 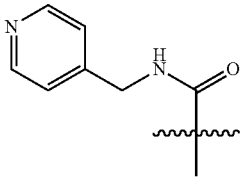 [SMILES: *C(=O)NCc1ccncc1] | 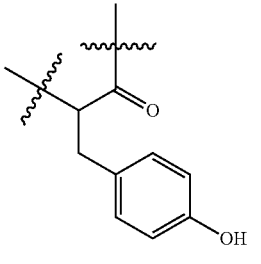 [SMILES: *C(=O)C(*)Cc1ccc(O)cc1] | H | 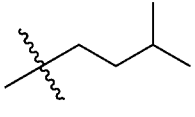 [SMILES: *CCC(C)C] |
| I-29 | 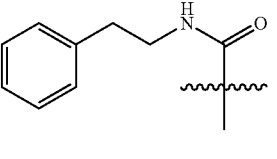 [SMILES: *C(=O)NCCc1ccccc1] | 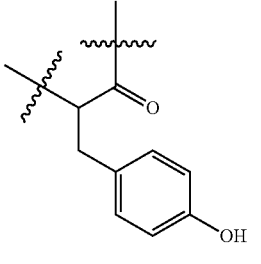 [SMILES: *C(=O)C(*)Cc1ccc(O)cc1] | H |  |

TABLE XIV-3-continued
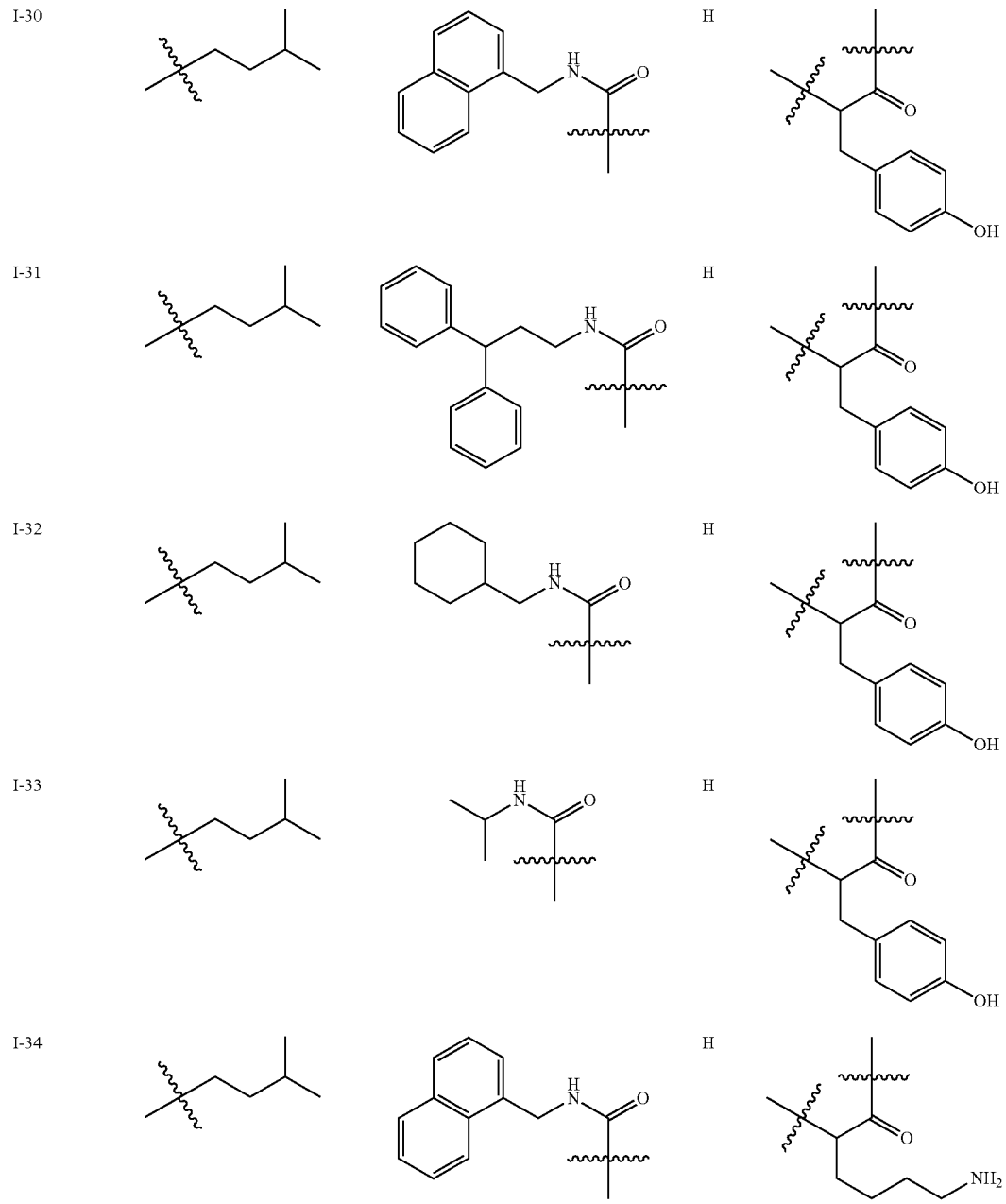
| Example No. | B | Syn. | Int | method | RT | Mass |
|---|---|---|---|---|---|---|
| I-24 | 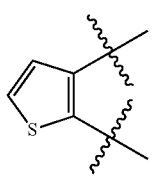 [SMILES: *c1ccsc1*] | I-1 | II-24 | A | 5.36 | 659 |

TABLE XIV-3-continued
| | | | | | | |
|---|---|---|---|---|---|---|
| I-25 | 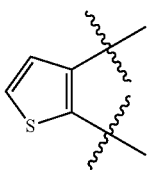 [SMILES: *c1ccsc1*] | I-1 | II-25 | A | 4.53 | 547 |
| I-26 | 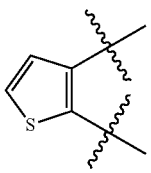 [SMILES: *c1ccsc1*] | I-1 | II-26 | A | 5.18 | 491 |
| I-27 | 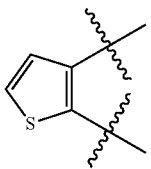 [SMILES: *c1ccsc1*] | I-1 | II-27 | A | 4.77 | 533 |
| I-28 | 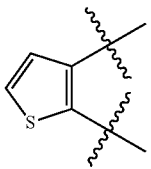 [SMILES: *c1ccsc1*] | I-1 | II-28 | A | 3 | 534 |
| I-29 | 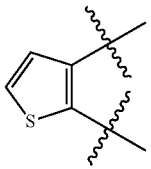 [SMILES: *c1ccsc1*] | I-1 | II-29 | A | 4.95 | 547 |
| I-30 | 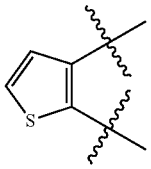 [SMILES: *c1ccsc1*] | I-1 | II-30 | A | 5.17 | 583 |
| I-31 | 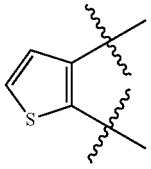 [SMILES: *c1ccsc1*] | I-1 | II-31 | A | 5.47 | 637 |
| I-32 | 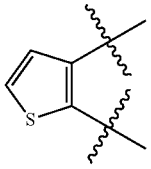 [SMILES: *c1ccsc1*] | I-1 | II-32 | A | 5.27 | 539 |
| I-33 | 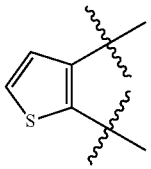 [SMILES: *c1ccsc1*] | I-1 | II-33 | A | 4.5 | 485 |

TABLE XIV-3-continued
| | | | | | | |
|---|---|---|---|---|---|---|
| I-34 | 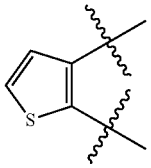 [SMILES: *c1ccsc1*] | I-1 | II-34 | A | 3.6 | 548 |
TABLE XIV-4
| Example No. | R1 | R2 | R3 | 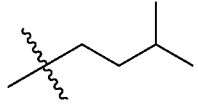 |
|---|---|---|---|---|
| I-35 | 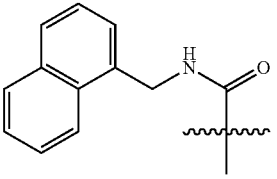 [SMILES: *C(=O)NCc1cccc2ccccc12] | 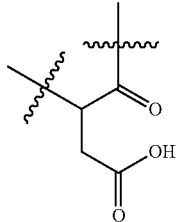 [SMILES: *C(=O)C(*)CC(=O)O] | H | 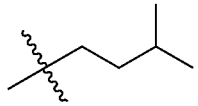 |
| I-36 | 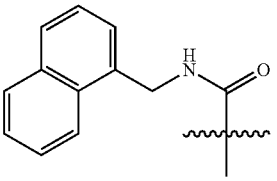 [SMILES: *C(=O)NCc1cccc2ccccc12] | 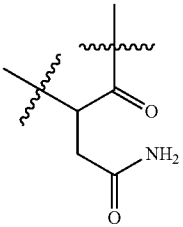 [SMILES: *C(=O)C(*)CC(N)=O] | H | 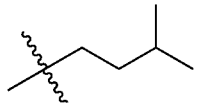 [SMILES: *CCC(C)C] |
| I-37 | 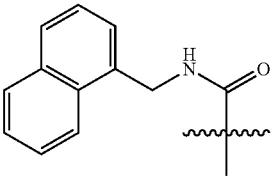 [SMILES: *C(=O)NCc1cccc2ccccc12] | 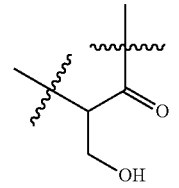 | H | 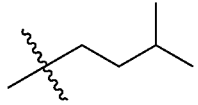 [SMILES: *CCC(C)C] |
| I-38 | 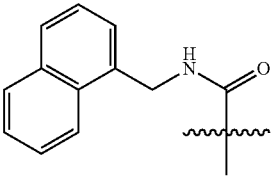 [SMILES: *C(=O)NCc1cccc2ccccc12] | 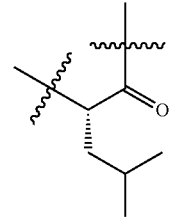 | H | 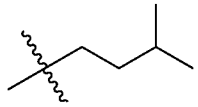 [SMILES: *CCC(C)C] |
| I-39 | 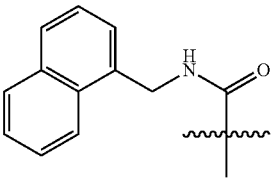 [SMILES: *C(=O)NCc1cccc2ccccc12] | 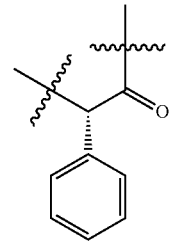 | H |  |

TABLE XIV-4-continued
| | | | | |
|---|---|---|---|---|
| I-40 | 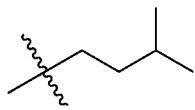 | 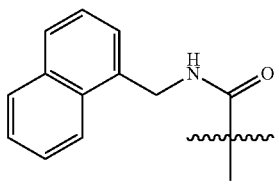 [SMILES: *C(=O)NCc1cccc2ccccc12] | H | 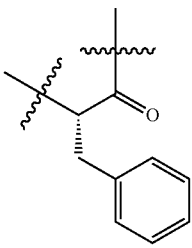 [SMILES: *C(=O)[C@@H](*)Cc1ccccc1] |
| I-41 | 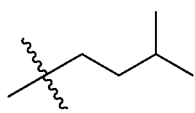 [SMILES: *CCC(C)C] | 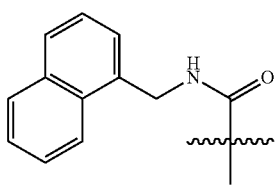 [SMILES: *C(=O)NCc1cccc2ccccc12] | H | 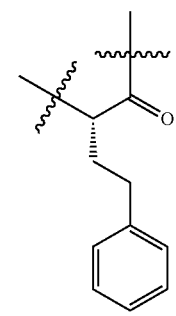 |
| I-42 | 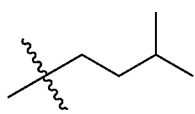 [SMILES: *CCC(C)C] | 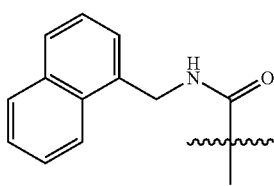 [SMILES: *C(=O)NCc1cccc2ccccc12] | H | 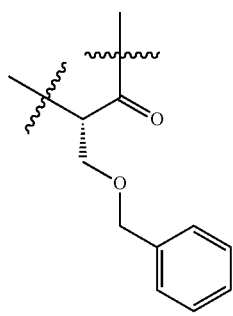 [SMILES: *C(=O)[C@@H](*)COCc1ccccc1] |
| I-43 | 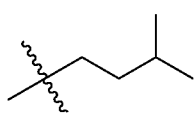 [SMILES: *CCC(C)C] | 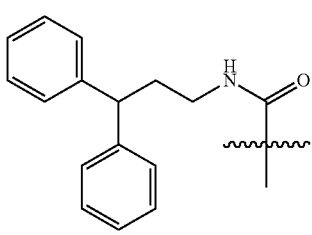 [SMILES: *C(=O)NCCC(c1ccccc1)c1ccccc1] | H | 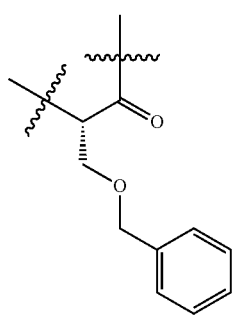 [SMILES: *C(=O)[C@@H](*)COCc1ccccc1] |
| I-44 | 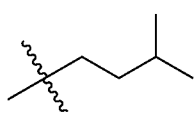 [SMILES: *CCC(C)C] | 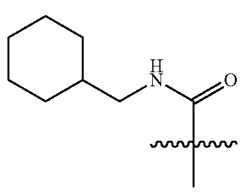 [SMILES: *C(=O)NCC1CCCCC1] | H | 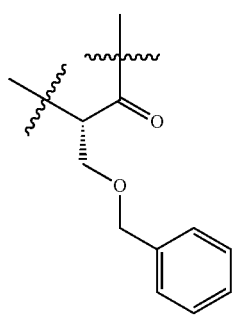 [SMILES: *C(=O)[C@@H](*)COCc1ccccc1] |

TABLE XIV-4-continued

| Example No. | B-G=Y | Syn. | Int | method | RT | Mass |
|---|---|---|---|---|---|---|
| I-35 | thiophene | I-1 | II-35 | A | 4.87 | 535 |
| I-36 | thiophene | I-1 | II-36 | A | 4.67 | 534 |
| I-37 | thiophene | I-1 | II-37 | A | 4.87 | 507 |
| I-38 | thiophene | I-1 | II-38 | A | 5.67 | 533 |
| I-39 | thiophene | I-1 | II-39 | A | 5.62 | 553 |
| I-40 | thiophene | I-1 | II-40 | A | 5.65 | 567 |

TABLE XIV-4-continued

| | | | | | | | |
|---|---|---|---|---|---|---|---|
| I-41 | | thiophene | I-1 | II-41 | A | 5.8 | 581 |
| I-42 | | thiophene | I-1 | II-42 | A | 5.78 | 597 |
| I-43 | | thiophene | I-1 | II-43 | A | 5.93 | 651 |
| I-44 | | thiophene | I-1 | II-44 | A | 5.88 | 553 |
| I-45 | | thiophene | I-1 | II-45 | A | 5.15 | 499 |

TABLE XIV-5

| Example No. | R1 | R2 | R3 | E—A |
|---|---|---|---|---|
| I-46 | isohexyl | naphthylmethyl-NH-C(O)- | H | naphthylmethyl branch |

TABLE XIV-5-continued
| | | | | |
|---|---|---|---|---|
| I-47 | 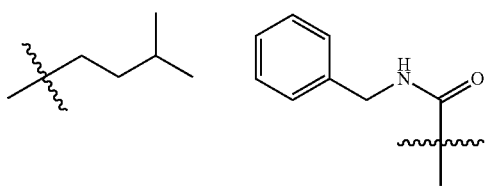 | 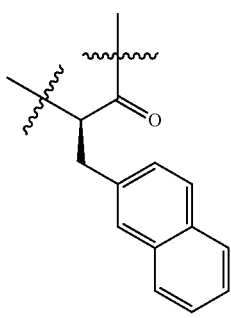 [SMILES: *C(=O)[C@H](*)Cc1ccc2ccccc2c1] | H | 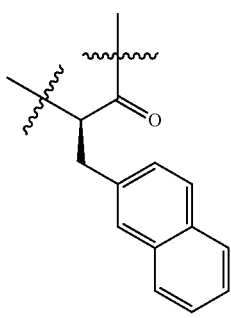 [SMILES: *C(=O)[C@H](*)Cc1ccc2ccccc2c1] |
| I-48 | 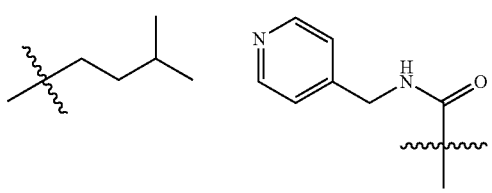 | 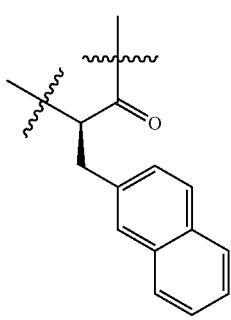 [SMILES: *C(=O)[C@H](*)Cc1ccc2ccccc2c1] | H | 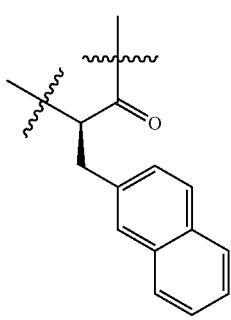 [SMILES: *C(=O)[C@H](*)Cc1ccc2ccccc2c1] |
| I-49 | 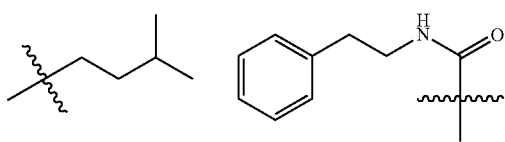 | 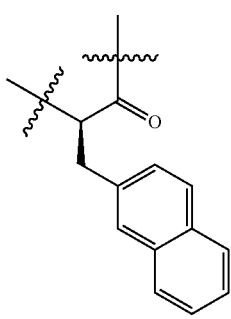 | H | 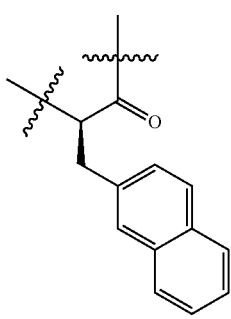 |
| I-50 | 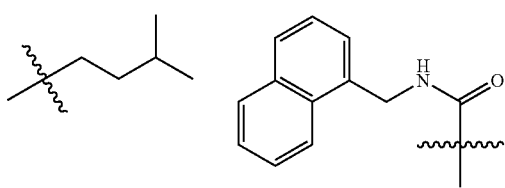 | 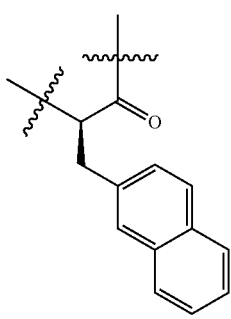 | H | 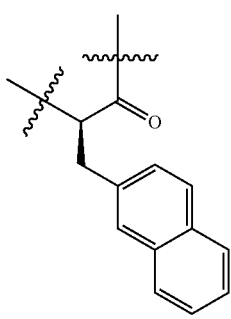 |
| I-51 | 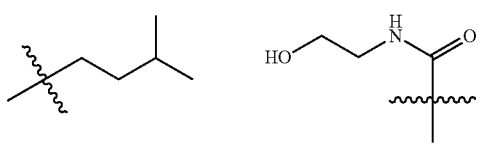 | 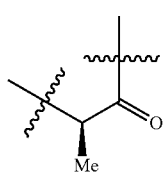 [SMILES: *C(=O)[C@H](*)C] | H | 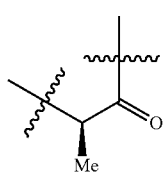 [SMILES: *C(=O)[C@H](*)C] |
| I-52 | 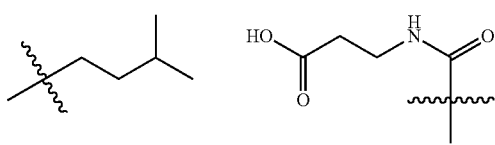 | 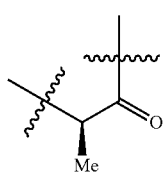 | H | 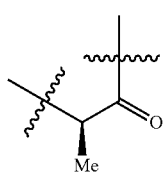 |

TABLE XIV-5-continued
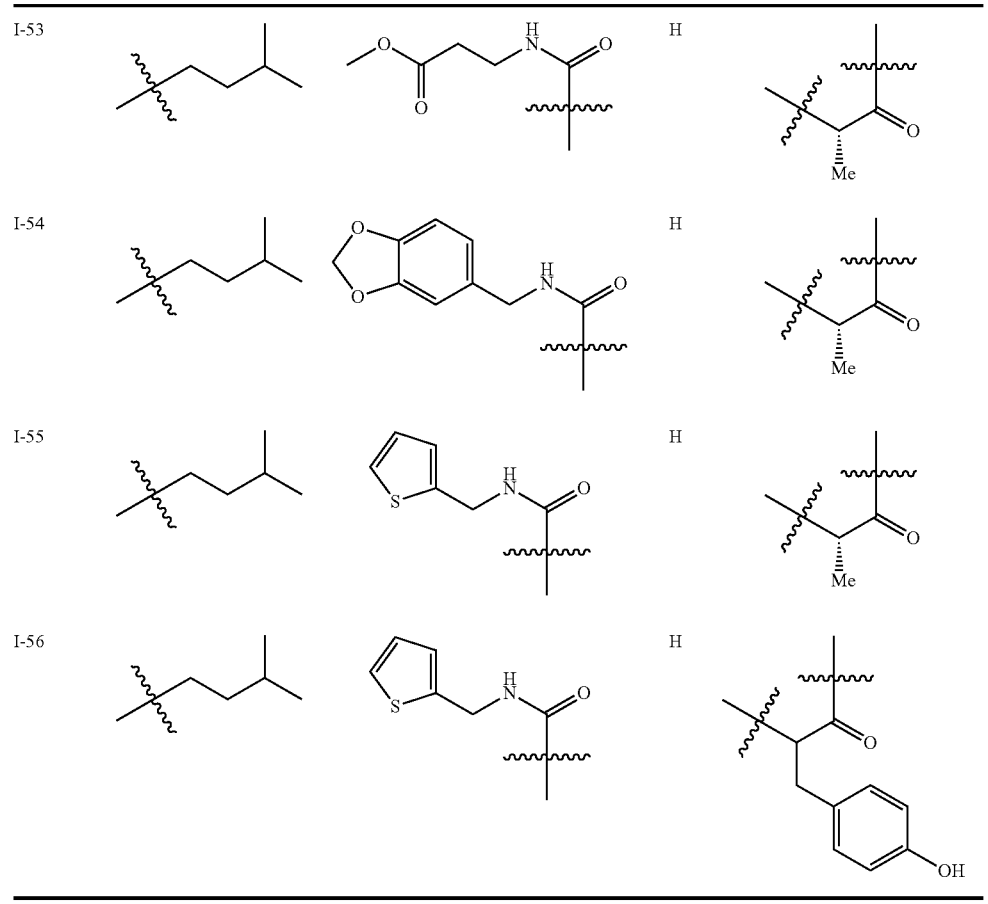
| Example No. | | Syn. | Int | method | RT | Mass |
|---|---|---|---|---|---|---|
| I-46 | | I-1 | II-46 | A | 6 | 617 |
| I-47 | | I-1 | II-47 | A | 5.6 | 567 |
| I-48 | | I-1 | II-48 | A | 3.82 | 568 |
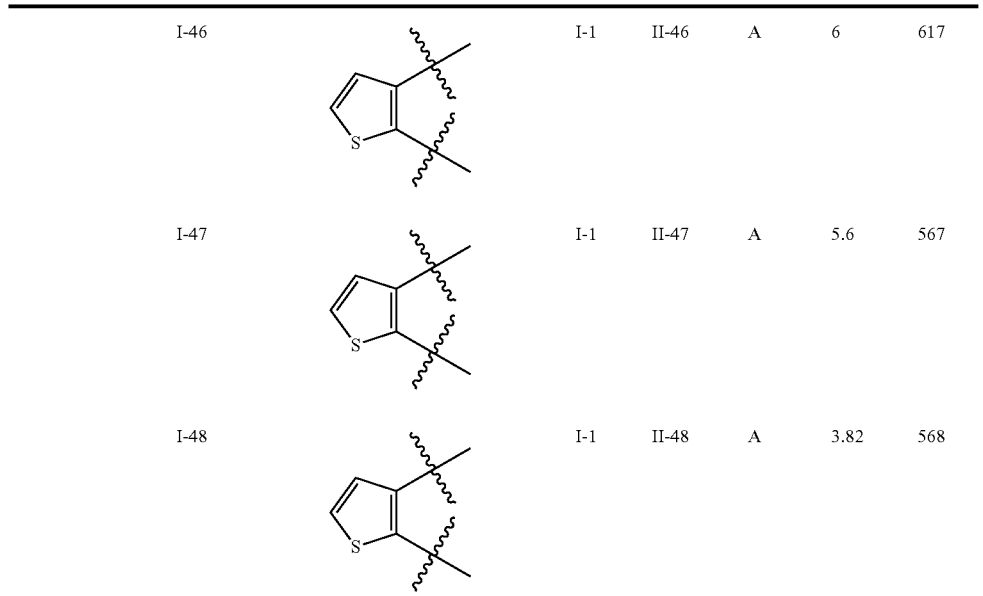

TABLE XIV-5-continued
| | | | | | | |
|---|---|---|---|---|---|---|
| I-49 | 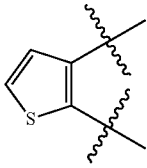 [SMILES: *c1ccsc1*] | I-1 | II-49 | A | 5.75 | 581 |
| I-50 | 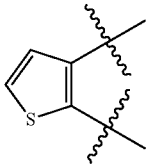 [SMILES: *c1ccsc1*] | I-1 | II-50 | A | 5.98 | 617 |
| I-51 | 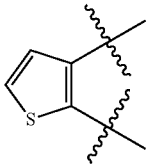 [SMILES: *c1ccsc1*] | I-1 | II-51 | A | 3.43 | 395 |
| I-52 | 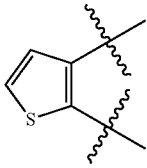 [SMILES: *c1ccsc1*] | I-1 | II-52 | A | 3.58 | 423 |
| I-53 | 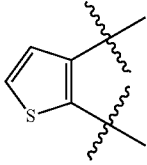 [SMILES: *c1ccsc1*] | I-1 | II-53 | A | 4.03 | 437 |
| I-54 | 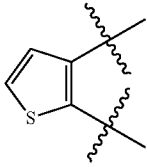 [SMILES: *c1ccsc1*] | I-1 | II-54 | A | 4.62 | 485 |
| I-55 | 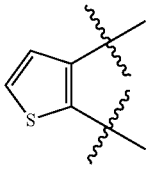 [SMILES: *c1ccsc1*] | I-1 | II-55 | A | 4.62 | 447 |
| I-56 | 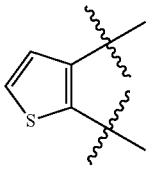 [SMILES: *c1ccsc1*] | I-1 | II-56 | A | 4.75 | 539 |

TABLE XIV-6

| Example No. | R1 | R2 | R3 | E-A (C=O) |
|---|---|---|---|---|
| I-57 | isohexyl | 4-methylbenzyl-NHC(O)- | H | -CH(CH2-C6H4-OH)-C(O)- |
| I-58 | isohexyl | thiophen-2-ylmethyl-NHC(O)- | H | -CH((CH2)4NH2)-C(O)- |
| I-59 | isohexyl | thiophen-2-ylmethyl-NHC(O)- | H | -CH(CH2COOH)-C(O)- |
| I-60 | isohexyl | thiophen-2-ylmethyl-NHC(O)- | H | -CH(CH2C(O)NH2)-C(O)- |
| I-61 | isohexyl | thiophen-2-ylmethyl-NHC(O)- | H | -CH(CH2OH)-C(O)- |
| I-62 | isohexyl | thiophen-2-ylmethyl-NHC(O)- | H | -CH(CH2CH(CH3)2)-C(O)- |

TABLE XIV-6-continued
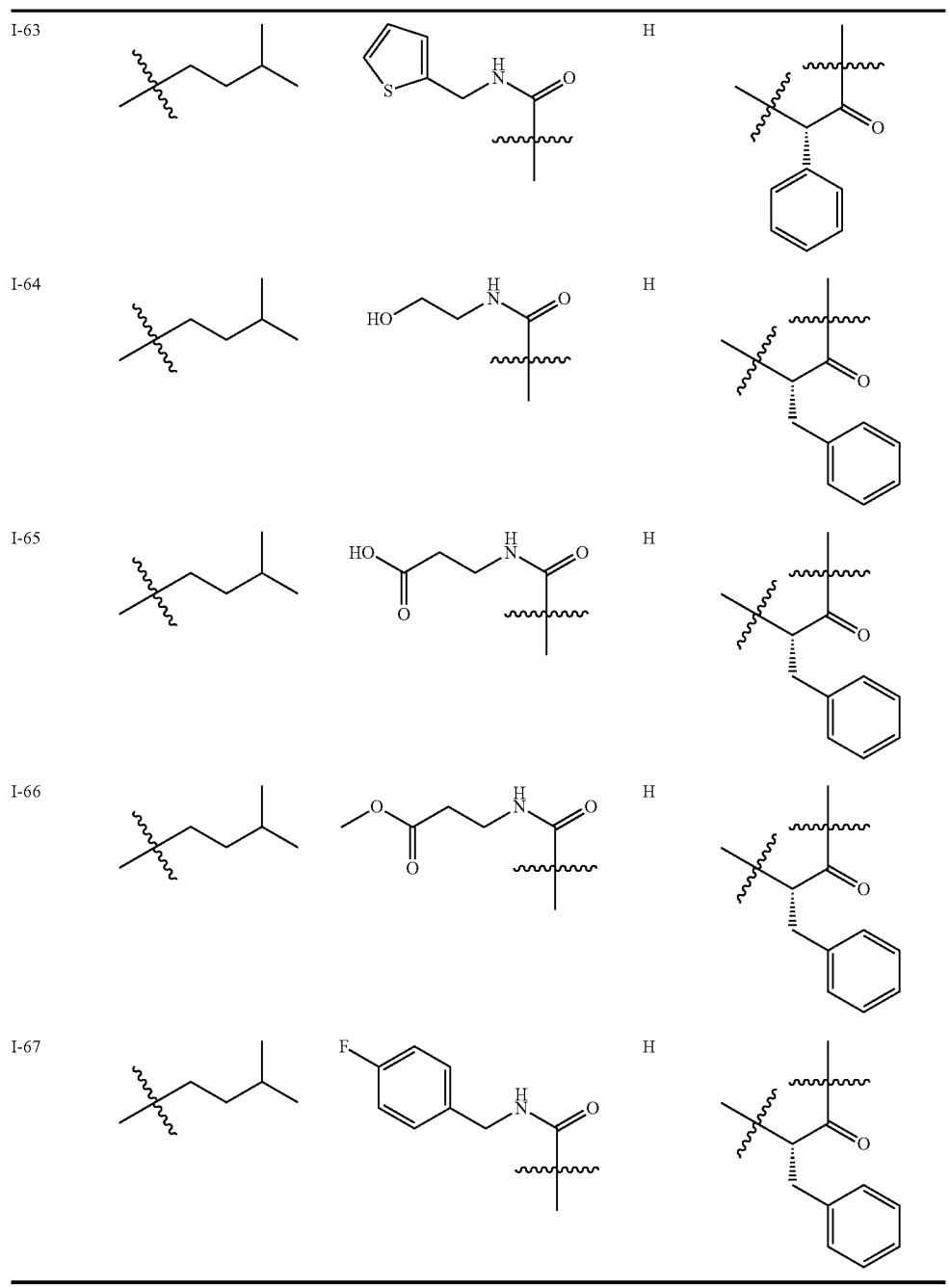
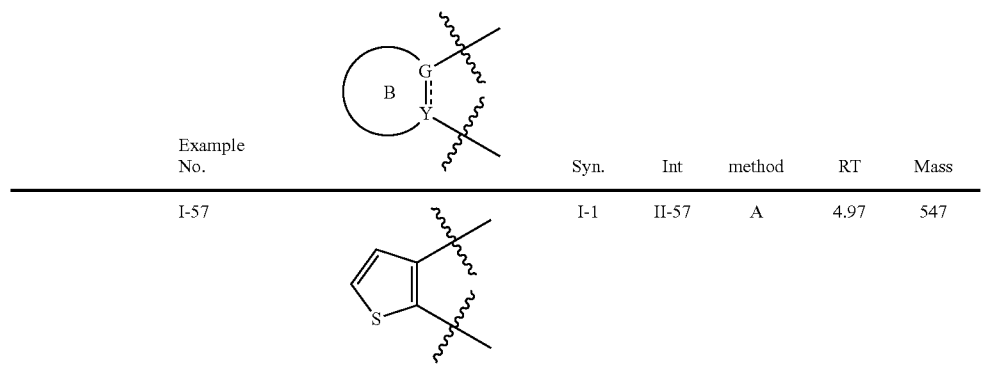
| Example No. | | Syn. | Int | method | RT | Mass |
|---|---|---|---|---|---|---|
| I-57 | | I-1 | II-57 | A | 4.97 | 547 |

TABLE XIV-6-continued
| I-58 | 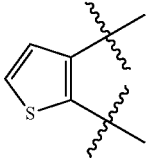 [SMILES: *c1ccsc1*] | I-1 | II-58 | A | 3.27 | 504 |
| I-59 | 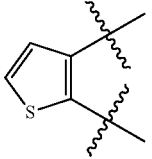 [SMILES: *c1ccsc1*] | I-1 | II-59 | A | 4.4 | 491 |
| I-60 | 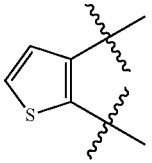 [SMILES: *c1ccsc1*] | I-1 | II-60 | A | 4.12 | 490 |
| I-61 | 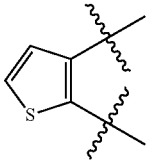 [SMILES: *c1ccsc1*] | I-1 | II-61 | A | 4.32 | 463 |
| I-62 | 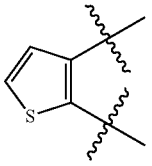 [SMILES: *c1ccsc1*] | I-1 | II-62 | A | 5.15 | 489 |
| I-63 | 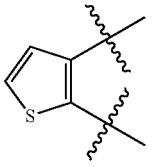 [SMILES: *c1ccsc1*] | I-1 | II-63 | A | 5.13 | 509 |
| I-64 | 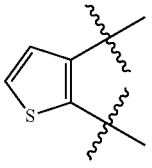 [SMILES: *c1ccsc1*] | I-1 | II-64 | A | 4.03 | 471 |
| I-65 | 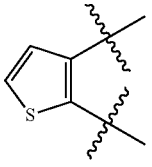 [SMILES: *c1ccsc1*] | I-1 | II-65 | A | 4.13 | 499 |
| I-66 | 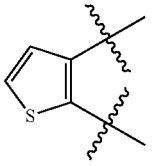 [SMILES: *c1ccsc1*] | I-1 | II-66 | A | 4.63 | 513 |

TABLE XIV-6-continued

| | | | | | | |
|---|---|---|---|---|---|---|
| I-67 | (thiophene structure) | I-1 | II-67 | A | 5.25 | 535 |

10

TABLE XIV-7

| Example No. | R1 | R2 | R3 | E—A |
|---|---|---|---|---|
| I-68 | (isohexyl) | (thiophen-2-ylmethyl amide) | H | (benzyl ketone) |
| I-69 | (isohexyl) | (4-fluorobenzylamide) | H | (naphthalen-1-ylmethyl ketone) |
| I-70 | (isohexyl) | (benzo[d][1,3]dioxol-5-ylmethyl amide) | H | (naphthalen-1-ylmethyl ketone) |

TABLE XIV-7-continued
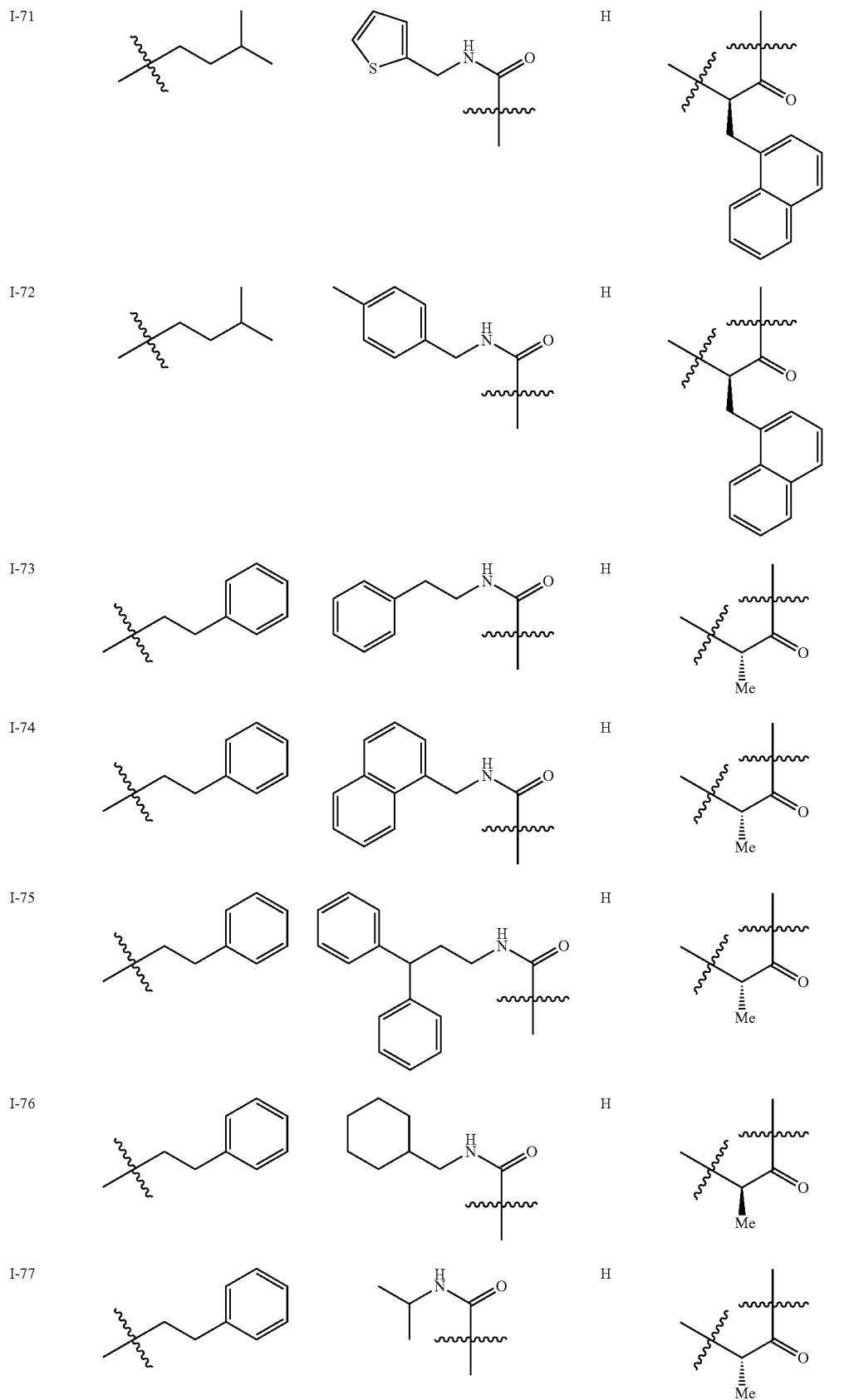

TABLE XIV-7-continued

| I-78 | (phenethyl) | (benzyl-NH-C(O)-) | H | (isobutyl with 4-hydroxybenzyl ketone) |

| Example No. | [B-G=Y ring structure] | Syn. | Int | method | RT | Mass |
|---|---|---|---|---|---|---|
| I-68 | thiophene | I-1 | II-68 | A | 5.13 | 523 |
| I-69 | thiophene | I-1 | II-69 | A | 5.62 | 585 |
| I-70 | thiophene | I-1 | II-70 | A | 5.52 | 611 |
| I-71 | thiophene | I-1 | II-71 | A | 5.53 | 573 |
| I-72 | thiophene | I-1 | II-72 | A | 5.83 | 581 |
| I-73 | thiophene | I-1 | II-73 | A | 4.78 | 489 |

TABLE XIV-7-continued
| Ex. | | | | | | |
|---|---|---|---|---|---|---|
| I-74 | 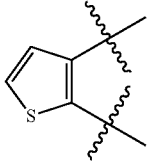 [SMILES: *c1ccsc1*] | I-1 | II-74 | A | 5.1 | 525 |
| I-75 | 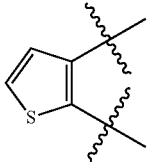 [SMILES: *c1ccsc1*] | I-1 | II-75 | A | 5.37 | 579 |
| I-76 | 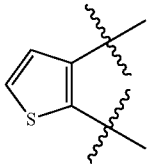 [SMILES: *c1ccsc1*] | I-1 | II-76 | A | 5.15 | 481 |
| I-77 | 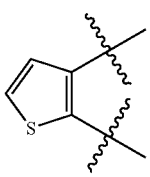 [SMILES: *c1ccsc1*] | I-1 | II-77 | A | 4.28 | 427 |
| I-78 | 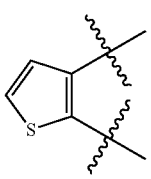 [SMILES: *c1ccsc1*] | I-1 | II-78 | A | 4.67 | 567 |
TABLE XIV-8
| Example No. | R1 | R2 | R3 | 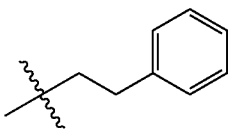 [SMILES: *CCc1ccccc1] | 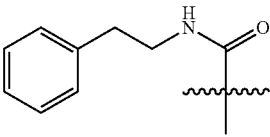 [SMILES: *C(=O)NCCc1ccccc1] |
|---|---|---|---|---|---|
| I-79 | 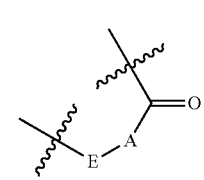 | 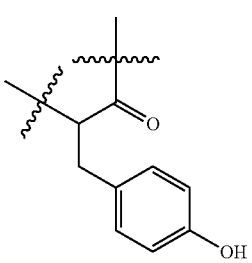 [SMILES: *C(=O)C(*)Cc1ccc(O)cc1] | H | | |

TABLE XIV-8-continued
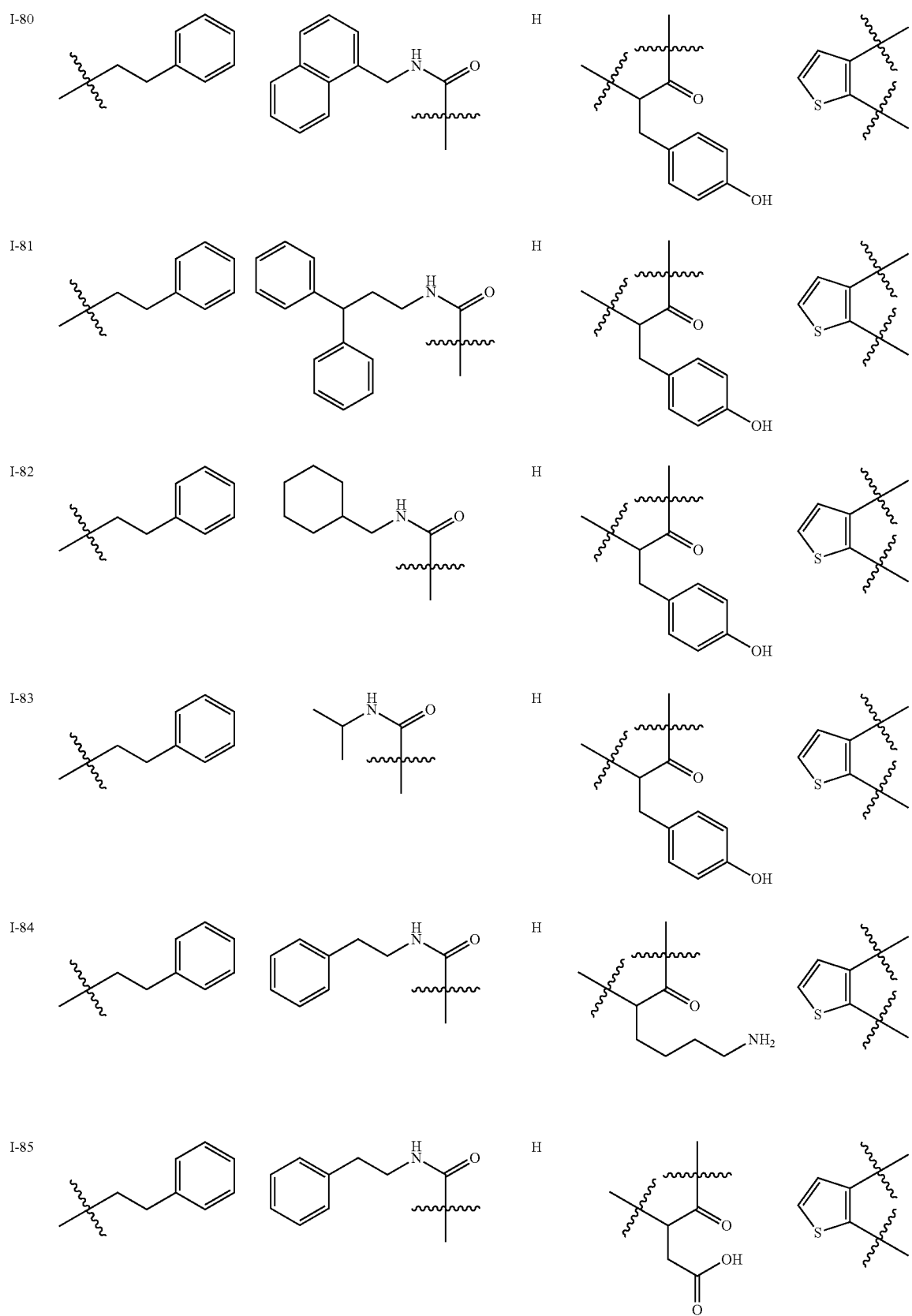

TABLE XIV-8-continued
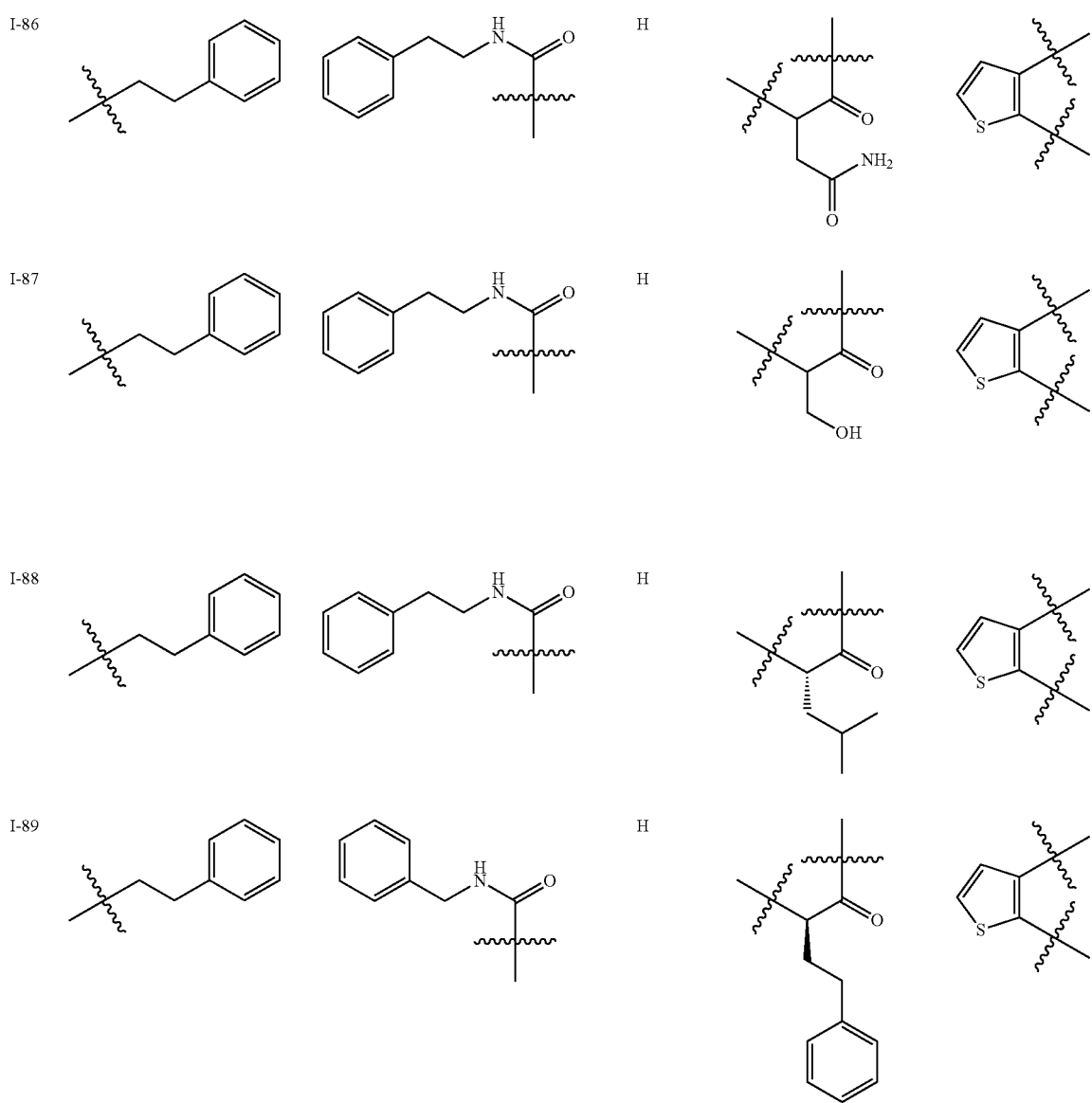
| Example No. | Syn. | Int | method | RT | Mass |
|---|---|---|---|---|---|
| I-79 | I-1 | II-79 | A | 4.83 | 581 |
| I-80 | I-1 | II-80 | A | 5.08 | 617 |
| I-81 | I-1 | II-81 | A | 5.37 | 671 |
| I-82 | I-1 | II-82 | A | 5.13 | 573 |
| I-83 | I-1 | II-83 | A | 4.4 | 519 |
| I-84 | I-1 | II-84 | A | 3.9 | 546 |
| I-85 | I-1 | II-85 | A | 4.33 | 519 |
| I-86 | I-1 | II-86 | A | 4.48 | 533 |
| I-87 | I-1 | II-87 | A | 4.47 | 505 |
| I-88 | I-1 | II-88 | A | 5.32 | 531 |
| I-89 | I-1 | II-89 | A | 5.28 | 565 |

TABLE XIV-9

| Example No. | R1 | R2 | R3 | E-A-C(=O)- | B/G/Y ring |
|---|---|---|---|---|---|
| I-90 | phenethyl | -C(=O)CH2-NH-CH2CH2-phenyl | H | -CH(CH2CH2Ph)-C(=O)- | thiophene |
| I-91 | phenethyl | -C(=O)CH2-NH-CH2CH2-OH | H | -CH(Me)-C(=O)- | thiophene |
| I-92 | phenethyl | -C(=O)CH2-NH-CH2CH2-COOH | H | -CH(Me)-C(=O)- | thiophene |
| I-93 | phenethyl | -C(=O)CH2-NH-CH2CH2-C(=O)OMe | H | -CH(Me)-C(=O)- | thiophene |
| I-94 | phenethyl | -C(=O)CH2-NH-CH2CH2-OH | H | -CH(CH2-C6H4-OH)-C(=O)- | thiophene |
| I-95 | phenethyl | -C(=O)CH2-NH-CH2CH2-COOH | H | -CH(CH2-C6H4-OH)-C(=O)- | thiophene |

TABLE XIV-9-continued
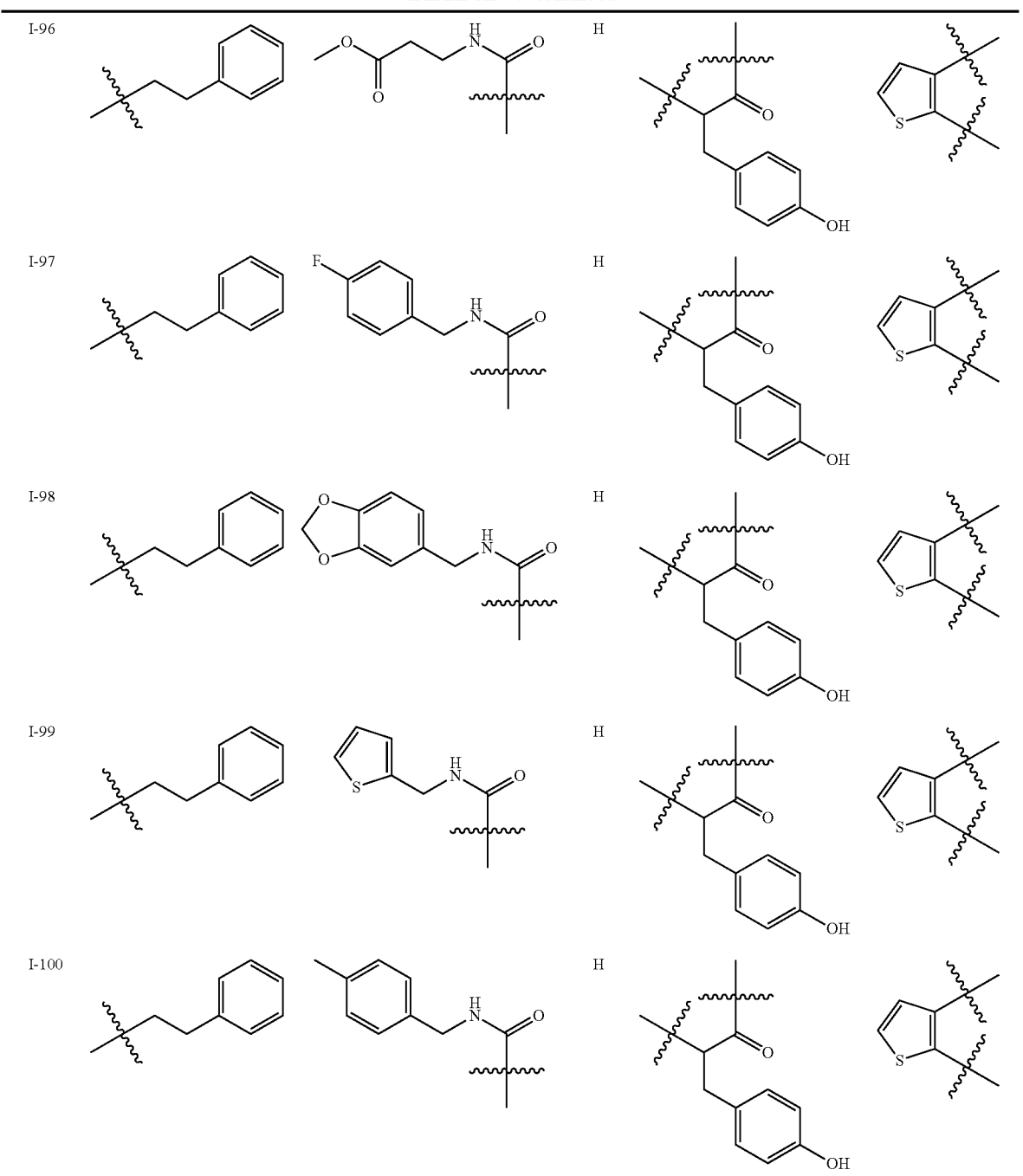
| Example No. | Syn. | Int | method | RT | Mass |
|---|---|---|---|---|---|
| I-90 | I-1 | II-90 | A | 5.43 | 579 |
| I-91 | I-1 | II-91 | A | 3.4 | 429 |
| I-92 | I-1 | II-92 | A | 3.53 | 457 |
| I-93 | I-1 | II-93 | A | 3.95 | 471 |
| I-94 | I-1 | II-94 | A | 3.65 | 521 |
| I-95 | I-1 | II-95 | A | 3.75 | 549 |
| I-96 | I-1 | II-96 | A | 4.13 | 563 |
| I-97 | I-1 | II-97 | A | 4.75 | 585 |
| I-98 | I-1 | II-98 | A | 4.62 | 611 |
| I-99 | I-1 | II-99 | A | 4.6 | 573 |
| I-100 | I-1 | II-100 | A | 4.88 | 581 |

TABLE XIV-10

| Example No. | R1 | R2 | R3 | (E-A-C(O)-) | (B-G-Y ring) |
|---|---|---|---|---|---|
| I-101 | phenethyl | 4-fluorobenzyl-NH-C(O)-CH(CH3)- | H | -CH(C(O)-)-CH2CH2CH2CH2-NH2 | thiophene |
| I-102 | phenethyl | (thiophen-2-yl)methyl-NH-C(O)-CH(CH3)- | H | -CH(C(O)-)-CH2CH2CH2CH2-NH2 | thiophene |
| I-103 | phenethyl | 4-fluorobenzyl-NH-C(O)-CH(CH3)- | H | -CH(C(O)-)-CH2-C(O)OH | thiophene |
| I-104 | phenethyl | (thiophen-2-yl)methyl-NH-C(O)-CH(CH3)- | H | -CH(C(O)-)-CH2-C(O)OH | thiophene |
| I-105 | phenethyl | 4-fluorobenzyl-NH-C(O)-CH(CH3)- | H | -CH(C(O)-)-CH2-C(O)NH2 | thiophene |
| I-106 | phenethyl | (thiophen-2-yl)methyl-NH-C(O)-CH(CH3)- | H | -CH(C(O)-)-CH2-C(O)NH2 | thiophene |

TABLE XIV-10-continued
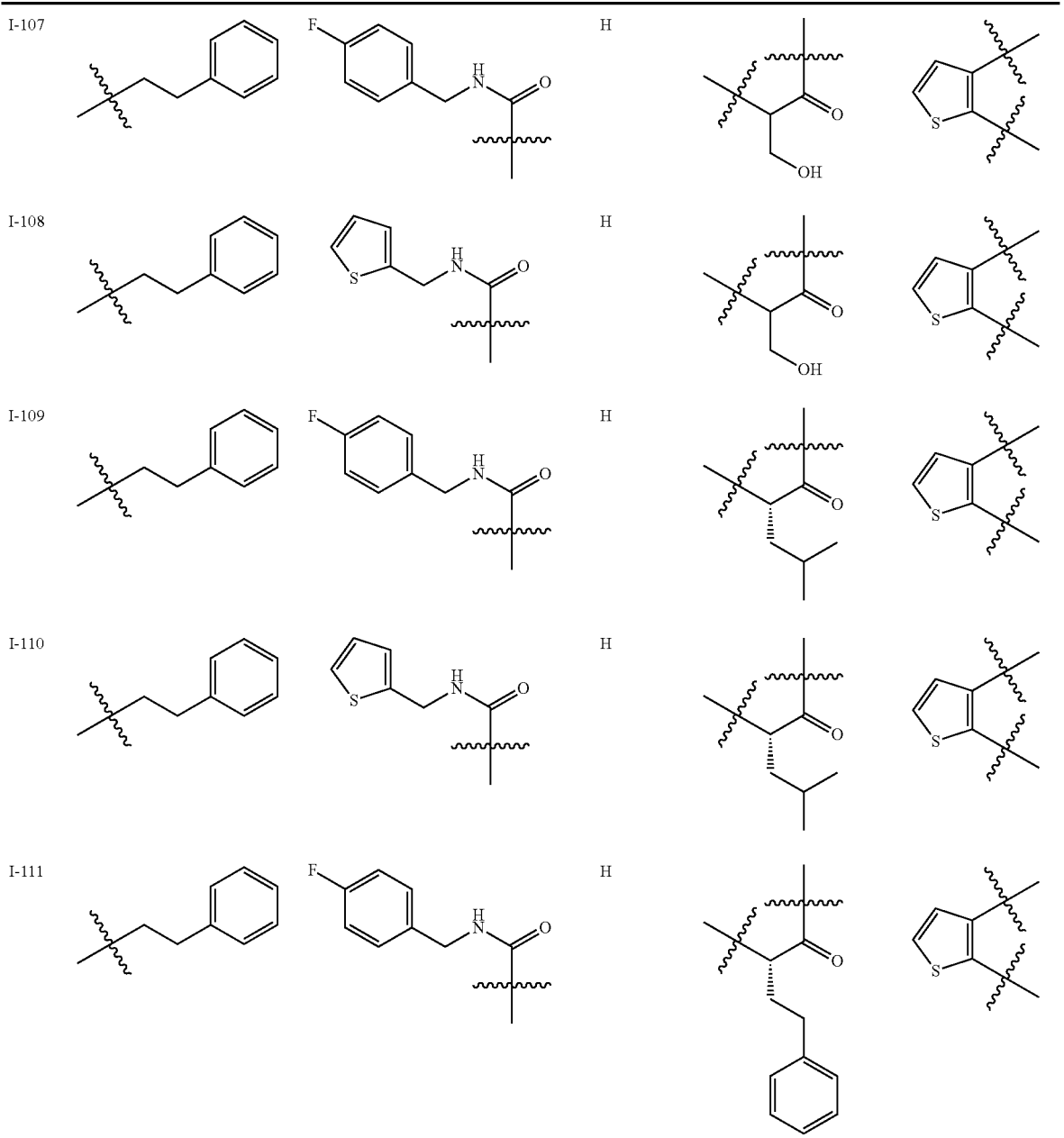
| Example No. | Syn. | Int | method | RT | Mass |
|---|---|---|---|---|---|
| I-101 | I-1 | II-101 | A | 3.82 | 550 |
| I-102 | I-1 | II-102 | A | 3.7 | 538 |
| I-103 | I-1 | II-103 | A | 4.43 | 537 |
| I-104 | I-1 | II-104 | A | 4.25 | 525 |
| I-105 | I-1 | II-105 | A | 4.18 | 536 |
| I-106 | I-1 | II-106 | A | 4.05 | 524 |
| I-107 | I-1 | II-107 | A | 4.37 | 509 |
| I-108 | I-1 | II-108 | A | 4.23 | 497 |
| I-109 | I-1 | II-109 | A | 5.15 | 535 |
| I-110 | I-1 | II-110 | A | 5.05 | 523 |
| I-111 | I-1 | II-111 | A | 5.3 | 583 |

TABLE XIV-11
| Example No. | R1 | R2 | R3 | 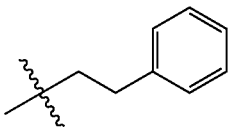 | 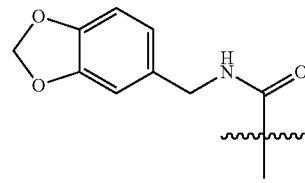 [SMILES: *C(=O)NCc1ccc2c(c1)OCO2] |
|---|---|---|---|---|---|
| I-112 | 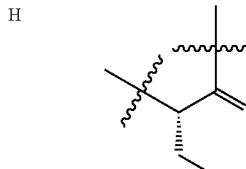 | 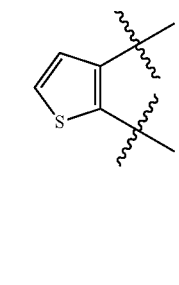 [SMILES: *c1ccsc1*] | H | 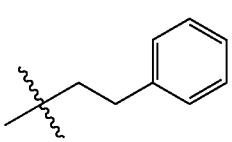 [SMILES: *CCc1ccccc1] | 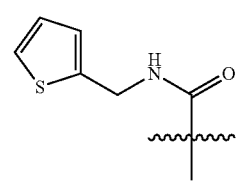 [SMILES: *C(=O)NCc1cccs1] |
| I-113 | 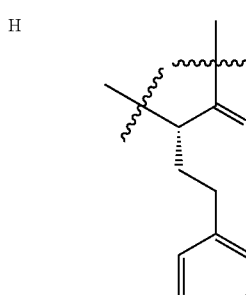 | 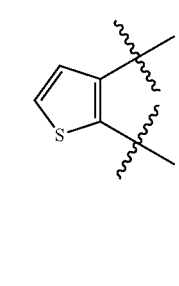 [SMILES: *c1ccsc1*] | H | 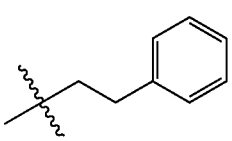 | 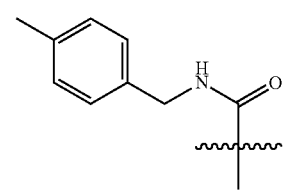 [SMILES: *C(=O)NCc1ccc(C)cc1] |
| I-114 | 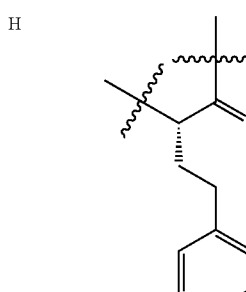 | 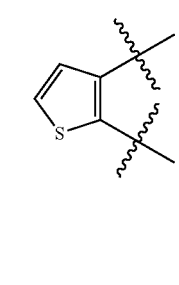 [SMILES: *c1ccsc1*] | H | 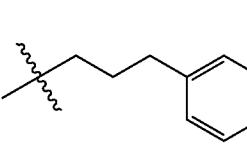 | 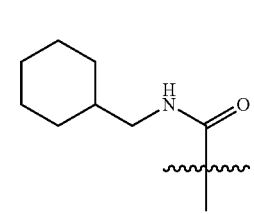 [SMILES: *C(=O)NCC1CCCCC1] |
| I-115 | 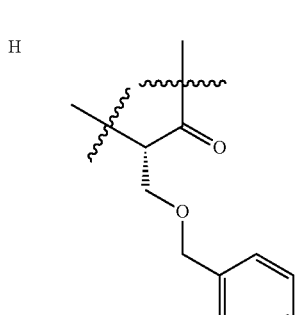 | 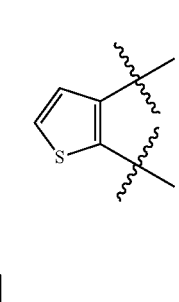 | H | | |

TABLE XIV-11-continued
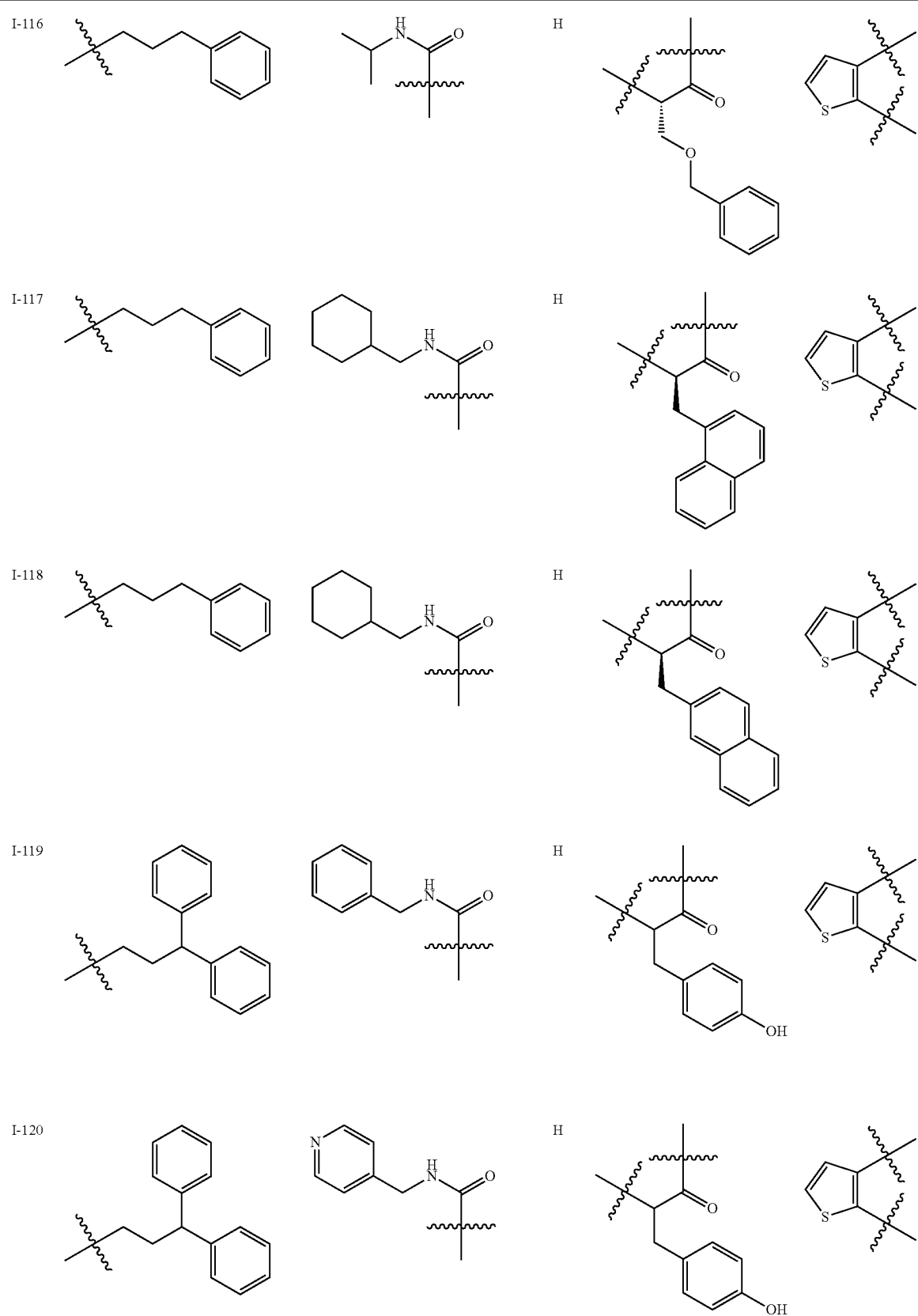

TABLE XIV-11-continued
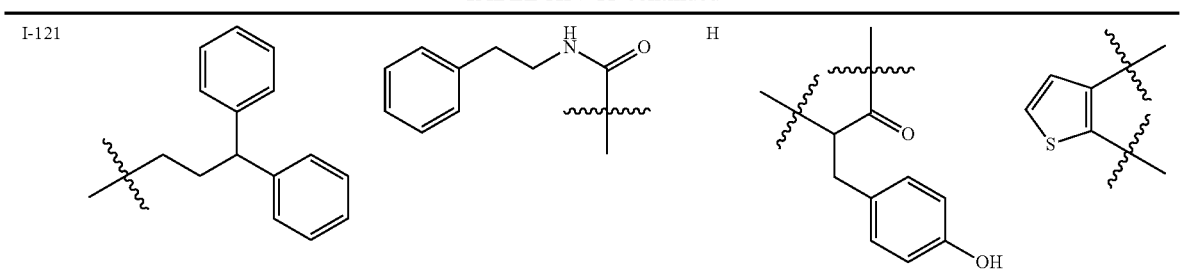
| Example No. | Syn. | Int | method | RT | Mass |
|---|---|---|---|---|---|
| I-112 | I-1 | II-112 | A | 5.18 | 609 |
| I-113 | I-1 | II-113 | A | 5.27 | 571 |
| I-114 | I-1 | II-114 | A | 5.52 | 579 |
| I-115 | I-1 | II-115 | A | 5.98 | 601 |
| I-116 | I-1 | II-116 | A | 5.25 | 547 |
| I-117 | I-1 | II-117 | A | 6.2 | 621 |
| I-118 | I-1 | II-118 | A | 6.17 | 621 |
| I-119 | I-1 | II-119 | A | 5.25 | 657 |
| I-120 | I-1 | II-120 | A | 3.87 | 658 |
| I-121 | I-1 | II-121 | A | 5.4 | 671 |
| I-122 | I-1 | II-122 | A | 5.6 | 707 |
TABLE XIV-12
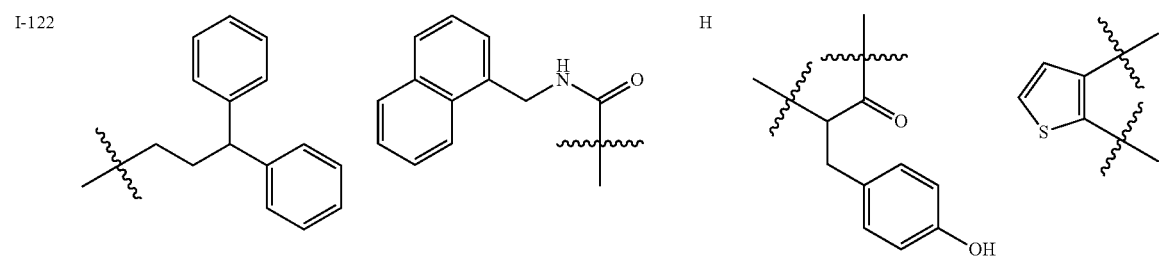

TABLE XIV-12-continued
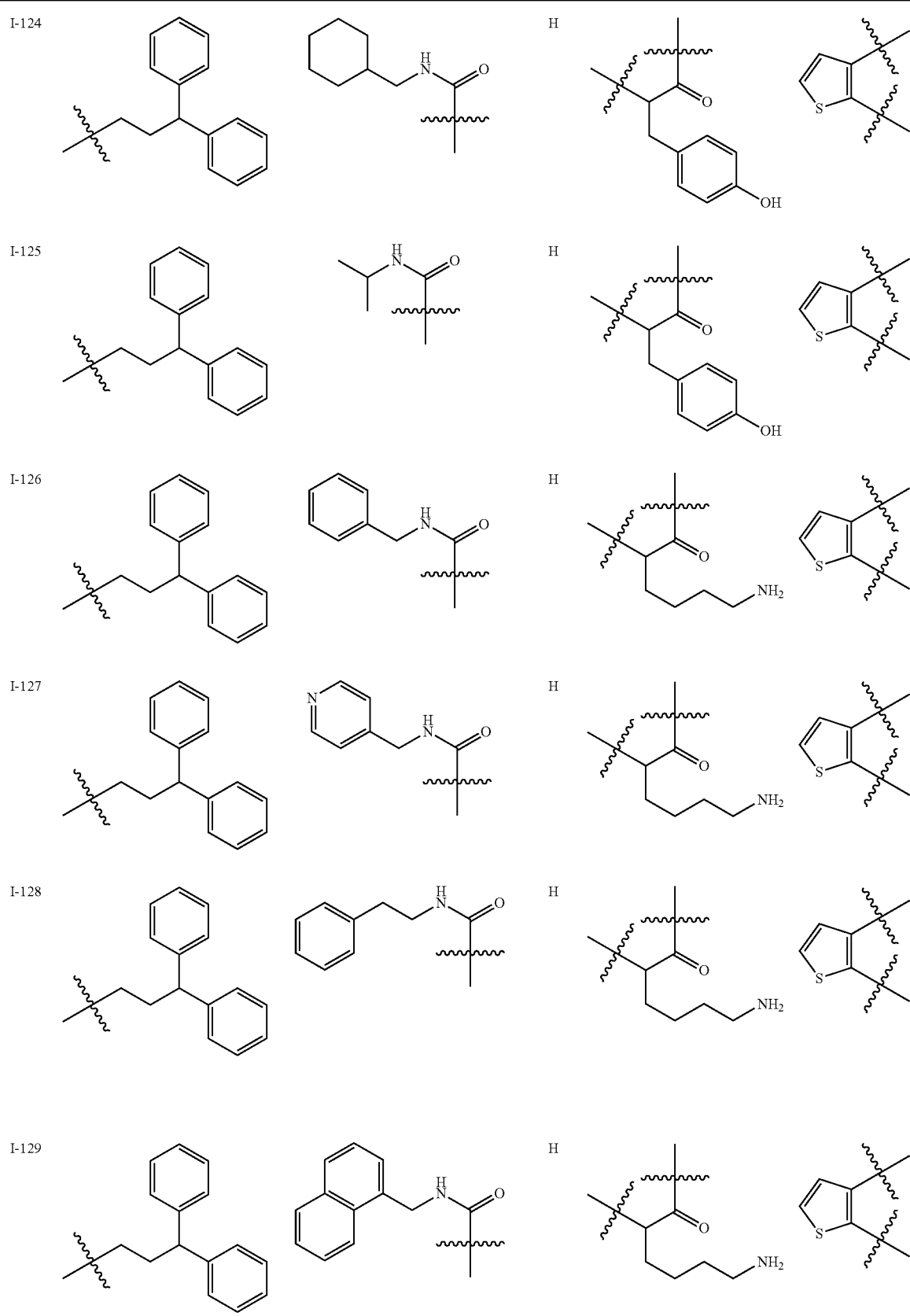

TABLE XIV-12-continued
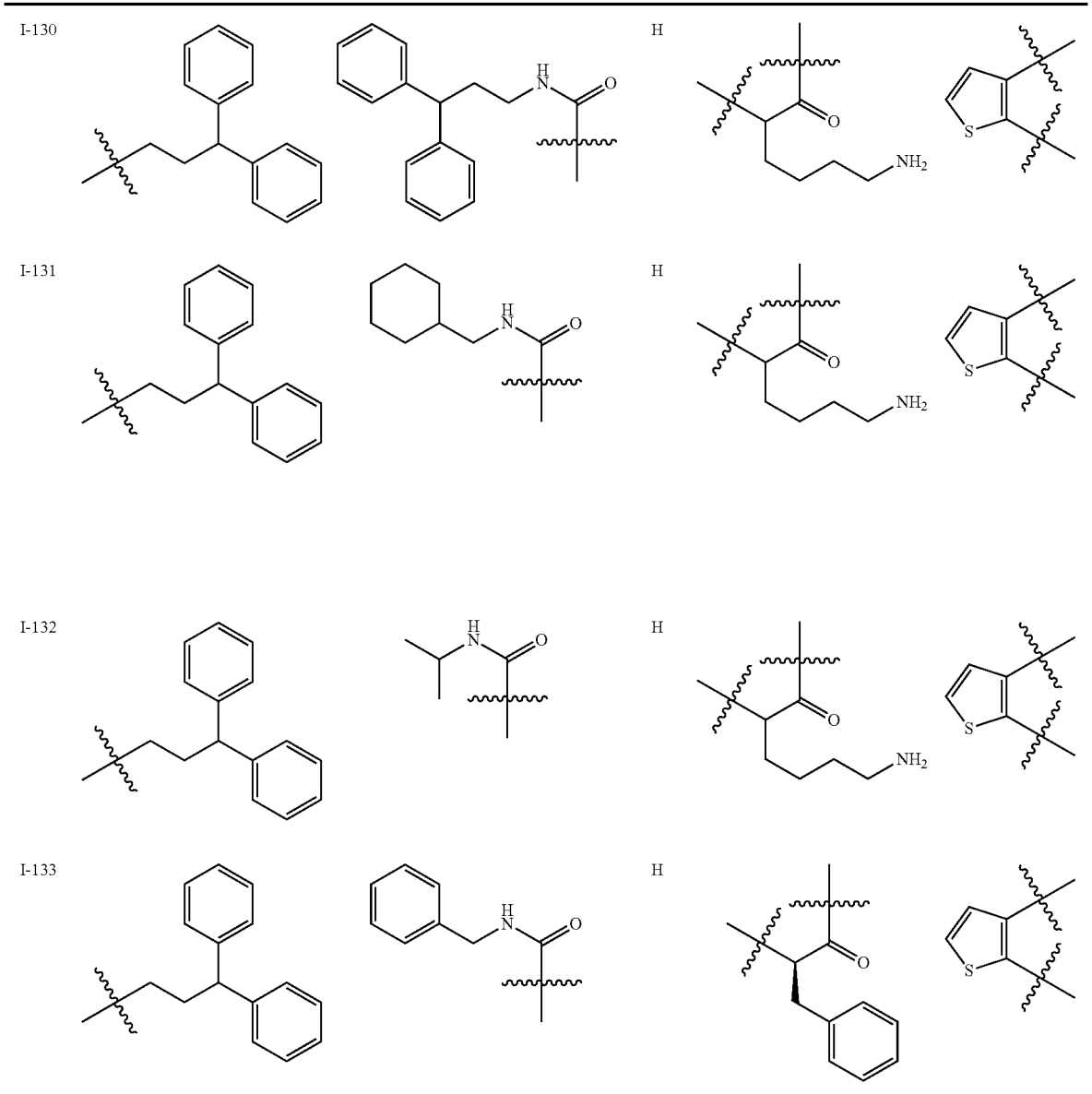
| Example No. | Syn. | Int | method | RT | Mass |
|---|---|---|---|---|---|
| I-123 | I-1 | II-123 | A | 5.8 | 761 |
| I-124 | I-1 | II-124 | A | 5.68 | 663 |
| I-125 | I-1 | II-125 | A | 5.07 | 609 |
| I-126 | I-1 | II-126 | A | 4.27 | 622 |
| I-127 | I-1 | II-127 | A | 4.23 | 623 |
| I-128 | I-1 | II-128 | A | 4.4 | 636 |
| I-129 | I-1 | II-129 | A | 4.53 | 672 |
| I-130 | I-1 | II-130 | A | 4.77 | 726 |
| I-131 | I-1 | II-131 | A | 4.57 | 628 |
| I-132 | I-1 | II-132 | A | 4.07 | 574 |
| I-133 | I-1 | II-133 | A | 5.67 | 641 |

TABLE XIV-13

| Example No. | R1 | R2 | R3 | ⦚-E-A(=O)-⦚ | ⦚-B=Y(G)-⦚ |
|---|---|---|---|---|---|
| I-134 | 1,1-diphenylpropyl | 4-pyridylmethyl-NH-C(=O)-C(CH3)- | H | benzyl-CH-C(=O)- | thiophene-2,3-diyl |
| I-135 | 1,1-diphenylpropyl | phenethyl-NH-C(=O)-C(CH3)- | H | benzyl-CH-C(=O)- | thiophene-2,3-diyl |
| I-136 | 1,1-diphenylpropyl | 1-naphthylmethyl-NH-C(=O)-C(CH3)- | H | benzyl-CH-C(=O)- | thiophene-2,3-diyl |
| I-137 | 1,1-diphenylpropyl | 3,3-diphenylpropyl-NH-C(=O)-C(CH3)- | H | benzyl-CH-C(=O)- | thiophene-2,3-diyl |
| I-138 | 1,1-diphenylpropyl | cyclohexylmethyl-NH-C(=O)-C(CH3)- | H | benzyl-CH-C(=O)- | thiophene-2,3-diyl |

TABLE XIV-13-continued
| | | | | |
|---|---|---|---|---|
| I-139 | 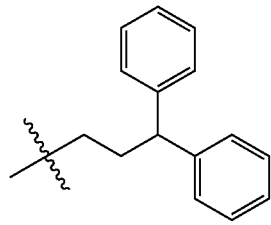 [SMILES: *CCC(c1ccccc1)c1ccccc1] | 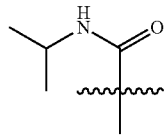 [SMILES: *C(=O)NC(C)C] | H | 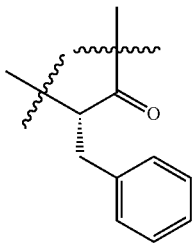 [SMILES: *C(=O)[C@@H](*)Cc1ccccc1] 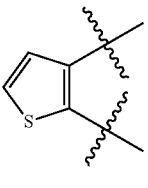 [SMILES: *c1ccsc1*] |
| I-140 | 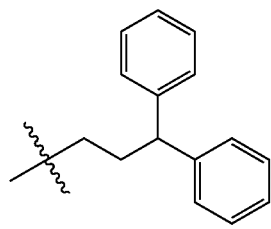 [SMILES: *CCC(c1ccccc1)c1ccccc1] | 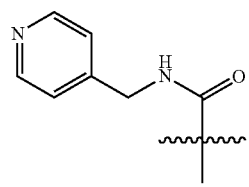 [SMILES: *C(=O)NCc1ccncc1] | H | 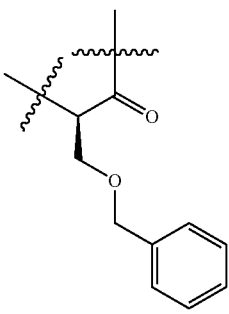 [SMILES: *C(=O)[C@H](*)COCc1ccccc1] 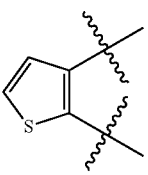 [SMILES: *c1ccsc1*] |
| I-141 | 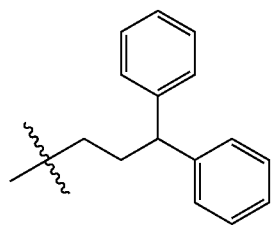 [SMILES: *CCC(c1ccccc1)c1ccccc1] | 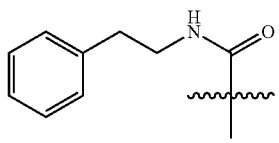 [SMILES: *C(=O)NCCc1ccccc1] | H | 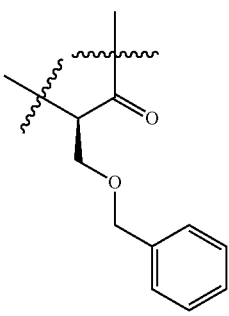 [SMILES: *C(=O)[C@H](*)COCc1ccccc1] 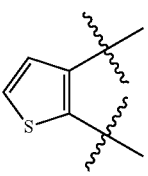 [SMILES: *c1ccsc1*] |
| I-142 | 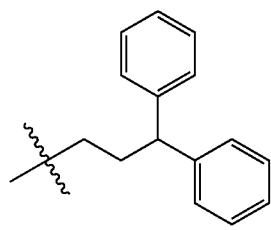 [SMILES: *CCC(c1ccccc1)c1ccccc1] | 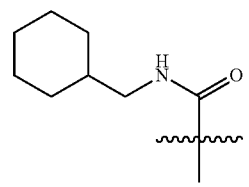 [SMILES: *C(=O)NCC1CCCCC1] | H | 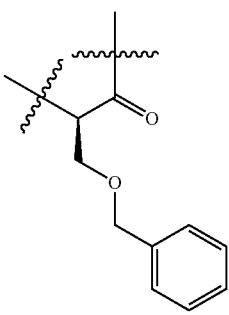 [SMILES: *C(=O)[C@H](*)COCc1ccccc1] 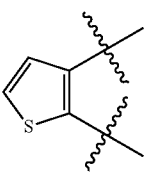 [SMILES: *c1ccsc1*] |
| I-143 | 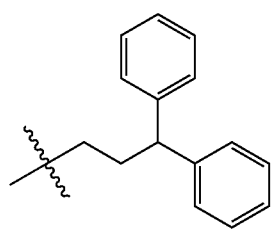 [SMILES: *CCC(c1ccccc1)c1ccccc1] | 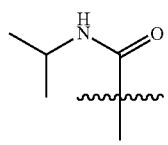 [SMILES: *C(=O)NC(C)C] | H | 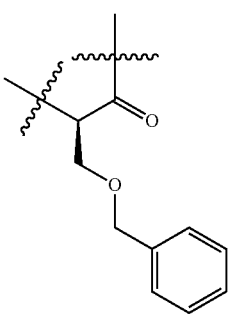 [SMILES: *C(=O)[C@H](*)COCc1ccccc1] 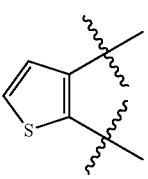 [SMILES: *c1ccsc1*] |

TABLE XIV-13-continued

| Example No. | Syn. | Int | method | RT | Mass |
|---|---|---|---|---|---|
| I-134 | I-1 | II-134 | A | 4.07 | 642 |
| I-135 | I-1 | II-135 | A | 5.82 | 655 |
| I-136 | I-1 | II-136 | A | 6 | 691 |
| I-137 | I-1 | II-137 | A | 6.15 | 745 |
| I-138 | I-1 | II-138 | A | 6.13 | 647 |
| I-139 | I-1 | II-139 | A | 5.53 | 593 |
| I-140 | I-1 | II-140 | A | 4.15 | 672 |
| I-141 | I-1 | II-141 | A | 5.92 | 667 |
| I-142 | I-1 | II-142 | A | 6.2 | 677 |
| I-143 | I-1 | II-143 | A | 5.6 | 623 |
| I-144 | I-1 | II-144 | A | 4.32 | 692 |

TABLE XIV-14

TABLE XIV-14-continued
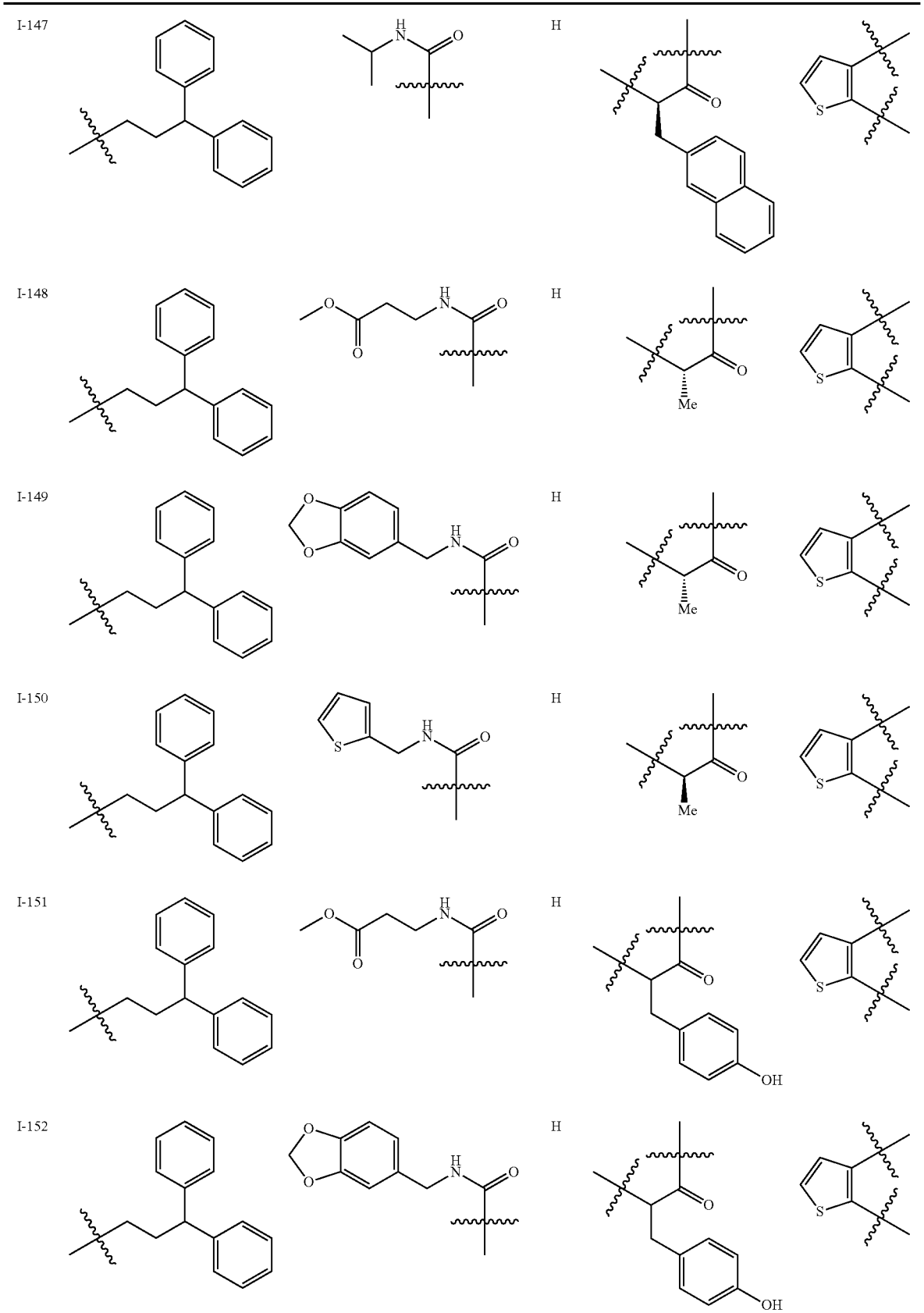

TABLE XIV-14-continued

| Example No. | Syn. | Int | method | RT | Mass |
|---|---|---|---|---|---|
| I-145 | I-1 | II-145 | A | 6.07 | 705 |
| I-146 | I-1 | II-146 | A | 6.42 | 697 |
| I-147 | I-1 | II-147 | A | 5.85 | 643 |
| I-148 | I-1 | II-148 | A | 4.72 | 561 |
| I-149 | I-1 | II-149 | A | 5.15 | 609 |
| I-150 | I-1 | II-150 | A | 5.22 | 571 |
| I-151 | I-1 | II-151 | A | 4.82 | 653 |
| I-152 | I-1 | II-152 | A | 5.2 | 701 |
| I-153 | I-1 | II-153 | A | 5.2 | 663 |
| I-154 | I-1 | II-154 | A | 3.93 | 618 |
| I-155 | I-1 | II-155 | A | 4.23 | 666 |

TABLE XIV-15

TABLE XIV-15-continued

TABLE XIV-15-continued
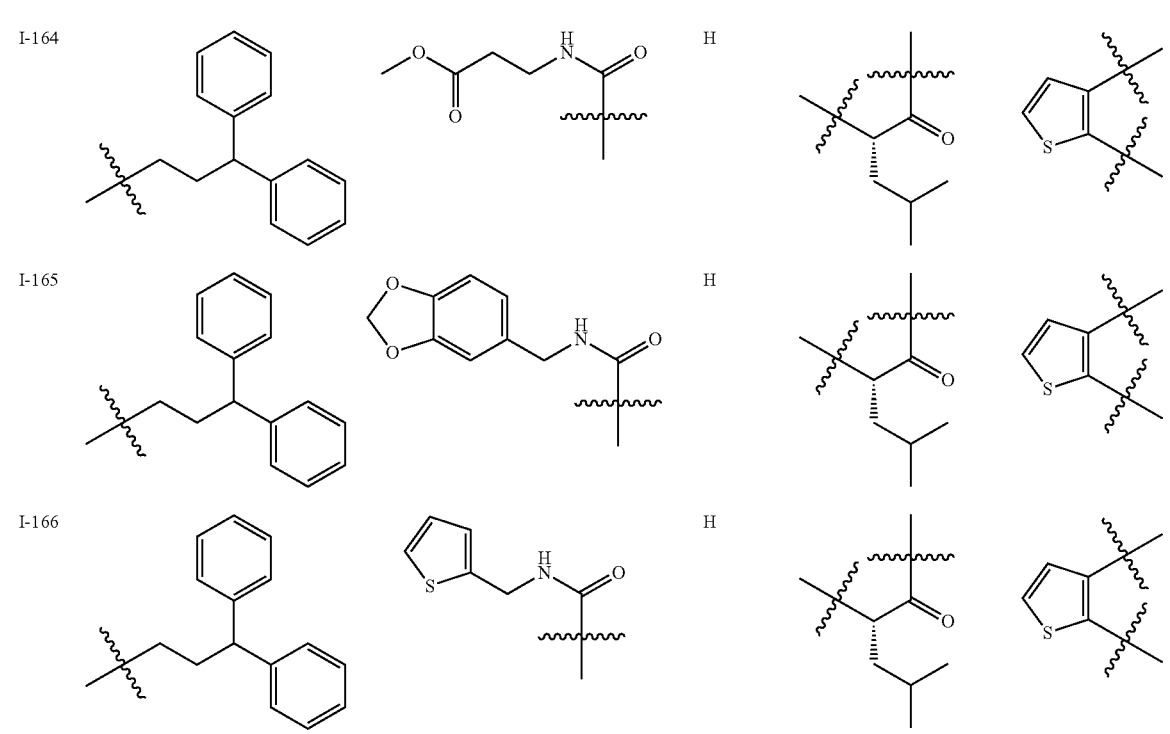
| Example No. | Syn. | Int | method | RT | Mass |
|---|---|---|---|---|---|
| I-156 | I-1 | II-156 | A | 4.25 | 628 |
| I-157 | I-1 | II-157 | A | 4.48 | 605 |
| I-158 | I-1 | II-158 | A | 4.9 | 653 |
| I-159 | I-1 | II-159 | A | 4.92 | 615 |
| I-160 | I-1 | II-160 | A | 4.32 | 604 |
| I-161 | I-1 | II-161 | A | 4.47 | 577 |
| I-162 | I-1 | II-162 | A | 4.7 | 561 |
| I-163 | I-1 | II-163 | A | 4.75 | 589 |
| I-164 | I-1 | II-164 | A | 5.22 | 603 |
| I-165 | I-1 | II-165 | A | 5.58 | 651 |
| I-166 | I-1 | II-166 | A | 5.62 | 613 |
TABLE XIV-16
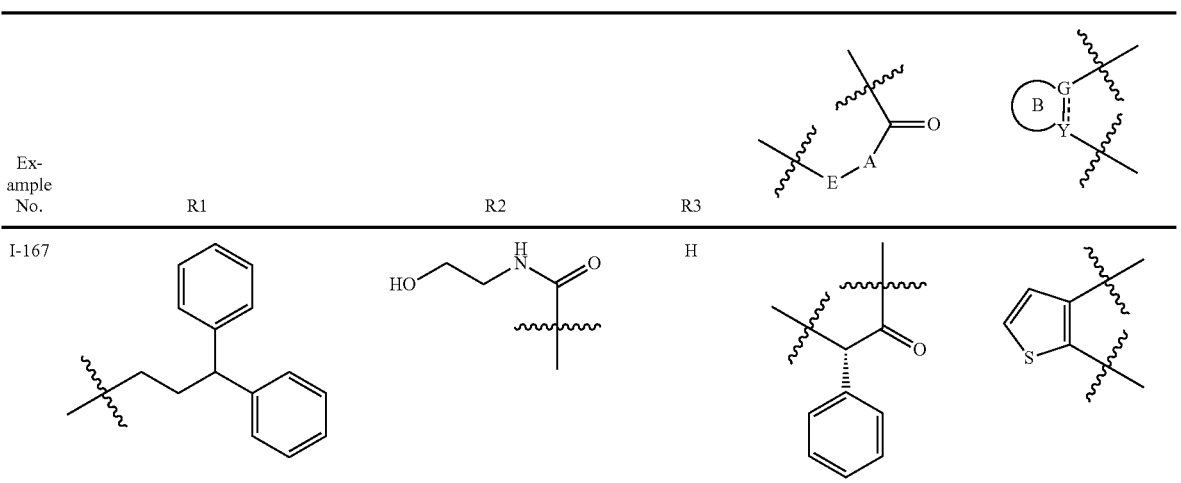

TABLE XIV-16-continued
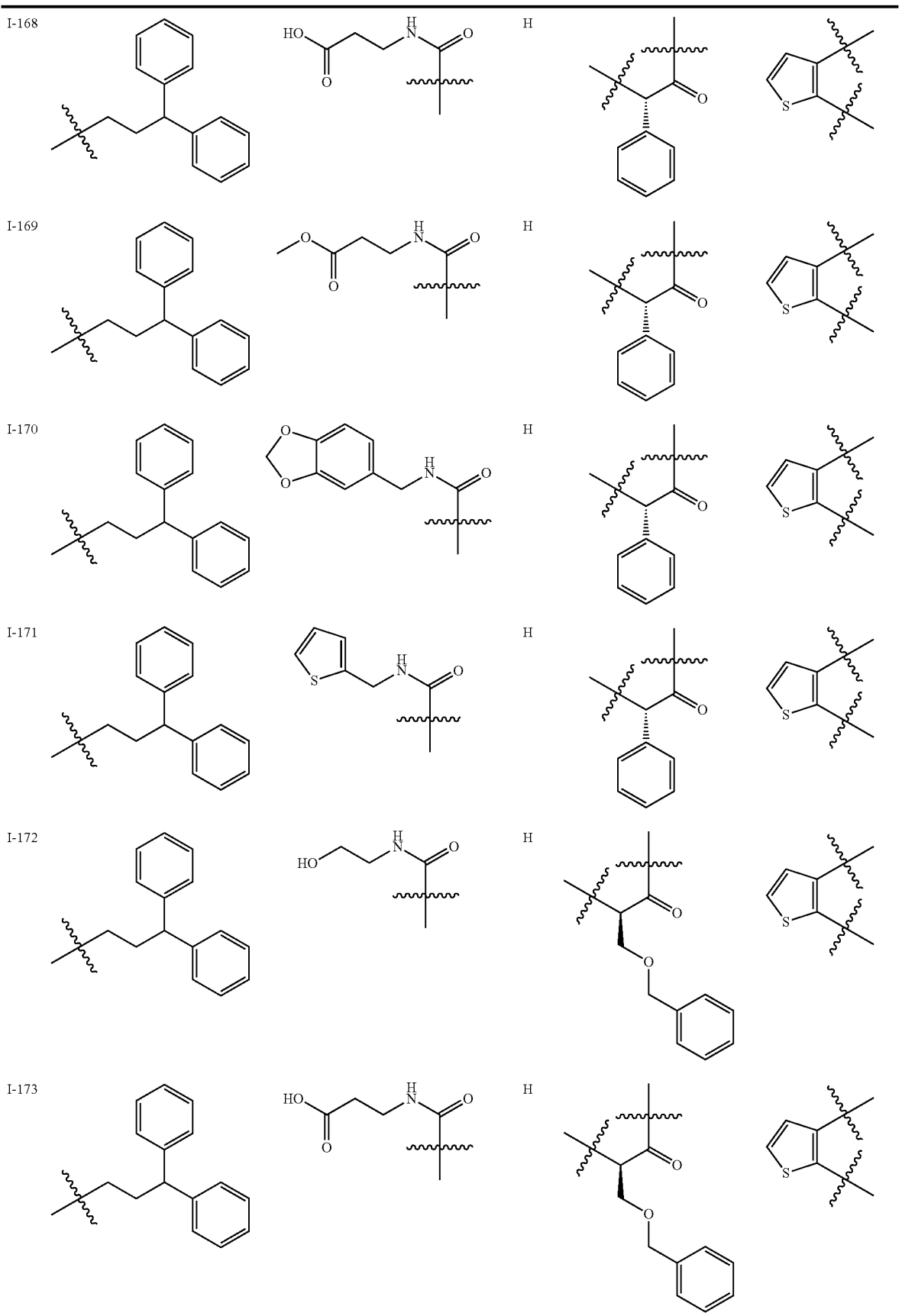

TABLE XIV-16-continued
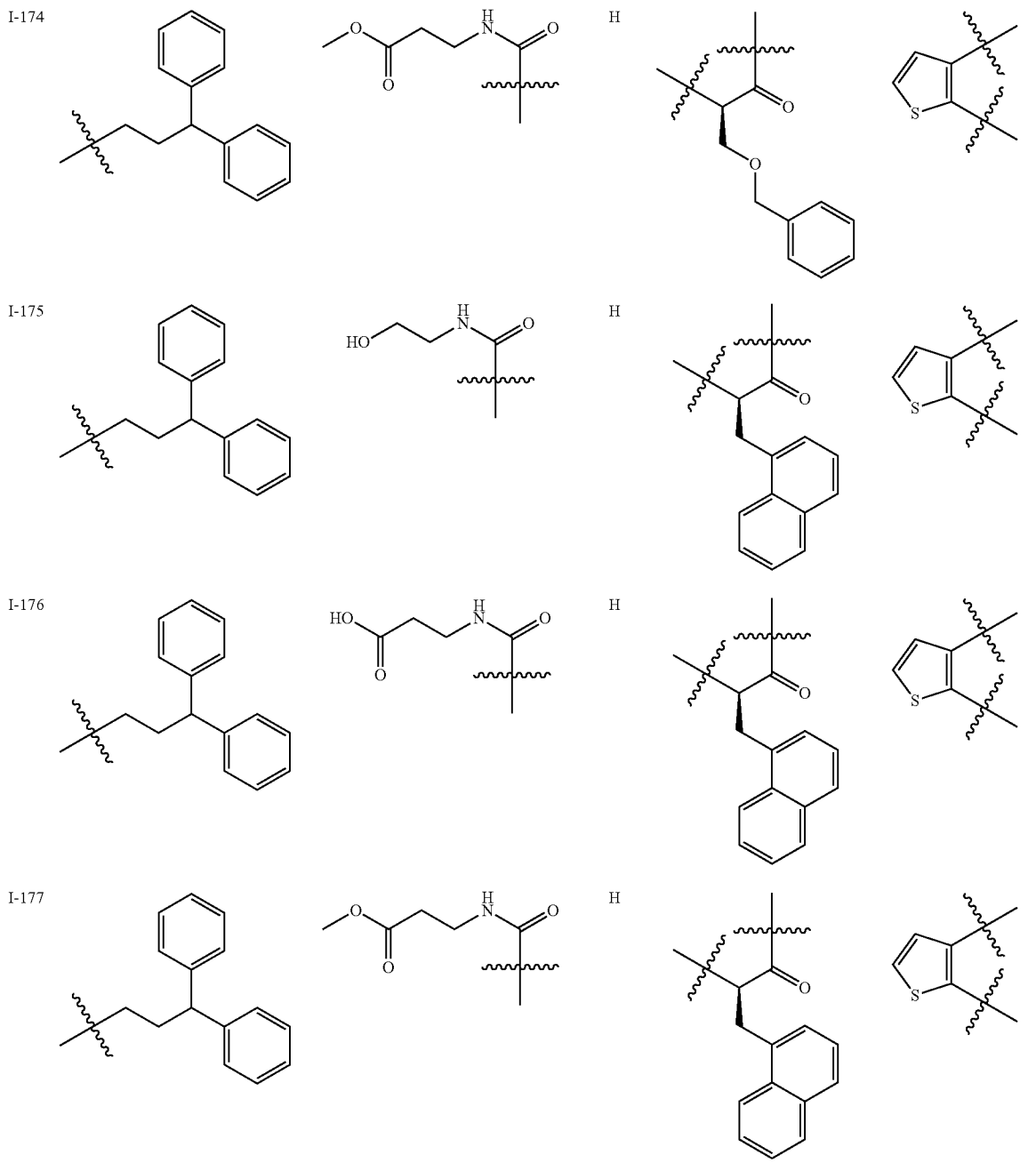
| Example No. | Syn. | Int | method | RT | Mass |
|---|---|---|---|---|---|
| I-167 | I-1 | II-167 | A | 4.68 | 581 |
| I-168 | I-1 | II-168 | A | 4.75 | 609 |
| I-169 | I-1 | II-169 | A | 5.17 | 623 |
| I-170 | I-1 | II-170 | A | 5.53 | 671 |
| I-171 | I-1 | II-171 | A | 5.57 | 633 |
| I-172 | I-1 | II-172 | A | 4.82 | 625 |
| I-173 | I-1 | II-173 | A | 4.83 | 653 |
| I-174 | I-1 | II-174 | A | 5.28 | 667 |
| I-175 | I-1 | II-175 | A | 5.05 | 645 |
| I-176 | I-1 | II-176 | A | 5.07 | 673 |
| I-177 | I-1 | II-177 | A | 5.55 | 687 |

TABLE XIV-17

| Example No. | R1 | R2 | R3 | E-A | B/G/Y |
|---|---|---|---|---|---|
| I-178 | naphthalen-2-ylmethyl | benzyl-NH-C(O)- | H | -C(Me)H-C(O)- | thiophene |
| I-179 | naphthalen-2-ylmethyl | cyclohexylmethyl-NH-C(O)- | H | -C(Me)H-C(O)- | thiophene |
| I-180 | naphthalen-2-ylmethyl | benzyl-NH-C(O)- | H | -CH(CH2-C6H4-OH)-C(O)- | thiophene |
| I-181 | naphthalen-2-ylmethyl | cyclohexylmethyl-NH-C(O)- | H | -CH(CH2-C6H4-OH)-C(O)- | thiophene |
| I-182 | naphthalen-2-ylmethyl | isopropyl-NH-C(O)- | H | -CH(CH2-C6H4-OH)-C(O)- | thiophene |
| I-183 | naphthalen-2-ylmethyl | benzyl-NH-C(O)- | H | -CH(CH2CH2CH2CH2NH2)-C(O)- | thiophene |

TABLE XIV-17-continued
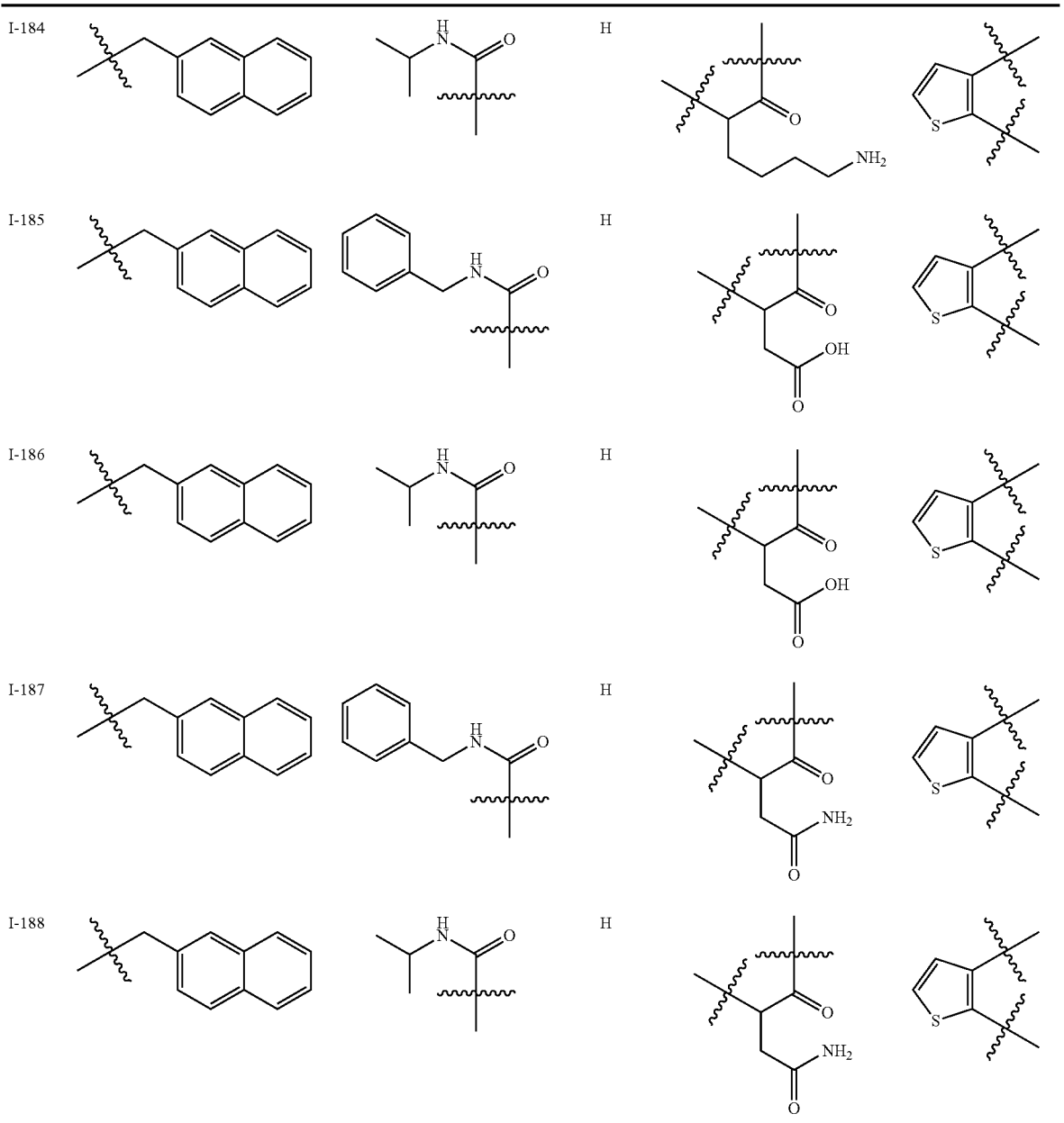
| Example No. | Syn. | Int | method | RT | Mass |
|---|---|---|---|---|---|
| I-178 | I-1 | II-178 | A | 4.98 | 511 |
| I-179 | I-1 | II-179 | A | 5.55 | 517 |
| I-180 | I-1 | II-180 | A | 5.03 | 603 |
| I-181 | I-1 | II-181 | A | 5.48 | 609 |
| I-182 | I-1 | II-182 | A | 4.82 | 555 |
| I-183 | I-1 | II-183 | A | 4.05 | 568 |
| I-184 | I-1 | II-184 | A | 3.85 | 520 |
| I-185 | I-1 | II-185 | A | 4.7 | 555 |
| I-186 | I-1 | II-186 | A | 4.45 | 507 |
| I-187 | I-1 | II-187 | A | 4.52 | 554 |
| I-188 | I-1 | II-188 | A | 4.25 | 506 |

TABLE XIV-18
| Example No. | R1 | R2 | R3 | E-A | G=Y | Syn. | Int | method | RT | Mass |
|---|---|---|---|---|---|---|---|---|---|---|
| I-189 | 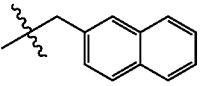 [SMILES: *Cc1ccc2ccccc2c1] | 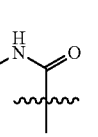 | H | 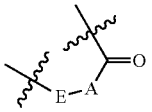 | 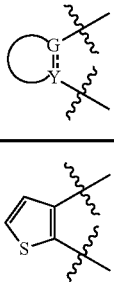 | I-1 | II-189 | A | 4.72 | 527 |
| I-190 | 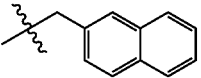 [SMILES: *Cc1ccc2ccccc2c1] | 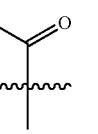 | H | 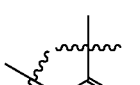 | 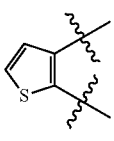 | I-1 | II-190 | A | 4.42 | 479 |
| I-191 | 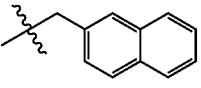 | 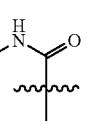 | H | 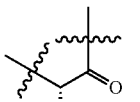 | 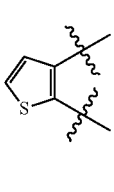 | I-1 | II-191 | A | 5.5 | 553 |
| I-192 | 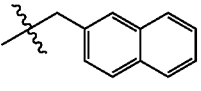 [SMILES: *Cc1ccc2ccccc2c1] | 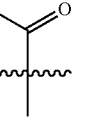 | H |  | 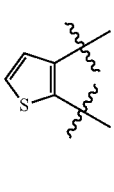 | I-1 | II-192 | A | 5.28 | 505 |
| I-193 | 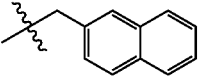 [SMILES: *Cc1ccc2ccccc2c1] | 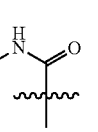 | H | 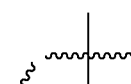 | 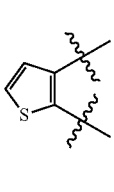 | I-1 | II-193 | A | 5.43 | 573 |
| I-194 | 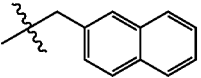 [SMILES: *Cc1ccc2ccccc2c1] | 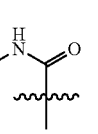 | H |  | 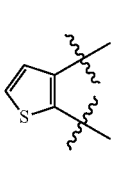 | I-1 | II-194 | A | 5.93 | 579 |
| I-195 | 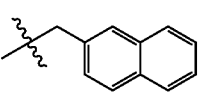 | 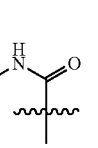 | H |  | 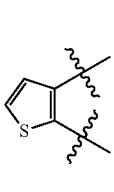 | I-1 | II-195 | A | 5.5 | 587 |

TABLE XIV-18-continued

| Example No. | R1 | R2 | R3 | E–A | G=Y ring | Syn. | Int | method | RT | Mass |
|---|---|---|---|---|---|---|---|---|---|---|
| I-196 | naphthalen-2-ylmethyl | cyclohexylmethyl-NHC(O)- | H | benzyl-CH-C(O) | thiophene | I-1 | II-196 | A | 6 | 593 |
| I-197 | naphthalen-2-ylmethyl | benzyl-NHC(O)- | H | phenethyl-CH-C(O) | thiophene | I-1 | II-197 | A | 5.62 | 601 |
| I-198 | naphthalen-2-ylmethyl | cyclohexylmethyl-NHC(O)- | H | phenethyl-CH-C(O) | thiophene | I-1 | II-198 | A | 6.12 | 607 |
| I-199 | naphthalen-2-ylmethyl | MeOC(O)CH₂CH₂-NHC(O)- | H | Me-CH-C(O) | thiophene | I-1 | II-199 | A | 4.42 | 507 |

TABLE XIV-19

| Example No. | R1 | R2 | R3 | E–A | B, G=Y ring | Syn. | Int | method | RT | Mass |
|---|---|---|---|---|---|---|---|---|---|---|
| I-200 | naphthalen-2-ylmethyl | benzo[1,3]dioxol-5-ylmethyl-NHC(O)- | H | Me-CH-C(O) | thiophene | I-1 | II-200 | A | 4.92 | 555 |
| I-201 | naphthalen-2-ylmethyl | 4-methylbenzyl-NHC(O)- | H | Me-CH-C(O) | thiophene | I-1 | II-201 | A | 5.27 | 525 |

TABLE XIV-19-continued

| Example No. | R1 | R2 | R3 | E-A | B G Y | Syn | Int | method | RT | Mass |
|---|---|---|---|---|---|---|---|---|---|---|
| I-202 | naphthyl-CH2 | methyl propanoate-NHC(O) | H | CH2-C6H4-OH ketone | thiophene | I-1 | II-202 | A | 4.55 | 599 |
| I-203 | naphthyl-CH2 | benzodioxole-CH2-NHC(O) | H | CH2-C6H4-OH ketone | thiophene | I-1 | II-203 | A | 4.98 | 647 |
| I-204 | naphthyl-CH2 | HO-CH2CH2-NHC(O) | H | phenyl ketone | thiophene | I-1 | II-204 | A | 4.4 | 527 |
| I-205 | naphthyl-CH2 | HOOC-CH2CH2-NHC(O) | H | phenyl ketone | thiophene | I-1 | II-205 | A | 4.48 | 555 |
| I-206 | naphthyl-CH2 | methyl propanoate-NHC(O) | H | phenyl ketone | thiophene | I-1 | II-206 | A | 4.93 | 569 |
| I-207 | naphthyl-CH2 | 4-F-C6H4-CH2-NHC(O) | H | phenyl ketone | thiophene | I-1 | II-207 | A | 5.45 | 591 |
| I-208 | naphthyl-CH2 | benzodioxole-CH2-NHC(O) | H | phenyl ketone | thiophene | I-1 | II-208 | A | 5.35 | 617 |

TABLE XIV-19-continued

| Example No. | R1 | R2 | R3 | E-A (=O) | B-G-Y | Syn | Int | method | RT | Mass |
|---|---|---|---|---|---|---|---|---|---|---|
| I-209 | naphthylmethyl | HOCH₂CH₂-NH-C(=O)- | H | phenethyl-substituted | thiophene | I-1 | II-209 | A | 4.58 | 555 |
| I-210 | naphthylmethyl | HOOC-CH₂CH₂-NH-C(=O)- | H | phenethyl-substituted | thiophene | I-1 | II-210 | A | 4.67 | 583 |

TABLE XIV-20

| Example No. | R1 | R2 | R3 | E-A (=O) | B-G-Y | Syn | Int | method | RT | Mass |
|---|---|---|---|---|---|---|---|---|---|---|
| I-211 | naphthylmethyl | MeO-C(=O)-CH₂CH₂-NH-C(=O)- | H | phenethyl-substituted | thiophene | I-1 | II-211 | A | 5.1 | 597 |
| I-212 | naphthylmethyl | 4-F-C₆H₄-CH₂-NH-C(=O)- | H | phenethyl-substituted | thiophene | I-1 | II-212 | A | 5.62 | 619 |
| I-213 | naphthylmethyl | 3,4-methylenedioxybenzyl-NH-C(=O)- | H | phenethyl-substituted | thiophene | I-1 | II-213 | A | 5.5 | 645 |

TABLE XIV-20-continued

| Example No. | R1 | R2 | R3 | E-A (structure) | B-G-Y (structure) | Syn | Int | method | RT | Mass |
|---|---|---|---|---|---|---|---|---|---|---|
| I-214 | benzyl | pyridin-4-ylmethyl-NHC(O)- | Me | CH(Me)C(O) | thiophene | I-1 | II-214 | A | 3.17 | 476 |
| I-215 | benzyl | 4-Cl-benzyl-NHC(O)- | Me | CH(Me)C(O) | thiophene | I-1 | II-215 | A | 4.95 | 510 |
| I-216 | benzyl | naphthalen-1-ylmethyl-NHC(O)- | Me | CH(Me)C(O) | thiophene | I-1 | II-216 | A | 5.13 | 525 |
| I-217 | benzyl | pyridin-4-ylmethyl-NHC(O)- | Me | CH(CH2-4-OH-Ph)C(O) | thiophene | I-1 | II-217 | A | 3.35 | 568 |
| I-218 | benzyl | 4-Cl-benzyl-NHC(O)- | Me | CH(CH2-4-OH-Ph)C(O) | thiophene | I-1 | II-218 | A | 5 | 602 |
| I-219 | benzyl | naphthalen-1-ylmethyl-NHC(O)- | Me | CH(CH2-4-OH-Ph)C(O) | thiophene | I-1 | II-219 | A | 5.15 | 617 |
| I-220 | benzyl | pyridin-4-ylmethyl-NHC(O)- | Me | CH(CH2COOH)C(O) | thiophene | I-1 | II-220 | A | 3.12 | 520 |
| I-221 | benzyl | 4-Cl-benzyl-NHC(O)- | Me | CH(CH2COOH)C(O) | thiophene | I-1 | II-221 | A | 4.62 | 554 |

TABLE XIV-21
| Example No. | R1 | R2 | R3 | 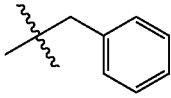 [SMILES: *Cc1ccccc1] | 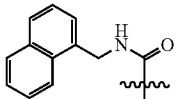 | Syn. | Int | method | RT | Mass |
|---|---|---|---|---|---|---|---|---|---|---|
| I-222 | 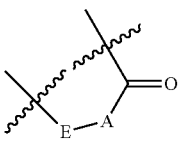 | 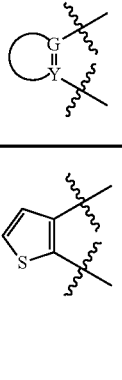 | Me | 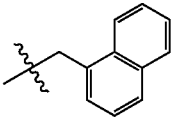 [SMILES: *Cc1cccc2ccccc12] | 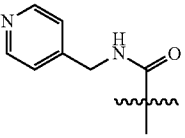 | I-1 | II-222 | A | 4.77 | 569 |
| I-223 | 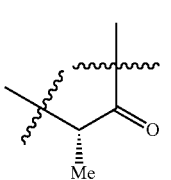 | 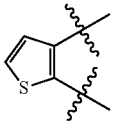 [SMILES: *c1ccsc1*] | Me | 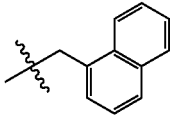 | 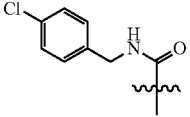 [SMILES: *C(=O)NCc1ccc(Cl)cc1] | I-1 | II-223 | A | 3.48 | 526 |
| I-224 | 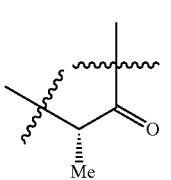 | 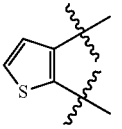 [SMILES: *c1ccsc1*] | Me | 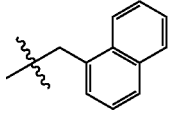 [SMILES: *Cc1cccc2ccccc12] | 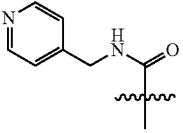 | I-1 | II-224 | A | 5.37 | 560 |
| I-225 | 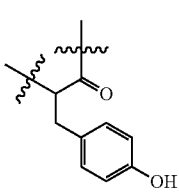 [SMILES: *C(=O)C(*)Cc1ccc(O)cc1] | 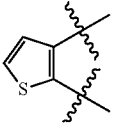 | Me | 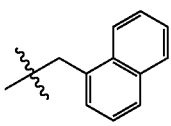 [SMILES: *Cc1cccc2ccccc12] | 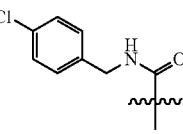 | I-1 | II-225 | A | 3.68 | 618 |
| I-226 | 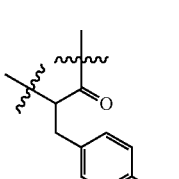 | 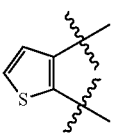 | Me | 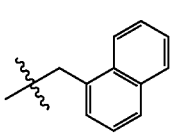 [SMILES: *Cc1cccc2ccccc12] | 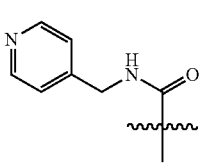 | I-1 | II-226 | A | 5.35 | 652 |
| I-227 | 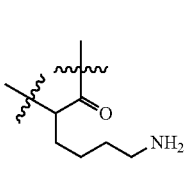 [SMILES: *C(=O)C(*)CCCCN] | 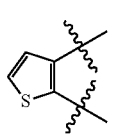 | Me | 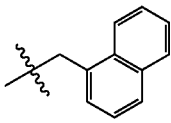 [SMILES: *Cc1cccc2ccccc12] | 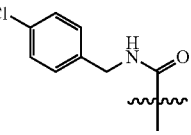 | I-1 | II-227 | A | 3.13 | 583 |
| I-228 | 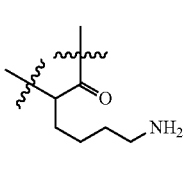 [SMILES: *C(=O)C(*)CCCCN] | 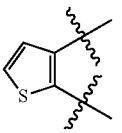 [SMILES: *c1ccsc1*] | Me | | | I-1 | II-228 | A | 4.23 | 617 |

TABLE XIV-21-continued
| Example No. | R1 | R2 | R3 | 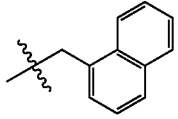 [SMILES: *Cc1cccc2ccccc12] | 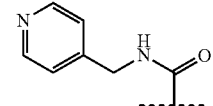 | Syn. | Int | method | RT | Mass |
|---|---|---|---|---|---|---|---|---|---|---|
| I-229 | 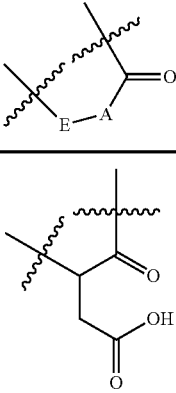 | 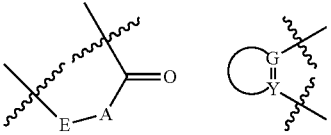 | Me | 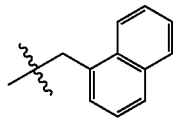 [SMILES: *Cc1cccc2ccccc12] | 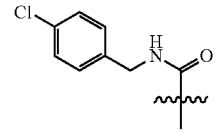 | I-1 | II-229 | A | 3.45 | 570 |
| I-230 | 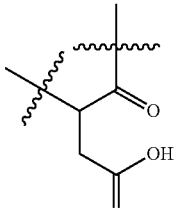 | 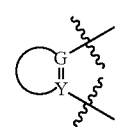 | Me | 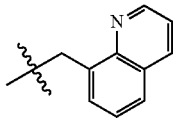 [SMILES: *Cc1cccc2cccnc12] | 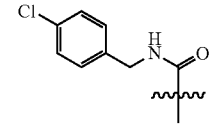 | I-1 | II-230 | A | 4.95 | 604 |
| I-231 | 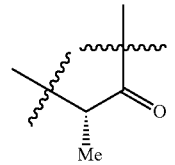 | 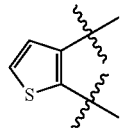 | Me | 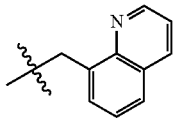 | 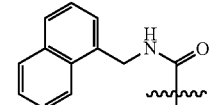 | I-1 | II-231 | A | 4.35 | 561 |
| I-232 | 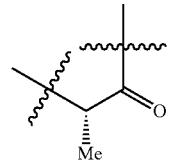 | 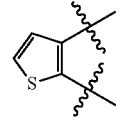 [SMILES: *c1ccsc1*] | Me | 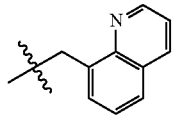 [SMILES: *Cc1cccc2cccnc12] | 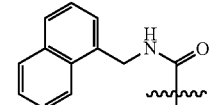 | I-1 | II-232 | A | 4.53 | 576 |
TABLE XIV-22
| Example No. | R1 | R2 | R3 | E—A | 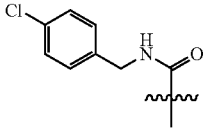 | Syn. | Int | method | RT | Mass |
|---|---|---|---|---|---|---|---|---|---|---|
| I-233 | 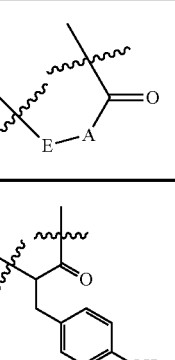 | 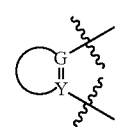 | Me | 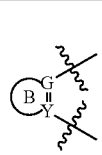 | 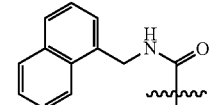 | I-1 | II-233 | A | 4.47 | 653 |

TABLE XIV-22-continued

| Example No. | R1 | R2 | R3 | E—A (with C=O) | B=Y ring | Syn. | Int | method | RT | Mass |
|---|---|---|---|---|---|---|---|---|---|---|
| I-234 | 8-quinolinyl-CH2 | 4-Cl-benzyl-NH-C(O) | Me | CH(CH2CH2CH2NH2)-C(O) | thieno | I-1 | II-234 | A | 3.67 | 618 |
| I-235 | 8-quinolinyl-CH2 | 1-naphthyl-CH2-NH-C(O) | Me | CH(CH2CH2CH2NH2)-C(O) | thieno | I-1 | II-235 | A | 3.78 | 633 |
| I-236 | 8-quinolinyl-CH2 | 4-Cl-benzyl-NH-C(O) | Me | CH(CH2C(O)NH2)-C(O) | thieno | I-1 | II-236 | A | 3.95 | 604 |
| I-237 | 8-quinolinyl-CH2 | 1-naphthyl-CH2-NH-C(O) | Me | CH(CH2C(O)NH2)-C(O) | thieno | I-1 | II-237 | A | 4.02 | 619 |
| I-238 | benzothiophen-3-yl-CH2 | 4-Cl-benzyl-NH-C(O) | Me | CH(CH2-4-OH-C6H4)-C(O) | thieno | I-1 | II-238 | A | 3.65 | 624 |
| I-239 | benzothiophen-3-yl-CH2 | 1-naphthyl-CH2-NH-C(O) | Me | CH(CH2-4-OH-C6H4)-C(O) | thieno | I-1 | II-239 | A | 5.43 | 673 |
| I-240 | benzothiophen-3-yl-CH2 | pyridin-3-yl-CH2-NH-C(O) | Me | CH(CH2CH2CH2NH2)-C(O) | thieno | I-1 | II-240 | A | 3.1 | 569 |

TABLE XIV-22-continued

| Example No. | R1 | R2 | R3 | E—A | B=Y ring | Syn. | Int | method | RT | Mass |
|---|---|---|---|---|---|---|---|---|---|---|
| I-241 | benzothiophene-CH2 | naphthyl-CH2-NH-C(O)- | Me | -CH(-)CH2CH2CH2NH2 with C=O | thiophene | I-1 | II-241 | A | 4.27 | 638 |
| I-242 | benzothiophene-CH2 | pyridyl-CH2-NH-C(O)- | Me | -CH(-)CH2C(O)OH with C=O | thiophene | I-1 | II-242 | A | 3.42 | 576 |
| I-243 | benzothiophene-CH2 | naphthyl-CH2-NH-C(O)- | Me | -CH(-)CH2C(O)OH with C=O | thiophene | I-1 | II-243 | A | 5.05 | 625 |

TABLE XIV-23

| Example No. | R1 | R2 | R3 | E—A | B=Y ring | Syn. | Int | method | RT | Mass |
|---|---|---|---|---|---|---|---|---|---|---|
| I-244 | benzothiophene-CH2 | pyridyl-CH2-NH-C(O)- | Me | -CH(-)CH2C(O)NH2 with C=O | thiophene | I-1 | II-244 | A | 3.28 | 575 |
| I-245 | benzothiophene-CH2 | naphthyl-CH2-NH-C(O)- | Me | -CH(-)CH2C(O)NH2 with C=O | thiophene | I-1 | II-245 | A | 4.87 | 624 |

TABLE XIV-23-continued

| Example No. | R1 | R2 | R3 | E-A (with C=O) | B-G=Y ring | Syn. Int | method | RT | Mass |
|---|---|---|---|---|---|---|---|---|---|
| I-246 | naphthalen-1-ylmethyl | benzylamide | H | 4-hydroxybenzyl ketone | pyrrolidine | I-1 | II-246 A | 4.93 | 590 |
| I-247 | 2-(NHBoc)-benzothiazol-4-ylmethyl | benzylamide | H | 4-hydroxybenzyl ketone | pyrrolidine | I-1 | II-247 A | 4 | 612 |
| I-248 | naphthalen-1-ylmethyl | benzylamide | H | 4-hydroxybenzyl ketone | pyrrolidine | I-1 | II-248 A | 4.85 | 590 |
| I-249 | 2-(NHBoc)-benzothiazol-4-ylmethyl | benzylamide | H | 4-hydroxybenzyl ketone | pyrrolidine | I-1 | II-249 A | 3.82 | 612 |
| I-250 | naphthalen-1-ylmethyl | benzylamide | H | 4-hydroxybenzyl ketone | thiophene | I-1 | II-250 A | 5.1 | 603 |
| I-251 | 2-(NHBoc)-benzothiazol-4-ylmethyl | benzylamide | H | 4-hydroxybenzyl ketone | thiophene | I-1 | II-251 A | 4.38 | 625 |
| I-252 | 2-(NHBoc)-benzothiazol-4-ylmethyl | benzylamide | H | 4-hydroxybenzyl ketone | thiophene | I-1 | II-252 A | 4.47 | 625 |

TABLE XIV-23-continued

| Example No. | R1 | R2 | R3 | (E-A structure) | (B-G-Y structure) | Syn. Int | method | RT | Mass |
|---|---|---|---|---|---|---|---|---|---|
| I-253 | naphthalen-1-ylmethyl | benzylaminocarbonyl | H | 4-hydroxybenzyl ketone | pyridyl | I-1 II-253 | A | 4.73 | 598 |

TABLE XIV-24

| Example No. | R1 | R2 | R3 | (E-A structure) | (G-Y structure) | Syn. Int | method | RT | Mass |
|---|---|---|---|---|---|---|---|---|---|
| I-254 | naphthalen-1-ylmethyl | benzylaminocarbonyl | H | 4-hydroxybenzyl ketone | N-pyrrolyl | I-1 II-254 | A | 5.02 | 586 |
| I-255 | naphthalen-1-ylmethyl | benzylaminocarbonyl | H | 4-hydroxybenzyl ketone | 1H-pyrazolyl | I-1 II-255 | A | 4.68 | 587 |
| I-256 | naphthalen-1-ylmethyl | benzylaminocarbonyl | H | 4-hydroxybenzyl ketone | N-formyl-pyrazolyl | I-1 II-255 | A | 4.63 | 587 |
| I-257 | 1-phenylethyl | benzylaminocarbonyl | H | 4-hydroxybenzyl ketone | thienyl | I-1 II-256 | A | 4.8 | 567 |

TABLE XIV-24-continued
| Example No. | R1 | R2 | R3 | 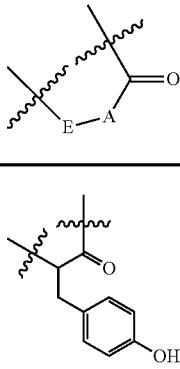 | 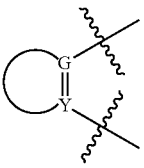 | Syn. | Int | method | RT | Mass |
|---|---|---|---|---|---|---|---|---|---|---|
| I-258 | 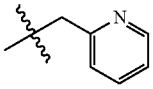 | 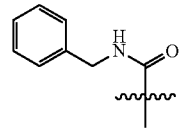 [SMILES: *C(=O)NCc1ccccc1] | H | 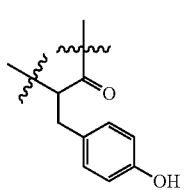 [SMILES: *C(=O)C(*)Cc1ccc(O)cc1] | 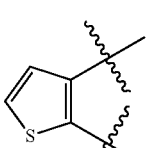 | I-1 | II-257 | A | 2.98 | 554 |
| I-259 | 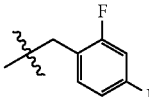 | 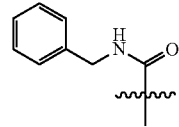 [SMILES: *C(=O)NCc1ccccc1] | H | 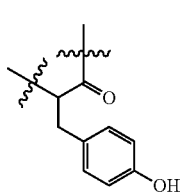 [SMILES: *C(=O)C(*)Cc1ccc(O)cc1] | 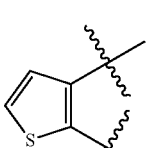 | I-1 | II-258 | A | 3.67 | 554 |
| I-260 | 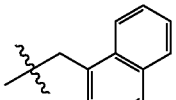 | 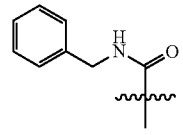 [SMILES: *C(=O)NCc1ccccc1] | H | 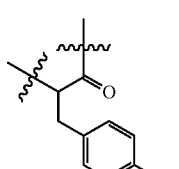 | 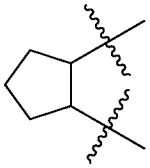 | I-1 | II-259 | A | 4.75 | 589 |
| I-261 | 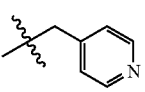 | 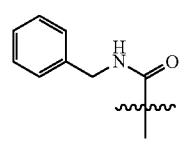 [SMILES: *C(=O)NCc1ccccc1] | H | 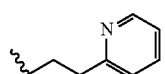 | 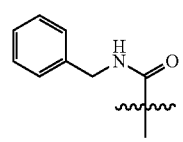 [SMILES: *C(=O)NCc1ccccc1] | I-1 | II-260 | A | 4.78 | 589 |
| I-262 | 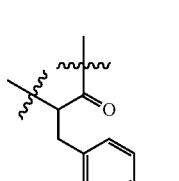 | 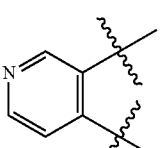 | H | | | I-1 | II-261 | A | 3.93 | 599 |

TABLE XIV-25
| Example No. | R1 | R2 | R3 | 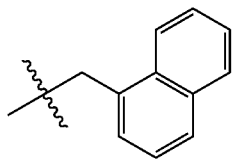 |
|---|---|---|---|---|
| I-263 | 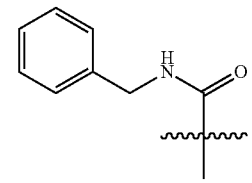 [SMILES: *C(=O)NCc1ccccc1] | 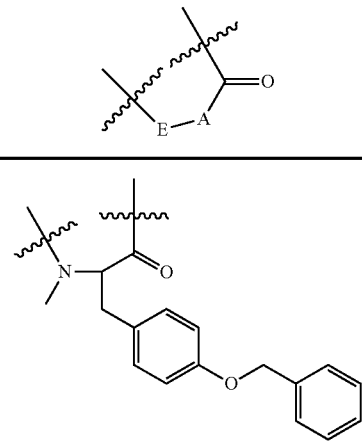 | H | 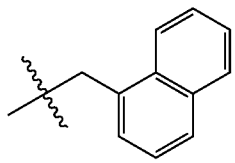 [SMILES: *Cc1cccc2ccccc12] |
| I-264 | 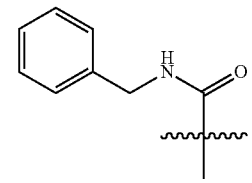 [SMILES: *C(=O)NCc1ccccc1] | 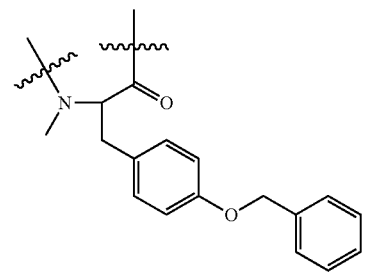 [SMILES: *C(=O)C(Cc1ccc(OCc2ccccc2)cc1)N(*)C] | H | 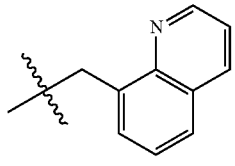 [SMILES: *Cc1cccc2cccnc12] |
| I-265 | 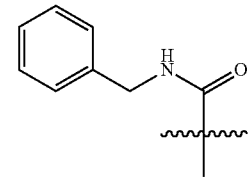 [SMILES: *C(=O)NCc1ccccc1] | 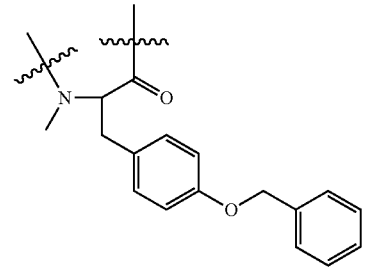 [SMILES: *C(=O)C(Cc1ccc(OCc2ccccc2)cc1)N(*)C] | H | 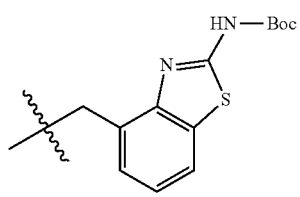 [SMILES: *Cc1cccc2sc(NC(=O)OC(C)(C)C)nc12] |
| I-266 | 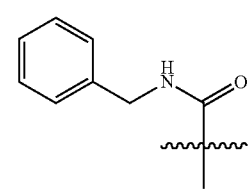 [SMILES: *C(=O)NCc1ccccc1] | 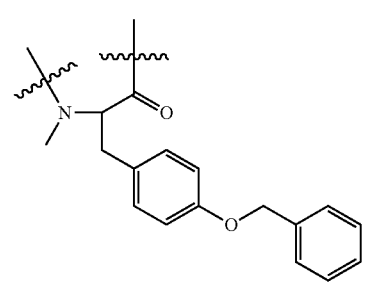 [SMILES: *C(=O)C(Cc1ccc(OCc2ccccc2)cc1)N(*)C] | H | 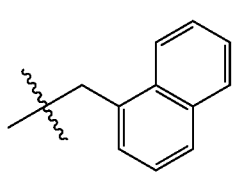 [SMILES: *Cc1cccc2ccccc12] |
| I-267 | 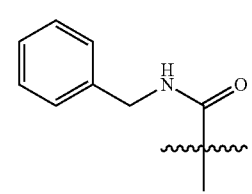 [SMILES: *C(=O)NCc1ccccc1] | 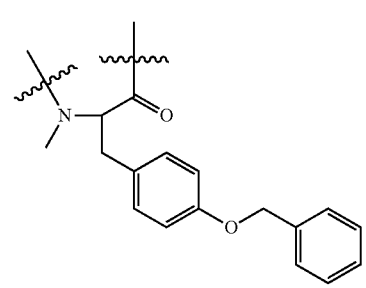 [SMILES: *C(=O)C(Cc1ccc(OCc2ccccc2)cc1)N(*)C] | H |  |

TABLE XIV-25-continued
| I-268 | 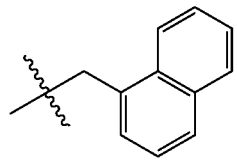 [SMILES: *Cc1cccc2ccccc12] | 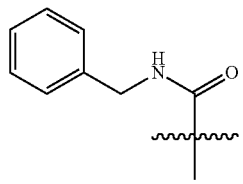 [SMILES: *C(=O)NCc1ccccc1] | H | 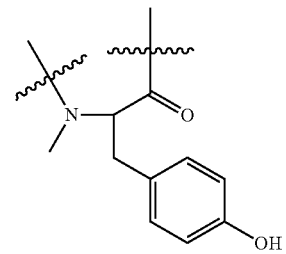 [SMILES: *C(=O)C(Cc1ccc(O)cc1)N(*)C] |
| I-269 | 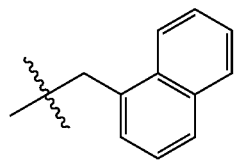 [SMILES: *Cc1cccc2ccccc12] | 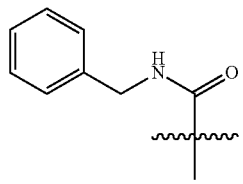 [SMILES: *C(=O)NCc1ccccc1] | H | 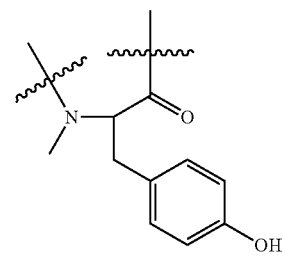 [SMILES: *C(=O)C(Cc1ccc(O)cc1)N(*)C] |
| I-270 | 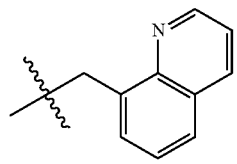 [SMILES: *Cc1cccc2cccnc12] | 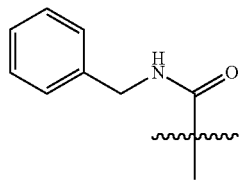 [SMILES: *C(=O)NCc1ccccc1] | H | 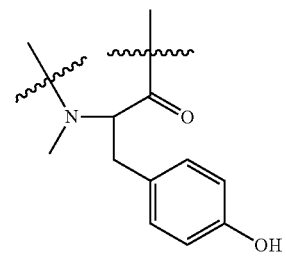 [SMILES: *C(=O)C(Cc1ccc(O)cc1)N(*)C] |
| I-271 | 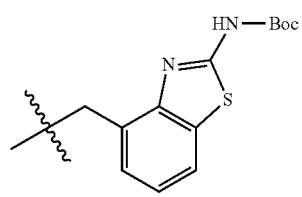 [SMILES: *Cc1cccc2sc(NC(=O)OC(C)(C)C)nc12] | 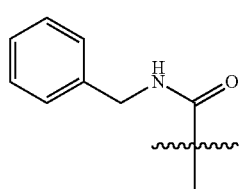 [SMILES: *C(=O)NCc1ccccc1] | H | 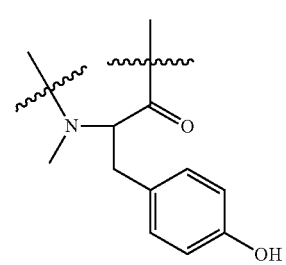 [SMILES: *C(=O)C(Cc1ccc(O)cc1)N(*)C] |

TABLE XIV-25-continued
| I-272 | 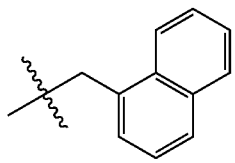 [SMILES: *Cc1cccc2ccccc12] | 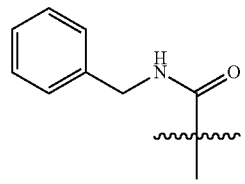 [SMILES: *C(=O)NCc1ccccc1] | H | 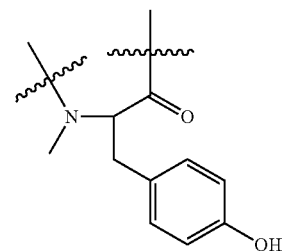 [SMILES: *C(=O)C(Cc1ccc(O)cc1)N(*)C] |
| Example No. | 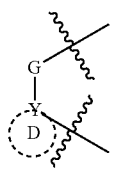 | Syn. | Int | method | RT | Mass |
|---|---|---|---|---|---|---|
| I-263 | 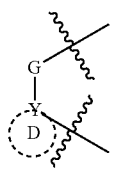 | I-1 | II-262 | A | 5.93 | 668 |
| I-264 | 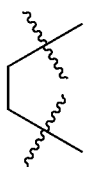 [SMILES: *CC*] | I-1 | II-263 | A | 6.15 | 683 |
| I-265 | 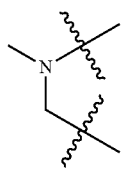 [SMILES: *CN(*)C] | I-1 | II-264 | A | 5.85 | 684 |
| I-266 | 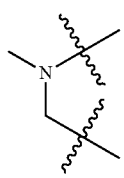 [SMILES: *CN(*)C] | I-1 | II-265 | A | 5.05 | 705 |
| I-267 | 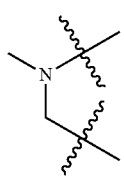 [SMILES: *CN(*)C] | I-1 | II-266 | A | 6.59 | 723 |
| I-268 | 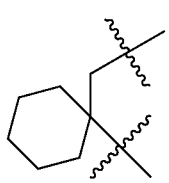 [SMILES: *CC1(*)CCCCC1] | I-2 | II-267 | A | 4.92 | 578 |

TABLE XIV-25-continued

| | | | | | | |
|---|---|---|---|---|---|---|
| I-269 | (structure) | I-2 | II-268 | A | 5.17 | 593 |
| I-270 | (structure) | I-2 | II-269 | A | 3.64 | 594 |
| I-271 | (structure) | I-2 | II-270 | A | 3.87 | 615 |
| I-272 | 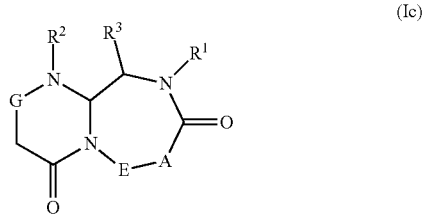 | I-2 | II-271 | A | 7.05 | 633 |

INDUSTRIAL APPLICABILITY

The compound of the formula (I) in the present invention blocks TCF4/β-catenin transcriptional pathway by inhibiting CBP, and therefore can be used for treatment of cancer, especially colorectal cancer, and fibrotic diseases.

This application is based on provisional application Nos. 61/176,348 and 61/176,363 filed in U.S.A., the contents of which are hereby incorporated by reference.

Although only some exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

The invention claimed is:

1. A compound having the following general formula (Ic):

(Ic)

wherein
A is —CHR$^7$—,
   wherein
   R$^7$ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl or optionally substituted heterocycloalkylalkyl;

E is —NR$^8$—,
   wherein
   R$^8$ is hydrogen, optionally substituted alkyl, optionally substituted alkenyl or optionally substituted alkynyl;

G is —NR$^6$—, —O—, —CHR$^6$— or —C(R$^6$)$_2$—,
   wherein
   each R$^6$ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl;

R$^1$ is optionally substituted alkyl, optionally substituted alkenyl, optionally substituted alkynyl, optionally substituted arylalkyl, optionally substituted heteroarylalkyl, optionally substituted cycloalkylalkyl or optionally substituted heterocycloalkylalkyl;

R$^2$ is —W$^{21}$—W$^{22}$—Rb—R$^{20}$,
   wherein
   W$^{21}$ is —(CO)— or —(SO$_2$)—,
   W$^{22}$ is bond, —O—, —NH— or optionally substituted lower alkylene, Rb is bond or optionally substituted alkylene, and
R$^{20}$ is optionally substituted alkyl, optionally substituted alkenyl, optionally substituted alkynyl, optionally substituted aryl, optionally substituted heteroaryl, optionally substituted cycloalkyl or optionally substituted heterocycloalkyl; and
R$^3$ is hydrogen or optionally substituted alkyl;
or a pharmaceutically acceptable salt thereof.

2. The compound of claim 1,
wherein
R$^8$ is hydrogen or optionally substituted alkyl.

3. The compound of claim 1,
wherein
R$^1$ is —Ra—R$^{10}$,
wherein
Ra is optionally substituted lower alkylene and
R$^{10}$ is hydrogen, optionally substituted alkyl, optionally substituted cycloalkyl, optionally substituted aryl or optionally substituted heteroaryl.

4. The compound of claim 3,
wherein
R$^{10}$ is hydrogen, optionally substituted methyl, optionally substituted ethyl, optionally substituted propyl, optionally substituted isopropyl, optionally substituted isobutyl, optionally substituted cyclohexyl, optionally substituted biphenyl, optionally substituted phenyl, optionally substituted benzhydryl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furanyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuranyl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

5. The compound of claim 3, wherein R$^3$ is hydrogen or C$_{1-4}$ alkyl group.

6. The compound of claim 1,
wherein
R$^2$ is —W$^{21}$—W$^{22}$—Rb—R$^{20}$,
wherein
W$^{21}$ is —(CO)— or —(SO$_2$)—,
W$^{22}$ is bond, —O—, —NH— or optionally substituted lower alkylene,
Rb is bond or optionally substituted lower alkylene, and
R$^{20}$ is optionally substituted alkyl, optionally substituted cycloalkyl, optionally substituted aryl or optionally substituted heteroaryl.

7. The compound of claim 6, wherein
R$^{20}$ is optionally substituted methyl, optionally substituted ethyl, optionally substituted propyl, optionally substituted isopropyl, optionally substituted isobutyl, optionally substituted cyclohexyl, optionally substituted benzhydryl, optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furanyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuranyl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl, optionally substituted benzodioxolyl or optionally substituted imidazopyridinyl.

8. The compound of claim 6, wherein R$^3$ is hydrogen or C$_{1-4}$ alkyl group.

9. The compound of claim 8,
wherein
R$^1$ is —Ra—R$^{10}$,
wherein
Ra is optionally substituted lower alkylene; and
R$^{10}$ is hydrogen, optionally substituted methyl, optionally substituted ethyl, optionally substituted propyl, optionally substituted isopropyl, optionally substituted isobutyl, optionally substituted cyclohexyl, optionally substituted biphenyl, optionally substituted phenyl, optionally substituted benzhydryl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furanyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuranyl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

10. The compound of claim 1,
wherein
$R^8$ is hydrogen or alkyl.

11. The compound of claim 10,
wherein
$R^3$ is hydrogen or $C_{1-4}$ alkyl group, and
$R^1$ is —Ra—$R^{10}$,
wherein
Ra is optionally substituted lower alkylene, and
$R^{10}$ is hydrogen, optionally substituted methyl, optionally substituted ethyl, optionally substituted propyl, optionally substituted isopropyl, optionally substituted isobutyl, optionally substituted cyclohexyl, optionally substituted biphenyl, optionally substituted phenyl, optionally substituted benzhydryl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furanyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuranyl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

12. The compound of claim 9,
wherein
$R^7$ of A is —Rc—$R^{70}$
wherein
Rc is optionally substituted lower alkylene, and
$R^{70}$ is hydrogen, optionally substituted alkyl, optionally substituted aryl or optionally substituted heteroaryl.

13. The compound of claim 12,
wherein
$R^{70}$ is hydrogen, optionally substituted methyl, optionally substituted ethyl, optionally substituted propyl, optionally substituted isopropyl, optionally substituted isobutyl, optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thiophenyl, optionally substituted furanyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuranyl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

14. A pharmaceutical composition comprising a compound according to claim 1 or a pharmaceutically acceptable salt thereof, and optionally a pharmaceutically acceptable carrier or diluent.

15. The pharmaceutical composition of claim 14, wherein the composition comprises an effective amount of the compound.

16. A method for treating a disease or condition, comprising administration of a therapeutically effective amount of a compound according to claim 1 or a pharmaceutically acceptable salt thereof to a subject in need thereof having a disease or condition selected from the group consisting of restenosis associated with angioplasty, polycystic kidney disease, aberrant angiogenesis disease, tuberous sclerosis complex (TSC), KSHV-associated tumor, and hair loss.

17. A process for preparing a compound having the following general formula (Ic):

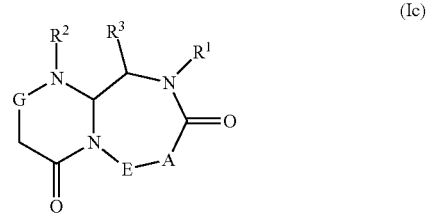

(Ic)

wherein

A is —CHR$^7$—,
wherein
$R^7$ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substi tuted cycloalkylalkyl or optionally substituted heterocycloalkylalkyl;

E is NR$^8$—,
wherein
R$^8$ is hydrogen, optionally substituted alkyl, optionally substituted alkenyl or optionally substituted alkynyl;

G is NR$^6$—, —O—, —CHR$^6$— or —C(R$^6$)$_2$—,
wherein
each R$^6$ is independently hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl or optionally substituted heteroarylalkyl;

R$^1$ is optionally substituted alkyl, optionally substituted alkenyl, optionally substituted alkynyl, optionally substituted arylalkyl, optionally substituted heteroarylalkyl, optionally substituted cycloalkylalkyl or optionally substituted heterocycloalkylalkyl;

R$^2$ is —W$^{21}$—W$^{22}$—Rb—R$^{20}$,
wherein
W$^{21}$ is —(CO)— or —(SO$_2$)—,
W$^{22}$ is bond, —O—, —NH— or optionally substituted lower alkylene,
Rb is bond or optionally substituted alkylene, and
R$^{20}$ is optionally substituted alkyl, optionally substituted alkenyl, optionally substituted alkynyl, optionally substituted aryl, optionally substituted heteroaryl, optionally substituted cycloalkyl or optionally substituted heterocycloalkyl; and R$^3$ is hydrogen or optionally substituted alkyl;

or a salt thereof, which comprises reacting a compound having the following general formula (II):

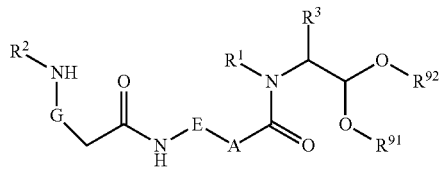

wherein
R$^{91}$ is selected from optionally substituted alkyl, linker and solid support;
R$^{92}$ is selected from optionally substituted alkyl, linker and solid support; and
the other symbols are as defined above, or a salt thereof, with an acid.

\* \* \* \* \*